United States Patent
Ponda et al.

(10) Patent No.: US 10,538,512 B2
(45) Date of Patent: Jan. 21, 2020

(54) AMINOACYLINDAZOLE IMMUNOMODULATORS FOR TREATMENT OF AUTOIMMUNE DISEASES

(71) Applicant: The Rockefeller University, New York, NY (US)

(72) Inventors: Manish P. Ponda, New York, NY (US); Jan L. Breslow, Scarsdale, NY (US); Harold Selnick, Ambler, PA (US); Melissa Egbertson, Ambler, PA (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 16/304,011

(22) PCT Filed: May 22, 2017

(86) PCT No.: PCT/US2017/033850
§ 371 (c)(1),
(2) Date: Nov. 21, 2018

(87) PCT Pub. No.: WO2017/205296
PCT Pub. Date: Nov. 30, 2017

(65) Prior Publication Data
US 2019/0202811 A1 Jul. 4, 2019

Related U.S. Application Data

(60) Provisional application No. 62/340,187, filed on May 23, 2016.

(51) Int. Cl.

| | | |
|---|---|---|
| *C07D 231/56* | (2006.01) | |
| *C07D 403/12* | (2006.01) | |
| *C07D 401/12* | (2006.01) | |
| *C07D 405/12* | (2006.01) | |
| *C07D 409/12* | (2006.01) | |
| *C07D 417/12* | (2006.01) | |
| *C07D 471/04* | (2006.01) | |

(52) U.S. Cl.
CPC ......... *C07D 403/12* (2013.01); *C07D 231/56* (2013.01); *C07D 401/12* (2013.01); *C07D 405/12* (2013.01); *C07D 409/12* (2013.01); *C07D 417/12* (2013.01); *C07D 471/04* (2013.01)

(58) Field of Classification Search
CPC .. C07D 403/12; C07D 405/12; C07D 471/04; C07D 401/12; C07D 409/12; C07D 231/56; C07D 417/12
USPC .............................................. 548/361, 361.1
See application file for complete search history.

(56) References Cited

U.S. PATENT DOCUMENTS

| 5,086,070 A | 2/1992 | Clemence et al. |
| 6,429,205 B1 | 8/2002 | Jacobson et al. |
| 7,326,791 B2 | 2/2008 | Gillard et al. |

FOREIGN PATENT DOCUMENTS

| EP | 0885883 A1 | 12/1998 |
| WO | 2011126903 A2 | 10/2011 |

OTHER PUBLICATIONS

International Search Report and Written Opinion issued in PCT/US2017/033850, dated Aug. 31, 2017.
Lucija Peterlin-Masic et al., "Novel Thrombin Inhibitors Incorporating Non-basic Partially Saturated Heterobicyclic P₁-Arginine Mimetics," Bioorganic & Medicinal Chemistry Letters, 2003, pp. 789-794.
Chris S. Constantinescu et al., "Experimental autoimmune encephalomyelitis (EAE) as a model for multiple sclerosis (MS)," British Journal of Pharmacology, 164, 2011, pp. 1079-1106.
Anton Matafonov et al., "Factor XII inhibition reduces thrombus formation in a primate thrombosis model," The American Society of Hematology, Blood Journal, Mar. 13, 2014, vol. 123, No. 11, pp. 1739-1746.
Kerstin Gobel et al., "Blood coagulation factor XII drives adaptive immunity during neuroinflammation via CD87-mediated modulation of dendritic cells," Nature Communications, May 18, 2016, pp. 1-15.
Extended European Search Report for PCT/US2011/030585 dated Oct. 15, 2019.

*Primary Examiner* — Taylor V Oh
(74) *Attorney, Agent, or Firm* — Heslin Rothenberg Farley & Mesiti, P.C.

(57) ABSTRACT

2-Acylindazole compounds of formula I or formula II are disclosed:

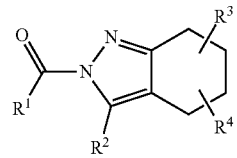

Formula I

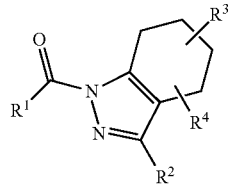

Formula II

These compounds inhibit Coagulation Factor XIIa. They are useful to treat autoimmune diseases.

18 Claims, No Drawings

AMINOACYLINDAZOLE IMMUNOMODULATORS FOR TREATMENT OF AUTOIMMUNE DISEASES

CROSS-REFERENCE TO RELATED APPLICATIONS

This application is a U.S. National Phase filing under 35 U.S.C. § 371 of International Application PCT/US2017/033850, filed May 22, 2017, and published as WO2017/205296 A1 on Nov. 30, 2017. PCT/US2017/033850 claims priority from U.S. provisional application 62/340,187, filed May 23, 2016. The entire contents of each of these applications are hereby incorporated herein by reference.

FIELD OF THE INVENTION

The invention relates to 2-acylindazoles that inhibit Coagulation Factor XIIa. These compounds are useful to treat autoimmune diseases.

BACKGROUND

Chemotaxis is directional movement in response to a specific chemical gradient. This cellular ability is necessary for immune homeostasis and the response to inflammation, among other critical biologic processes. Several chemokines have been identified along with their receptors, providing a molecular mechanism to orchestrate movement of distinct cell types in response to diverse stimuli. For example, chemokine receptor 7 (CCR7) and its ligands, CCL19 and CCL21, comprise a signaling axis required for chemotaxis of T-cells into and within lymphoid organs. CCR7-mediated chemotaxis is important in developing adaptive immunity, as well as maintaining tolerance and memory.

Chemokines are broadly grouped as homeostatic or inflammatory. For the latter, acutely increasing production may be sufficient to control a chemotactic response. For homeostatic chemokines, such as CCL19/21, signal modulation occurs by altering receptor density or effective ligand concentration. This is achieved either directly (e.g. increased receptor expression) or indirectly (e.g. atypical chemokine receptor scavenging of ligands). Indeed, for CCR7, exposure to serum promotes cell migration, and there is an enhanced chemotactic response of T-cells to CCL19/21 in the presence of serum, although the basis for this acceleration has not been previously described in the literature.

BRIEF SUMMARY OF THE INVENTION

It has now been found that a fragment from high molecular weight kininogen (HK) is a potent cofactor that accelerates CCL19-mediated chemotaxis. This HK fragment is necessary and sufficient for accelerated chemotaxis towards CCL19, and for serum or plasma, the activity is dependent on coagulation factor XIIa. High molecular weight kininogen (HK) is well-known for a role in inflammation, particularly as the parent molecule of the nonapeptide bradykinin.

Mechanistically, serum-accelerated chemotaxis is dependent on active coagulation factor XII (FXIIa), which is known to promote cleavage of HK. It has now been discovered that pre-treatment of native murine lymphocytes with this HK-derived fragment peptide enhances in vivo homing of T-cells to lymph nodes. A circulating cofactor that is activated at sites of inflammation and injury to enhance lymphocyte chemotaxis represents a new and powerful mechanism coupling inflammation to adaptive immunity. In particular, small molecule therapeutic agents that can modulate FXIIa function—and thereby production of the HK fragment—without significantly affecting thrombin activation offer a means of safely regulating immune cell chemotaxis through humoral cofactors. Small molecule therapeutic agents that inhibit both FXIIa and thrombin are useful for treating thromboses.

In one aspect, the invention relates to compounds of the following formula I or formula II:

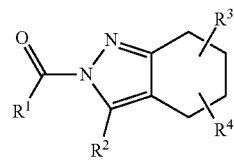

Formula I

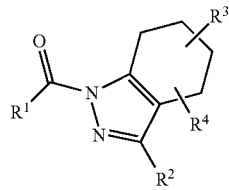

Formula II wherein
$R^1$ is an optionally substituted bicyclic ring system, attached to the carbonyl through a carbon, or, when $R^2$ is amino, $R^1$ may additionally be meta- or para-substituted phenyl or an optionally substituted monocyclic heteroaryl ring;
$R^2$ is chosen from hydrogen, amino and methyl; and
$R^3$ and $R^4$ are chosen independently from hydrogen, halogen, hydroxy, amino, cyano, $(C_1-C_4)$alkyl, $(C_1-C_4)$alkoxy, $(C_1-C_4)$alkylamino, $di(C_1-C_4)$alkylamino, $(C_1-C_7)$acylamino, $((C_1-C_7)$hydrocarbyloxy)carbonylamino, $(C_1-C_4)$fluoroalkyl, $(C_1-C_4)$fluoroalkoxy, and $(C_1-C_6)$oxaalkyl or, taken together, $R^3$ and $R^4$ on adjacent carbons form a double bond.

In another aspect, the invention relates to a method for inhibiting Factor XIIa in a subject including, for example, administering to the subject an inhibitory amount of a compound of formula I or formula II described above.

In another aspect, the invention relates to a method for selectively inhibiting Factor XIIa in the presence of thrombin and kallikrein including, for example, contacting an inhibitory amount of a compound of formula I or formula II described above with Factor XIIa.

In another aspect, the invention relates to a method for treating inflammation in a patient including, for example, administering to the patient a therapeutically effective amount of a compound of formula I or formula II as described above.

In another aspect, the invention relates to a method for treating an immunological disorder in a patient including, for example, administering to the patient a therapeutically effective amount of a compound of formula I or formula II as described above.

In another aspect, the invention relates to a method for treating vasodilatation in a patient including, for example, administering to the patient a therapeutically effective amount of a compound of formula I or formula II as described above.

In another aspect, the invention relates to a method for treating thrombosis in a patient including, for example, administering to the patient a therapeutically effective amount of a compound of formula I or formula II as described above.

These and other objects, features, and advantages of the invention will become apparent from the following detailed description of the various aspects of the invention.

DETAILED DESCRIPTION OF THE INVENTION

In one aspect, the invention relates to compounds of formula I or formula II:

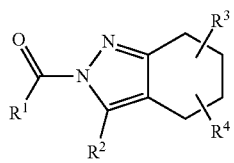

Formula I

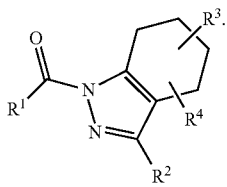

Formula II

In the compounds of formula I or formula II, $R^1$ may be an optionally substituted bicyclic ring system. Examples of bicyclic ring systems that may be optionally substituted, include indole, isoindole, oxindole, tetrahydroindole, tetralin, indoline, isoindoline, tetrahydroquinoline, tetrahydroisoquinoline, 3,4-dihydro-1H-isochromene, 3,4-dihydro-2H-chromene, benzofuran, dihydrobenzofuran, tetrahydrobenzofuran, benzothiophene, tetrahydrobenzothiophene, indazole, tetrahydroindazole, 2,3-dihydro-1H-indene, naphthalene, tetrahydronaphthalene, and isochroman. For instance, in some embodiments, $R^1$ may be an optionally substituted indole, benzofuran, or benzothiophene.

In some embodiments, $R^1$ may be a bicyclic ring system optionally substituted with one or more of halogen, hydroxy, amino, cyano, $(C_1-C_8)$hydrocarbyl, $(C_1-C_8)$hydrocarbyloxy, $(C_1-C_4)$alkylamino, di$(C_1-C_4)$alkylamino, $(C_1-C_4)$acylamino, $(C_1-C_4)$fluoroalkyl, $(C_1-C_4)$fluoroalkoxy, $(C_1-C_6)$oxaalkyl, $(C_3-C_6)$carbocycle, and $(C_1-C_4)$alkenyl. In certain embodiments, the $(C_1-C_8)$hydrocarbyl substituent may be chosen from straight chain $(C_1-C_8)$alkyl, branched $(C_1-C_8)$alkyl, $(C_3-C_6)$cycloalkyl, and $(C_3-C_6)$cycloalkyl$(C_1-C_3)$alkyl.

An exemplary embodiment of the optionally substituted bicyclic ring system includes a compound of formula I or formula II, where: $R^1$ may be

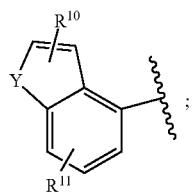

$R^{10}$ may be —H, halogen, —O—$(C_1-C_8)$hydrocarbyl, or —$(C_1-C_8)$hydrocarbyl; Y may be chosen from S, O, NH, and N$(C_1-C_8)$hydrocarbyl; and $R^{11}$ may be —H, halogen, —$(C_1-C_8)$hydrocarbyl, or —O$(C_1-C_8)$hydrocarbyl. For example, $R^1$ may be

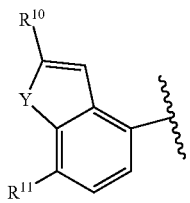

and $R^{10}$ may be —H, —$(C_1-C_4)$alkyl, or —$(C_3-C_6)$cycloalkyl, and $R^{11}$ may be —H, or —O$(C_1-C_4)$alkyl.

In another exemplary embodiment of the optionally substituted bicyclic ring system includes a compound of formula I or formula II, where: $R^1$ may be

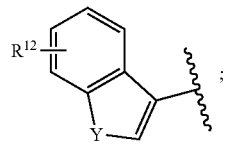

Y may be chosen from S, O, NH, and N$(C_1-C_8)$hydrocarbyl; and $R^{12}$ may be chosen from —H, —$(C_1-C_8)$hydrocarbyl and —O$(C_1-C_8)$hydrocarbyl. For example, $R^1$ may be

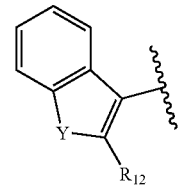

and $R^{12}$ may be —H or $(C_1-C_4)$alkyl.

In some embodiments, where $R^1$ is an optionally substituted bicyclic ring system, $R^1$ may be optionally substituted naphthalene, tetralin, tetrahydrobenzofuran, benzothiophene, tetrahydroquinoline, or 3,4-dihydro-1H-isochromene.

In the compounds of formula I or formula II, $R^2$ may be —$NH_2$.

In the compounds of formula I or formula II, when $R^2$ is amino, $R^1$ may additionally be substituted phenyl or an optionally substituted monocyclic heteroaryl ring. For example, in some embodiments, $R^2$ may be —$NH_2$ and $R^1$ may be thiophene or furan, optionally substituted with —$(C_1-C_8)$hydrocarbyl, —O$(C_1-C_8)$hydrocarbyl, or halogen.

In the compounds of formula I or formula II, $R^2$ may be chosen from hydrogen, amino, or methyl. For example, in some embodiments, $R^2$ may be —$NH_2$.

In the compounds of formula I or formula II, $R^3$ and $R^4$ may be chosen independently from hydrogen, halogen, hydroxy, amino, cyano, $(C_1-C_4)$alkyl, $(C_1-C_4)$alkoxy, $(C_1-C_4)$alkylamino, di$(C_1-C_4)$alkylamino, $(C_1-C_4)$acylamino, $(C_1-C_4)$fluoroalkyl, $(C_1-C_4)$fluoroalkoxy, or $(C_1-C_6)$oxaalkyl. Preferably $R^3$ and $R^4$ may be chosen independently from hydrogen, halogen, hydroxy, amino, $(C_1-C_4)$alkoxy, ($C_1$-$C_4$)alkylamino, di($C_1$-$C_4$)alkylamino, ($C_1$-$C_4$)acylamino, ($C_1$-$C_4$)fluoroalkyl, ($C_1$-$C_4$)fluoroalkoxy, and ($C_1$-$C_6$)oxaalkyl. In other embodiments, $R^3$ and $R^4$ on adjacent carbons form a double bond and the resulting indazole is a dihydroindazole rather than a tetrahydroindazole, as in examples 194-196 below.

In some embodiments the dihydroindazole is of formula III

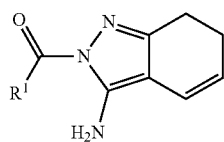

In some embodiments of the compounds of formula I or formula II, $R^2$ may be —$NH_2$ and $R^1$ may be thiophene or furan, optionally substituted with —($C_1$-$C_8$)hydrocarbyl, —O($C_1$-$C_8$)hydrocarbyl, or halogen.

In some embodiments of the compounds of formula I, $R^2$ may be —$NH_2$ and the compounds have the formula

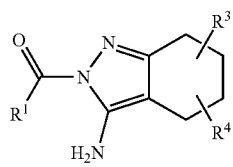

wherein (1) $R^3$ is hydrogen and $R^4$ is chosen from fluorine, hydroxy, and amino; or (2) $R^3$ and $R^4$ are both hydroxy or (3) $R^3$ and $R^4$ together form a double bond as in III. In these compounds, $R^1$ may be

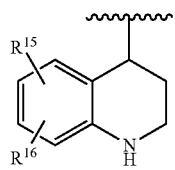

wherein $R^{15}$ and $R^{16}$ are independently selected from hydrogen, halogen, hydroxy, amino, cyano, ($C_1$-$C_4$)alkyl, ($C_1$-$C_4$)alkoxy, ($C_1$-$C_4$)fluoroalkyl, and ($C_1$-$C_4$)fluoroalkoxy.

In some embodiments, the substituent $R^1$ may be an optionally substituted 6,5-5,6- or 6,6 bicycle AB, in which ring A is non-aromatic and the carbon at its point of attachment is of a specific absolute configuration as shown in the depiction:

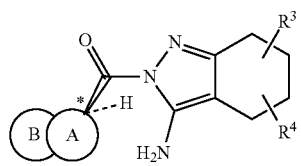

The configuration at the chiral center * is such that the ring A is in the plane of the paper and the substituents H and carbonyl are disposed above and below that plane. (As would be understood by the person of skill in the art, the nomenclature (R) or (S) may vary according to the hierarchy of the atoms adjacent to the chiral carbon in the ring.)

The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. For nomenclature in the text corresponding to wedge outlines and dotted or broken lines, we define R* and S* as indicating single enantiomers of uncertain absolute configuration. Thus, for example, in Example 125 below, the synthesis of ((5R*)-3-amino-5-hydroxy-4,5,6,7-tetrahydroindazol-2-yl) ((4R*)-2-chloro-4,5,6,7-tetrahydro-1H-indol-4-yl)methanone is described. The (5R*) and (4R*) are intended to indicate that the product is a single enantiomer possessing the characteristics described (e.g. NMR, HPLC retention time, etc.), in which each of the chiral centers is believed on the basis of circumstantial evidence to be of the configuration shown, but the absolute configuration has not been confirmed at either the 5-position of the indazole component or the 4-position of the indole component. Thus, the depiction:

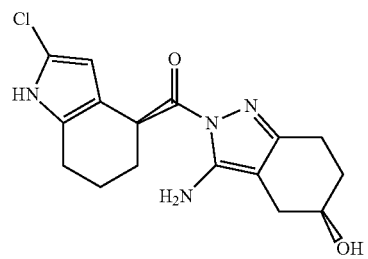

means that the product is a single one of the four following isomers, probably the first:

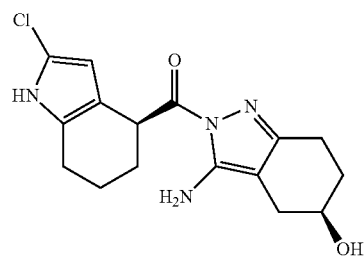 [SMILES: Nc1c2c(nn1C(=O)[C@H]1CCCc3[nH]c(Cl)cc31)CC[C@@H](O)C2]

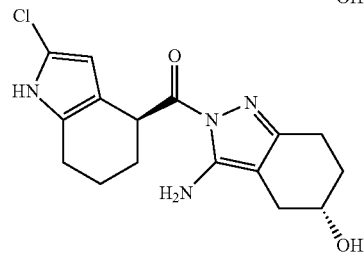

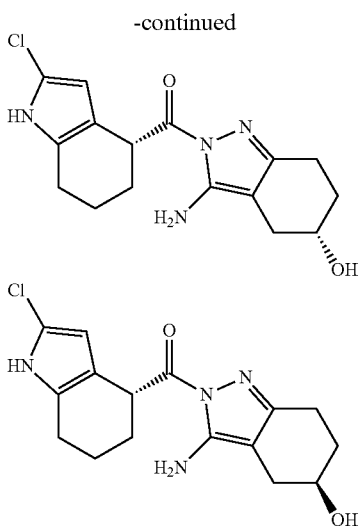

When a compound possesses a center of asymmetry, its depiction in the claims of this patent with simple lines, (e.g.

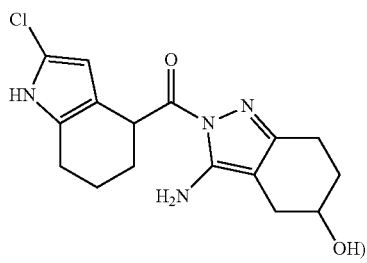

is intended to indicate that the structure includes any and all isomers without regard to enantiomeric purity. When its depiction in the claims of this patent includes wedges, dashed lines etc. (e.g.

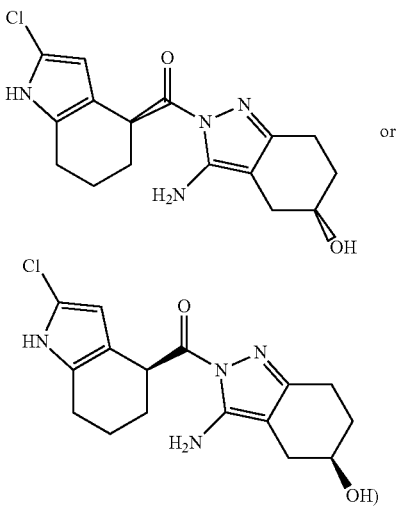

it is intended to indicate that the structure encompasses isomers of that relative or absolute configuration of at least 80% ee, preferably >90% ee.

Throughout this specification the terms and substituents retain their definitions.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbyl refers to any substituent comprised of hydrogen and carbon as the only elemental constituents. Aliphatic hydrocarbons are hydrocarbons that are not aromatic; they may be saturated or unsaturated, cyclic, linear or branched. Examples of aliphatic hydrocarbons include isopropyl, 2-butenyl, 2-butynyl, cyclopentyl, norbornyl, etc. Aromatic hydrocarbons include benzene (phenyl), naphthalene (naphthyl), anthracene, etc.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cy-propyl, cy-butyl, cy-pentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons. The term "halogen" means fluorine, chlorine, bromine or iodine atoms.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Loweracyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, hydrocarbyl, acyl, alkoxyalkyl, hydroxy lower alkyl, carbonyl, phenyl, heteroaryl, benzenesulfonyl, hydroxy, hydrocarbyloxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In particular embodiments, substituents are halogen, halo($C_1$-$C_4$)hydrocarbyl, halo($C_1$-$C_4$)hydrocarbyloxy, cyano, thiocyanato, ($C_1$-$C_4$)hydrocarbylsulfinyl, ($C_1$-$C_4$)hydrocarbyl-sulfonyl, aminosulfonyl, nitro, acetyl, and acetamido. Preferred substituents are halogen, ($C_1$-$C_4$)alkyl, ($C_1$-$C_4$)alkoxy, ($C_1$-$C_4$)fluoroalkyl, ($C_1$-$C_4$)fluoroalkoxy, hydroxy, amino, ($C_1$-$C_4$)alkylamino, di($C_1$-$C_4$)alkylamino, ($C_1$-$C_4$)acylamino, ($C_1$-$C_4$)fluoroalkyl and ($C_1$-$C_4$)fluoroalkoxy.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Substituents $R''$ are generally defined when introduced and retain that definition throughout the specification and claims.

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as *Protective Groups in Organic Synthesis* by T. W. Greene and P. G. M. Wuts [John Wiley & Sons, New York, 1999], in *Protecting Group Chemistry*, 1$^{st}$ Ed., Oxford University Press, 2000; and in *March's Advanced Organic chemistry: Reactions, Mechanisms, and Structure*, 5$^{th}$ Ed., Wiley-Interscience Publication, 2001.

In general, compounds of formula I or formula II can be prepared from as shown below. The appropriately substituted starting materials and intermediates used in the preparation of compounds of the invention are either commercially available or readily prepared by methods known in the literature to those skilled in the art.

The compounds described herein will, in most instances, contain an asymmetric center and may thus give rise to enantiomers, diastereomers, and other stereoisomeric forms. The present invention is meant to include all such possible isomers as racemates, optically pure forms and intermediate mixtures. Optically active (R)- and (S)-isomers may be prepared using homo-chiral synthons or homo-chiral reagents, or optically resolved using conventional techniques as described below. All tautomeric forms are intended to be included.

As used herein, and as would be understood by the person of skill in the art, the recitation of "a compound"—unless expressly further limited—is intended to include salts of that compound. In a particular embodiment, the term "compound of formula" refers to the compound or a pharmaceutically acceptable salt thereof.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

Also provided herein is a pharmaceutical composition comprising a compound disclosed above, or a pharmaceutically acceptable salt form thereof, and a pharmaceutically acceptable carrier or diluent.

While it may be possible for the compounds of formula I or formula II to be administered as the raw chemical, it is preferable to present them as a pharmaceutical composition. According to a further aspect, the present invention provides a pharmaceutical composition comprising a compound of formula I or formula II, or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or formula II, or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

General Methods.

All solvents used were commercially available and were used without further purification. Reactions were typically run using anhydrous solvents under an inert atmosphere of nitrogen.

$^1$H spectra were recorded at 300 or 400 MHz for proton on a Bruker Mercury Plus 400 NMR Spectrometer equipped with a Bruker 400 BBO probe. All deuterated solvents contained typically 0.03% to 0.05% v/v tetramethylsilane, which was used as the reference signal (set at δ 0.00 for both $^1$H and $^{13}$C).

LCMS analyses were performed on a SHIMADZU LCMS consisting of an UFLC 20-AD and LCMS 2020 MS detector. The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.2 min with a total run time of 3.6 min. The column temperature was at 40° C. with the flow rate of 1.0 mL/min. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 0.7 s.

HPLC analyses were performed on a SHIMADZU UFLC with two LC20 AD pump and a SPD-M20A Photodiiode Array Detector. The column used was an XBridge $C_{18}$, 3.5 μm, 4 60×100 mm. A linear gradient was applied, starting at 90% A (A: 0.05% TFA in water) and ending at 95% B (B: 0.05% TFA in MeCN) over 10 min with a total run time of 15 min. The column temperature was at 40° C. with the flow rate of 1.5 mL/min. The Diode Array Detector was scanned from 200-400 nm.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24}·4H_2O$, 5 g $(NH_4)_2Ce(IV)(NO_3)_6$ in 450 mL water and 50 mL concentrated $H_2SO_4$) to visualize the compound. Flash chromatography was performed using 40-63 μm (230-400 mesh) silica gel from Silicycle following analogous techniques to those disclosed in Still, W. C.; Kahn, M.; and Mitra, M. *Journal of Organic Chemistry*, 1978, 43, 2923. Typical solvents used for flash chromatography or thin layer chromatography were mixtures of chloroform/methanol, dichloromethane/methanol, ethyl acetate/methanol and hexanes/ethyl acetate.

Examples 1 and 2: (3-Amino-4,5,6,7-tetrahydro-2H-indazol-2-yl)(1H-indol-4-yl)methanone and (3-amino-4,5,6,7-tetrahydroindazol-1-yl)(1H-indol-4-yl)methanone

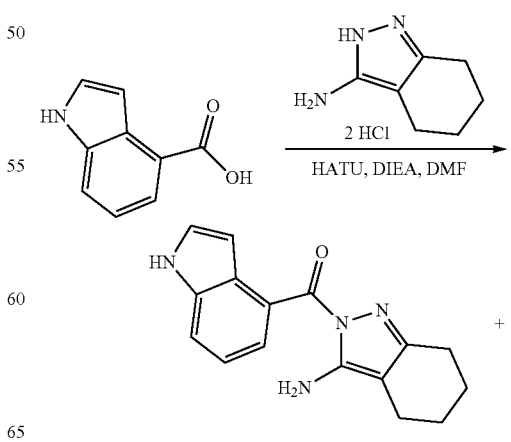

1

-continued

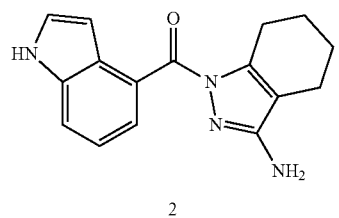

2

Into a 50-mL round-bottom flask, was placed 1H-indole-4-carboxylic acid (40 mg, 0.25 mmol, 1.00 eq.), N,N-dimethylformamide (3 mL), HATU (143 mg, 0.38 mmol, 1.50 eq.), and DIEA (97 mg, 0.75 mmol, 3.00 eq.). The mixture was stirred for 30 min. Then 4,5,6,7-tetrahydro-2H-indazol-3-amine (79.8 mg, 0.38 mmol, 1.20 eq.) was added. The resulting solution was stirred overnight at room temperature. The reaction mixture was diluted with DCM (50 mL), washed with water (50 mL×3) and brine (50 mL×3), dried over anhydrous sodium sulfate, filtered and concentrated under vacuum. The residue was purified by Pre-TLC with DCM/MeOH (20:1). The crude product was purified by Prep-HPLC with the following conditions: Column, XBridge Shield RP18 OBD Column, 5 um, 19×150 mm; mobile phase, water (0.1% FA) and ACN (30.0% ACN up to 60.0% in 7 min); Detector, UV 254 nm to give the title compounds.

Fraction A (Example 1): Rt=6.45 min; Yield: 1.7 mg (2%) as a light yellow solid. MS (ES, m/z) [M+H]$^+$: 281; $^1$HNMR (DMSO-d$_6$, 400 MHz, ppm): δ 11.42 (s, 1H), 7.66-7.58 (m, 2H), 7.49-7.48 (m, 1H), 7.18-7.14 (m, 1H), 6.40-6.21 (m, 3H), 2.37-2.30 (m, 4H), 1.66 (m, 4H).

Fraction B (Example 2): Rt=5.35 min; Yield: 4.3 mg (6%) as a gray solid. MS (ES, m/z) [M+H]$^+$: 281; $^1$HNMR (DMSO-d$_6$, 400 MHz, ppm): δ 11.30 (s, 1H), 7.55 (d, J=8.0 Hz, 1H), 7.47 (d, J=6.8 Hz, 1H), 7.42-7.41 (m, 1H), 7.15-7.11 (m, 1H), 6.46 (s, 1H), 5.34 (s, 2H), 2.97-2.94 (m, 2H), 2.33-2.26 (s, 2H), 1.76-1.69 (m, 4H).

Examples 3 and 4: (1H-Indol-4-yl)(3-methyl-4,5,6,7-tetrahydroindazol-2-yl)methanone and (1H-indol-4-yl)(3-methyl-4,5,6,7-tetrahydroindazol-1-yl)methanone

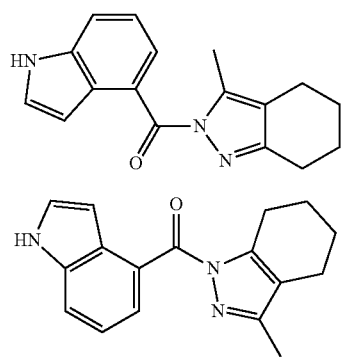

3

4

Step 1. 1H-Indole-4-carbohydrazide

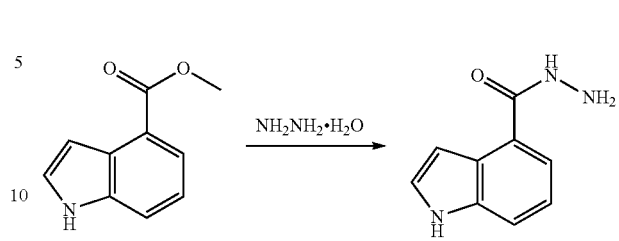

Into a 100-mL round-bottom flask, was placed methyl 1H-indole-4-carboxylate (500 mg, 2.85 mmol, 1.00 eq.) and hydrazine hydrate (10 mL). The resulting solution was stirred overnight at 80° C. After cooling down to room temperature, the reaction mixture was concentrated under vacuum to give 500 mg (crude) of the title compound as a yellow solid. MS (ES, m/z) [M+H]$^+$: 176.

Step 2. (3-Hydroxy-3-methyl-3,3a,4,5,6,7-hexahydroindazol-2-yl)(1H-indol-4-yl)methanone and (7a-hydroxy-3-methyl-3a,4,5,6,7,7a-hexahydroindazol-1-yl)(1H-indol-4-yl)methanone

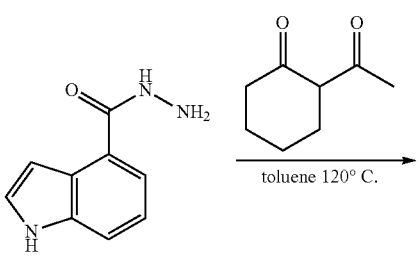

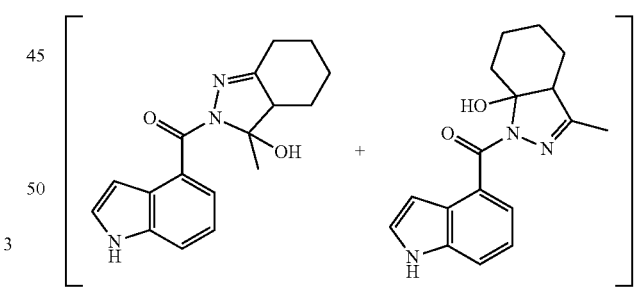

Into a 100-mL round-bottom flask, was placed 1H-indole-4-carbohydrazide (500 mg, 2.85 mmol, 1.20 eq.), 2-acetyl-cyclohexan-1-one (333 mg, 2.38 mmol, 1.00 eq.) and toluene (40 mL). The resulting solution was stirred overnight at 120° C. The reaction mixture was cooled to room temperature. The solids were filtered out. The filtrate was concentrated under vacuum. This resulted in 150 mg (22%) mixture of the title compounds as yellow oil. MS (ES, m/z) [M+H]$^+$: 298.

Step 3. (1H-Indol-4-yl)(3-methyl-4,5,6,7-tetrahydroindazol-2-yl)methanone (Example 3) and (1H-indol-4-yl)(3-methyl-4,5,6,7-tetrahydroindazol-1-yl)methanone (Example 4)

Examples 5 and 6: (S*)-(3-Amino-4,5,6,7-tetrahydroindazol-2-yl)(1,2,3,4-tetrahydronaphthalen-1-yl)methanone and (R*)-(3-amino-4,5,6,7-tetrahydroindazol-2-yl)(1,2,3,4-tetrahydronaphthalen-1-yl)methanone

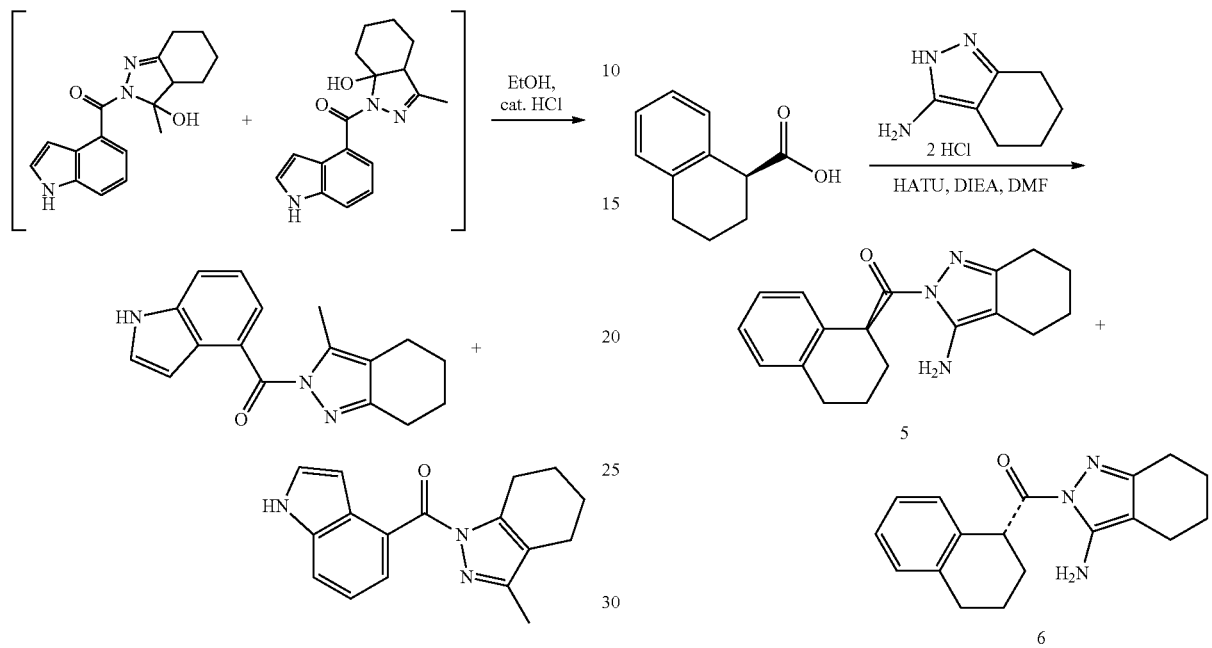

Into a 100-mL round-bottom flask, was placed the mixture of 1-[(1H-indol-4-yl)carbonyl]-3-methyl-3a,4,5,6,7,7a-hexahydro-1H-indazol-7a-ol and 2-[(1H-indol-4-yl)carbonyl]-3-methyl-3,3a, 4,5,6,7-hexahydro-2H-indazol-3-ol (150 mg, 0.25 mmol, 1.00 eq.) in ethanol (3 mL), and hydrochloric acid (catalytic amount, 12 M). The resulting solution was stirred for 1.5 h at 84° C., cooled down to room temperature and concentrated under reduced pressure. The crude product was purified by Prep-HPLC with the following conditions: Column, XBridge Shield RP18 OBD Column 5 um 19×150 nm; mobile phase, Water (0.05% FA) and CAN (30.0% ACN up to 60.0% in 8 min); Detector, 245 nm. The mixture was separated by Chiral-Prep-HPLC with the following conditions: Column, Chiralpak IB4.6×250 nm 5 um HPLC chiral (ALIB)001IB00CE-LA026; mobile phase, Hex (0.1% DEA): EtOH=85:15; Detector, 254 nm to give the title compounds.

Fraction A (Example 3): Rt=5.20 min; Yield: 14.2 mg (20%) as an off-white solid. MS (ES, m/z) [M+H]$^+$: 280; $^1$HNMR (DMSO-d6, 400 MHz, ppm): δ 11.42 (s, 1H), 7.72-7.63 (m, 1H), 7.53-7.47 (m, 2H), 7.19-7.15 (m, 1H), 6.49 (s, 1H), 2.58-2.51 (m, 4H), 2.49 (s, 3H), 1.72-1.71 (m, 4H).

Fraction B (Example 4): Rt=6.26 min; Yield: 3 mg (4%) as an off-white solid. MS (ES, m/z) [M+H]$^+$: 280; $^1$HNMR (DMSO-d6, 400 MHz, ppm): δ 11.41 (s, 1H), 7.64 (d, 1=8.0 Hz, 1H), 7.54 (d, J=7.2 Hz, 1H), 7.49-7.48 (m, 1H), 7.20-7.16 (m, 1H), 6.51 (s, 1H), 3.01-2.98 (m, 2H), 2.41-2.39 (m, 2H), 2.08 (s, 3H), 1.79-1.73 (m, 4H).

Into a 50-mL round-bottom flask, was placed 1,2,3,4-tetrahydronaphthalene-1-carboxylic acid (54.6 mg, 0.31 mmol, 0.90 eq.), N,N-dimethylformamide (3 mL), HATU (193 mg, 0.51 mmol, 1.50 eq.), and DIEA (132 mg, 1.02 mmol, 3.00 eq.). After stirring for 30 min at ambient temperature, 4,5,6,7-tetrahydro-2H-indazol-3-amine hydrochloride (73.5 mg, 0.35 mmol, 1.00 eq.) was added. The reaction was stirred overnight at ambient temperature, diluted with EA (30 mL), washed with brine (100 mL×2), dried over anhydrous sodium sulfate, filtered and concentrated under vacuum. The crude product was purified by Prep-HPLC with the following conditions: Column, XBridge Shield RP18 OBD Column, 5 um, 19×150 mm; mobile phase, water (0.1% FA) and ACN (45.0% ACN up to 65.0% in 7 min); Detector, UV 254 nm. The collected fraction was lyophilized to give 15 mg of a racemic mixture. The racemized product was separated by Chiral-Prep-HPLC with the following conditions: Column: CHIRAL ART Cellulose-SB, 250*20 mmI.D.; Mobile Phase A: Hex-HPLC, Mobile Phase B: IPA-HPLC; Flow rate: 20 mL/min; Gradient: 30 B to 30 B in 9.5 min; 254/220 nm to give the two single enantiomers.

Enantiomer A (Example 6): Rt: 6.28 min; Yield: 7.7 mg (8%) as a white solid; MS (ES, m/z): [M+H]$^+$ 296; $^1$HNMR (300 MHz, DMSO-d$_6$, ppm): δ 7.15-7.02 (m, 3H), 6.91 (d, J=9.9 Hz, 1H), 6.35 (s, 2H), 5.13-5.08 (m, 1H), 2.84-2.61 (m, 2H), 2.49 (d, J=1.5 Hz, 2H), 2.28-2.34 (m, 2H), 2.11-1.86 (m, 3H), 1.70 (s, 5H).

Enantiomer B (Example 5): Rt: 8.54 min; Yield: 2.8 mg (3%) as a white solid; MS (ES, m/z): [M+H]$^+$ 296; $^1$HNMR (300 MHz, DMSO-d$_6$, ppm): δ 7.15-7.02 (m, 3H), 6.91 (d, J=9.9 Hz, 1H), 6.35 (s, 2H), 5.13-5.08 (m, 1H), 2.84-2.61 (m, 2H), 2.49 (d, J=1.5 Hz, 2H), 2.28-2.34 (m, 2H), 2.11-1.86 (m, 3H), 1.70 (s, 5H).

Examples 7 and 8: (3-Amino-4,5,6,7-tetrahydroindazol-2-yl)(1-methyl-1H-indol-4-yl)methanone and (3-amino-4,5,6,7-tetrahydroindazol-1-yl)(1-methyl-1H-indol-4-yl)methanone

Step 1. Methyl-1-methyl-1H-indole-4-carboxylate

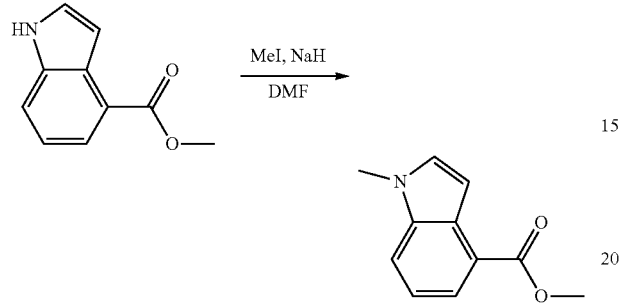

Into a 40-mL vial, was placed a solution of methyl 1H-indole-4-carboxylate (400 mg, 2.28 mmol, 1.00 eq.) in N,N-dimethylformamide (10 mL). This was followed by the addition of sodium hydride (275 mg, 6.88 mmol, 3.00 eq., 60%) in several portions at 0° C. After stirring for 0.5 hour at 0° C., iodomethane (1.298 g, 9.14 mmol, 4.00 eq.) was added dropwise with stirring at 0° C. After stirring for 15 h at 25° C., the reaction mixture was poured into ice-water (50 mL), extracted with ethyl acetate (50 mL×3), washed with brine (100 mL), dried over anhydrous sodium sulfate, filtered and concentrated under vacuum. This resulted in 429 mg (99%) of the title compound as a red oil. MS: (ES, m/z) [M+H]$^+$: 190.

Step 2. 1-Methyl-1H-indole-4-carboxylic Acid

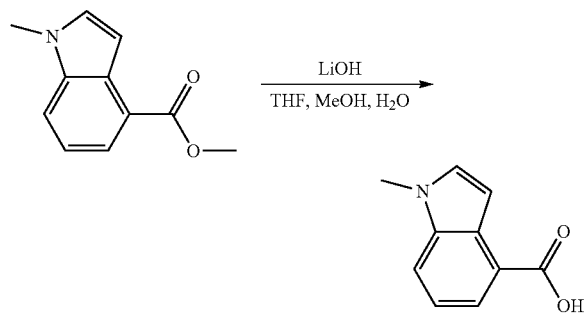

Into a 250-mL round-bottom flask, was placed a solution of methyl 1-methyl-1H-indole-4-carboxylate (429 mg, 2.27 mmol, 1.00 eq.) in tetrahydrofuran (50 mL) and MeOH (10 mL). LiOH (aq. 2 mol/L, 22.7 mL, 45.4 mmol, 20.0 eq.) was added. The resulting solution was stirred for 18 h at 30° C. After removal of the solvents under reduced pressure and extraction with ethyl acetate (60 mL), the pH value of the solution was adjusted to 5-6 with HCl (1N). The solid was collected by filtration and dried in vacuo. This resulted in 373 mg (94%) of the title compound as a white solid. MS: (ES, m/z) [M+H]$^+$: 176.

Step 3. (3-Amino-4,5,6,7-tetrahydroindazol-2-yl)(1-methyl-1H-indol-4-yl)methanone (Example 7) and (3-amino-4,5,6,7-tetrahydroindazol-1-yl)(1-methyl-1H-indol-4-yl)methanone (Example 8)

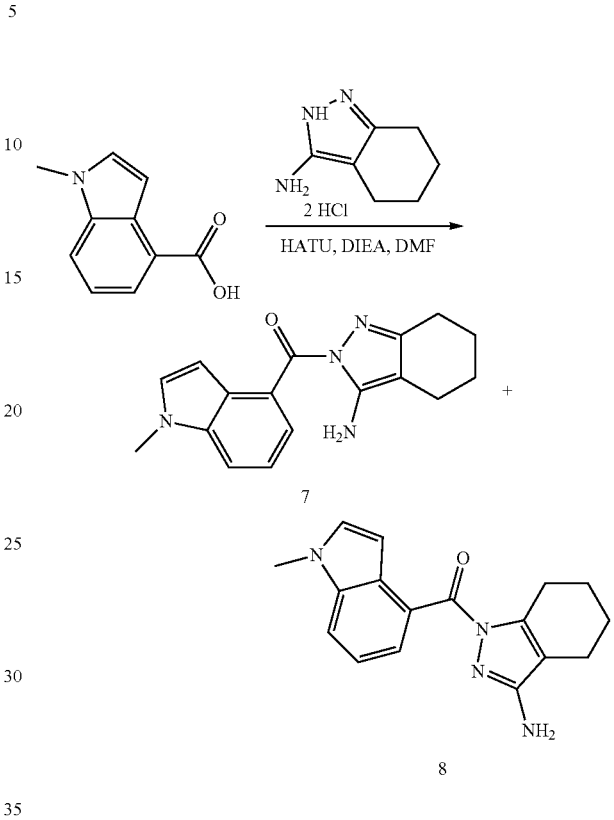

Into a 40-mL vial, was placed a solution of 1-methyl-1H-indole-4-carboxylic acid (100 mg, 0.57 mmol, 1.00 eq.) in N,N-dimethylformamide (6 mL), HATU (325 mg, 0.86 mmol, 1.50 eq.), and DIEA (368 mg, 2.85 mmol, 5.00 eq.). After stirring for 1 h at 25° C. 4,5,6,7-tetrahydro-2H-indazol-3-amine hydrochloride (119.7 mg, 0.57 mmol, 1.00 eq.) was added. The resulting solution was stirred for 18 h at 25° C. The reaction mixture was diluted with water (40 mL), extracted with ethyl acetate (40 mL×3), washed with brine (100 mL×2), dried over anhydrous sodium sulfate, filtered and concentrated under vacuum. The crude product was purified by Prep-HPLC with the following conditions: Column, XBridge Shield RP18 OBD Column, 5 um, 19×150 mm; mobile phase, water (0.1% FA) and ACN (30.0% ACN up to 55.0% in 12 min); Detector, UV 254 nm to give two isomers.

Fraction A (Example 7): Rt=10.40 min; Yield: 15.4 mg (9%) as a light yellow solid. (ES, m/z) [M+H]$^+$: 295; $^1$HNMR (DMSO-d$_6$, 400 MHz, ppm): δ 7.65 (d, J=8.0 Hz, 1H), 7.61-7.59 (m, 1H), 7.44 (d, J=2.8 Hz, 1H), 7.24-7.21 (m, 1H), 6.49-6.48 (m, 1H), 6.40 (s, 2H), 3.84 (s, 3H), 2.36-2.30 (m, 4H), 1.69-1.66 (m, 4H).

Fraction B (Example 8): Rt=8.35 min; Yield: 21.2 mg (13%) as a white solid. (ES, m/z) [M+H]$^+$: 295; $^1$HNMR (DMSO-d$_6$, 400 MHz ppm): δ 7.60 (d, J=8.0 Hz, 1H), 7.49-7.47 (m, 1H), 7.39 (d, J=2.8 Hz, 1H), 7.21-7.18 (m, 1H); 6.42-6.41 (m, 1H), 5.35 (s, 2H); 3.83-3.81 (m, 3H), 2.96-2.94 (m, 2H), 2.28-2.26 (m, 2H), 1.74-1.69 (m, 4H).

Examples 9 and 10: (3-Amino-4,5,6,7-tetrahydroindazol-2-yl)(2-methyl-1H-indol-4-yl)methanone and (3-amino-3a,4,5,6,7,7a-hexahydroindazol-1-yl)(2-methyl-1H-indol-4-yl)methanone Step 1. 2-Methyl-1H-indole-4-carboxylate

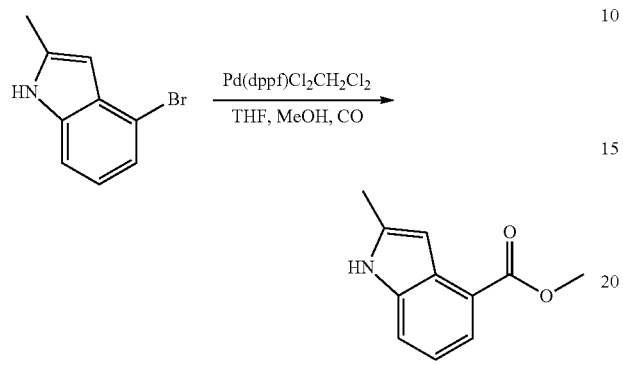

Into a 30-mL pressure tank reactor (60 atm), was placed 4-bromo-2-methyl-1H-indole (300 mg, 1.43 mmol, 1.00 eq.), methanol (5 mL), TEA (720 mg, 7.12 mmol, 5.00 eq.), and Pd(dppf)Cl$_2$CH$_2$Cl$_2$ (585 mg, 0.50 eq.). To the above mixture CO (g) was introduced in. The resulting mixture was stirred for 5 days at 120° C. After cooling down to room temperature, the solid was filtered out. The filtrate was concentrated under vacuum. The residue was purified by Pre-TLC with ethyl acetate/petroleum ether (1:1). This resulted in 0.3 g (crude) of the title compound as a red solid. MS (ES, m/z) [M+H]$^+$: 190

Step 2. 2-Methyl-1H-indole-4-carboxylic

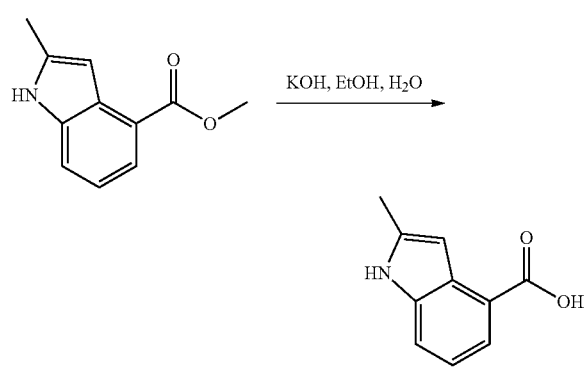

Into a 100-mL round-bottom flask, was placed methyl 2-methyl-1H-indole-4-carboxylate (0.3 g, crude), ethanol (10 mL), potassium hydroxide (0.445 g, 7.93 mmol) and water (5 mL). The resulting solution was stirred overnight at 80° C. After cooling down to room temperature, the reaction mixture was diluted with water (100 mL), and extracted with ethyl acetate (60 mL). The pH value of the aqueous phase was adjusted to 5-6 with HCl (1N). The resulting solution was extracted with ethyl acetate (60 mL). The organic phase was dried over anhydrous sodium sulfate, filtered and concentrated under vacuum. The residue was purified by Pre-TLC with ethyl acetate/petroleum ether (1/1). This resulted in 106 mg of the title compound as a red solid. MS (ES, m/z) [M+H]$^+$: 176.

Step 3. (3-Amino-4,5,6,7-tetrahydroindazol-2-yl)(2-methyl-1H-indol-4-yl)methanone and (3-amino-3a,4,5,6,7,7a-hexahydroindazol-1-yl)(2-methyl-1H-indol-4-yl)methanone

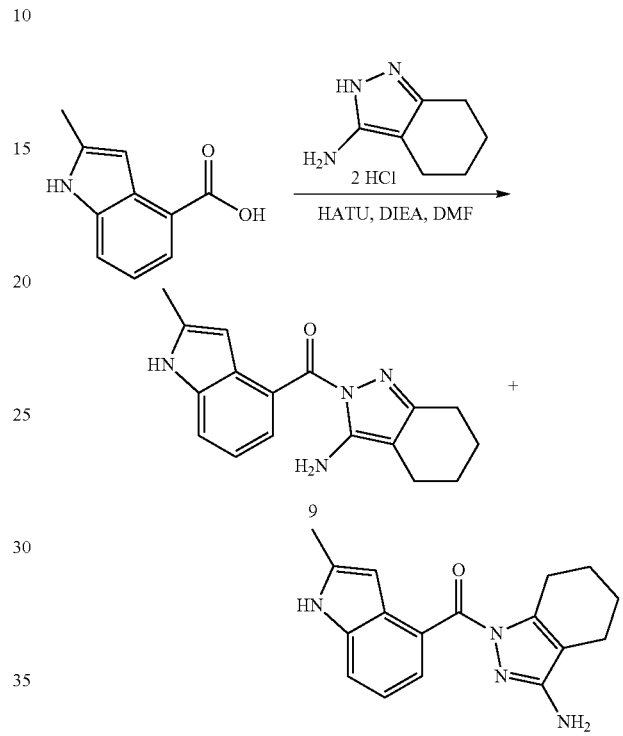

Into a 50-mL round-bottom flask, was placed 2-methyl-1H-indole-4-carboxylic acid (40 mg, 0.23 mmol, 0.90 eq.), N,N-dimethylformamide (3 mL), HATU (143 mg, 0.38 mmol, 1.50 eq.), and DIEA (97 mg, 0.75 mmol, 3.00 eq.). After stirring for 30 min at room temperature, 4,5,6,7-tetrahydro-2H-indazol-3-amine hydrochloride (52.5 mg, 0.25 mmol, 1.00 eq.) was added. The resulting solution was stirred overnight at room temperature, diluted with EA (50 mL), washed with brine (100 mL×2), dried over anhydrous sodium sulfate, filtered and concentrated under vacuum. The crude product was purified by Prep-HPLC with the following conditions: Column, XBridge Shield RP18 OBD Column, 5 um, 19×150 mm; mobile phase, water (0.1% FA) and ACN (35.0% ACN up to 65.0% in 7 min); Detector, UV 254 nm to give the following two isomers.

Fraction A (Example 9): Rt=6.20 min; Yield: 5.7 mg (8%) as an off-white solid. MS (ES, m/z) [M+1]+: 295; 1HNMR (400 MHz, DMSO-d6, ppm): δ 11.20 (s, 1H), 7.63 (d, J=7.6 Hz, 1H), 7.55 (d, J=7.6 Hz, 1H), 7.07-7.03 (m, 1H), 6.37 (s, 2H), 6.27 (s, 1H), 2.40-2.36 (m, 5H), 2.33-2.24 (m, 2H), 1.66 (m, 4H).

Fraction B (Example 10): Rt=5.12 min; Yield: 7.0 mg (10%) as an off-white solid. MS (ES, m/z) [M+H]$^+$: 295; $^1$HNMR (400 MHz, DMSO-d6, ppm): δ 11.10 (s, 1H), 7.42-7.39 (m, 2H), 7.04-7.00 (m, 1H), 6.18 (s, 1H), 5.32 (s, 2H), 2.95-2.92 (m, 2H), 2.38 (s, 3H), 2.27 (d, J=5.6 Hz, 2H), 1.75-1.70 (m, 4H).

Examples 11 and 12: (3-Amino-4,5,6,7-tetrahydroindazol-2-yl)(4-ethylthiophen-3-yl)methanone and (3-amino-4,5,6,7-tetrahydroindazol-1-yl)(4-ethylthiophen-3-yl)methanone Step 1. 4-Vinylthiophene-3-carboxylic Acid

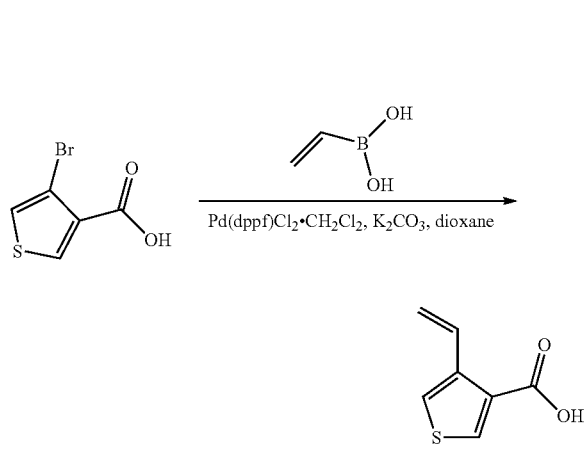

Into a 100-mL round-bottom flask purged and maintained with an inert atmosphere of nitrogen, was placed 4-bromothiophene-3-carboxylic acid (900 mg, 4.35 mmol, 1.00 eq.), Pd(dppf)Cl$_2$.CH$_2$Cl$_2$ (357 mg, 0.44 mmol, 0.10 eq.), potassium carbonate (1.8 g, 13.02 mmol, 3.00 eq.), 1,4-dioxane (40 mL), water (4 mL), and ethenylboronic acid (1.566 g, 21.75 mmol, 5.0 eq.). The resulting mixture was stirred overnight at 100° C. and then cooled to room temperature. The solid was filtered out. The pH value of the filtrate was adjusted to 5-6 with HCl (1 N). The resulting solution was extracted with dichloromethane (100 mL×2), dried over anhydrous sodium sulfate, filtered and concentrated under vacuum. The residue was purified by column chromatography on silica gel eluting with ethyl acetate/petroleum ether (0-25%). The collected fraction was concentrated to give 240 mg (36%) of the title compound as a yellow solid. GCMS (ES, m/z): 154.

Step 2. 4-Ethylthiophene-3-carboxylic Acid

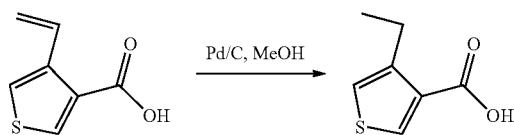

5-Ethenylthiophene-2-carboxylic acid (240 mg, 1.56 mmol, 1.00 eq.) in methanol (10 mL) was hydrogenated overnight at room temperature, in the presence of palladium carbon (120 mg, 10%). The reaction mixture was filtered through Celite and the filtrate was concentrated under vacuum. The residue was purified by Pre-TLC with ethyl acetate/petroleum ether (1:20). The collected fraction was concentrated to give 180 mg (74%) of the title compound as a white solid. MS (ES, m/z) [M+H]$^+$: 157.

Step 3. (3-Amino-4,5,6,7-tetrahydroindazol-2-yl)(4-ethylthiophen-3-yl)methanone (11) and (3-amino-4,5,6,7-tetrahydroindazol-1-yl)(4-ethylthiophen-3-yl)methanone (12)

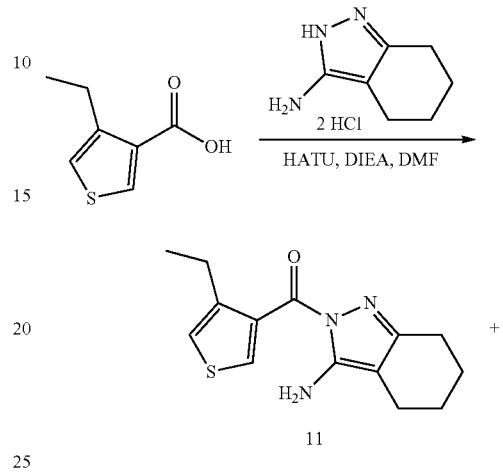

Into a 50-mL round-bottom flask, was placed 4-ethylthiophene-3-carboxylic acid (70 mg, 0.45 mmol, 0.90 eq.), HATU (284.2 mg, 0.75 mmol, 1.50 eq.), N,N-dimethylformamide (5 mL), and DIEA (289.4 mg, 2.24 mmol, 5.00 eq.). After stirring for 30 min at room temperature, 4,5,6,7-tetrahydro-2H-indazol-3-amine hydrochloride (105 mg, 0.50 mmol, 1.00 eq.) was added. The resulting mixture was stirred overnight at room temperature, diluted with EA (100 mL), washed with brine (120 mL×2), dried over anhydrous sodium sulfate, filtered and concentrated under vacuum. The crude product was purified by Prep-HPLC with the following conditions: Column, XBridge Shield RP18 OBD Column, 5 um, 19×150 mm; mobile phase, water (0.1% FA) and ACN (45.0% ACN up to 70.0% in 7 min); Detector, 254 & 220 nm to give the following two isomers.

Fraction A (Example 11): Rt=8.35 min; Yield: 14.2 mg (10%) as a gray solid. MS (ES, m/z) [M+H]$^+$: 276; $^1$H-NMR (DMSO-d6, 400 MHz, ppm): δ 8.24 (d, J=3.2 Hz, 1H); 7.25 (d, J=2.8 Hz, 1H); 2.74-2.69 (m, 2H); 2.44-2.41 (m, 2H); 2.31-2.28 (m, 2H); 1.66 (d, J=5.6 Hz, 4H); 1.17-1.13 (m, 3H).

Fraction B (Example 12): Rt=6.90 min; Yield: 15.7 mg (11%) of as a gray solid. (ES, m/z) [M+H]$^+$: 276; $^1$H-NMR (DMSO-d6, 400 MHz, ppm): δ 8.05 (d, J=3.2 Hz, 1H); 7.21 (d, J=3.2 Hz, 1H); 2.91-2.89 (M, 2H); 2.69-2.64 (m, 2H); 2.28-2.25 (m, 2H); 1.74-1.67 (m, 4H); 1.18-1.11 (m, 3H).

Examples 13, 14 and 15: (3-Amino-4,5,6,7-tetrahydroindazol-2-yl)(isochroman-1-yl)methanone; N-(4,5,6,7-tetrahydro-2H-indazol-3-yl)isochroman-1-carboxamide and (3-amino-4,5,6,7-tetrahydroindazol-1-yl)(isochroman-1-yl)methanone

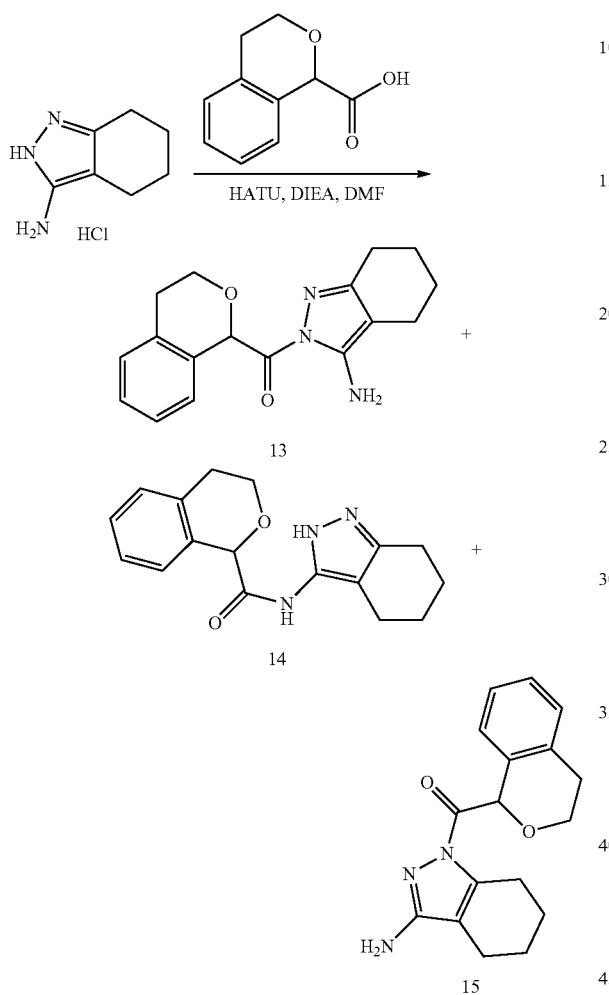

Into a 50-mL round-bottom flask, was placed 3,4-dihydro-1H-2-benzopyran-1-carboxylic acid (304 mg, 1.71 mmol, 3.00 eq.), and N,N-dimethylformamide (4 mL). DMT-MM (382 mg, 3.00 eq.) was added at 0° C. After the mixture was stirred for 30 min at 35° C., 4,5,6,7-tetrahydro-2H-indazol-3-amine hydrochloride (80 mg, 0.46 mmol, 1.00 eq.) was added. The resulting mixture was stirred overnight at room temperature, diluted with EA (30 mL), washed with brine (50 mL×2), dried over anhydrous sodium sulfate, filtered and concentrated under vacuum. The crude product was purified by Prep-HPLC with the following conditions: Column, XBridge Shield RP18 OBD Column, 5 um, 19×150 mm; mobile phase, water (10 mmol/L $NH_4HCO_3$) and ACN (40.0% ACN up to 65.0% in 7 min); Detector, UV 254 nm to give the following three isomers.

Fraction A (Example 13): Rt=6.73 min; Yield: 8.3 mg (6%) as a white solid. MS (ES, m/z) [M+H]$^+$: 298; $^1$HNMR (400 MHz, DMSO-d$_6$, ppm): δ 7.15 (d, J=3.2 Hz, 2H), 7.07 (d, J=3.2 Hz, 1H), 6.98 (d, J=7.6 Hz, 1H), 6.48 (s, 1H), 6.33 (s, 2H), 4.28-4.27 (m, 1H), 3.88-3.85 (m, 1H), 2.79-2.77 (m, 2H), 2.46-2.43 (m, 2H), 2.23-2.20 (m, 2H), 1.65-1.58 (m, 4H).

Fraction B (Example 15): Rt=5.62 min; Yield: 5.6 mg (4%) as an off-white solid. MS (ES, m/z): 298 [M+H]$^+$; $^1$HNMR (400 MHz, DMSO-d$_6$, ppm): (400 MHz, DMSO-d$_6$, ppm): δ 718-713 (m, 2H), 7.11-7.07 (m, 1H), 7.05-6.99 (m, 1H), 6.41 (s, 1H), 5.64 (s, 2H), 4.34-4.29 (m, 1H), 3.86-3.81 (m, 1H), 2.78-2.64 (m, 4H), 2.20 (s, 2H), 1.62-1.58 (m, 4H).

Fraction C (Example 14): Rt=6.10 min; Yield: 0.2 mg (0.14%) as a yellow oil. MS (ES, m/z): 298 [M+H]$^+$; $^1$HNMR (400 MHz, DMSO-d$_6$, ppm): δ 11.94 (s, 1H), 9.63 (s, 1H), 7.28-7.26 (m, 1H), 7.17-7.09 (m, 3H), 5.19 (s, 1H), 4.19-4.14 (m, 1H), 3.79-3.71 (m, 1H), 3.40 (m, 2H), 2.93-2.87 (m, 1H), 2.70-2.64 (m, 1H), 2.19-2.07 (m, 2H), 1.68-1.32 (m, 4H).

Examples 16 and 17: (3-Amino-4,5,6,7-tetrahydroindazol-2-yl)(2,4-dimethylthiophen-3-yl)methanone and (3-amino-4,5,6,7-tetrahydroindazol-1-yl)(2,4-dimethylthiophen-3-yl)methanone

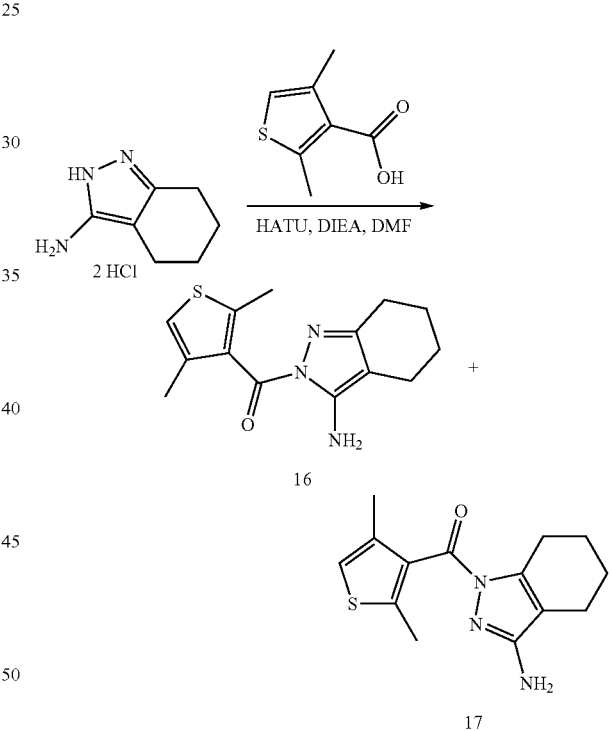

Into a 40-mL vial, was placed a solution of 2,4-dimethylthiophene-3-carboxylic acid (90 mg, 0.58 mmol, 1.00 eq.) in N,N-dimethylformamide (5.0 mL), HATU (329 mg, 0.87 mmol, 1.50 eq.), and DIEA (372 mg, 2.88 mmol, 5.00 eq.). After stirring for 0.5 hour at room temperature, 4,5,6,7-tetrahydro-2H-indazol-3-amine hydrochloride (121.8 mg, 0.58 mmol, 1.00 eq.) was added. The reaction mixture was stirred for 24 h at room temperature, poured into water (40 mL), extracted with ethyl acetate (40 mL×4), washed with brine (100 mL×2), dried over anhydrous sodium sulfate, filtered and concentrated under vacuum. The crude product was purified by Prep-HPLC with the following conditions: Column, XBridge Shield RP18 OBD Column, 5 um, 19×150 mm; mobile phase, water (0.1% FA) and ACN (35.0% ACN up to 60.0% in 9 min); Detector, UV 254 nm to give two isomers.

Fraction A (Example 16): Rt=8.17 min; Yield: 4.7 mg (3%) as a white solid. MS (ES, m/z) [M+H]$^+$: 276; $^1$HNMR (400 MHz, DMSO-d$_6$, ppm): δ 6.94 (d, J=0.8 Hz, 1H); 2.39-2.33 (m, 2H); 2.29-2.27 (m, 5H); 2.03 (s, 3H); 1.64-1.63 (m, 4H).

Fraction B (Example 17): Rt=6.38 min; Yield: 10.9 mg (7%) as a white solid. MS (ES, m/z) [M+H]$^+$: 276; $^1$HNMR (400 MHz, DMSO-d$_6$, ppm): δ 6.90 (s, 1H); 2.89 (s, 2H); 2.33-2.24 (m, 5H); 2.02 (s, 3H), 1.74-1.67 (m, 4H).

Examples 18 and 19: (3-Amino-4,5,6,7-tetrahydroindazol-2-yl)(4-ethyl-2-methylthiophen-3-yl)methanone and (3-amino-4,5,6,7-tetrahydroindazol-1-yl)(4-ethyl-2-methylthiophen-3-yl)methanone

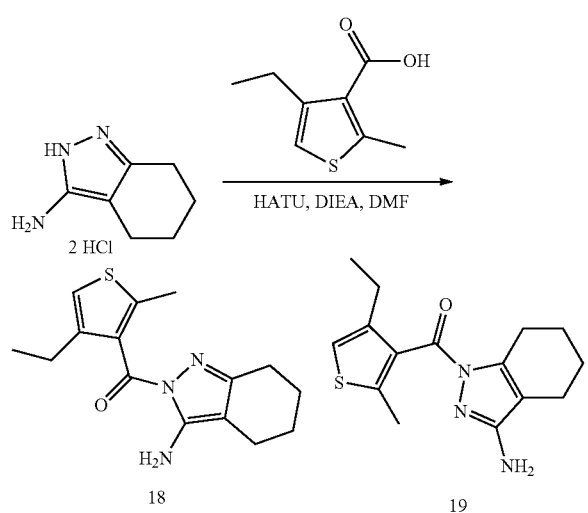

Into a 40-mL vial, was placed a solution of 4-ethyl-2-methylthiophene-3-carboxylic acid (100 mg, 0.59 mmol, 1.00 eq.) in N,N-dimethylformamide (6 mL), HATU (335 mg, 0.88 mmol, 1.50 eq.), and DIEA (380 mg, 2.95 mmol, 5.00 eq.). After stirring for 0.5 hour at room temperature, 4,5,6,7-tetrahydro-2H-indazol-3-amine hydrochloride (102 mg, 0.59 mmol, 1.00 eq.) was added. The reaction was stirred for 18 h at room temperature, poured into water (40 mL), and extracted with ethyl acetate (40 mL×3). The combined organic layers was washed with brine (100 mL×2), dried over anhydrous sodium sulfate, filtered and concentrated under vacuum. The crude product was purified by Prep-HPLC with the following conditions: Column, XBridge Shield RP18 OBD Column, 5 um, 19×150 mm; mobile phase, water (0.1% FA) and ACN (40.0% ACN up to 60.0% in 7 min, up to 75.0% in 3 min); Detector, UV 254 nm to give two isomers.

Fraction A (Example 18): Rt=8.00 min; Yield: 7.4 mg (4%) as an off-white solid. MS (ES, m/z) [M+H]$^+$: 290; $^1$HNMR (400 MHz, DMSO-d$_6$, ppm): 6.95 (s, 1H); 6.41 (s, 2H); 2.44-2.33 (m, 4H); 2.32-2.28 (m, 5H); 1.64 (d, J=5.2 Hz, 4H); 1.07-1.03 (m, 3H).

Fraction B (Example 19): Rt=6.30 min; Yield: 21.8 mg (13%) as an off-white solid. MS (ES, m/z) [M+H]$^+$: 290; $^1$HNMR (400 MHz, DMSO-d$_6$, ppm): 6.91 (s, 1H); 5.52 (s, 2H); 2.88 (d, J=6.0 Hz, 2H), 2.43-2.37 (m, 2H); 2.26-2.23 (m, 5H); 1.74-1.66 (m, 4H); 1.07-1.03 (m, 3H).

Examples 20 and 21: (3-amino-4,5,6,7-tetrahydroindazol-2-yl)(1-phenyl-1H-indol-4-yl)methanone and (3-amino-4,5,6,7-tetrahydroindazol-1-yl)(1-phenyl-1H-indol-4-yl)methanone Step 1. Methyl 1-phenyl-1H-indole-4-carboxylate

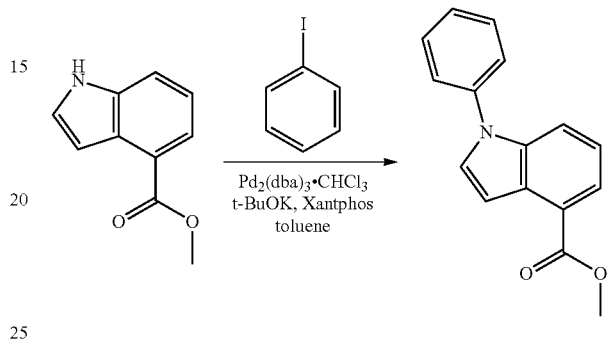

Into a 15-mL sealed tube, was placed methyl 1H-indole-4-carboxylate (874 mg, 4.99 mmol, 1.50 eq.), iodobenzene (500 mg, 2.45 mmol, 1.00 eq.), Pd$_2$(dba)$_3$·CHCl$_3$ (296 mg, 0.29 mmol, 0.10 eq.), Xantphos (330 mg, 0.57 mmol, 0.20 eq.), t-BuOK (960 mg, 8.57 mmol, 3.00 eq.) and toluene (5 mL). The resulting mixture was irradiated with microwave radiation for 1.5 h at 120° C. After cooled to room temperature, the reaction mixture was concentrated under vacuum. The residue was diluted with water (25 mL). The pH value of the solution was adjusted to 8 with HCl (1 N). The resulting solution was extracted with dichloromethane (50 mL×3). The combined organic phases was washed with brine (100 mL×3), dried with Na$_2$SO$_4$, filtered and concentrated under vacuum. The crude product was purified by Pre-TLC with EA:PE (1:3) to afford 180 mg (29%) of the title compound as a red solid. MS (ES, m/z) [M+H]$^+$: 252.

Step 2. 1-Phenyl-1H-indole-4-carboxylic Acid

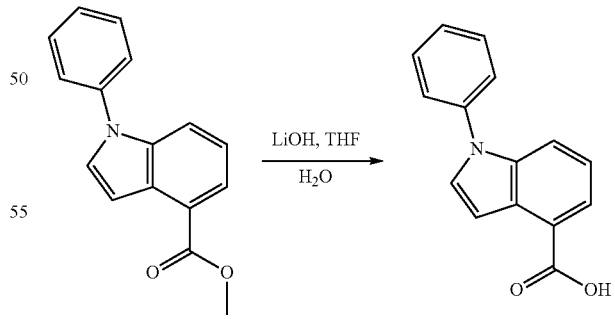

Into a 100-mL round-bottom flask, was placed methyl 1-phenyl-1H-indole-4-carboxylate (125 mg, 0.50 mmol, 1.00 eq.), tetrahydrofuran (20 mL), a solution of LiOH (238 mg, 9.94 mmol, 20.00 eq.) in water (10 mL). After stirring overnight at ambient temperature, the reaction mixture was diluted with water (30 mL), and extraction with DCM (20 mL×2). The pH value of the aqueous layers was adjusted to 5-6 with HCl (1 N). The resulting solution was extracted with EA (30 mL×3). The organic layers were combined and concentrated under vacuum. The residue was purified by Pre-TLC with ethyl acetate/Petroleum ether (1/1) to afford 55 mg (47%) of the title compound as a yellow solid. MS (ES, m/z) [M+H]$^+$: 238.

Step 3. (3-Amino-4,5,6,7-tetrahydroindazol-2-yl)(1-phenyl-1H-indol-4-yl)methanone and (3-amino-4,5,6,7-tetrahydroindazol-1-yl)(1-phenyl-1H-indol-4-yl)methanone

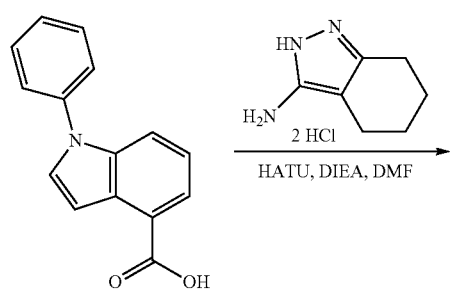

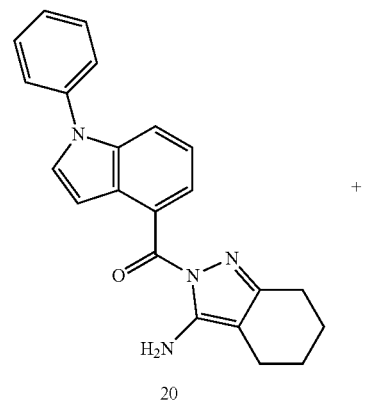

Into a 5-mL round-bottom flask, was placed 1-phenyl-1H-indole-4-carboxylic acid (55 mg, 0.23 mmol, 1.00 eq.), HATU (131 mg, 0.34 mmol, 1.50 eq.), DIEA (89 mg, 0.69 mmol, 3.00 eq.), and N,N-dimethylformamide (5 L). After stirring for 30 min at room temperature, 4,5,6,7-tetrahydro-2H-indazol-3-amine dihydrochloride (53.1 mg, 0.253 mmol, 1.10 eq.) was added. The reaction mixture was stirred overnight at room temperature, diluted with DCM (80 mL), washed with water (50 mL×3) and brine (50 mL×3), dried with Na$_2$SO$_4$, filtered and concentrated under vacuum. The crude product was purified by Prep-HPLC with the following conditions: Column, XBridge Shield RP18 OBD Column, 5 um, 19×150 mm; mobile phase, water (0.1% FA) and ACN (55.0% ACN up to 70.0% in 7 min); Detector, uv 254/220 nm to give the two isomers.

Fraction A (Example 20): Rt=7.60 min; Yield: 5.3 mg (6.4%) as a yellow solid. MS (ES, m/z) [M+H]$^+$: 357; $^1$HNMR (DMSO-d$_6$, 400 MHz, ppm): δ 7.77-7.72 (m, 2H), 7.65-7.59 (m, 5H), 7.48-7.43 (m, 1H), 7.30-7.26 (m, 1H), 6.71 (d, J=3.2, 1H), 2.38-2.33 (m, 4H), 1.72-1.66 (m, 4H).

Fraction B (Example 21): Rt=5.85 min; Yield: 10.2 mg (12.4%) as a yellow solid. MS (ES, m/z) [M+H]$^+$: 357; $^1$HNMR (DMSO-d$_6$, 400 MHz, ppm): δ 7.73-7.72 (m, 1H), 7.69-7.67 (m, 1H), 7.62-7.61 (m, 4H), 7.58-7.52 (m, 1H), 7.47-7.42 (m, 1H), 7.27-7.70 (m, 1H), 6.65 (d, J=2.8, 1H), 2.99-2.98 (m, 2H), 2.33-2.29 (m, 2H), 1.78-1.71 (m, 4H).

Example 22: (3-Amino-4,5,6,7-tetrahydroindazol-2-yl)(1,2-dimethyl-1H-indol-4-yl)methanone Step 1: 1,2-Dimethyl-1H-indole-4-carboxylic Acid

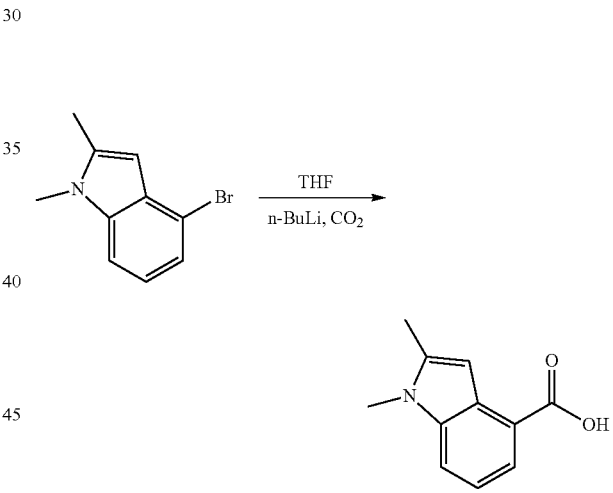

Into a 100-mL 3-necked round-bottom flask, was placed 4-bromo-1,2-dimethyl-1H-indole (100 mg, 0.45 mmol, 1.00 eq.), and tetrahydrofuran (10 mL). n-BuLi (0.25 mL, 1.40 eq.) was added dropwise at −78° C. The mixture was stirred for 30 min at −78° C. and then CO$_2$ was added. The resulting solution was stirred overnight at room temperature. The reaction was then quenched by the addition of ice-water (40 mL). The resulting solution was extracted with ethyl acetate (30 mL×2). The pH value of the aqueous phase was adjusted to 5-6 with HCl (1N). The aqueous phase was extracted with ethyl acetate (50 mL×2). The combined organic layers were dried over anhydrous sodium sulfate filtered, filtered and concentrated under vacuum. The crude product was purified by Prep-TLC with ethyl acetate/petroleum ether (1/3). This resulted in 50 mg (58.8%) of the title compound as a yellow solid. MS (ES, m/z) [M+H]$^+$: 190

Step 2: (3-Amino-4,5,6,7-tetrahydroindazol-2-yl)(1,2-dimethyl-1H-indol-4-yl)methanone

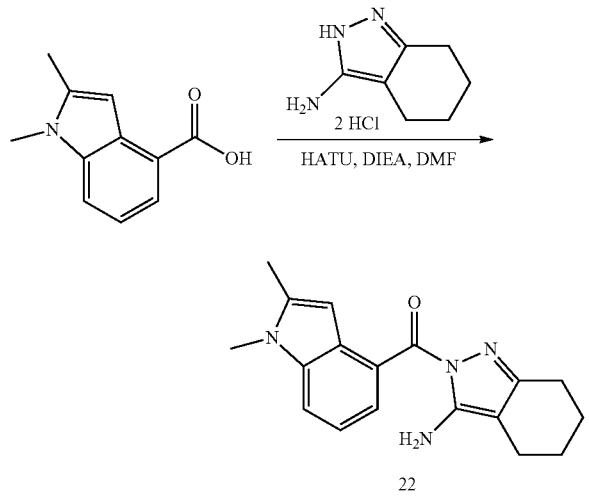

22

Into a 50-mL round-bottom flask, was placed 1,2-dimethyl-1H-indole-4-carboxylic acid (49 mg, 0.26 mmol, 1.00 eq.), N,N-dimethylformamide (3 mL), DIEA (112 mg, 0.87 mmol, 3.60 eq.), and HATU (165 mg, 0.43 mmol, 1.65 eq.). After the mixture was stirred for 30 min, 4,5,6,7-tetrahydro-2H-indazol-3-amine dihydrochloride (50 mg, 0.24 mmol, 0.90 eq.) was added. The resulting solution was stirred overnight at room temperature. The reaction mixture was diluted with EA (30 mL), washed with brine (100 mL×2), dried over anhydrous sodium sulfate, filtered and concentrated under vacuum. The crude product was purified by Pre-TLC with ethyl acetate/petroleum ether (2/1). The crude product was purified by Prep-HPLC with the following conditions: Column, XBridge C18 OBD Prep Column, 5 µm, 19 mm×250 mm; mobile phase, Waters (0.1% FA) and ACN (50.0% ACN up to 70.0% in 8 min); Detector, uv 254 nm. Rt: 6.74; The collected fraction was lyophilized to give 11.5 mg (14%) of the title compound as a yellow solid. MS (ES, m/z): 309 [M+H]$^+$; $^1$HNMR (400 MHz, DMSO-d$_6$, ppm): δ 7.60-7.56 (m, 2H), 7.14-7.10 (m, 1H), 6.37 (s, 2H), 6.33 (s, 1H), 3.71 (s, 3H), 2.46-2.31 (m, 7H), 1.66 (s, 4H).

Examples 23 and 24: (3-Amino-4,5,6,7-tetrahydroindazol-2-yl)(2-methylbenzo[b]thiophen-3-yl)methanone and (3-amino-4,5,6,7-tetrahydroindazol-1-yl)(2-methylbenzo[b]thiophen-3-yl)methanone Step 1: 2-Methylbenzo[b]thiophene-3-carboxylic Acid

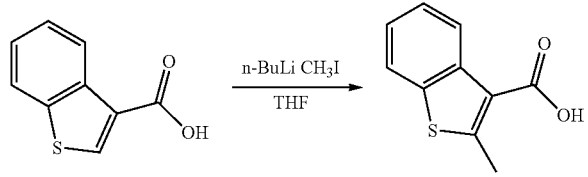

Into a 50-mL 3-necked round-bottom flask purged and maintained with an inert atmosphere of nitrogen, was placed a solution of 1-benzothiophene-3-carboxylic acid (270 mg, 1.52 mmol, 1.00 eq.) in tetrahydrofuran (10 mL). This was followed by the addition of n-BuLi (2.5 M, 2.12 mL, 5.3 mmol, 3.50 eq.) dropwise with stirring at −78° C. The resulting solution was stirred for 30 min at −78° C. To this was added a solution of iodomethane (863 mg, 6.08 mmol, 4.00 eq.) in tetrahydrofuran (5 mL) dropwise with stirring at −78° C. The temperature was increased to room temperature naturally and the resulting solution was allowed to react for an additional 15 h. The reaction mixture was then poured into 40 mL of saturated NH$_4$Cl (aq.). The pH value of the solution was adjusted to 2 with HCl (1 N). The resulting solution was extracted with ethyl acetate (40 mL×4). The combined organic layers was dried over anhydrous sodium sulfate, filtered and concentrated under vacuum. The residue was purified by Prep-TLC with MeOH/CH$_2$Cl$_2$ (1/12). This resulted in 270 mg (93%) of the title compound as a yellow solid. (ES, m/z) [M+H]$^+$: 193.

Step 2: (3-Amino-4,5,6,7-tetrahydroindazol-2-yl)(2-methylbenzo[b]thiophen-3-yl)methanone and (3-amino-4,5,6,7-tetrahydroindazol-1-yl)(2-methylbenzo[b]thiophen-3-yl)methanone

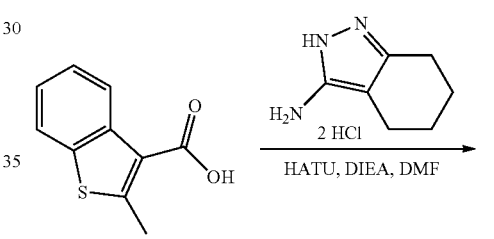

23

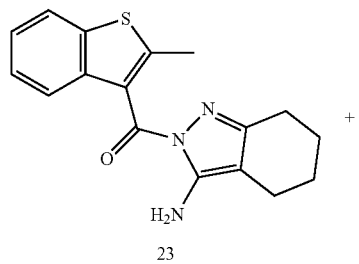

24

Into a 40-mL vial, was placed a solution of 2-methyl-1-benzothiophene-3-carboxylic acid (150 mg, 0.78 mmol, 1.00 eq.) in N,N-dimethylformamide (10 mL), HATU (593 mg, 1.56 mmol, 2.00 eq.), and DIEA (503 mg, 3.90 mmol, 5.00 eq.). After stirring for 1 h at 35° C., 4,5,6,7-tetrahydro-2H-indazol-3-amine hydrochloride (163.8 mg, 0.78 mmol, 1.00 eq.) was added. The resulting solution was stirred for 48 h at 35° C., diluted with water (40 mL) and extracted with ethyl acetate (40 mL×3). The combined organic phases was washed with brine (100 mL×2), dried over anhydrous sodium sulfate, filtered and concentrated under vacuum. The crude product was purified by Prep-HPLC with the following conditions: Column, XBridge C18 OBD Prep Column; 5 μm, 19 mm×250 mm; mobile phase, water (0.1% FA) and ACN (45.0% ACN up to 70.0% in 8 min); Detector, UV 254 nm to give the two isomers.

Fraction A (Example 23): Rt=5.14 min; Yield: 5.5 mg (2%) as a white solid. MS (ES, m/z): 312 [M+H]$^+$; $^1$HNMR (DMSO-d$_6$, 400 MHz, ppm): δ 7.95-7.92 (m, 1H); 7.45-7.43 (m, 1H); 7.38-7.32 (m, 2H); 6.48 (s, 2H); 2.50-2.48 (m, 3H); 2.38 (s, 4H); 1.64 (s, 4H).

Fraction A (Example 24): Rt=4.35 min; Yield: 24.8 mg (10%) as a white solid. MS (ES, m/z): 312 [M+H]$^+$; $^1$HNMR (DMSO-d$_6$, 400 MHz, ppm): δ 7.91-7.88 (m, 1H); 7.43-7.40 (m, 1H); 7.35-7.29 (m, 2H); 5.48 (s, 2H); 2.98 (d, J=6.0 Hz, 2H); 2.50-2.47 (m, 3H); 2.33-2.26 (m, 2H); 1.78-1.70 (m, 4H).

Examples 25 and 26: (3-Amino-4,5,6,7-tetrahydroindazol-2-yl)(1-methyl-1,2,3,4-tetrahydroquinolin-4-yl)methanone and (3-amino-4,5,6,7-tetrahydroindazol-1-yl)(1-methyl-1,2,3,4-tetrahydroquinolin-4-yl)methanone Step 1.
1-Methyl-1,2,3,4-tetrahydroquinoline-4-carboxylic Acid

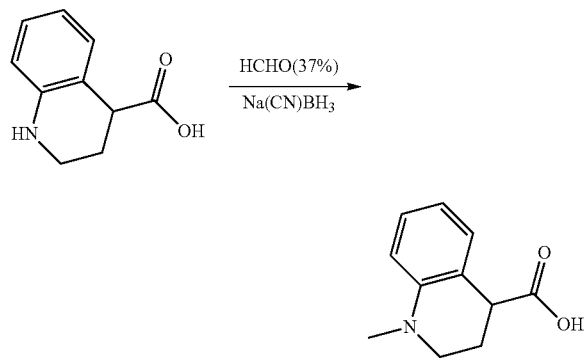

Into a 100-mL round-bottom flask, was placed 1,2,3,4-tetrahydroquinoline-4-carboxylic acid (200 mg, 1.13 mmol, 1.00 eq.), HCHO (37%, 458 mg, 253 mmol, 5.00 eq.), and methanol/AcOH (10 mL, 20/1). The mixture was stirred for 30 min at room temperature and then Na(CN)BH$_3$ (214 mg, 3.40 mmol, 3.00 eq.) was added. The resulting solution was stirred overnight at room temperature. The reaction mixture was poured into water (80 mL), and extracted with ethyl acetate (100 mL×3). The combined organic phases was dried with anhydrous sodium sulfate, filtered and concentrated under vacuum. This resulted in 180 mg (crude) of the title compound as yellow oil. MS (ES, m/z): [M+H]$^+$: 192.

Step 2. (3-Amino-4,5,6,7-tetrahydroindazol-2-yl)(1-methyl-1,2,3,4-tetrahydroquinolin-4-yl)methanone and (3-amino-4,5,6,7-tetrahydroindazol-1-yl)(1-methyl-1,2,3,4-tetrahydroquinolin-4-yl)methanone

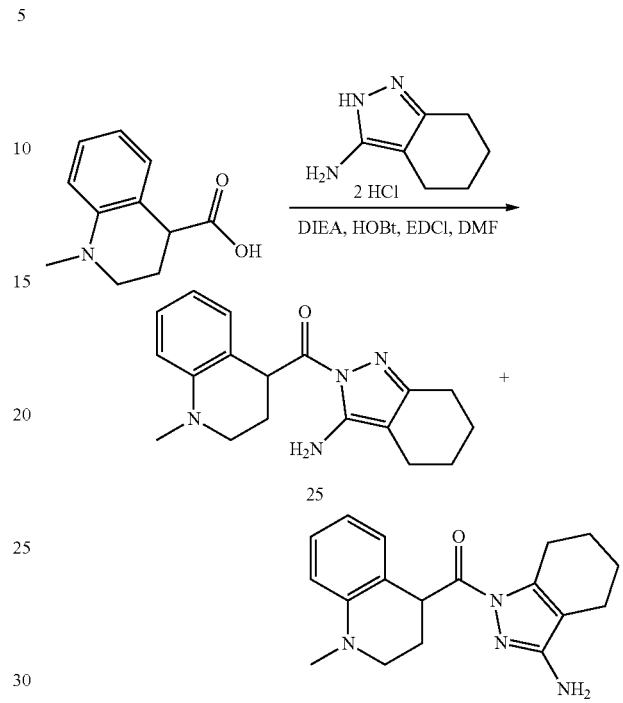

Into a 50-mL round-bottom flask, was placed 1-methyl-1,2,3,4-tetrahydroquinoline-4-carboxylic acid (50 mg, 0.26 mmol, 1.00 eq.), HOBt (53 mg, 0.39 mmol, 1.50 eq.), EDCI (75 mg, 0.39 mmol, 1.50 eq.), DIEA (101 mg, 0.78 mmol, 3.00 eq.), and N,N-dimethylformamide (5 mL). After stirring for 30 min at room temperature, 4,5,6,7-tetrahydro-2H-indazol-3-amine dihydrochloride (60.1 mg, 0.286 mmol, 1.10 eq.) was added. The resulting solution was stirred overnight at 25° C. The reaction mixture was diluted with DCM (80 mL), washed with water (50 mL×3) and brine (50 mL×3) and dried with Na$_2$SO$_4$. After filtration, the filtrate was concentrated under vacuum. The crude product was purified by Prep-HPLC with the following conditions: Column, XBridge Shield RP18 OBD Column, 5 um, 19×150 mm; mobile phase, water (0.1% FA) and ACN (25.0% ACN up to 55.0% in 7 min); Detector, uv 254/220 nm to give two isomers.

Fraction A (Example 25): Rt=5.77 min; Yield: 21.1 mg (26.1%) as an off-white solid. MS (ES, m/z) [M+H]$^+$: 311; $^1$HNMR (DMSO-d$_6$, 400 MHz, ppm): δ 7.07-7.03 (m, 1H), 6.81 (d, J=7.2, 1H), 6.64 (d, J=8.4, 1H), 6.55-6.49 (m, 1H), 6.37 (s, 2H), 5.07-5.04 (m, 1H), 3.31-3.28 (m, 1H), 3.21-3.15 (m, 1H), 2.85 (s, 3H), 2.47-2.44 (m, 2H), 2.28-2.25 (m, 2H), 2.14-2.10 (m, 2H), 1.71-1.64 (m, 4H).

Fraction B (Example 26): Rt=5.15 min; Yield: 8.0 mg (9.9%) as an off-white solid. MS (ES, m/z) [M+H]$^+$: 311; $^1$HNMR (DMSO-d$_6$, 400 MHz, ppm): δ 7.05-7.01 (m, 1H), 6.80 (d, J=7.2, 1H), 6.63 (d, J=8.0, 1H), 6.55-6.48 (m, 1H), 5.57 (s, 2H), 5.00-4.98 (m, 1H), 3.32-3.28 (m, 1H), 3.19-3.13 (m, 1H), 2.85 (s, 3H), 2.79-2.75 (m, 2H), 2.26-2.24 (m, 2H), 2.10-2.06 (m, 2H), 1.66-1.65 (m, 4H).

Table 1: The following compounds in Table 1 (Examples 27-46) were prepared by procedures similar to those described above in Examples 1-26 and well known to those skilled in the art.

| Example | Structure | Name | ¹HNMR |
|---|---|---|---|
| Example 27 | 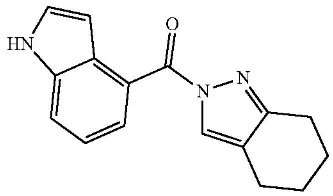 [SMILES: O=C(c1cccc2[nH]ccc12)n1cc2c(n1)CCCC2] | (1H-indol-4-yl)(4,5,6,7-tetrahydroindazol-2-yl)methanone | (DMSO-d₆, 300 MHz, ppm): δ 11.51 (s, 1H), 8.19 (s, 1H), 7.72-7.68 (m, 2H), 7.53-7.51 (m, 1H), 7.24-7.19 (m, 1H), 6.61 (d, J = 0.9 Hz, 1H), 2.64-2.57 (m, 4H), 1.78-1.69 (m, 4H). |
| Example 28 | 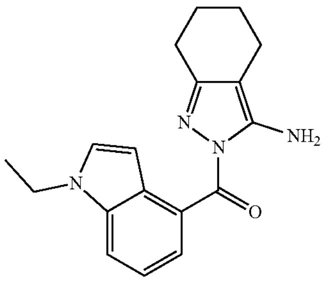 [SMILES: CCn1ccc2c(C(=O)n3nc4c(c3N)CCCC4)cccc21] | (3-amino-4,5,6,7-tetrahydroindazol-2-yl)(1-ethyl-1H-indol-4-yl)methanone | (300 MHz, DMSO-d₆, ppm): 7.76-7.67 (m, 1H), 7.57-7.49 (m, 2H), 7.22-7.16 (m, 1H), 6.53 (s, 1H), 6.30 (s, 2H), 4.29-4.19 (m, 2H), 2.40-2.19 (m, 4H), 1.64 (m, 4H), 1.54-1.33 (m, 3H). |
| Example 29 | 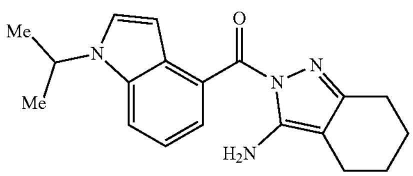 [SMILES: CC(C)n1ccc2c(C(=O)n3nc4c(c3N)CCCC4)cccc21] | (3-amino-4,5,6,7-tetrahydroindazol-2-yl)(1-isopropyl-1H-indol-4-yl)methanone | (DMSO-d₆, 400 MHz, ppm): δ 7.74 (d, J = 8.4 Hz, 1H); 7.61 (d, J = 3.2 Hz, 1H); 7.55 (d, J = 7.2 Hz, 1H); 7.22-7.18 (m, 1H); 6.51 (d, J = 3.2 Hz, 1H); 6.41 (s, 2H); 4.87-4.80 (m, 1H); 2.36-2.31 (m, 4H); 1.65 (m, 4H); 1.47 (d, J = 6.8 Hz, 6H). |
| Example 30 | 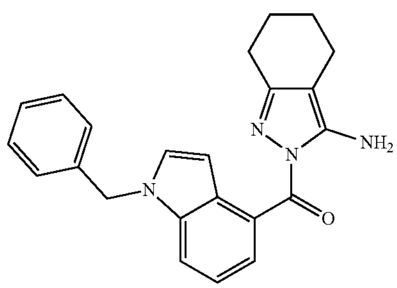 [SMILES: Nc1c2c(nn1C(=O)c1cccc3c1ccn3Cc1ccccc1)CCCC2] | (3-amino-4,5,6,7-tetrahydroindazol-2-yl)(1-benzyl-1H-indol-4-yl)methanone | (300 MHz, DMSO-d₆, ppm): δ 7.72-7.60 (m, 3H), 7.39-7.19 (m, 6H), 6.55 (s, 1H), 5.48 (s, 2H), 2.36-2.50 (m, 4H), 1.64 (m, 4H). |
| Example 31 | 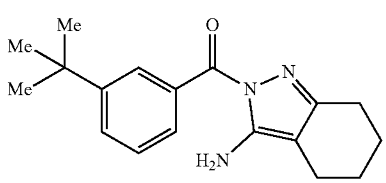 [SMILES: CC(C)(C)c1cccc(C(=O)n2nc3c(c2N)CCCC3)c1] | (3-amino-4,5,6,7-tetrahydroindazol-2-yl)(3-tert-butylphenyl)methanone | (DMSO-d₆, 300 MHz, ppm): δ 7.89 (s, 1H); 7.73 (d, J = 7.8 Hz, 1H); 7.62 (d, J = 8.1 Hz, 1H); 7.43-7.38 (m, 1H); 6.42 (s, 2H); 2.51-2.31 (m, 4H); 1.66 (m, 4H); 1.31 (s, 9H). |
| Example 32 | 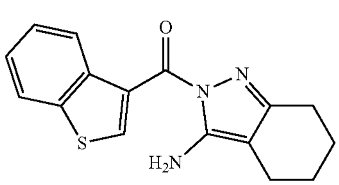 [SMILES: Nc1c2c(nn1C(=O)c1csc3ccccc13)CCCC2] | (3-amino-4,5,6,7-tetrahydroindazol-2-yl)(benzo[b]thiophen-3-yl)methanone | (DMSO-d₆, 400 MHz, ppm): δ 9.05 (s, 1H); 8.33-8.31 (m, 1H); 8.11-8.09 (m, 1H); 7.52-7.44 (m, 2H); 6.52 (s, 2H); 2.46 (d, J = 6.0 Hz, 2H); 2.33-2.31 (m, 2H); 1.71-1.66 (m, 4H). |
| Example 35 | 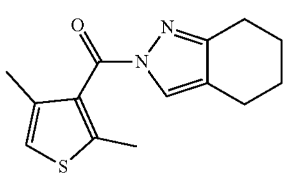 [SMILES: Cc1csc(C)c1C(=O)n1cc2c(n1)CCCC2] | 2-[(2,4-dimethylthiophen-3-yl)carbonyl]-4,5,6,7-tetrahydro-2H-indazole | (DMSO-d₆, 400 MHz, ppm): δ 8.13 (s, 1H), 7.02 (d, J = 0.8 Hz, 1H), 2.61-2.56 (m, 4H), 2.29 (s, 3H), 2.03 (s, 3H), 1.78-1.65 (m, 4H). |

| Example | Structure | Name | ¹HNMR |
|---|---|---|---|
| Example 36 | 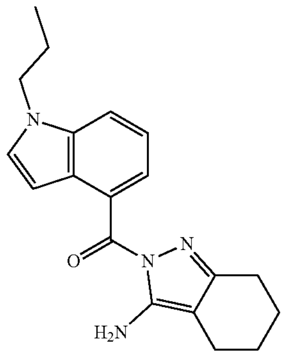 [SMILES: CCCn1ccc2c(C(=O)n3nc4c(c3N)CCCC4)cccc21] | (3-amino-4,5,6,7-tetrahydroindazol-2-yl)(1-propyl-1H-indol-4-yl)methanone | (DMSO-d$_6$, 400 MHz, ppm): δ 7.71 (d, J = 8.4, 1H), 7.58 (d, J = 7.2, 1H), 7.49 (d, J = 2.8, 1H), 7.22-7.18 (m, 1H), 6.50 (d, J = 2.8, 1H), 6.40 (s, 2H), 4.21-4.18 (m, 2H), 2.37-2.31 (m, 4H), 1.83-1.74 (m, 2H), 1.66-1.65 (m, 4H), 0.86-0.81 (m, 3H). |
| Example 37 | 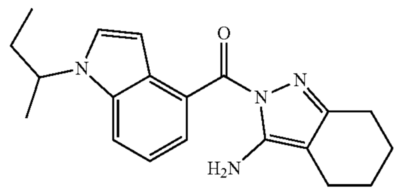 [SMILES: CCC(C)n1ccc2c(C(=O)n3nc4c(c3N)CCCC4)cccc21] | (3-amino-4,5,6,7-tetrahydroindazol-2-yl)(1-sec-butyl-1H-indol-4-yl)methanone | (DMSO-d$_6$, 400 MHz, ppm): δ 7.80-7.75 (m, 1H), 7.67-7.55 (m, 2H), 7.21-7.17 (m, 1H), 6.55 (d, J = 3.2, 1H), 4.64-4.55 (m, 1H), 2.37-2.32 (m, 4H), 1.91-1.79 (m, 2H), 1.65-1.66 (m, 4H), 1.52-1.45 (m, 3H), 0.80-0.72 (m, 3H). |
| Example 38 | 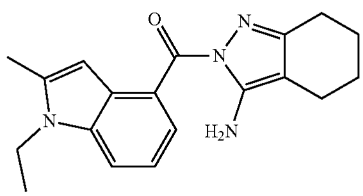 [SMILES: CCn1c(C)cc2c(C(=O)n3nc4c(c3N)CCCC4)cccc21] | (3-amino-4,5,6,7-tetrahydroindazol-2-yl)(1-ethyl-2-methyl-1H-indol-4-yl)methanone | (400 MHz, DMSO-d$_6$, ppm): δ 7.61 (d, J = 8.0 Hz, 1H), 7.55 (d, J = 7.2 Hz, 1H), 7.14-7.10 (m, 1H), 6.38 (s, 2H), 6.32 (s, 1H), 4.24-4.18 (m, 2H), 2.43 (s, 3H), 2.37-2.31 (m, 4H), 1.66 (s, 4H), 1.27-1.23 (m, 3H). |
| Example 39 | 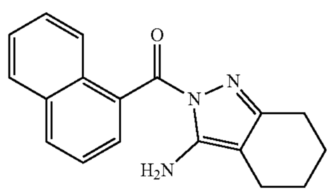 [SMILES: Nc1c2c(nn1C(=O)c1cccc3ccccc13)CCCC2] | (3-amino-4,5,6,7-tetrahydroindazol-2-yl)(naphthalen-1-yl)methanone | (DMSO-d$_6$, 400 MHz, ppm): δ 8.14-8.06 (m, 1H), 8.03-8.01 (m, 1H), 7.77-7.71 (m, 1H), 7.69-7.60 (m, 1H), 7.58-7.52 (m, 3H), 6.49 (s, 2H), 2.40-2.25 (m, 4H), 1.62-1.61 (m, 4H). |
| Example 40 | 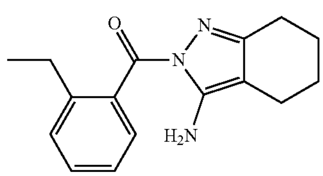 [SMILES: CCc1ccccc1C(=O)n1nc2c(c1N)CCCC2] | (3-amino-4,5,6,7-tetrahydroindazol-2-yl)(2-ethylphenyl)methanone | (400 MHz, DMSO-d$_6$, ppm): δ 7.43-7.20 (m, 4H), 6.00-6.70 (brs, 2H), 2.54-2.50 (m, 2H), 2.32-2.29 (m, 4H), 1.63 (m, 4H), 1.12-1.08 (m, 3H) |
| Example 41 | 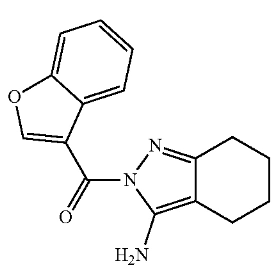 [SMILES: Nc1c2c(nn1C(=O)c1coc3ccccc13)CCCC2] | (3-amino-4,5,6,7-tetrahydroindazol-2-yl)(benzofuran-3-yl)methanone | (400 MHz, DMSO-d$_6$, ppm): δ 9.26 (s, 1H), 8.26-8.22 (m, 1H), 7.77-7.72 (m, 1H), 7.48-7.41 (m, 2H), 6.20-6.90 (brs, 2H), 2.56-2.50 (m, 2H), 2.32-2.30 (m, 2H), 1.73-1.66 (m, 4H) |

| Example | Structure | Name | ¹HNMR |
|---|---|---|---|
| Example 42 | 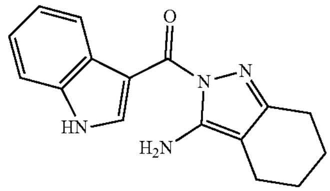 [SMILES: Nc1c2c(nn1C(=O)c1c[nH]c3ccccc13)CCCC2] | (3-amino-4,5,6,7-tetrahydroindazol-2-yl)(1H-indol-3-yl)methanone | (400 MHz, DMSO-d₆, ppm): δ 12.00 (s, 1H), 8.90 (d, J = 3.2 Hz, 1H), 8.31-8.28 (m, 1H), 7.55-7.50 (m, 1H), 7.25-7.19 (m, 2H), 6.47 (s, 2H), 2.67-2.50 (m, 2H), 2.32-2.29 (m, 2H), 1.73-1.66 (m, 4H). |
| Example 43 | 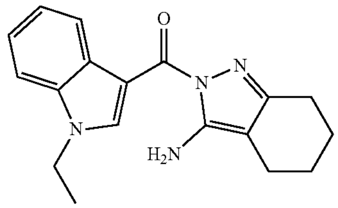 [SMILES: CCn1cc(C(=O)n2nc3c(c2N)CCCC3)c2ccccc21] | (3-amino-4,5,6,7-tetrahydroindazol-2-yl)(1-ethyl-1H-indol-3-yl)methanone | (400 MHz, DMSO-d₆, ppm): δ 8.93 (s, 1H), 8.34 (d, J = 7.2 Hz, 1H), 7.62 (d, J = 8 Hz, 1H), 7.31-7.23 (m, 2H), 6.46 (s, 2H), 4.38-4.32 (m, 2H), 2.56-2.53 (m, 2H), 2.32-2.29 (m, 2H), 1.73-1.67 (m, 4H), 1.43-1.24 (m, 3H). |
| Example 44 | 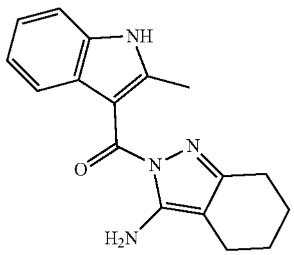 [SMILES: Cc1[nH]c2ccccc2c1C(=O)n1nc2c(c1N)CCCC2] | (3-amino-4,5,6,7-tetrahydroindazol-2-yl)(2-methyl-1H-indol-3-yl)methanone | (300 MHz, DMSO-d₆, ppm): δ 11.79 (s, 1H), 7.51 (d, J = 7.5 Hz, 1H), 7.35 (d, J = 7.5 Hz, 1H), 7.10-7.03 (m, 2H), 6.19 (s, 2H), 2.46 (s, 3H), 2.39-2.32 (m, 4H), 1.68 (m, 4H) |
| Example 45 | 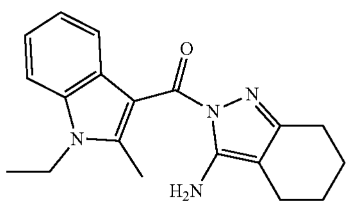 [SMILES: CCn1c(C)c(C(=O)n2nc3c(c2N)CCCC3)c2ccccc21] | (3-amino-4,5,6,7-tetrahydroindazol-2-yl)(1-ethyl-2-methyl-1H-indol-3-yl)methanone | (DMSO-d₆, 400 MHz, ppm): δ 7.44 (d, J = 8.0, 1H), 7.37 (d, J = 7.6, 1H), 7.09-7.07 (m, 1H), 7.01-7.00 (m, 1H), 6.12 (s, 2H), 4.20-4.18 (m, 2H), 2.44 (s, 3H), 2.31-2.24 (m, 4H), 1.60-1.59 (m, 4H), 1.24-1.20 (m, 3H). |
| Example 46 | 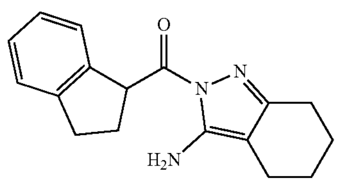 [SMILES: Nc1c2c(nn1C(=O)C1CCc3ccccc31)CCCC2] | (3-amino-4,5,6,7-tetrahydroindazol-2-yl)(2,3-dihydro-1H-inden-1-yl)methanone | (DMSO-d₆, 400 MHz, ppm): δ 7.27 (d, J = 7.2, 1H), 7.21-7.10 (m, 3H), 6.35 (s, 2H), 5.21-5.24 (m, 1H), 3.10-3.02 (m, 1H), 2.96-2.89 (m, 1H), 2.51-2.50 (m, 1H), 2.48-2.49 (m, 1H), 2.37-2.26 (m, 4H), 1.72-1.67 (m, 4H). |

Example 47: (3-amino-4,5,6,7-tetrahydroindazol-2-yl)(1H-indazol-4-yl)methanone

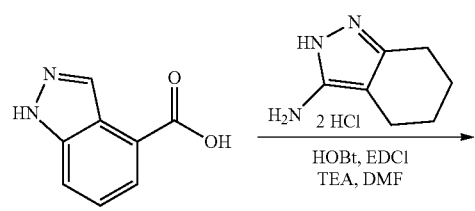

-continued

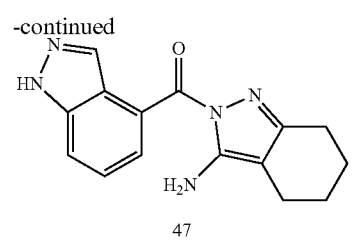

47

Into a 50-mL round-bottom flask, was placed 1H-indazole-4-carboxylic acid (3 g, 18.50 mmol, 1.20 equiv), 4,5,6,7-tetrahydro-2H-indazol-3-amine dihydrochloride (3.25 g, 15.47 mmol, 1.00 equiv), HOBT (3.75 g, 27.75 mmol, 1.80 equiv), EDCI (5.35 g, 27.91 mmol, 1.80 equiv), TEA (5.5 g, 54.35 mmol, 3.00 equiv), N,N-dimethylformamide (100 mL). The resulting solution was stirred overnight at 25° C. The reaction mixture was diluted with DCM (500 mL), washed with H$_2$O (500 mL×3) and brine (500 mL×3) and dried with Na$_2$SO$_4$. After filtration, the filtrate was concentrated under vacuum. The crude product was purified by Prep-HPLC with the following conditions (Analyse HPLC-SHIMADZU): Column, SunFire Prep C18, 19*150 mm; mobile phase, Phase A: water (0.1% FA), Phase B: CH$_3$CN (10% CH$_3$CN up to 40%); Detector, UV220&254 nm. The collected fraction was lyophilized to give 1.2141 g (28%) of (3-amino-4,5,6,7-tetrahydroindazol-2-yl)(1H-indazol-4-yl)methanone (Example 47) as a light yellow solid. Rt=37.5 min; MS (ES, m/z) [M+H]$^+$: 282; $^1$HNMR (DMSO-d$_6$, 300 MHz, ppm): δ 13.32 (s, 1H); 8.07 (s, 1H); 7.81-7.75 (m, 2H); 7.47-7.42 (m, 1H); 6.47 (s, 2H); 2.38-2.31 (m, 4H); 1.26-1.45 (m, 4H).

Example 48: (3-amino-4,5,6,7-tetrahydroindazol-2-yl)(1H-benzo[d]imidazol-4-yl)methanone

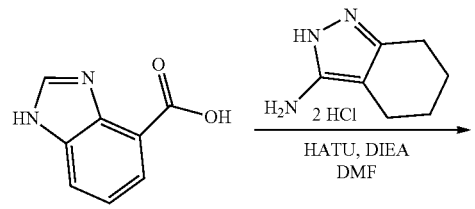

Into a 50-mL round-bottom flask, was placed 1H-1,3-benzodiazole-4-carboxylic acid (42 mg, 0.26 mmol, 1.00 equiv), HATU (164 mg, 0.43 mmol, 1.50 equiv), DIEA (111 mg, 0.86 mmol, 3.00 equiv), 4,5,6,7-tetrahydro-2H-indazol-3-amine dihydrochloride (60.6 mg, 0.29 mmol, 1.10 equiv), N,N-dimethylformamide (5 mL). The resulting solution was stirred overnight at 25° C. The reaction mixture was diluted with DCM (50 mL), washed with H$_2$O (50 mL×3) and brine (50 mL×3) and dried with Na$_2$SO$_4$. After filtration, the filtrate was concentrated under vacuum. The crude product was purified by Prep-HPLC with the following conditions (Analyse HPLC-SHIMADZU): Column: XBridge Shield RP18 OBD Column, 5 um, 19*150 mm; Mobile Phase A: water (0.1% FA), Mobile Phase B: ACN; Flow rate: 20 mL/min; Gradient: 3% B to 20% B in 17 min; 254 nm. The collected fraction was lyophilized to give 18.5 mg (25%) of (3-amino-4,5,6,7-tetrahydroindazol-2-yl)(1H-benzo[d]imidazol-4-yl)methanone (Example 48) as an off-white solid. Rt=15.5 min; MS (ES, m/z) [M+H]$^+$: 282; $^1$HNMR (DMSO-d$_6$, 400 MHz, ppm): δ 11.57 (s, 1H); 8.71 (s, 1H); 8.02 (d, J=7.6, 1H); 7.87 (d, J=8.0, 1H); 7.47-7.43 (m, 1H); 2.61-2.58 (m, 2H); 2.45-2.46 (m, 2H); 1.76-1.67 (m, 4H).

Example 49: (3-amino-4,5,6,7-tetrahydroindazol-2-yl)(1-isopropyl-2-methyl-1H-indol-4-yl)methanone Step 1. 4-bromo-1-isopropyl-2-methyl-1H-indole

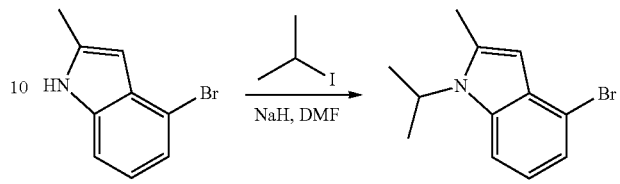

Into a 50-mL 3-necked round-bottom flask, was placed 4-bromo-2-methyl-1H-indole (200 mg, 0.95 mmol, 1.00 equiv), N,N-dimethylformamide (8 mL). This was followed by the addition of sodium hydride (60% in oil) (58 mg, 1.45 mmol, 1.50 equiv) at 0° C. The mixture was stirred for 30 min at this temperature. To the above was added 2-iodopropane (326 mg, 1.92 mmol, 2.00 equiv) at 0° C. The resulting solution was stirred overnight at room temperature (19° C.). The reaction was quenched by the addition of water (10 ml). The resulting solution was extracted with dichloromethane (50 mL×2) and dried with Na$_2$SO$_4$. After filtration, the filtrate was concentrated under vacuum. The residue was applied onto a silica gel column with ethyl acetate/petroleum ether (1/10). The collected fraction was concentrated to give 130 mg (54%) of 4-bromo-1-isopropyl-2-methyl-1H-indole as yellow oil. MS (ES, m/z) [M+H]$^+$: 252, 254

Step 2. 1-isopropyl-2-methyl-1H-indole-4-carboxylic Acid

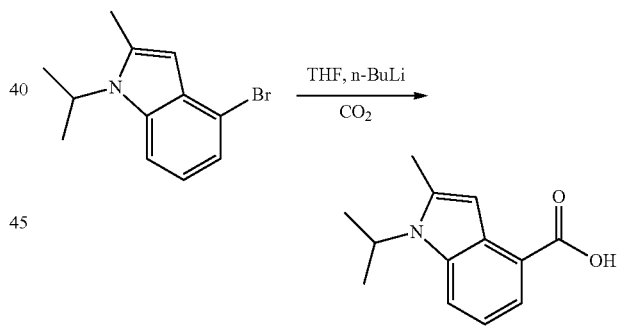

Into a 100-mL 3-necked round-bottom flask purged and maintained with an inert atmosphere of nitrogen, was placed 4-bromo-1-isopropyl-2-methyl-1H-indole (130 mg, 0.52 mmol, 1.00 equiv), tetrahydrofuran (10 mL). This was followed by the addition of n-BuLi (2.5 mol/L in hexane, 0.33 mL) dropwised at −78° C. The above mixture was stirred for 30 min at −78° C. To the above CO$_2$ (0.5 g) was added at −78° C. The resulting solution was stirred overnight at room temperature (20° C.). The reaction was then quenched by the addition of water/ice (10 mL). The resulting mixture was washed with EA (60 mL×2). The pH value of the aqueous layers was adjusted to 4 with HCl (1 mol/L). The resulting solution was extracted with dichloromethane (60 mL×2) and dried over anhydrous sodium sulfate. The solids were filtered out. The filtrate was concentrated under vacuum to give 54 mg (48%) of 1-isopropyl-2-methyl-1H-indole-4-carboxylic acid as brown oil.

MS (ES, m/z): [M+H]$^+$: 218

Step 3. (3-amino-4,5,6,7-tetrahydroindazol-2-yl)(1-isopropyl-2-methyl-1H-indol-4-yl)methanone

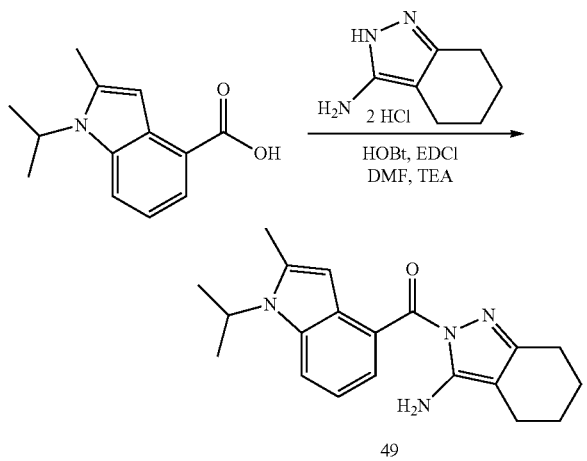

Into a 50-mL round-bottom flask, was placed 2-methyl-1-(propan-2-yl)-1H-indole-4-carboxylic acid (50 mg, 0.23 mmol, 0.90 equiv) in N,N-dimethylformamide (3 mL), HOBt (88 mg, 0.65 mmol, 2.50 equiv), EDCI (75 mg, 0.39 mmol, 1.50 equiv), TEA (131 mg, 1.29 mmol, 5.00 equiv). The above mixture was stirred for 30 min at room temperature (20° C.). To the above was added 4,5,6,7-tetrahydro-2H-indazol-3-amine dihydrochloride (54.3 mg, 0.26 mmol, 1.00 equiv). The resulting solution was stirred overnight at room temperature (20° C.). The resulting solution was diluted with EA (30 mL), washed with washed with H$_2$O (50 mL×3) and brine (50 mL×3), dried with Na$_2$SO$_4$ and concentrated under vacuum. The crude product was purified by Prep-TLC with ethyl acetate/petroleum ether (1/1.5). The crude product was purified by Prep-HPLC with the following conditions (AnalyseHPLC-SHIMADZU): Column, XBridge C18 OBD Prep Column, 100 A, 5 um, 19×250 mm; mobile phase, water (0.1% FA) and ACN (50.0% ACN up to 70.0% in 7 min); Detector, UV 254 nm. The collected fraction was lyophilized to give 11.6 mg (13%) of (3-amino-4,5,6,7-tetrahydroindazol-2-yl)(1-isopropyl-2-methyl-1H-indol-4-yl)methanone (49) as a yellow solid. Rt=7.85 min; MS (ES, m/z) [M+H]$^+$: 337; $^1$HNMR (400 MHz, DMSO-d$_6$, ppm): δ 7.73 (d, J=8.4 Hz, 1H); 7.47 (d, J=7.2 Hz, 1H); 7.08-7.04 (m, 1H); 6.37 (s, 2H); 6.27 (s, 1H); 4.77-4.20 (m, 1H); 2.43 (s, 3H); 2.35-2.29 (m, 4H); 1.64 (s, 4H); 1.55-1.52 (m, 6H).

Example 50: (3-amino-4,5,6,7-tetrahydroindazol-2-yl)(2-ethyl-1H-indol-4-yl)methanone Step 1: Methyl 2-bromo-1H-indole-4-carboxylate

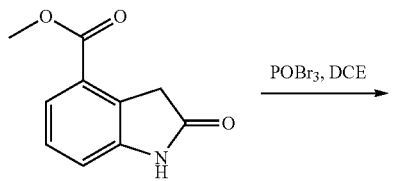

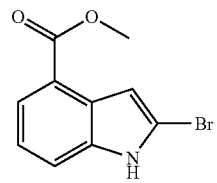

Into a 250-mL 3-necked round-bottom flask, was placed a solution of methyl 2-oxo-2,3-dihydro-1H-indole-4-carboxylate (3.0 g, 15.69 mmol, 1.00 equiv) in DCE (50 mL). This was followed by the addition of a solution of POBr$_3$ (7.36 g, 25.92 mmol, 1.65 equiv) in DCE (30 mL) at 0° C. The resulting solution was stirred for 1 h at 0° C. and heated to 80° C. for 2 h. Then 1H-imidazole (2.135 g, 31.36 mmol, 2.00 equiv) was added at 80° C. The resulting solution was allowed to react, with stirring, for an additional 15 h at 80° C. The reaction mixture was cooled to r.t. (25° C.) and slowly poured into 150 mL of sat. NaHCO$_3$. The resulting solution was extracted with dichloromethane (200 mL×3), washed with brine (500 mL), dried over anhydrous sodium sulfate, filtered and concentrated under vacuum. The residue was applied onto a silica gel column with ethyl acetate/hexane (0-10%). The collected fraction was concentrated to give 2.0 g (50%) of methyl 2-bromo-1H-indole-4-carboxylate as a light yellow solid. MS (ES, m/z) [M+H]$^+$: 254, 256.

Step 2: Methyl 2-vinyl-1H-indole-4-carboxylate

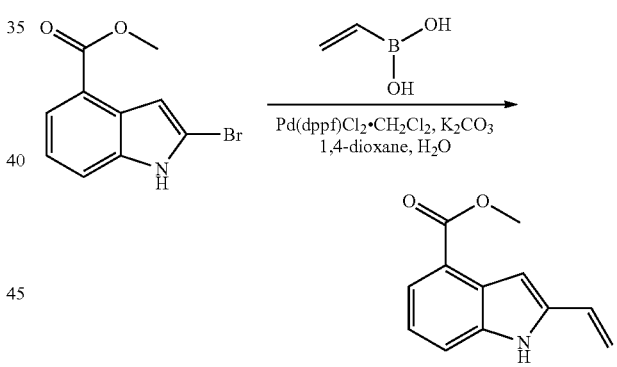

Into a 250-mL round-bottom flask purged and maintained with an inert atmosphere of nitrogen, was placed methyl 2-bromo-1H-indole-4-carboxylate (2 g, 7.87 mmol, 1.00 equiv), Pd(dppf)Cl$_2$.CH$_2$Cl$_2$ (1.29 g, 0.20 equiv), potassium carbonate (3.27 g, 23.66 mmol, 3.00 equiv), 1,4-dioxane (60 mL), vinylboronic acid (6.09 g, 43.50 mmol, 5.00 equiv), water (20 mL). The resulting mixture was stirred overnight at 80° C. The resulting mixture was cooled to room temperature. Then solvent was concentrated under vacuum, diluted with ethyl acetate (200 mL), washed with water (50 mL×3) and brine (50 mL×3), dried over anhydrous sodium sulfate and concentrated under vacuum. The residue was applied onto a silica gel column and eluted with ethyl acetate/petroleum ether (0-20%). The collected fraction was concentrated to give 1.0 g (63%) of methyl 2-ethenyl-1H-indole-4-carboxylate as a light yellow solid. MS (ES, m/z) [M+H]$^+$: 202.

Step 3: Methyl 2-ethyl-1H-indole-4-carboxylate

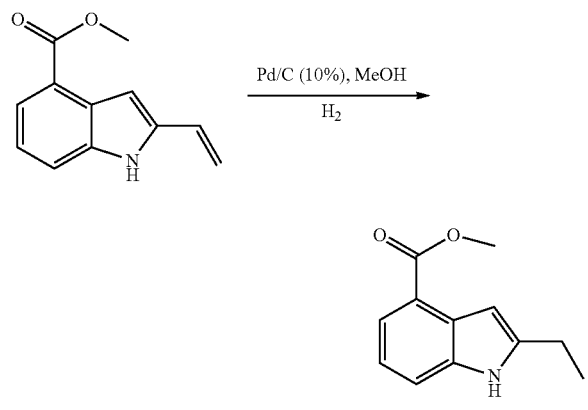

Into a 100-mL round-bottom flask, was placed methyl 2-ethenyl-1H-indole-4-carboxylate (1 g, 4.97 mmol, 1.00 equiv), methanol (25 mL), palladium carbon (10%, 200 mg). The mixture was evacuated and flushed three times with hydrogen. The resulting solution was stirred overnight at 20° C. under an atmosphere of hydrogen (4 atm). The solids were filtered out. The filtrate was concentrated under vacuum to give 0.9 g (89%) of methyl 2-ethyl-1H-indole-4-carboxylate as a yellow solid. MS (ES, m/z) [M+H]$^+$: 204.

Step 4: 2-ethyl-1H-indole-4-carboxylic Acid

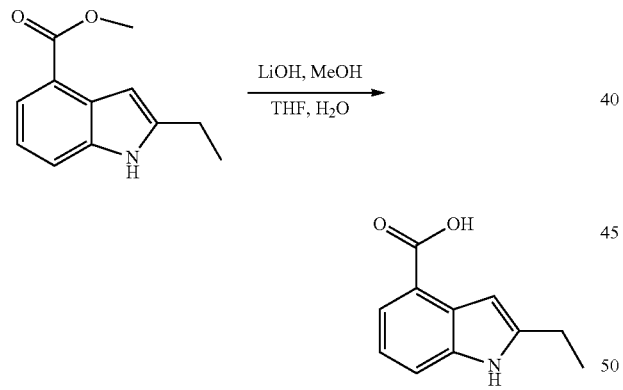

Into a 100-mL round-bottom flask, was placed methyl 2-ethyl-1H-indole-4-carboxylate (600 mg, 2.95 mmol, 1.00 equiv), tetrahydrofuran (20 mL), methanol (5 mL), a solution of LiOH (490 mg, 20.46 mmol, 6.00 equiv) in H$_2$O (15 mL). The resulting solution was stirred overnight at 35° C. The resulting mixture was concentrated under vacuum. The resulting solution was extracted with 40 mL of ethyl acetate and the aqueous layers collected. The pH value was adjusted to 6 with HCl (1 mol/L). The resulting solution was extracted with ethyl acetate (60 mL×3), dried over anhydrous sodium sulfate, filtered and concentrated under vacuum. This gave 470 mg (84%) of 2-ethyl-1H-indole-4-carboxylic acid as a light yellow solid. MS (ES, m/z) [M+H]$^+$: 190.

Step 5: (3-amino-4,5,6,7-tetrahydroindazol-2-yl)(2-ethyl-1H-indol-4-yl) methanone

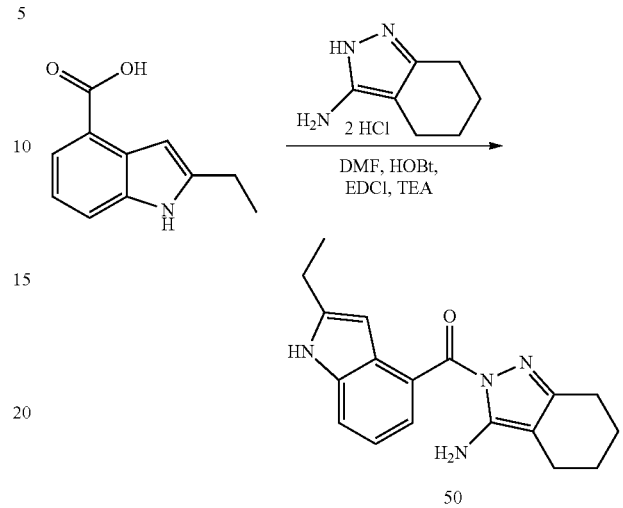

Into a 100-mL round-bottom flask, was placed 2-ethyl-1H-indole-4-carboxylic acid (1.2 g, 6.34 mmol, 1.00 equiv) in DMF (35 mL), HOBT (1.29 g, 9.55 mmol, 1.50 equiv), EDCI (1.83 g, 9.55 mmol, 1.50 equiv), TEA (3.0 g, 29.65 mmol, 5.00 equiv) and 4,5,6,7-tetrahydro-2H-indazol-3-amine dihydrochloride (1.62 g, 7.57 mmol, 1.20 equiv). The resulting solution was stirred overnight at room temperature (25° C.). The resulting solution was diluted with ethyl acetate (150 mL), washed with brine (200 mL×2), dried over anhydrous sodium sulfate and concentrated under vacuum. The residue was applied onto a silica gel column with ethyl acetate/petroleum ether (1:1). The crude product was re-purified by Prep-HPLC with the following conditions (AnalyseHPLC-SHIMADZU): Column, XBridge Prep C18 OBD Column, 5 um, 19×150 mm; mobile phase, water (10 mmol/L NH$_4$HCO$_3$) and ACN (30.0% ACN up to 60.0% in 12 min); Detector, UV 254 nm. The collected fraction was lyophilized to give 378 mg (19%) of (3-amino-4,5,6,7-tetrahydroindazol-2-yl)(2-ethyl-1H-indol-4-yl)methanone as a yellow solid. Rt=10.25 min; MS (ES, m/z) [M+H]$^+$: 309; $^1$HNMR (DMSO-d6, 400 MHz, ppm): δ 11.21 (s, 1H); 7.55 (d, J=6.8 Hz, 1H); 7.47 (d, J=7.6 Hz, 1H); 7.08-7.04 (m, 1H); 6.38 (s, 2H); 6.29 (s, 1H); 2.79-2.73 (m, 2H); 2.38-2.36 (m, 2H); 2.33-2.31 (m, 2H); 1.66 (s, 4H); 1.29-1.25 (m, 3H).

Examples 51 and 52: (3-amino-4,5,6,7-tetrahydroindazol-2-yl)(2-isopropyl-1H-indol-4-yl)methanone and (3-amino-4,5,6,7-tetrahydroindazol-1-yl)(2-isopropyl-1H-indol-4-yl)methanone

Step 1. Methyl 2-(prop-1-en-2-yl)-1H-indole-4-carboxylate

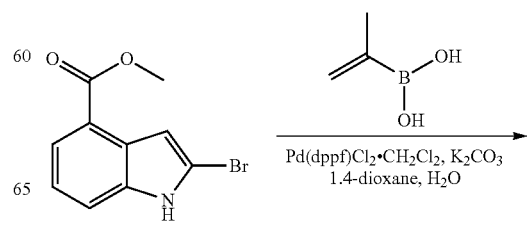

-continued

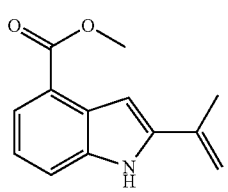

Into a 100-mL round-bottom flask purged and maintained with an inert atmosphere of nitrogen, was placed methyl 2-bromo-1H-indole-4-carboxylate (120 mg, 0.47 mmol, 1.00 equiv), 4,4,5,5-tetramethyl-2-(prop-1-en-2-yl)-1,3,2-dioxaborolane (796 mg, 4.74 mmol, 10.00 equiv), Pd(dppf)Cl$_2$·CH$_2$Cl$_2$ (39 mg, 0.05 mmol, 0.10 equiv), potassium carbonate (196 mg, 1.42 mmol, 3.00 equiv), dioxane (10 mL), water (1 mL). The resulting solution was stirred overnight at 100° C. After cooled to room temperature, the resulting mixture was concentrated under vacuum. The residue was purified by preparative TLC (EA:PE=1:3). This resulted in 86 mg (85%) of methyl 2-(prop-1-en-2-yl)-1H-indole-4-carboxylate as a yellow solid. MS (ES, m/z) [M+H]$^+$: 215.

Step 2. 2-(prop-1-en-2-yl)-1H-indole-4-carboxylic Acid

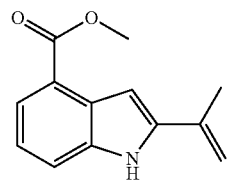

Into a 100-mL round-bottom flask, was placed methyl 2-(prop-1-en-2-yl)-1H-indole-4-carboxylate (86 mg, 0.40 mmol, 1.00 equiv), sodium hydroxide (80 mg, 2.00 mmol, 5.00 equiv), methanol (20 mL) and water (5 mL). The resulting solution was stirred overnight at room temperature. The methanol was removed under vacuum. The residue was diluted with water (20 mL). The resulting mixture was washed with DCM (20 mL×2). The pH value of the aqueous layers was adjusted to 5-6 with HCl (1 mol/L). The resulting solution was extracted with EA (30 mL×3) and concentrated under vacuum. The residue was purified by preparative TLC (EA:PE=1:1). This resulted in 35 mg (44%) of 2-(prop-1-en-2-yl)-1H-indole-4-carboxylic acid as a light yellow solid. MS (ES, m/z) [M+H]$^+$: 202.

Step 3. 2-(prop-1-en-2-yl)-1H-indole-4-carboxylic Acid

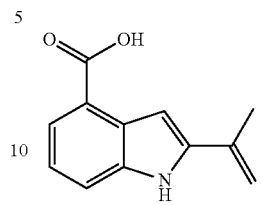

Into a 50-mL round-bottom flask, was placed 2-(prop-1-en-2-yl)-4,5,6,7-tetrahydro-1H-indole-4-carboxylic acid (35 mg, 0.17 mmol, 1.00 equiv), methanol (5 mL), palladium carbon (10%, 35 mg). To the above hydrogen was introduced in. The resulting solution was stirred for 4 h at 20° C. The solids were filtered out. The filtrate was concentrated under vacuum to give 30 mg (85%) of 2-(propan-2-yl)-4,5,6,7-tetrahydro-1H-indole-4-carboxylic acid as a yellow solid. MS (ES, m/z) [M+H]$^+$: 204;

Step 4. (3-amino-4,5,6,7-tetrahydroindazol-2-yl)(2-isopropyl-1H-indol-4-yl)methanone and (3-amino-4,5,6,7-tetrahydroindazol-1-yl)(2-isopropyl-1H-indol-4-yl)methanone

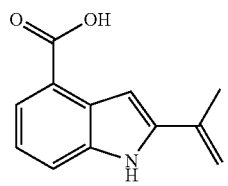

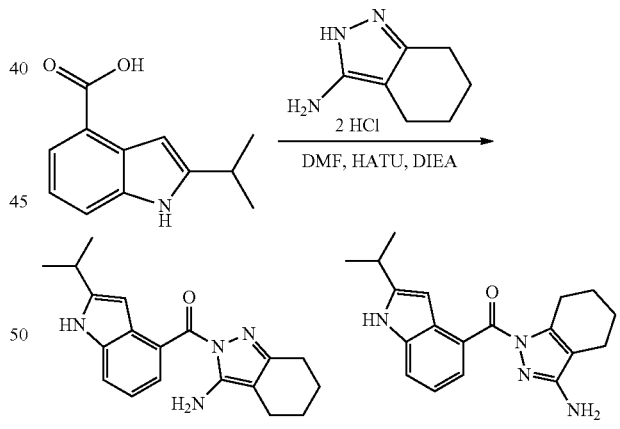

Into a 50-mL round-bottom flask, was placed 2-(propan-2-yl)-1H-indole-4-carboxylic acid (30 mg, 0.15 mmol, 1.00 equiv) in DMF (5 mL), HATU (84 mg, 0.22 mmol, 1.50 equiv) and DIEA (57 mg, 0.44 mmol, 3.00 equiv). The mixture was stirred for 30 min at room temperature (25° C.). Then 4,5,6,7-tetrahydro-2H-indazol-3-amine dihydrochloride (33.4 mg, 0.16 mmol, 1.10 equiv) was added. The resulting solution was stirred overnight at room temperature (25° C.). The reaction mixture was diluted with DCM (80 mL), washed with H$_2$O (50 mL×3) and brine (50 mL×3), dried with anhydrous sodium sulfate and concentrated under vacuum. The crude product was purified by Prep-HPLC with the following conditions (Analyse HPLC-SHIMADZU): Column: XBridge Shield RP18 OBD Column, 5 um, 19*150 mm; Mobile Phase A: water (0.1% FA), Mobile Phase B: ACN; Flow rate: 20 mL/min; Gradient: 30% B to 60% B in 12 min; 254 nm. The collected fractions were lyophilized.

Fraction A (Example 51): 3.3 mg (7%) of 2-[[2-(propan-2-yl)-1H-indol-4-yl]carbonyl]-4,5,6,7-tetrahydro-2H-indazol-3-amine as a yellow solid. Rt=11.1 min; MS (ES, m/z) [M+H]+: 323; 1HNMR (DMSO-d6, 400 MHz, ppm): δ 11.21 (s, 1H); 7.55 (d, J=7.2, 1H); 7.47 (d, J=8.0, 1H); 7.09-7.05 (m, 1H); 6.28 (s, 1H); 3.10-3.03 (m, 1H); 2.38-2.36 (m, 2H); 2.33-2.31 (m, 2H); 1.67-1.66 (m, 4H); 1.33- 1.23 (m, 6H).

Fraction B (Example 52): 2.0 mg (4%) of 1-[[2-(propan-2-yl)-1H-indol-4-yl]carbonyl]-4,5,6,7-tetrahydro-1H-indazol-3-amine as a yellow solid. Rt=8.25 min MS (ES, m/z) [M+H]+: 323; 1HNMR (DMSO-d6, 400 MHz, ppm): δ 11.12 (s, 1H); 7.44-7.41 (m, 2H); 7.07-6.95 (m, 1H); 6.22 (s, 1H); 3.08-3.01 (m, 1H); 2.94-2.93 (m, 2H); 2.33-2.27 (m, 2H); 1.75-1.70 (m, 4H); 1.30-1.23 (m, 6H).

Examples 53 and 54: (3-amino-4,5,6,7-tetrahydroindazol-2-yl)(2-cyclopropyl-1H-indol-4-yl)methanone and (3-amino-4,5,6,7-tetrahydroindazol-1-yl)(2-cyclopropyl-1H-indol-4-yl)methanone Step 1: 2-cyclopropyl-1H-indole-4-carboxylic Acid

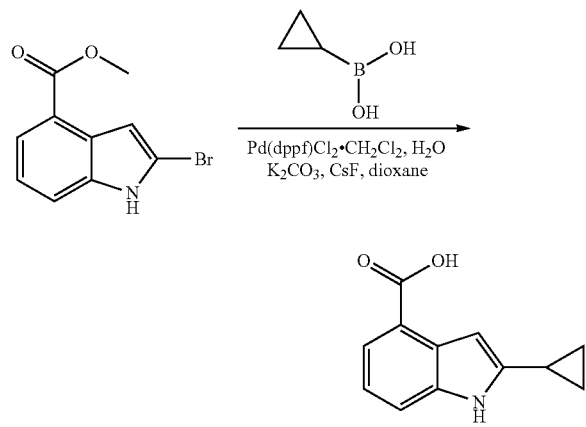

Into a 100-mL round-bottom flask purged and maintained with an inert atmosphere of nitrogen, was placed methyl 2-bromo-1H-indole-4-carboxylate (150 mg, 0.59 mmol, 1.00 equiv) in 1,4-dioxane (10 mL), cyclopropylboronic acid (254.9 mg, 2.97 mmol, 5.00 equiv), Pd(dppf)Cl2.CH2Cl2 (48.4 mg, 0.10 equiv), potassium carbonate (245 mg, 1.77 mmol, 3.00 equiv), CsF (225.3 mg, 2.50 equiv) and water (2 mL). The resulting solution was stirred overnight at 110° C. The reaction mixture was cooled to room temperature. The solvent was removed under vacuum. The residue was diluted with water (80 mL) and washed with ethyl acetate (40 mL×2). The pH value of the aqueous layers was adjusted to 5 with HCl (1 mol/L). The resulting solution was extracted with ethyl acetate (60 mL×2), dried over anhydrous sodium sulfate and concentrated under vacuum to give 110 mg (crude) of 2-cyclopropyl-1H-indole-4-carboxylic acid as brown oil. MS (ES, m/z) [M+H]+: 202.

Step 2: (3-amino-4,5,6,7-tetrahydroindazol-2-yl)(2-cyclopropyl-1H-indol-4-yl)methanone: and (3-amino-4,5,6,7-tetrahydroindazol-1-yl)(2-cyclopropyl-1H-indol-4-yl)methanone

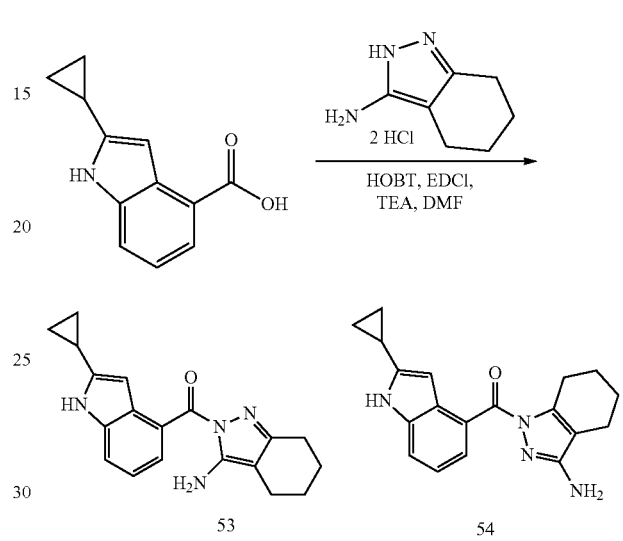

Into a 50-mL round-bottom flask, was placed 2-cyclopropyl-1H-indole-4-carboxylic acid (110 mg, 0.55 mmol, 1.00 equiv) in DMF (5 mL), HOBT (111 mg, 0.82 mmol, 1.50 equiv), EDCI (156 mg, 0.82 mmol, 1.50 equiv), TEA (275.5 mg, 2.72 mmol, 5.00 equiv) and 4,5,6,7-tetrahydro-2H-indazol-3-amine dihydrochloride (137 mg, 0.66 mmol, 1.20 equiv). The resulting solution was stirred overnight at room temperature (25° C.). The resulting solution was diluted with ethyl acetate (100 mL), washed with brine (150 mL×2), dried over anhydrous sodium sulfate and concentrated under vacuum. The crude product was purified by Prep-HPLC with the following conditions (AnalyseHPLC-SHIMADZU): Column, XBridge Shield RP18 OBD Column, 5 um, 19×150 mm; mobile phase, water (0.1% FA) and ACN (45.0% ACN up to 75.0% in 7 min); Detector, UV 254 nm to give two fractions. The collected fraction was lyophilized.

Fraction A (Example 53): 15.4 mg (9%) of (3-amino-4,5,6,7-tetrahydroindazol-2-yl)(2-cyclopropyl-1H-indol-4-yl)methanone as a yellow solid. Rt=6.1 min; MS (ES, m/z) [M+H]+: 321; 1HNMR (DMSO-d6, 400 MHz, ppm): δ 11.17 (s, 1H); 7.62 (d, J=7.2 Hz, 1H); 7.55 (d, J=7.6 Hz, 1H); 7.48-7.42 (m, 1H); 6.37 (s, 2H); 6.22 (s, 1H); 2.43-2.36 (m, 2H); 2.35-2.28 (m, 2H); 2.08-2.02 (m, 1H); 1.66 (s, 4H); 1.06-0.96 (m, 2H); 0.85-0.75 (m, 2H).

Fraction B (Example 54): 11.9 mg (7%) of (3-amino-4,5,6,7-tetrahydroindazol-1-yl)(2-cyclopropyl-1H-indol-4-yl)methanone as a dark yellow solid. Rt=5.0 min; MS (ES, m/z) [M+H]+: 321; 1HNMR (DMSO-d6, 400 MHz, ppm): δ 11.07 (s, 1H); 7.43-7.36 (m, 2H); 7.02-6.99 (m, 1H); 6.16 (s, 1H); 5.34 (s, 2H); 2.93-2.92 (m, 2H); 2.31-2.19 (m, 2H); 2.08-2.00 (m, 1H); 1.75-1.70 (m, 4H); 1.04-0.95 (m, 2H); 0.81-0.75 (m, 2H).

Examples 55 and 56: (3-amino-4,5,6,7-tetrahydroindazol-2-yl)(2-chloro-1H-indol-4-yl)methanone and (3-amino-4,5,6,7-tetrahydroindazol-1-yl)(2-chloro-1H-indol-4-yl)methanone Step 1. Methyl 2-chloro-1H-indole-4-carboxylate

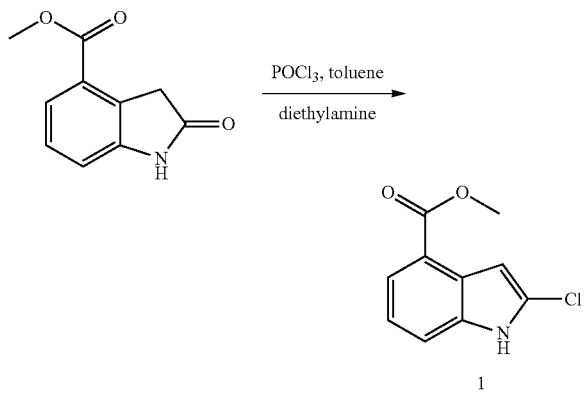

Into a 100-mL round-bottom flask, was placed methyl 2-oxoindoline-4-carboxylate (300 mg, 1.57 mmol, 1.00 equiv) and toluene (10 mL). This was followed by the addition of POCl₃ (0.25 mL) dropwise with stirring at 0° C. To this was added diethylamine (0.25 mL). The resulting solution was stirred overnight at 110° C. After cooled to room temperature, the resulting mixture was concentrated under vacuum. Then the mixture was quenched with water (20 mL). The solution was extracted with dichloromethane (30 mL×3), washed with brine, dried over anhydrous sodium sulfate, filtered and concentrated under vacuum to give 150 mg (46%) of methyl 2-chloro-1H-indole-4-carboxylate as a yellow solid. MS (ES, m/z) [M+H]$^+$: 210, 212.

Step 2. 2-chloro-1H-indole-4-carboxylic Acid

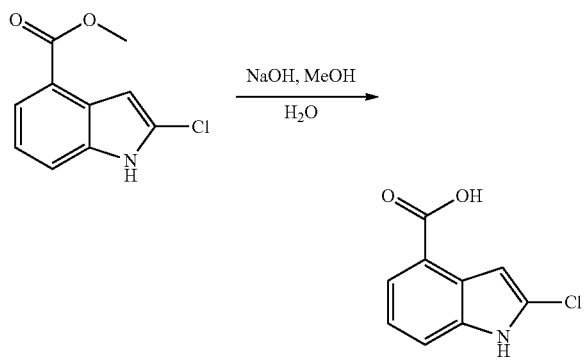

Into a 100-mL round-bottom flask, was placed methyl 2-chloro-1H-indole-4-carboxylate (150 mg, 0.72 mmol, 1.00 equiv), methanol (10 mL), a solution of sodium hydroxide (586 mg, 14.65 mmol, 20.00 equiv) in water (10 mL). The resulting solution was stirred overnight at room temperature (20° C.). The resulting solution was washed with DCM (20 mL×2). The pH value of the aqueous layers was adjusted to 5-6 with HCl (6 mol/L). The resulting solution was extracted with ethyl acetate (30 mL×3) and concentrated under vacuum. This gave 100 mg (71%) of 2-chloro-1H-indole-4-carboxylic acid as a yellow solid. MS (ES, m/z) [M+H]+: 196, 198.

Step 3. (3-amino-4,5,6,7-tetrahydroindazol-2-yl)(2-chloro-1H-indol-4-yl)methanone (Example 55) and (3-amino-4,5,6,7-tetrahydroindazol-1-yl)(2-chloro-1H-indol-4-yl)methanone (Example 56)

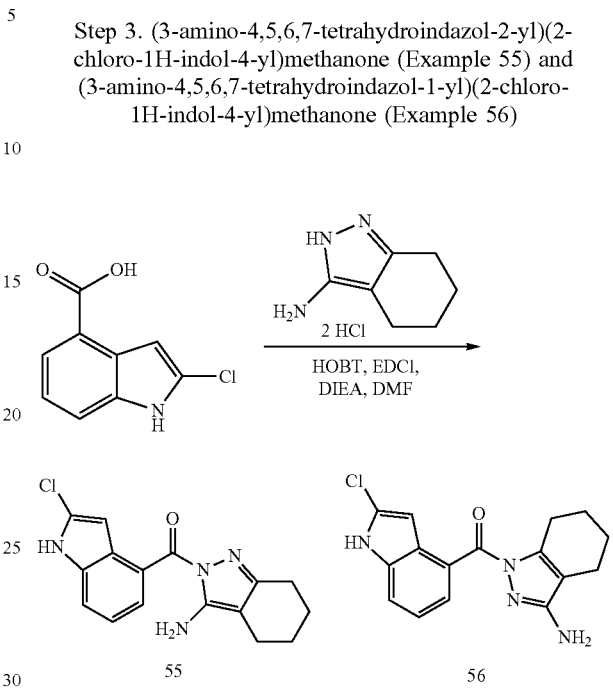

Into a 50-mL round-bottom flask, was placed 2-methyl-1-benzofuran-4-carboxylic acid; 2-methyl-1-benzofuran-6-carboxylic acid (60 mg, 0.17 mmol, 1.00 equiv) in DMF (5 mL), HOBT (69 mg, 0.51 mmol, 1.50 equiv), EDCI (98 mg, 0.51 mmol, 1.50 equiv), DIEA (132 mg, 1.02 mmol, 3.00 equiv). The mixture was stirred for 30 min at room temperature (25° C.). Then 4,5,6,7-tetrahydro-2H-indazol-3-amine dihydrochloride (79.4 mg, 0.38 mmol, 1.10 equiv) was added. The resulting solution was stirred overnight at room temperature (25° C.). The reaction mixture was diluted with DCM (80 mL), washed with H₂O (50 mL×3) and brine (50 mL×3), dried with anhydrous sodium sulfate and concentrated under vacuum. The crude product was purified by Prep-HPLC with the following conditions (Analyse HPLC-SHIMADZU): Column: XBridge Prep C18 OBD Column 19×150 mm 5 um; Mobile Phase A: water (0.1% FA), Mobile Phase B: ACN; Flow rate: 20 mL/min; Gradient: 25% B to 55% B in 7 min; 254/220 nm. The collected fractions were lyophilized.

The Fraction A (Example 55): 8.5 mg (13%) of (3-amino-4,5,6,7-tetrahydroindazol-2-yl)(2-chloro-1H-indol-4-yl) methanone as an off-white solid. Rt=6.3 min; MS (ES, m/z) [M+H]$^+$: 315, 317; $^1$HNMR (DMSO-d$_6$, 400 MHz, ppm): δ 12.20 (s, 1H); 7.65 (d, J=7.6, 1H); 7.51 (d, J=8.0, 1H); 7.23-7.18 (m, 1H); 6.49 (s, 1H); 6.41 (s, 2H); 2.38-2.37 (m, 2H); 2.32-2.31 (m, 2H); 1.68-1.66 (m, 4H).

The Fraction B (Example 56): 7.1 mg (11%) of (3-amino-4,5,6,7-tetrahydroindazol-1-yl)(2-chloro-1H-indol-4-yl) methanone as an off-white solid. Rt=5.1 min; MS (ES, m/z) [M+H]$^+$: 315, 317; $^1$HNMR (DMSO-d$_6$, 400 MHz, ppm): δ 12.10 (s, 1H); 7.52 (d, J=7.6, 1H); 7.45 (d, J=8.0, 1H); 7.19-7.15 (m, 1H); 6.41 (s, 2H); 6.40 (s, 2H); 2.95-2.94 (m, 2H); 2.28-2.27 (m, 2H); 1.76-1.71 (m, 4H).

Example 57: (3-Amino-4,5,6,7-tetrahydro-indazol-2-yl)-(2-methyl-benzo[b]thiophen-4-yl)-methanone

Step 1. Methyl benzo[b]thiophene-4-carboxylate

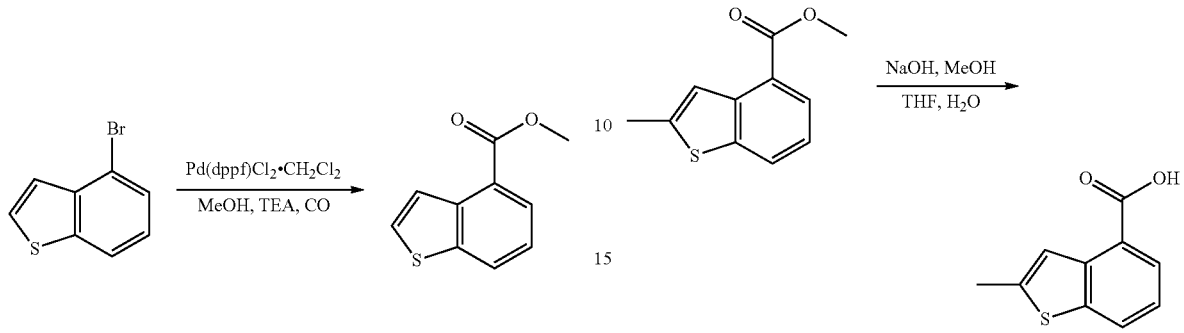

Into a 30-mL pressure tank reactor (60 atm) purged and maintained with an inert atmosphere of CO, was placed 4-bromo-1-benzothiophene (3 g, 14.08 mmol, 1.00 equiv), Pd(dppf)Cl$_2$.CH$_2$Cl$_2$ (5.8 g, 0.50 equiv), TEA (7.2 g, 71.15 mmol, 5.00 equiv), methanol (15 mL). The resulting solution was stirred overnight at 120° C. The resulting mixture was cooled to room temperature and concentrated under vacuum. The residue was applied onto a silica gel column and eluted with ethyl acetate/petroleum ether (1/10). The collected fraction was concentrated to give 1.18 g (44%) of methyl benzo[b]thiophene-4-carboxylate as a yellow solid. MS (ES, m/z): [M+H]$^+$: 193

Step 2. Methyl 2-methylbenzo[b]thiophene-4-carboxylate

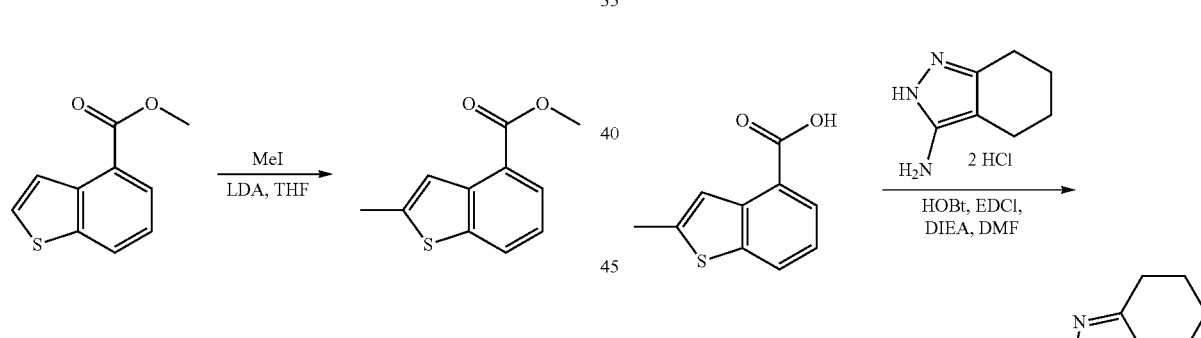

Into a 100-mL 3-necked round-bottom flask purged and maintained with an inert atmosphere of nitrogen, was placed methyl 1-benzothiophene-4-carboxylate (311 mg, 1.62 mmol, 1.00 equiv), tetrahydrofuran (10 mL). The mixture was cooled to −78° C., Then LDA (0.9 mL, 1.10 equiv 2 mol/1) was added with dropwise at −78° C. The mixture was stirred for 30 min at −78° C., then MeI was added (253 mg, 1.10 equiv). The resulting solution was stirred overnight at room temperature. The reaction was then quenched by the addition of water/ice (10 mL). The resulting solution was extracted with ethyl acetate (50 ml×2), dried over anhydrous sodium sulfate and concentrated under vacuum. The crude product was purified by Prep-TLC with ethyl acetate/petroleum ether (1/1). The collected fraction was concentrated to give 200 mg (60%) of methyl 2-methylbenzo[b]thiophene-4-carboxylate as a yellow solid. MS (ES, m/z): [M+H]$^+$: 207.

Step 3. 2-methylbenzo[b]thiophene-4-carboxylic Acid

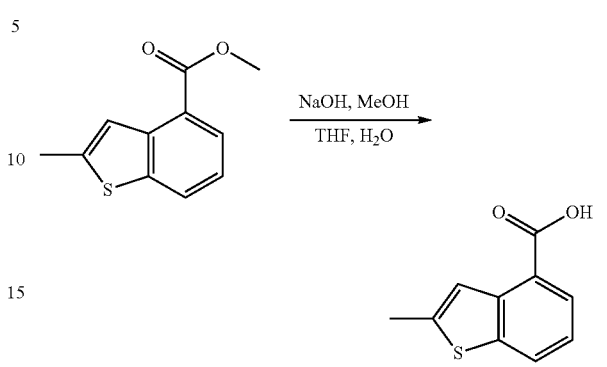

Into a 100-mL round-bottom flask, was placed methyl 2-methyl-1-benzothiophene-4-carboxylate (100 mg, 0.48 mmol, 1.00 equiv) in methanol (10 mL), sodium hydroxide (97 mg, 2.42 mmol, 5.00 equiv), tetrahydrofuran (2.5 mL), water (2.5 mL). The resulting solution was stirred overnight at room temperature. The resulting solution was diluted with water (10 mL). The pH value of the solution was adjusted to 4 with HCl (1 mol/L). The solids were collected by filtration. This gave 90 mg (97%) of 2-methylbenzo[b]thiophene-4-carboxylic acid as a white solid. MS (ES, m/z): [M+H]$^+$: 193.

Step 4. (3-amino-4,5,6,7-tetrahydroindazol-2-yl)(2-methylbenzo[b]thiophen-4-yl)methanone

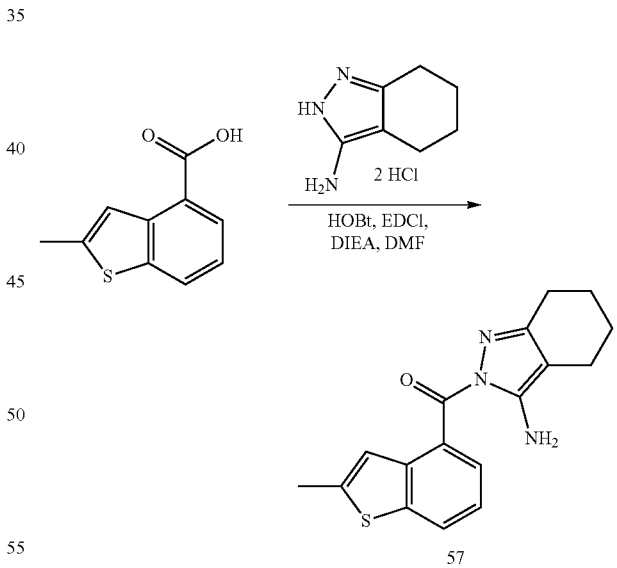

Into a 50-mL round-bottom flask, was placed 2-methyl-1-benzothiophene-4-carboxylic acid (50 mg, 0.26 mmol, 0.90 equiv) in DMF (3 mL), HOBt (88 mg, 0.65 mmol, 2.00 equiv), EDCI (75 mg, 0.48 mmol, 1.50 equiv), TEA (131.3 mg, 1.30 mmol, 5.00 equiv). The mixture was stirred for 30 min at r.t (20° C.). Then 4,5,6,7-tetrahydro-2H-indazol-3-amine dihydrochloride (61 mg, 0.29 mmol, 1.00 equiv) was added. The resulting solution was stirred overnight at room temperature (20° C.). The resulting solution was diluted with EA (30 mL), washed with H$_2$O (50 mL×3) and brine (50 mL×3), dried with Na₂SO₄ and concentrated under vacuum. The crude product was purified by Prep-HPLC with the following conditions (AnalyseHPLC-SHIMADZU): Column, XBridge Prep C18 OBD Column, 5 um, 19×150 mm; mobile phase, water (0.1% FA) and ACN (40.0% ACN up to 51.0% in 10 min); Detector, UV 254 nm. The collected fraction was lyophilized to give 2.6 mg (4%) of (3-amino-4,5,6,7-tetrahydroindazol-2-yl)(2-methylbenzo[b]thiophen-4-yl)methanone (Example 57) as a white solid. Rt=8.9 min; MS (ES, m/z): [M+H]⁺: 312. ¹HNMR (300 MHz, DMSO-d₆, ppm): δ 8.06 (d, J=8.1 Hz, 1H); 7.64-7.62 (m, 1H); 7.38-7.33 (m, 1H); 7.09 (s, 1H); 6.50 (s, 2H); 2.58 (d, J=0.9 Hz, 3H); 2.33 (d, J=5.7 Hz, 4H); 1.65 (s, 4H).

Examples 58, 59, 60 and 61: (3-amino-4,5,6,7-tetrahydroindazol-2-yl)(2-methylbenzofuran-4-yl)methanone and (3-amino-4,5,6,7-tetrahydroindazol-1-yl)(2-methylbenzofuran-4-yl)methanone and (3-amino-4,5,6,7-tetrahydroindazol-2-yl)(2-methylbenzofuran-6-yl)methanone and (3-amino-4,5,6,7-tetrahydroindazol-1-yl)(2-methylbenzofuran-6-yl)methanone Step 1. Methyl 3-(prop-2-ynyloxy)benzoate

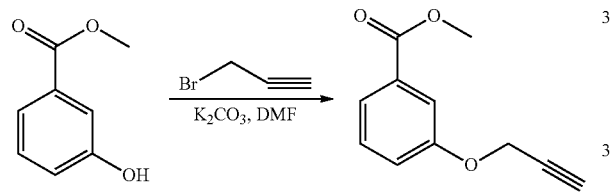

Into a 100-mL round-bottom flask, was placed a solution of methyl 3-hydroxybenzoate (4.44 g, 29.18 mmol, 1.00 equiv) in DMF (20 mL), 3-bromoprop-1-yne (5.0 g, 42.03 mmol, 1.45 equiv), potassium carbonate (6.29 g, 45.58 mmol, 1.56 equiv). The resulting mixture was stirred for 18 h at room temperature (25° C.). The resulting solution was diluted with ethyl acetate (50 mL), washed with H₂O (100 mL×3) and brine (100 mL×3), dried with Na₂SO₄ and concentrated under reduced pressure. The residue was applied onto a silica gel column and eluted with ethyl acetate/petroleum ether (0-10%). The collected fraction was concentrated to give 5.4 g (97%) of methyl 3-(prop-2-yn-1-yloxy)benzoate as a light yellow liquid. MS (ES, m/z) [M+H]⁺: 191.

Step 2. Methyl 2-methylbenzofuran-4-carboxylate and methyl 2-methylbenzofuran-6-carboxylate

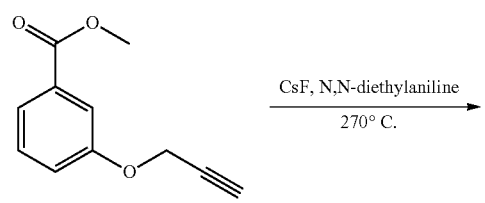

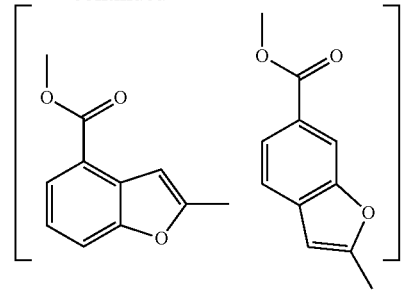

Into a 100-mL round-bottom flask, was placed methyl 3-(prop-2-yn-1-yloxy)benzoate (1.0 g, 5.26 mmol, 1.00 equiv) in N,N-diethylaniline (15 mL), CsF (1.06 g, 6.97 mmol, 1.32 equiv). The resulting solution was stirred for 5.0 h at 270° C. The reaction mixture was cooled to 25 degree C. The resulting solution was diluted with EA (150 mL). The resulting mixture was washed with HCl (3.0 mol/L, 150 mL×4). The mixture was dried over anhydrous sodium sulfate. The solids were filtered out. The filtrate was concentrated under vacuum. The residue was applied onto a silica gel column and eluted with ethyl acetate/petroleum ether (0-10%). The collected fraction was concentrated to give 660 mg (66%) of the mixture of methyl 2-methylbenzofuran-4-carboxylate and methyl 2-methylbenzofuran-6-carboxylate as a light yellow solid. MS (ES, m/z) [M+H]⁺: 191.

Step 3. 2-methylbenzofuran-4-carboxylic acid and 2-methylbenzofuran-6-carboxylic Acid

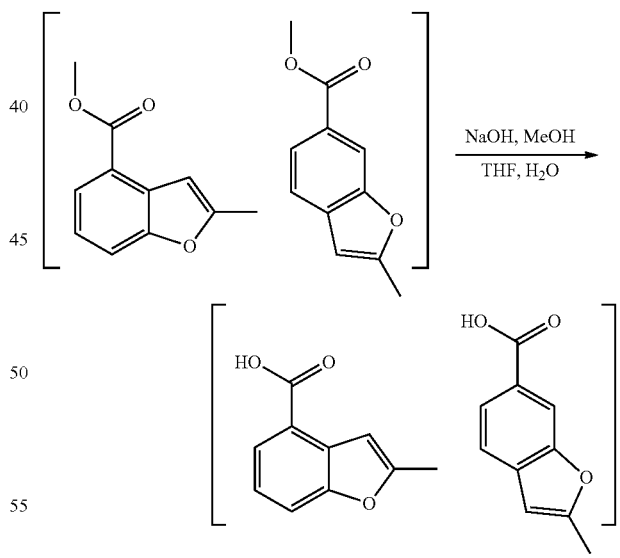

Into a 100-mL round-bottom flask, was placed the mixture of methyl 2-methyl-1-benzofuran-4-carboxylate and methyl 2-methylbenzofuran-6-carboxylate (300 mg, 1.58 mmol, 1.00 equiv), a solution of sodium hydroxide (1.2 g, 30.00 mmol, 20.00 equiv) in water (10 mL), tetrahydrofuran (2 mL), methanol (8 mL). The resulting solution was stirred overnight at room temperature (20° C.). The resulting solution was washed with DCM (20 mL×2). The pH value of the aqueous layers was adjusted to 5-6 with HCl (1 mol/L). The resulting solution was extracted with EA (30 mL×3) and concentrated under vacuum. The residue was purified by Prep-TLC with ethyl acetate/Petroleum ether (1/1) to afford 250 mg (89%) of a mixture of 2-methyl-1-benzofuran-4-carboxylic acid and 2-methylbenzofuran-6-carboxylic acid as an off-white solid. MS (ES, m/z) [M+H]+: 177.

Step 4. (3-amino-4,5,6,7-tetrahydroindazol-2-yl)(2-methylbenzofuran-4-yl)methanone (Example 58) and (3-amino-4,5,6,7-tetrahydroindazol-1-yl)(2-methylbenzofuran-4-yl)methanone (Example 59) and (3-amino-4,5,6,7-tetrahydroindazol-2-yl)(2-methylbenzofuran-6-yl)methanone (Example 60) and (3-amino-4,5,6,7-tetrahydroindazol-1-yl)(2-methylbenzofuran-6-yl)methanone (Example 61)

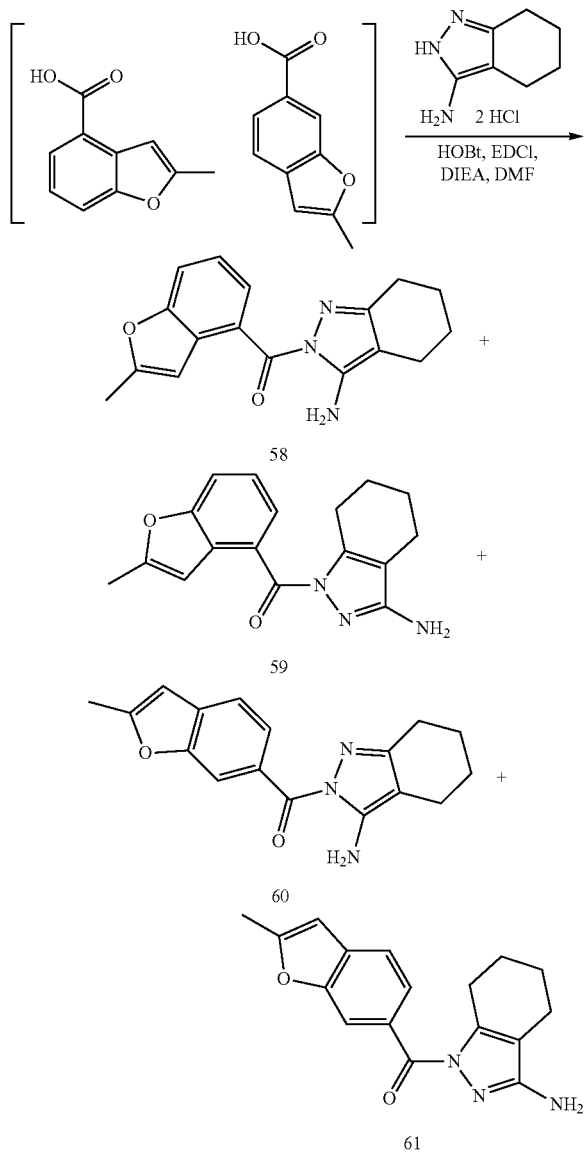

Into a 50-mL round-bottom flask, was placed the mixture of 2-methyl-1-benzofuran-4-carboxylic acid and 2-methyl-1-benzofuran-6-carboxylic acid (60 mg, 0.34 mmol, 1.00 equiv) in DMF (5 mL), HOBT (69 mg, 0.51 mmol, 1.50 equiv), EDCI (98 mg, 0.51 mmol, 1.50 equiv) and DIEA (132 mg, 1.02 mmol, 3.00 equiv). The mixture was stirred for 30 min at 25° C. Then 4,5,6,7-tetrahydro-2H-indazol-3-amine dihydrochloride (79.4 mg, 0.38 mmol, 1.10 equiv) was added. The resulting solution was stirred overnight at room temperature (25° C.). The reaction mixture was diluted with DCM (80 mL), washed with H₂O (50 mL×3) and brine (50 mL×3) and dried with Na₂SO₄. After filtration, the filtrate was concentrated under vacuum. The crude product was purified by Prep-HPLC with the following conditions (Analyse HPLC-SHIMADZU): Column: XBridge Prep C18 OBD Column 19×150 mm 5 um; Mobile Phase A: water (0.1% FA), Mobile Phase B: ACN; Flow rate: 20 mL/min; Gradient: 40% B to 60% B in 12 min; 254/220 nm. The collected fractions were lyophilized.

The Fraction A (Example 58): 6.0 mg (12%) of (3-amino-4,5,6,7-tetrahydroindazol-2-yl)(2-methylbenzofuran-4-yl)methanone as an off-white solid. Rt=8.57 min; MS (ES, m/z) [M+H]+: 295; ¹HNMR (DMSO-d₆, 400 MHz, ppm): δ 7.77 (d, J=7.6, 1H); 7.70 (d, J=8.0, 1H); 7.32-7.28 (m, 1H); 6.62-6.56 (m, 1H); 6.44 (s, 2H); 2.42 (s, 3H); 2.40-2.37 (m, 2H); 2.33-2.30 (m, 2H); 1.66-1.65 (m, 4H).

The Fraction B (Example 59): 13.5 mg (27%) of (3-amino-4,5,6,7-tetrahydroindazol-1-yl)(2-methylbenzofuran-4-yl)methanone as an off-white solid. Rt=7.00 min; MS (ES, m/z) [M+H]+: 295; ¹HNMR (DMSO-d₆, 400 MHz, ppm): δ 7.65-7.63 (m, 2H); 7.29-7.25 (m, 1H); 6.56 (s, 1H); 5.47 (s, 2H); 2.97-2.94 (m, 2H); 2.46 (s, 3H); 2.28-2.26 (m, 2H); 1.76-1.69 (m, 4H).

The Fraction C (Example 60): 2.1 mg (4%) of (3-amino-4,5,6,7-tetrahydroindazol-2-yl)(2-methylbenzofuran-6-yl)methanone as an off-white solid. Rt=9.63 min; MS (ES, m/z) [M+H]+: 295; ¹HNMR (DMSO-d₆, 400 MHz, ppm): δ 8.18 (s, 1H); 7.81 (d, J=9.2, 1H); 7.61 (d, J=8.0, 1H); 6.71 (s, 1H); 6.44 (s, 2H); 2.48 (s, 3H); 2.45-2.43 (m, 2H); 2.32-2.29 (m, 2H); 1.67-1.66 (m, 4H).

The Fraction D (Example 61): 2.8 mg (5%) of (3-amino-4,5,6,7-tetrahydroindazol-1-yl)(2-methylbenzofuran-6-yl)methanone as an off-white solid. Rt=7.66 min; MS (ES, m/z) [M+H]+: 295; ¹HNMR (DMSO-d₆, 400 MHz, ppm): δ 8.11 (s, 1H); 7.74 (d, J=9.6, 1H); 7.67 (d, J=8.0, 1H); 6.68 (s, 1H); 5.48 (s, 2H); 2.94-2.92 (m, 2H); 2.46 (s, 3H); 2.29-2.26 (m, 2H); 1.72-1.69 (m, 4H).

Examples 62 and 63: (3-amino-4,5,6,7-tetrahydroindazol-2-yl)(2-bromo-1H-indol-4-yl) methanone and (3-amino-4,5,6,7-tetrahydroindazol-1-yl) (2-bromo-1H-indol-4-yl)methanone Step 1: 2-bromo-1H-indole-4-carboxylic Acid

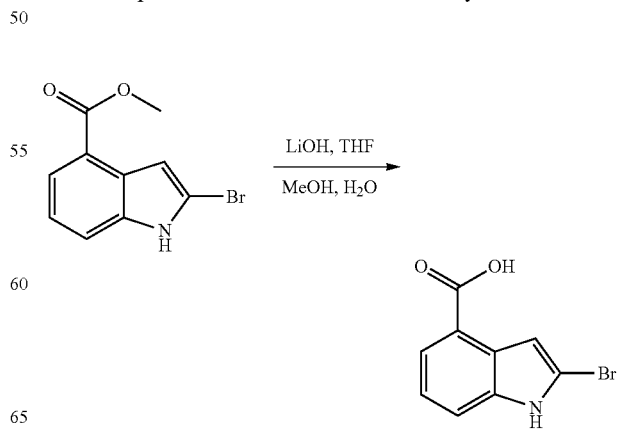

Into a 50-mL round-bottom flask, was placed methyl 2-bromo-1H-indole-4-carboxylate (100 mg, 0.39 mmol, 1.00 equiv), methanol (10 mL), a solution of sodium hydroxide (158.1 mg, 3.95 mmol, 10.00 equiv) in water (5 mL). The resulting solution was stirred overnight at 20° C. The resulting solvent was concentrated under vacuum. The residue was diluted with water (20 mL) and washed with ethyl acetate (30 mL). HCl (1 mol/L) was employed to adjust the pH to 6. The resulting solution was extracted with ethyl acetate (40 mL×2), dried over anhydrous sodium sulfate and concentrated under vacuum to give 75 mg (crude) of 2-bromo-1H-indole-4-carboxylic acid as a light yellow solid. MS (ES, m/z) [M+H]+: 240, 242.

Step 2: (3-amino-4,5,6,7-tetrahydroindazol-2-yl)(2-bromo-1H-indol-4-yl) methanone (Example 62) and (3-amino-4,5,6,7-tetrahydroindazol-1-yl) (2-bromo-1H-indol-4-yl)methanone (Example 63)

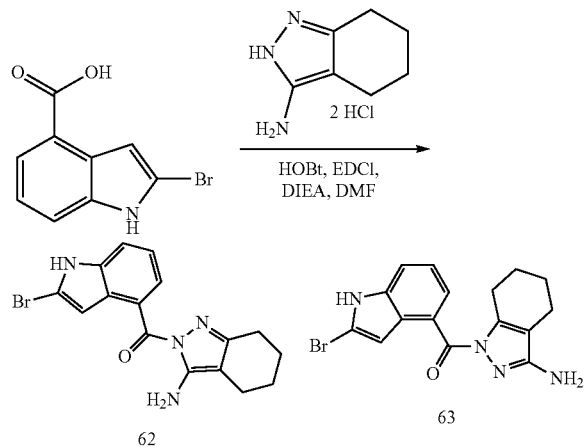

Into a 50-mL round-bottom flask, was placed 2-bromo-1H-indole-4-carboxylic acid (75 mg, 0.31 mmol, 1.00 equiv) in DMF (4 mL), HOBT (63.5 mg, 0.47 mmol, 1.50 equiv), EDCI (90.4 mg, 0.47 mmol, 1.50 equiv), TEA (158.5 mg, 1.57 mmol, 5.00 equiv), 4,5,6,7-tetrahydro-2H-indazol-3-amine dihydrochloride (77.3 mg, 0.37 mmol, 1.20 equiv). The resulting solution was stirred overnight at room temperature (25° C.). The resulting solution was diluted with 80 mL of ethyl acetate, washed with 2×120 mL of saturated brine, dried over anhydrous sodium sulfate and concentrated under vacuum. The crude product was purified by Prep-HPLC with the following conditions (AnalyseHPLC-SHIMADZU): Column, XBridge Prep C18 OBD Column, 19×150 mm 5 um; mobile phase, water (0.1% FA) and ACN (25.0% ACN up to 55.0% in 7 min); Detector, UV 254&220 nm. The collected fractions were lyophilized.

Fraction A (Example 62): 11.8 mg (11%) of (3-amino-4,5,6,7-tetrahydroindazol-2-yl)(2-bromo-1H-indol-4-yl) methanone as an off-white solid. Rt=5.83 min; MS (ES, m/z) [M+H]+: 359, 361; 1HNMR (DMSO-d6, 400 MHz, ppm): δ 12.18 (s, 1H); 7.64 (d, J=7.2 Hz, 1H); 7.52 (d, J=8.0 Hz, 1H); 7.20-7.16 (m, 1H); 6.58 (s, 1H); 6.41 (s, 2H); 2.42-2.36 (m, 2H); 2.35-2.29 (m, 2H); 1.66 (s, 4H).

Fraction B (Example 63): 10.3 mg (9%) of (3-amino-4,5,6,7-tetrahydroindazol-1-yl)(2-bromo-1H-indol-4-yl) methanone as an off-white solid. Rt=5.07 min; MS (ES, m/z) [M+H]+: 359, 361; 1HNMR (DMSO-d6, 400 MHz, ppm): δ 12.07 (s, 1H); 7.52-7.46 (m, 2H); 7.17-7.13 (m, 1H); 6.52 (s, 1H); 5.54 (s, 2H); 2.98-2.92 (m, 2H); 2.29-2.24 (m, 2H); 2.76-2.65 (m, 4H).

Examples 64 and 65: 4-(3-amino-4,5,6,7-tetrahydro-2H-indazole-2-carbonyl)indolin-2-one and 4-(3-amino-4,5,6,7-tetrahydro-1H-indazole-1-carbonyl)indolin-2-One Step 1: 2-oxoindoline-4-carboxylic Acid

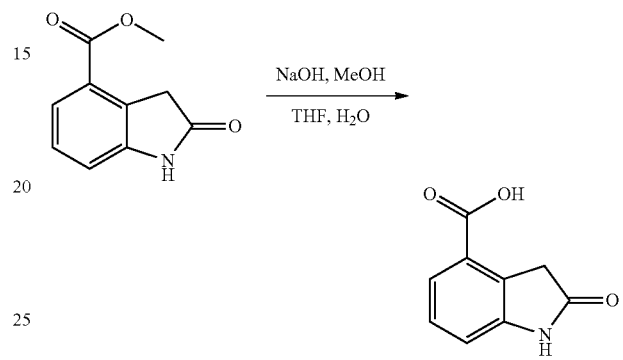

Into a 50-mL round-bottom flask, was placed methyl 2-oxo-2,3-dihydro-1H-indole-4-carboxylate (150 mg, 0.78 mmol, 1.00 equiv), methanol (2 mL), tetrahydrofuran (8 mL), a solution of LiOH (150.8 mg, 6.30 mmol, 8.00 equiv) in water (5 mL). The resulting solution was stirred overnight at 25° C. The resulting solvent was concentrated under vacuum. The residue was diluted with water (20 mL) and washed with ethyl acetate (30 mL). HCl (1 mol/L) was employed to adjust the pH to 6. The resulting solution was extracted with 2×40 mL of ethyl acetate, dried over anhydrous sodium sulfate and concentrated to give 85 mg (61%) of 2-oxo-2,3-dihydro-1H-indole-4-carboxylic acid as a light brown solid. MS (ES, m/z) [M+H]+: 178.

Step 2: 4-(3-amino-4,5,6,7-tetrahydro-2H-indazole-2-carbonyl)indolin-2-one (Example 64) and 4-(3-amino-4,5,6,7-tetrahydro-1H-indazole-1-carbonyl)indolin-2-one (Example 65)

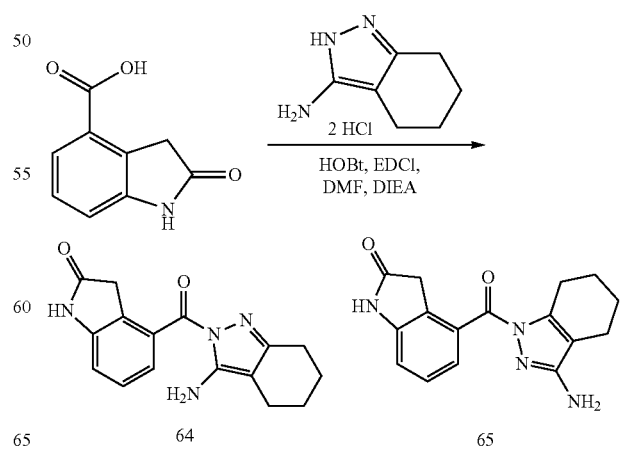

Into a 50-mL round-bottom flask, was placed 2-oxo-2,3-dihydro-1H-indole-4-carboxylic acid (80 mg, 0.45 mmol, 1.00 equiv) in DMF (5 mL), HOBT (91.5 mg, 0.68 mmol, 1.50 equiv), EDCI (130.2 mg, 0.68 mmol, 1.50 equiv), TEA (228.2 mg, 2.26 mmol, 5.00 equiv), 4,5,6,7-tetrahydro-2H-indazol-3-amine dihydrochloride (112.9 mg, 0.54 mmol, 1.20 equiv). The resulting solution was stirred overnight at room temperature (25° C.). The resulting solution was diluted with ethyl acetate (90 mL), washed with brine (130 mL×2), dried over anhydrous sodium sulfate and concentrated under vacuum. The crude product was purified by Prep-HPLC with the following conditions (AnalyseHPLC-SHIMADZU): Column, XBridge Shield RP18 OBD Column, 5 um, 19*150 mm; mobile phase, water (0.1% FA) and ACN (20.0% ACN up to 45.0% in 7 min); Detector, UV 254 nm give two fractions. The collected fractions were lyophilized.

Fraction A (Example 64): 12.5 mg (9%) of 4-(3-amino-4,5,6,7-tetrahydro-2H-indazole-2-carbonyl)indolin-2-one as a light yellow solid. Rt=6.03 min; MS (ES, m/z) [M+H]$^+$: 297; $^1$HNMR (DMSO-d6, 300 MHz, ppm): δ 10.53 (s, 1H); 7.28 (d, J=3.9 Hz, 2H); 6.99-6.96 (m, 1H); 6.42 (s, 2H); 3.53 (s, 2H); 2.41-2.37 (m, 2H); 2.31-2.27 (m, 2H); 1.65 (s, 4H).

Fraction B (Example 65): 18.2 mg (14%) of 4-(3-amino-4,5,6,7-tetrahydro-1H-indazole-1-carbonyl)indolin-2-one as a yellow solid. Rt=4.95 min; MS (ES, m/z) [M+H]$^+$: 297; $^1$HNMR (DMSO-d6, 300 MHz, ppm): δ 10.49 (s, 1H); 7.28-7.18 (m, 2H); 6.94-6.91 (m, 1H); 5.52 (s, 2H); 3.50 (s, 2H); 2.94-2.89 (m, 2H); 2.28-2.25 (m, 2H); 1.77-1.67 (m, 4H).

Examples 66 and 67: (3-amino-4,5,6,7-tetrahydroindazol-2-yl)(2-ethyl-1-methyl-1H-indol-4-yl)methanone and (3-amino-4,5,6,7-tetrahydroindazol-1-yl)(2-ethyl-1-methyl-1H-indol-4-yl)methanone Step 1: Methyl 2-ethyl-1-methyl-1H-indole-4-carboxylate

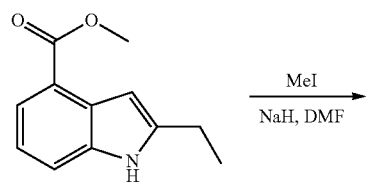

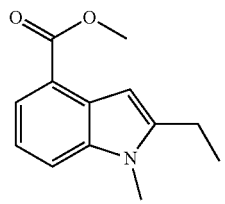

Into a 50-mL 3-necked round-bottom flask, was placed methyl 2-ethyl-1H-indole-4-carboxylate (100 mg, 0.49 mmol, 1.00 equiv) in DMF (5 mL), NaH (25.6 mg, 0.64 mmol, 1.30 equiv, 60%). This was followed by the addition of MeI (83.9 mg, 1.20 equiv) dropwise with stirring at 0° C. The resulting solution was stirred for 3 h at room temperature (20° C.). The reaction was then quenched by the addition water/ice (20 mL). The resulting solution was extracted with ethyl acetate (40 mL×2), washed with brine (100 mL×2), dried over anhydrous sodium sulfate and concentrated under vacuum to give 95 mg (89%) of methyl 2-ethyl-1-methyl-1H-indole-4-carboxylate as an off-white solid. MS (ES, m/z) [M+H]$^+$: 218.

Step 2: 2-ethyl-1-methyl-1H-indole-4-carboxylic Acid

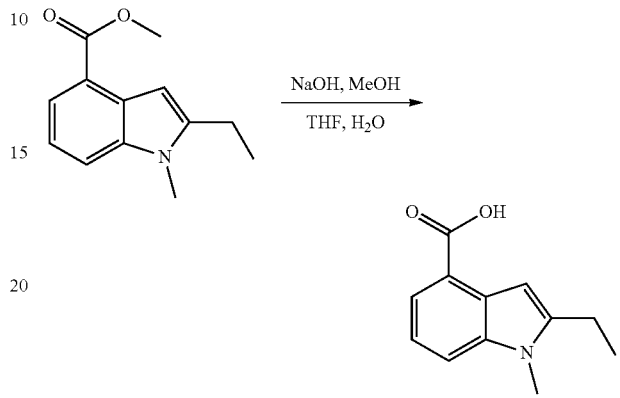

Into a 50-mL round-bottom flask, was placed methyl 2-ethyl-1-methyl-1H-indole-4-carboxylate (95 mg, 0.44 mmol, 1.00 equiv), tetrahydrofuran (6 mL), methanol (2 mL), a solution of LiOH (63 mg, 2.63 mmol, 6.00 equiv) in H$_2$O (4 mL). The resulting solution was stirred overnight at 35° C. The resulting solvent was concentrated under vacuum. The residue was diluted with water (20 mL) and washed with ethyl acetate (30 mL). HCl (1 mol/L) was employed to adjust the pH to 6. The resulting solution was extracted with ethyl acetate (40 mL×2), dried over anhydrous sodium sulfate and concentrated to give 55 mg (62%) of 2-ethyl-1-methyl-1H-indole-4-carboxylic acid as a light yellow solid. MS (ES, m/z) [M+H]$^+$: 204.

Step 3: (3-amino-4,5,6,7-tetrahydroindazol-2-yl)(2-ethyl-1-methyl-1H-indol-4-yl)methanone (Example 66) and (3-amino-4,5,6,7-tetrahydroindazol-1-yl)(2-ethyl-1-methyl-1H-indol-4-yl)methanone (Example 67)

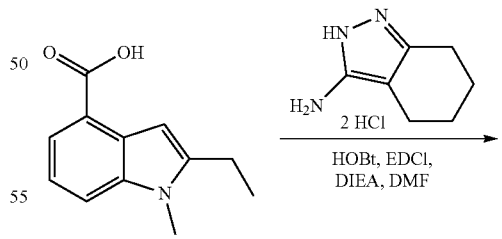

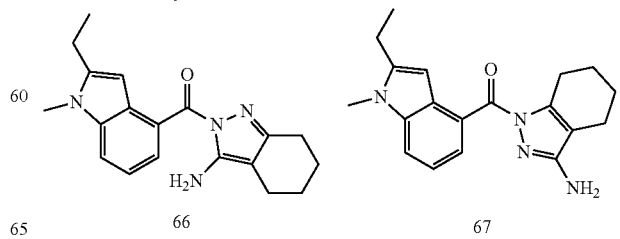

66   67

Into a 50-mL round-bottom flask, was placed 2-ethyl-1-methyl-1H-indole-4-carboxylic acid (55 mg, 0.27 mmol, 1.00 equiv) in DMF (4 mL), HOBT (54.9 mg, 0.41 mmol, 1.50 equiv), EDCI (78 mg, 0.41 mmol, 1.50 equiv), TEA (136.8 mg, 1.35 mmol, 5.00 equiv) and 4,5,6,7-tetrahydro-2H-indazol-3-amine dihydrochloride (64.8 mg, 0.31 mmol, 1.20 equiv). The resulting solution was stirred overnight at room temperature (25° C.). The resulting solution was diluted with EA (80 mL), washed with brine (120 mL×2), dried over anhydrous sodium sulfate and concentrated under vacuum. The crude product was purified by Prep-HPLC with the following conditions (AnalyseHPLC-SHIMADZU): Column, XBridge C18 OBD Prep Column, 5 μm, 19 mm×250 mm; mobile phase, water (0.1% FA) and ACN (50.0% ACN up to 70.0% in 10 min); Detector, UV 254 nm to give two fractions. The collected fractions were lyophilized.

Fraction A (Example 66): 16.3 mg (19%) of (3-amino-4,5,6,7-tetrahydroindazol-2-yl)(2-ethyl-1-methyl-1H-indol-4-yl)methanone as an off-white solid. Rt=9.93 min; MS (ES, m/z) [M+H]$^+$: 323; $^1$HNMR (DMSO-d6, 400 MHz, ppm): δ 7.62-7.57 (m, 2H); 7.15-7.11 (m, 1H); 6.39 (s, 2H); 6.33 (s, 1H); 3.72 (s, 3H); 2.82-2.76 (m, 2H); 2.37-2.35 (m, 2H); 2.33-2.30 (m, 2H); 1.65 (s, 4H); 1.29-1.25 (s, 3H).

Fraction B (Example 67): 17.4 mg (20%) of (3-amino-4,5,6,7-tetrahydroindazol-1-yl)(2-ethyl-1-methyl-1H-indol-4-yl)methanone as an off-white solid. Rt=7.86 min; MS (ES, m/z) [M+H]$^+$: 323; $^1$HNMR (DMSO-d6, 400 MHz, ppm): δ 7.54 (d, J=8.0 Hz, 1H); 7.45 (d, J=6.8 Hz, 1H); 7.12-7.08 (m, 1H); 6.27 (s, 1H); 5.34 (s, 2H); 3.70 (s, 3H); 2.96-2.93 (m, 2H); 2.80-2.75 (m, 2H); 2.28-2.26 (m, 2H); 1.76-1.69 (m, 4H); 1.28-1.24 (m, 3H).

Examples 68 and 69: (3-amino-4,5,6,7-tetrahydroindazol-2-yl)(1,2-diethyl-1H-indol-4-yl)methanone and (3-amino-4,5,6,7-tetrahydroindazol-1-yl)(1,2-diethyl-1H-indol-4-yl)methanone Step 1: Methyl 1,2-diethyl-1H-indole-4-carboxylate

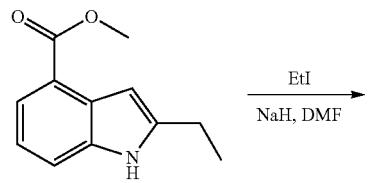

Into a 50-mL 3-necked round-bottom flask, was placed methyl 2-ethyl-1H-indole-4-carboxylate (100 mg, 0.49 mmol, 1.00 equiv) in N,N-dimethylformamide (5 mL), NaH (25.6 mg, 0.64 mmol, 1.30 equiv, 60%). This was followed by the addition of EtI (92.2 mg, 0.59 mmol, 1.20 equiv) dropwise with stirring at 0° C. The resulting solution was stirred for 4 h at room temperature (20° C.). The reaction was then quenched by the addition of water/ice (20 mL). The resulting solution was extracted with ethyl acetate (40 mL×2), washed with brine (100 mL×2), dried over anhydrous sodium sulfate and concentrated. The residue was purified by Prep-TLC with ethyl acetate/petroleum ether (1:1). This resulted in 60 mg (53%) of methyl 1,2-diethyl-1H-indole-4-carboxylate as a light yellow solid. MS (ES, m/z) [M+H]$^+$: 232.

Step 2: 1,2-diethyl-1H-indole-4-carboxylic Acid

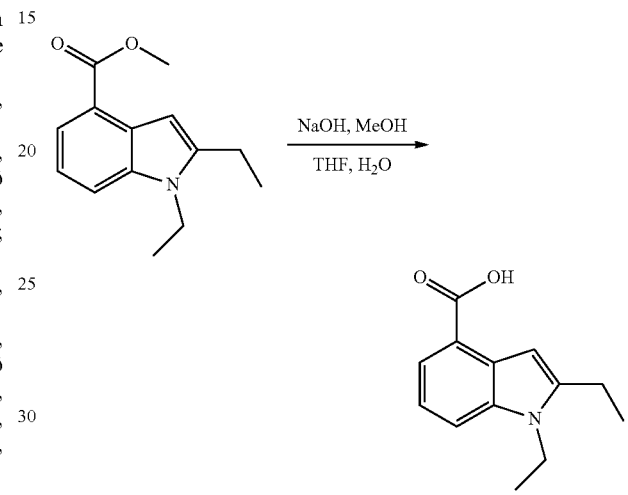

Into a 50-mL round-bottom flask, was placed methyl 1,2-diethyl-1H-indole-4-carboxylate (60 mg, 0.26 mmol, 1.00 equiv), tetrahydrofuran (6 mL), methanol (3 mL), a solution of LiOH (37.4 mg, 1.56 mmol, 6.00 equiv) in H$_2$O (3 mL). The resulting solution was stirred overnight at 35° C. The resulting mixture was concentrated under vacuum. The resulting solution was extracted with ethyl acetate (20 mL) and the aqueous layers collected. The pH value was adjusted to 6 with HCl (1 mol/L). The resulting solution was extracted with ethyl acetate (40 mL×2), dried over anhydrous sodium sulfate and concentrated to give 35 mg (62%) of 1,2-diethyl-1H-indole-4-carboxylic acid as a light yellow solid. MS (ES, m/z) [M+H]$^+$: 218.

Step 3: (3-amino-4,5,6,7-tetrahydroindazol-2-yl)(1,2-diethyl-1H-indol-4-yl)methanone (Example 68) and (3-amino-4,5,6,7-tetrahydroindazol-1-yl)(1,2-diethyl-1H-indol-4-yl)methanone (Example 69)

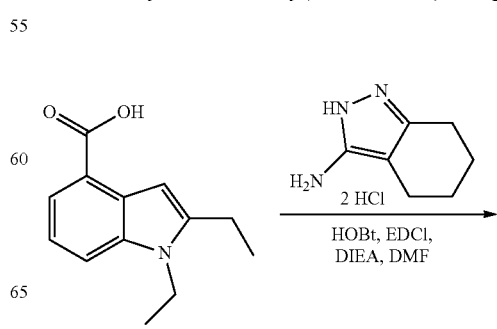

-continued

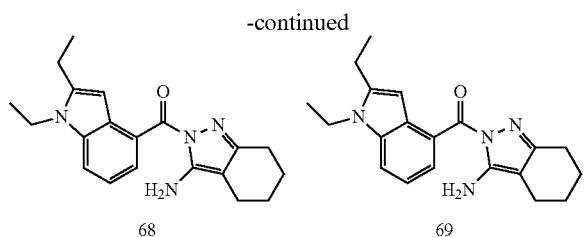

68   69

Into a 50-mL round-bottom flask, was placed 1,2-diethyl-1H-indole-4-carboxylic acid (35 mg, 0.16 mmol, 1.00 equiv) in DMF (4 mL), HOBT (32.7 mg, 0.24 mmol, 1.50 equiv), EDCI (46.5 mg, 0.24 mmol, 1.50 equiv), TEA (81.5 mg, 0.81 mmol, 5.00 equiv) and 4,5,6,7-tetrahydro-2H-indazol-3-amine dihydrochloride (39.7 mg, 0.19 mmol, 1.20 equiv). The resulting solution was stirred overnight at room temperature (25° C.). The resulting solution was diluted with EA (80 mL), washed with brine (120 mL×2), dried over anhydrous sodium sulfate and concentrated. The crude product was purified by Prep-HPLC with the following conditions (AnalyseHPLC-SHIMADZU): Column, XBridge C18 OBD Prep Column, 5 μm, 19×250 mm; mobile phase, water (0.1% FA) and ACN (55.0% ACN up to 75.0% in 7 min); Detector, UV 254 nm to give two fractions. The collected fractions were lyophilized.

Fraction A (Example 68): 13.5 mg (25%) of (3-amino-4,5,6,7-tetrahydroindazol-2-yl)(1,2-diethyl-1H-indol-4-yl)methanone as a light yellow solid. Rt=5.8 min; MS (ES, m/z) [M+H]+: 337; 1HNMR (DMSO-d6, 400 MHz, ppm): δ 7.62 (d, J=8.0 Hz, 1H); 7.56 (d, J=8.4 Hz, 1H); 7.15-7.11 (m, 1H); 6.39 (s, 2H); 6.33 (s, 1H); 4.24-4.19 (m, 2H); 2.82-2.76 (m, 2H); 2.40-2.35 (m, 2H); 2.34-2.28 (m, 2H); 1.66 (s, 4H); 1.31-1.24 (m, 6H).

Fraction B (Example 69): 4.6 mg (9%) of (3-amino-4,5,6,7-tetrahydroindazol-1-yl)(1,2-diethyl-1H-indol-4-yl)methanone as a white solid. Rt=4.71 min; MS (ES, m/z) [M+H]+: 337; 1HNMR (DMSO-d6, 400 MHz, ppm): δ 7.55 (d, J=8.0 Hz, 1H); 7.44 (d, J=6.8 Hz, 1H); 7.12-7.08 (m, 1H); 6.27 (s, 1H); 5.34 (s, 2H); 4.22-4.17 (m, 2H); 2.97-2.94 (m, 2H); 2.80-2.75 (m, 2H); 2.32-2.26 (m, 2H); 1.76-1.69 (m, 4H); 1.32-1.23 (m, 6H).

Examples 70 and 71: (3-amino-4,5,6,7-tetrahydroindazol-2-yl)(2-vinyl-1H-indol-4-yl)methanone and (3-amino-4,5,6,7-tetrahydroindazol-1-yl)(2-vinyl-1H-indol-4-yl)methanone Step 1: 2-vinyl-1H-indole-4-carboxylic Acid

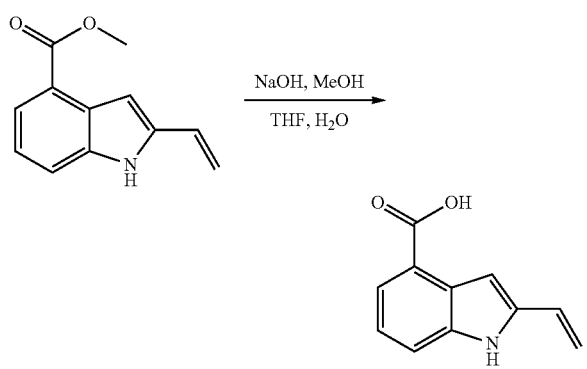

Into a 50-mL round-bottom flask, was placed methyl 2-ethenyl-1H-indole-4-carboxylate (80 mg, 0.40 mmol, 1.00 equiv), tetrahydrofuran (6 mL), methanol (2 mL), a solution of LiOH (57.3 mg, 2.39 mmol, 6.00 equiv) in H2O (4 mL). The resulting solution was stirred overnight at 30° C. The resulting solvent was concentrated under vacuum. The residue was diluted with water (20 mL) and washed with ethyl acetate (30 mL). HCl (1 mol/L) was employed to adjust the pH to 6. The resulting solution was extracted with 2×30 mL of ethyl acetate, dried over anhydrous sodium sulfate and concentrated to give 65 mg (87%) of 2-ethenyl-1H-indole-4-carboxylic acid as a light yellow solid. MS (ES, m/z) [M+H]+: 188.

Step 2: (3-amino-4,5,6,7-tetrahydroindazol-2-yl)(2-vinyl-1H-indol-4-yl)methanone (Example 70) and (3-amino-4,5,6,7-tetrahydroindazol-1-yl)(2-vinyl-1H-indol-4-yl)methanone (Example 71)

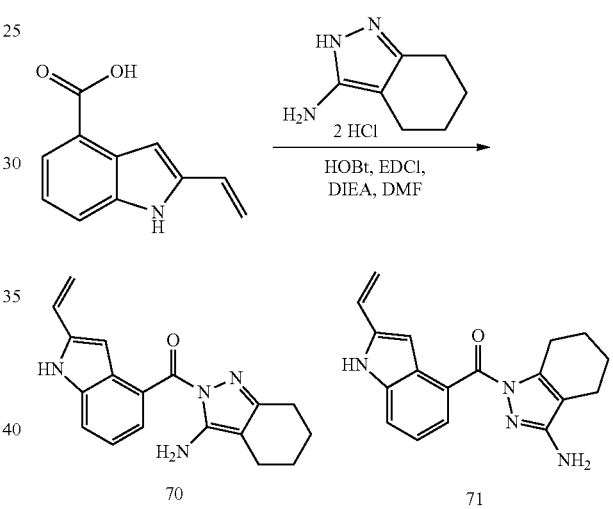

70   71

Into a 50-mL round-bottom flask, was placed 2-ethenyl-1H-indole-4-carboxylic acid (65 mg, 0.35 mmol, 1.00 equiv) in DMF (4 mL), HOBT (70.4 mg, 0.52 mmol, 1.50 equiv), EDCI (100 mg, 0.52 mmol, 1.50 equiv), 4,5,6,7-tetrahydro-2H-indazol-3-amine dihydrochloride (87.8 mg, 0.42 mmol, 1.20 equiv) and TEA (175.5 mg, 1.73 mmol, 5.00 equiv). The resulting solution was stirred overnight at 25° C. The resulting solution was diluted with 80 mL of EA, washed with saturated brine (120 mL×2), dried over anhydrous sodium sulfate and concentrated under vacuum. The crude product was purified by Prep-HPLC with the following conditions (AnalyseHPLC-SHIMADZU): Column, XBridge C18 OBD Prep Column, 5 μm, 19×250 mm; mobile phase, water (0.1% FA) and ACN (50.0% ACN up to 70.0% in 7 min); Detector, UV 254 nm to give two fractions. The collected fractions were lyophilized.

Fraction A (Example 70): 6.1 mg (6%) of (3-amino-4,5,6,7-tetrahydroindazol-2-yl)(2-vinyl-1H-indol-4-yl)methanone as a yellow solid. Rt=5.3 min; MS (ES, m/z) [M+H]+: 307; 1HNMR (DMSO-d6, 400 MHz, ppm): δ 11.58 (s, 1H);

7.58 (d, J=6.8 Hz, 1H); 7.53 (d, J=8.0 Hz, 1H); 7.19-7.15 (m, 1H); 6.81-6.74 (m, 1H); 6.58 (s, 1H); 6.40 (s, 2H); 5.88 (d, J=18 Hz, 1H); 5.33 (d, J=12.0 Hz, 1H); 2.38-2.36 (m, 2H); 2.33-2.31 (m, 2H); 1.66 (m, 4H).

Fraction B (Example 71): 2.4 mg (2%) of (3-amino-4,5,6,7-tetrahydroindazol-1-yl)(2-vinyl-1H-indol-4-yl)methanone as a yellow solid. Rt=4.21 min; MS (ES, m/z) [M+H]+: 307; $^1$HNMR (DMSO-d6, 400 MHz, ppm): δ 11.5 (s, 1H); 7.48-7.44 (m, 2H); 7.16-7.12 (m, 1H); 6.79-6.72 (m, 1H); 7.50 (s, 1H); 5.85 (d, J=17.6 Hz, 1H); 5.38 (s, 2H); 5.30 (d, J=11.6 Hz, 1H); 2.95-2.93 (m, 2H); 2.28-2.25 (m, 2H); 1.76-1.71 (m, 4H).

Examples 72 and 73: (S*)-(3-amino-4,5,6,7-tetrahydroindazol-2-yl)(1-methyl-1,2,3,4-tetrahydroquinolin-4-yl)methanone and (R*)-(3-amino-4,5,6,7-tetrahydroindazol-2-yl)(1-methyl-1,2,3,4-tetrahydroquinolin-4-yl)methanone

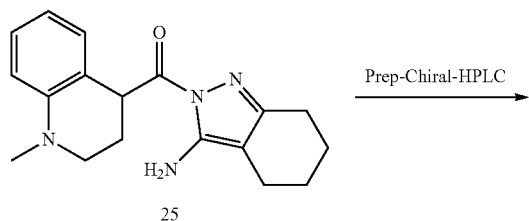

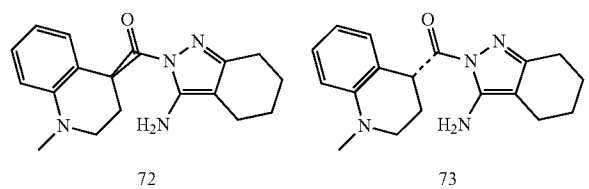

260 mg of Example 25 was separated by Prep-Chiral-HPLC with following condition: Column: Chiralpak IC, 2*25 cm, 5 um; Mobile Phase A: CO$_2$:70, Mobile Phase B: IPA: 30; Flow rate: 40 mL/min; 220 nm. The collected fractions were lyophilized.

Fraction A (Example 72): 104 mg (40%) of (S*)-(3-amino-4,5,6,7-tetrahydroindazol-2-yl)(1-methyl-1,2,3,4-tetrahydroquinolin-4-yl)methanone as an off white solid. Rt=7.7 min; MS (ES, m/z): 311 [M+H]+; $^1$HNMR (DMSO-d$_6$, 400 MHz, ppm): δ 7.08-7.04 (m, 1H); 6.82 (d, J=7.2, 1H); 6.65 (d, J=8.0, 1H); 6.53-6.49 (m, 1H); 6.37 (s, 2H); 5.08-5.05 (m, 1H); 3.32-3.27 (m, 1H); 3.21-3.16 (m, 1H); 2.86 (s, 3H); 2.50-2.48 (m, 2H); 2.29-2.26 (m, 2H); 2.15-2.11 (m, 2H); 1.71-1.64 (m, 4H).

Fraction B (Example 73): 107 mg (41.2%) of (R*)-(3-amino-4,5,6,7-tetrahydroindazol-2-yl)(1-methyl-1,2,3,4-tetrahydroquinolin-4-yl)methanone as an off white solid. Rt=5.94 min; MS (ES, m/z): 311 [M+H]+; $^1$HNMR (DMSO-d$_6$, 400 MHz, ppm): δ 7.08-7.03 (m, 1H); 6.82 (d, J=6.8, 1H); 6.65 (d, J=7.6, 1H); 6.53-6.49 (m, 1H); 6.37 (s, 2H); 5.08-5.05 (m, 1H); 3.33-3.27 (m, 1H); 3.21-3.16 (m, 1H); 2.86 (s, 3H); 2.50-2.48 (m, 2H); 2.28-2.26 (m, 2H); 2.15-2.08 (m, 2H); 1.71-1.65 (m, 4H).

Examples 74 and 75: (3-amino-4,5,6,7-tetrahydroindazol-2-yl)(1-ethyl-1,2,3,4-tetrahydroquinolin-4-yl)methanone and (3-amino-4,5,6,7-tetrahydroindazol-1-yl)(1-ethyl-1,2,3,4-tetrahydroquinolin-4-yl)methanone Step 1. 1-ethyl-1,2,3,4-tetrahydroquinoline-4-carboxylic Acid

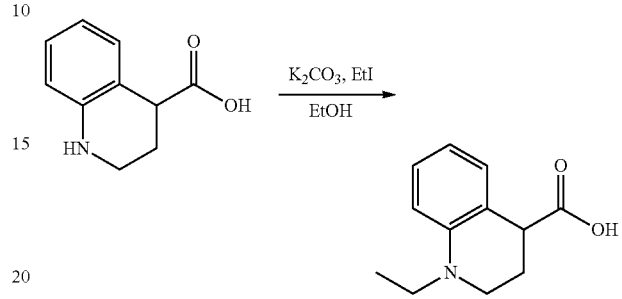

Into a 50-mL round-bottom flask, was placed 1,2,3,4-tetrahydroquinoline-4-carboxylic acid (150 mg, 0.85 mmol, 1.00 equiv) in ethanol (8 mL), iodoethane (160 mg, 1.03 mmol, 1.20 equiv), potassium carbonate (352 mg, 2.55 mmol, 3.00 equiv). The resulting mixture was stirred overnight at room temperature. The resulting solution was diluted with H$_2$O (8 mL). The pH value was adjusted to 4 with HCl (1 mol/L). The resulting solution was extracted with ethyl acetate (80 mL×2) and concentrated under vacuum. The residue was purified by silica gel column with ethyl acetate/petroleum ether (1/2). The collected fraction was concentrated to give 45 mg (26%) of 1-ethyl-1,2,3,4-tetrahydroquinoline-4-carboxylic acid as brown oil.

Step 2. (3-amino-4,5,6,7-tetrahydroindazol-2-yl)(1-ethyl-1,2,3,4-tetrahydroquinolin-4-yl)methanone (Example 74) and (3-amino-4,5,6,7-tetrahydroindazol-1-yl)(1-ethyl-1,2,3,4-tetrahydroquinolin-4-yl)methanone (Example 75)

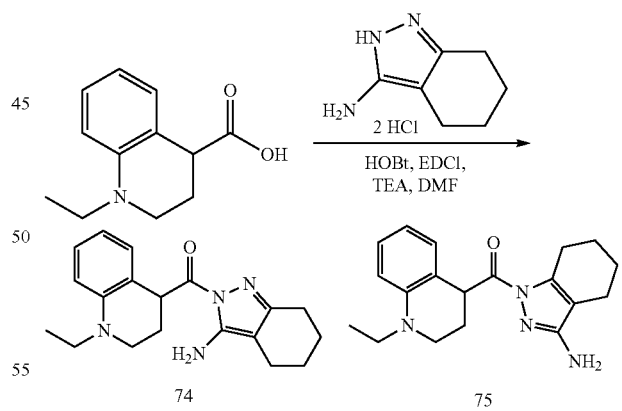

Into a 50-mL round-bottom flask, was placed 1-ethyl-1,2,3,4-tetrahydroquinoline-4-carboxylic acid (45 mg, 0.22 mmol, 1.00 equiv) in DMF (5 mL), HOBt (45 mg, 0.33 mmol, 1.50 equiv), EDCI (64 mg, 0.33 mmol, 1.50 equiv), TEA (67 mg, 0.66 mmol, 3.00 equiv). After stirring for 30 min, 4,5,6,7-tetrahydro-2H-indazol-3-amine dihydrochloride (55 mg, 0.26 mmol, 1.20 equiv) was added. The resulting solution was stirred overnight at room temperature. The resulting solution was diluted with EA (30 mL), washed with brine (100 mL×2), dried with Na$_2$SO$_4$ and concentrated under vacuum. The crude product was purified by Prep-HPLC with the following conditions (AnalyseHPLC-SHIMADZU): Column, XBridge Shield RP18 OBD Column, 5 um, 19×150 mm; mobile phase, water (0.1% FA) and ACN (45.0% ACN up to 65.0% in 7 min, up to 70.0% in 3 min); Detector, UV 254 nm. The collected fractions were lyophilized.

Fraction A (Example 74): 13.6 mg (19%) of (3-amino-4,5,6,7-tetrahydroindazol-2-yl)(1-ethyl-1,2,3,4-tetrahydroquinolin-4-yl)methanone as a white solid. Rt=7.5 min; MS (ES, m/z) [M+H]+: 325; 1HNMR (400 MHz, DMSO-$d_6$, ppm): δ 7.05-7.01 (m, 1H); 6.80 (d, J=6.8 Hz, 1H); 6.67 (d, J=8.0 Hz, 1H); 6.47-6.43 (m, 1H); 6.37 (s, 2H); 5.05-5.02 (m, 1H); 3.45-3.41 (m, 2H); 3.37-3.18 (m, 2H); 2.51-2.50 (m, 2H); 2.28-2.25 (s, 2H); 2.15-2.06 (m, 2H); 1.79-1.54 (m, 4H); 1.11-1.02 (m, 3H).

Fraction B (Example 75): 5.4 mg (8%) of (3-amino-4,5,6,7-tetrahydroindazol-1-yl)(1-ethyl-1,2,3,4-tetrahydroquinolin-4-yl)methanone as a white solid. Rt=6.35 min; MS (ES, m/z) [M+H]+: 325; 1HNMR (400 MHz, DMSO-$d_6$, ppm): δ 7.03-6.99 (m, 1H); 6.79 (d, J=6.8 Hz, 1H); 6.52 (d, J=8.0 Hz, 1H); 6.45-6.42 (m, 1H); 5.56 (s, 2H); 4.97-4.94 (m, 1H); 3.41-3.39 (m, 2H); 3.31-3.16 (m, 2H); 2.80 (m, 2H); 2.25 (d, J=5.6 Hz, 2H); 2.09-2.02 (m, 2H); 1.79-1.54 (m, 4H); 1.11-1.02 (m, 3H).

Examples 76 and 77: (3-amino-4,5,6,7-tetrahydroindazol-2-yl)(1,2,3,4-tetrahydroquinolin-4-yl)methanone and (3-amino-1H-indazol-1-yl)(1,2,3,4-tetrahydroquinolin-4-yl)methanone

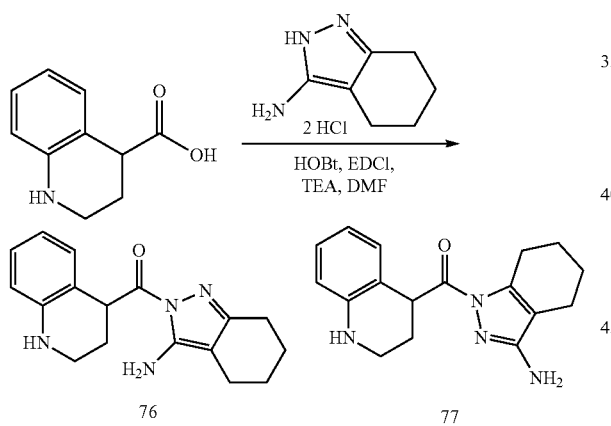

Into a 50-mL round-bottom flask, was placed 1,2,3,4-tetrahydroquinoline-4-carboxylic acid (56 mg, 0.32 mmol, 1.00 equiv), DMF (10 mL), HOBt (65 mg, 0.48 mmol, 1.50 equiv), EDCI (92 mg, 0.48 mmol, 1.50 equiv), TEA (97 mg, 0.96 mmol, 3.00 equiv). The mixture was stirred for 30 min. 4,5,6,7-tetrahydro-2H-indazol-3-amine dihydrochloride (80 mg, 0.38 mmol, 1.20 equiv) was added. The resulting solution was stirred overnight at room temperature (20° C.). The resulting solution was diluted with DCM (30 mL), washed with $H_2O$ (50 mL×3) and brine (50 mL×3), dried with $Na_2SO_4$ and concentrated under vacuum. The crude product was purified by Prep-HPLC with the following conditions (AnalyseHPLC-SHIMADZU): Column, XBridge C18 OBD Prep Column; 5 μm, 19 mm×250 mm; mobile phase, water (0.1% FA) and ACN (40.0% ACN up to 60.0% in 7 min); Detector, UV 254 nm. The collected fractions were lyophilized Fraction A (Example 76): 26.8 mg (29%) of (3-amino-4,5,6,7-tetrahydroindazol-2-yl)(1,2,3,4-tetrahydroquinolin-4-yl)methanone as a white solid. Rt=6.5 min; MS (ES, m/z): 297 [M+H]+; 1HNMR- (400 MHz, DMSO-d6, ppm): δ 6.92-6.81 (m, 1H); 6.76 (d, J=7.2 Hz, 1H); 6.51-6.37 (m, 4H); 5.84 (s, 1H); 5.05-5.02 (m, 1H); 3.31-3.17 (s, 2H); 2.48 (s, 2H); 2.29-2.27 (m, 2H); 2.09-2.00 (m, 2H); 2.00-1.66 (m, 4H).

Fraction B (Example 77): 15.2 mg (16.4%) of (3-amino-1H-indazol-1-yl)(1,2,3,4-tetrahydroquinolin-4-yl)methanone as a white solid. Rt=5.1 min; MS (ES, m/z): 297 [M+H]+; 1HNMR (400 MHz, DMSO-d6, ppm): δ 6.90-6.86 (m, 1H); 6.76 (d, J=7.2 Hz, 1H); 6.49 (d, J=8.4 Hz, 1H); 6.40-6.38 (m, 1H); 5.80 (s, 1H); 5.50 (s, 2H); 4.97-4.94 (m, 1H); 3.29-3.13 (m, 2H); 2.80 (s, 2H); 2.25 (s, 2H); 2.04-1.92 (m, 2H); 1.69 (m, 4H).

Example 78 & 79: (S*)-(3-amino-4,5,6,7-tetrahydroindazol-2-yl)(1,2,3,4-tetrahydroquinolin-4-yl)methanone and (R*)-(3-amino-4,5,6,7-tetrahydroindazol-2-yl)(1,2,3,4-tetrahydroquinolin-4-yl)methanone

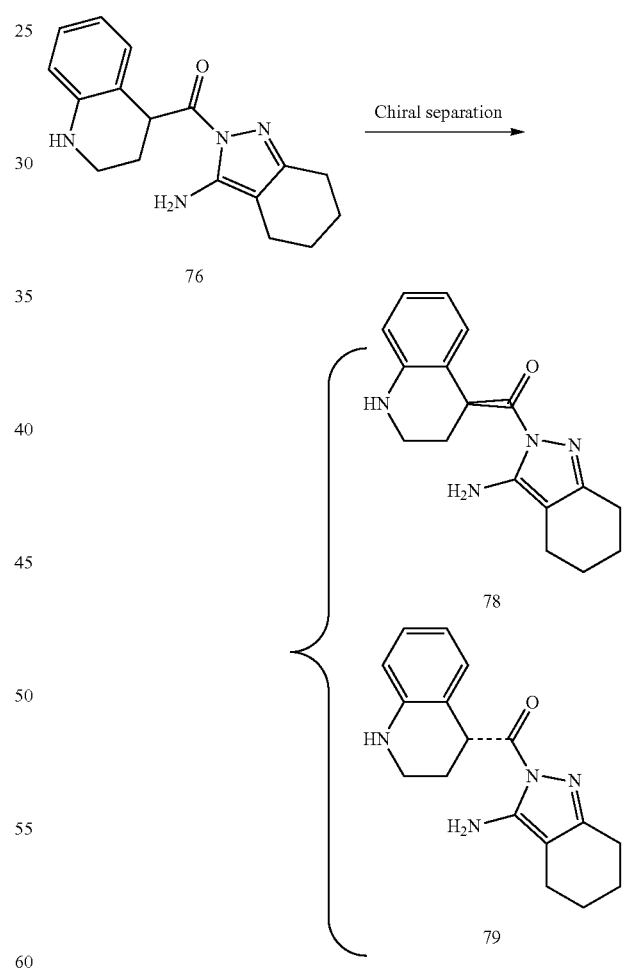

Racemic Example 76 (20 mg, 0.07 mmol, 1.00 equiv) was separated by Chiral-Prep-HPLC with the following conditions (Prep-HPLC-009): Column: Chiralpak IB, 2×25 cm, 5 um, Mobile Phase A: (0.1%) DEA (HPLC), Mobile Phase B: EtOH (HPLC), Flow rate: 20 mL/min, Gradient: 30 B to 30 B in 12 min, 220/254 nm.

Enantiomer A: the collected fraction was lyophilized to give 5.7 mg of (R*)-(3-amino-4,5,6,7-tetrahydroindazol-2-yl)(1,2,3,4-tetrahydroquinolin-4-yl)methanone (78): RT1: 7.41 min, MS (ES, m/z) [M+H]+: 297, (300 MHz, DMSO-d6, ppm): δ 6.93-6.88 (m, 1H), 6.76 (d, J=7.2 Hz, 1H), 6.52-6.50 (m, 1H), 6.42-5.37 (m, 3H), 5.83 (s, 1H), 5.06-5.02 (m, 1H), 3.32-3.20 (s, 2H), 2.48 (s, 2H), 2.29-2.26 (m, 2H), 2.05-2.00 (m, 2H), 1.70-1.68 (m, 4H).

Enantiomer B: the collected fraction was lyophilized to give 6 mg (30%) of (S*)-(3-amino-4,5,6,7-tetrahydroindazol-2-yl)(1,2,3,4-tetrahydroquinolin-4-yl)methanone (79): RT2:10.22, MS (ES, m/z) [M+H]+: 297 min, (300 MHz, DMSO-d6, ppm): δ 6.93-6.88 (m, 1H), 6.76 (d, J=7.2 Hz, 1H), 6.52-6.50 (m, 1H), 6.42-5.37 (m, 3H), 5.83 (s, 1H), 5.06-5.02 (m, 1H), 3.32-3.20 (s, 2H), 2.48 (s, 2H), 2.29-2.26 (m, 2H), 2.05-2.00 (m, 2H), 1.70-1.68 (m, 4H).

Example 80: (3-amino-4,5,6,7-tetrahydroindazol-2-yl)(7-methoxy-1H-indol-4-yl)methanone

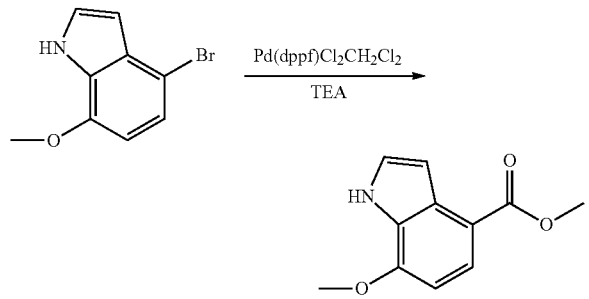

Step 1. Methyl 7-methoxy-1H-indole-4-carboxylate

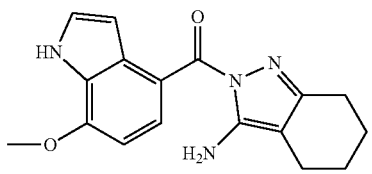

Into a 20-mL pressure tank reactor (60 atm) purged and maintained with an inert atmosphere of CO, was placed 4-bromo-7-methoxy-1H-indole (300 mg, 1.33 mmol, 1.00 equiv), ethanol (5 mL), TEA (670 mg, 6.62 mmol, 5.00 equiv), Pd(dppf)Cl2.CH2Cl2 (543 mg, 0.50 equiv). The resulting solution was stirred for 5 days at 120° C. The resulting mixture was cooled to r.t. and concentrated under vacuum. The residue was applied onto a silica gel column with ethyl acetate/petroleum ether (1:1). The solids were filtered out and the filtrate was concentrated under vacuum. This resulted in 1 g (crude) of ethyl 7-methoxy-1H-indole-4-carboxylate as a red solid. MS: (ES, m/z) [M+H]+: 206.

Step 2. 7-Methoxy-1H-indole-4-carboxylic Acid

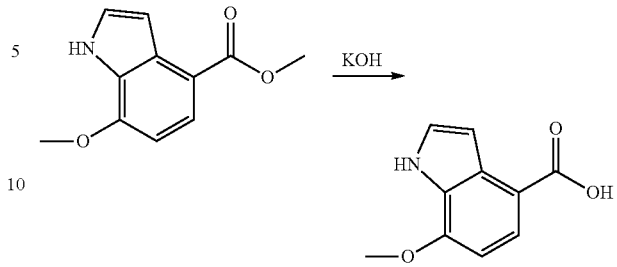

Into a 50-mL round-bottom flask, was placed ethyl 7-methoxy-1H-indole-4-carboxylate (1 g, 4.56 mmol, 1.00 equiv), ethanol (20 mL), KOH (1.28 g, 22.81 mmol, 5.00 equiv), water (4 mL). The resulting solution was stirred overnight at 80° C. The resulting solution was cooled to r.t. and extracted with dichloromethane (250 mL×2) and the aqueous layers collected. The pH value of the aqueous layers was adjusted to 5-6 with hydrochloric acid (1 mol/L). The resulting solution was extracted with ethyl acetate (100 mL×2) and the organic layers combined and concentrated under vacuum. This resulted in 63 mg (7%) of 7-methoxy-1H-indole-4-carboxylic acid as a yellow solid. MS: (ES, m/z) [M+H]+: 192.

Step 3. (3-amino-4,5,6,7-tetrahydroindazol-2-yl)(7-methoxy-1H-indol-4-yl)methanone

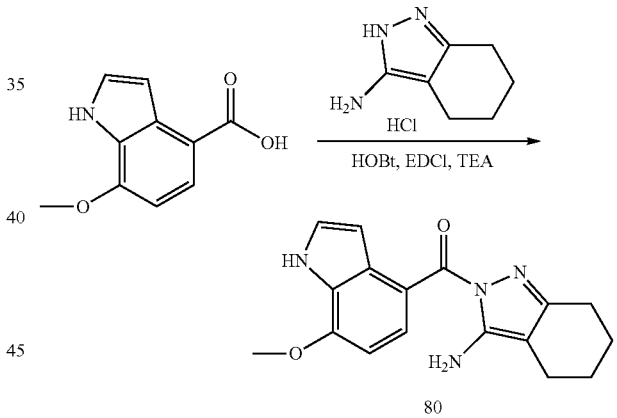

Into a 50-mL round-bottom flask, was placed 7-methoxy-1H-indole-4-carboxylic acid (30 mg, 0.16 mmol, 0.90 equiv), N,N-dimethylformamide (3 mL), HATU (97 mg, 0.26 mmol, 1.50 equiv), DIEA (66 mg, 0.51 mmol, 3.00 equiv). The mixture was stirred for 30 min at r.t. (20° C.). Then 4,5,6,7-tetrahydro-2H-indazol-3-amine hydrochloride (30 mg, 0.17 mmol, 1.00 equiv) was added. The resulting solution was stirred overnight at room temperature (20° C.). The resulting solution was diluted with EA (30 mL). The resulting mixture was washed with brine (100 mL×2). The resulting mixture was concentrated under vacuum. The crude product was purified by Prep-HPLC with the following conditions: Column, XBridge Shield RP18 OBD Column, 19×250 mm, 10 um, mobile phase, waters (0.1% FA) and ACN (35.0% ACN up to 65.0% in 7 min), Detector, UV 254/220 nm. The collected fraction was lyophilized to give 3.5 mg (7%) of (3-amino-4,5,6,7-tetrahydroindazol-2-yl)(7-methoxy-1H-indol-4-yl)methanone (80) as a white solid. RT: 6.65 min, MS (ES, m/z) [M+H]+: 311, (400 MHz, DMSO-d6, ppm): δ 11.50 (s, 1H), 7.87 (d, J=8.0 Hz, 1H), 7.37-7.35 (m, 1H), 6.76 (d, J=8.4 Hz, 1H), 6.68-6.67 (m, 1H), 6.31 (s, 2H), 4.00 (s, 3H), 2.43-2.40 (m, 2H), 2.33-2.30 (m, 2H), 1.67 (d, J=5.6 Hz, 4H).

Example 81: (3-amino-4,5,6,7-tetrahydroindazol-2-yl)(2-methyl-4,5,6,7-tetrahydro-1H-indol-4-yl) methanone

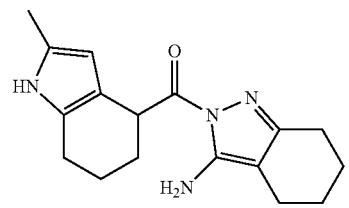

81

Step 1.
2-Methyl-4,5,6,7-tetrahydro-1H-indole-4-carboxylic Acid

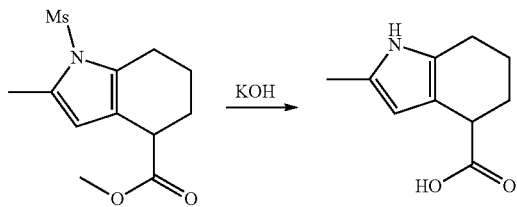

Into a 100-mL round-bottom flask purged and maintained with an inert atmosphere of nitrogen, was placed 1-(methylsulfonyl)-4,5,6,7-tetrahydro-1H-indole-4-carboxylic acid (157 mg, 0.65 mmol, 1.00 equiv) [see example 90 for synthesis], 1,4-dioxane (16 mL), water (8 mL), potassium hydroxide (724 mg, 12.92 mmol, 20.00 equiv). The resulting solution was stirred for 1 overnight at 130° C. The resulting mixture was washed with dichloromethane (80 mL×2). The pH value of the solution was adjusted to 4 with hydrogen chloride (6 mol/L). The resulting solution was extracted with dichloromethane (80 mL×3) and concentrated under vacuum. The residue was purified by Pre-TLC with dichloromethane/methanol (20/1). This resulted in 70 mg (61%) of 2-methyl-4,5,6,7-tetrahydro-1H-indole-4-carboxylic acid as brown oil. MS (ES, m/z) [M+H]$^+$: 180.

Step 2. (3-amino-4,5,6,7-tetrahydroindazol-2-yl)(2-methyl-4,5,6,7-tetrahydro-1H-indol-4-yl)methanone

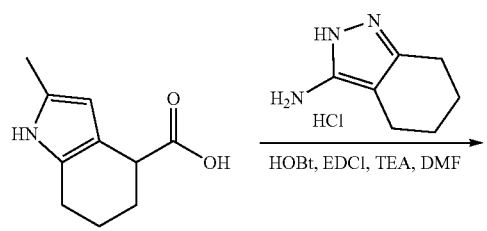

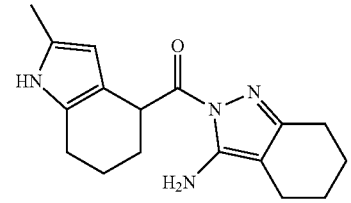

81

Into a 50-mL round-bottom flask, was placed 2-methyl-4,5,6,7-tetrahydro-1H-indole-4-carboxylic acid (71 mg, 0.40 mmol, 1.0 equiv), 4,5,6,7-tetrahydro-2H-indazol-3-amine dihydrochloride (75 mg, 0.44 mmol, 1.1 equiv), HOBt (80 mg, 0.60 mmol, 1.50 equiv), EDCI (114 mg, 0.60 mmol, 1.50 equiv), N,N-dimethylformamide (5 mL), TEA (200 mg, 2.0 mmol, 5.00 equiv). The resulting solution was stirred overnight at 25° C. The reaction mixture was diluted with DCM (80 mL), washed with H$_2$O (50 mL×3) and brine (50 mL×3) and dried with Na$_2$SO$_4$. After filtration, the filtrate was concentrated under reduced pressure. The crude product was purified by Prep-HPLC with the following conditions: Column: XSelect CSH Prep C18 OBD Column, 5 um, 19×150 mm, Mobile Phase A: water (0.1% FA), Mobile Phase B: ACN, Flow rate: 20 mL/min, Gradient: 40% B to 70% B in 7 min, 254 nm. The collected fraction was lyophilized to give 2 mg (1.7%) of (3-amino-4,5,6,7-tetrahydroindazol-2-yl)(2-methyl-4,5,6,7-tetrahydro-1H-indol-4-yl)methanone (81) as a pink solid. R.t: 6 min, MS (ES, m/z) [M+H]$^+$: 299, (300 MHz, DMSO-d$_6$, ppm): δ 10.05 (s, 1H), 6.28 (s, 2H), 5.25 (d, J=1.5 Hz, 1H), 4.73-4.69 (m, 1H), 2.49-2.47 (m, 4H), 2.28-2.26 (m, 2H), 2.05 (s, 3H), 1.99-1.96 (m, 2H), 1.84-1.66 (m, 6H).

Example 82 & 83 & 84: (3-amino-4,5,6,7-tetrahydroindazol-2-yl)(2-ethyl-4,5,6,7-tetrahydro-1H-indol-4-yl)methanone (82); (S*)-(3-amino-4,5,6,7-tetrahydroindazol-2-yl)(2-ethyl-4,5,6,7-tetrahydro-1H-indol-4-yl)methanone (83) and (R*)-(3-amino-4,5,6,7-tetrahydroindazol-2-yl)(2-ethyl-4,5,6,7-tetrahydro-1H-indol-4-yl)methanone (84)

82

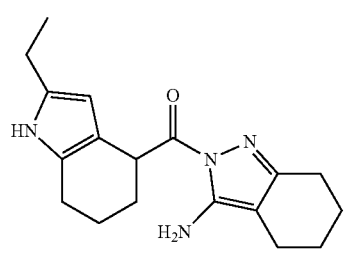

83

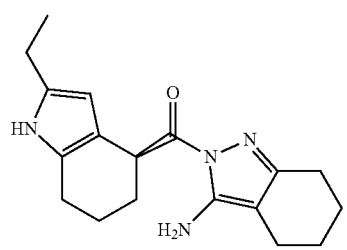

-continued

84

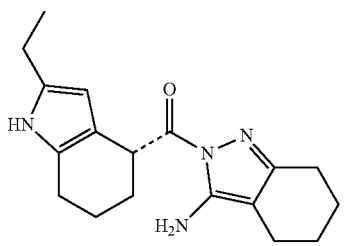

Step 1. tert-butyl
2-ethyl-5-formyl-1H-pyrrole-1-carboxylate

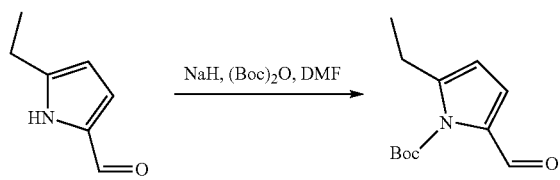

Into a 250-mL 3-necked round-bottom flask purged and maintained with an inert atmosphere of nitrogen, was placed 5-ethyl-1H-pyrrole-2-carbaldehyde (2.0 g, 16.24 mmol, 1.00 equiv), N,N-dimethylformamide (150 mL). This was followed by the addition of sodium hydride (780 mg, 19.50 mmol, 1.20 equiv, 60%) in several batches at 0° C. To this was added a solution of (Boc)₂O (3.9 g, 17.87 mmol, 1.10 equiv) in N,N-dimethylformamide (8 mL) dropwise with stirring at 5° C. The resulting solution was stirred overnight at 25° C. The reaction was then quenched by the addition of ice/water (250 mL). The resulting solution was extracted with ethyl acetate (250 mL×2) and the organic layers combined. The resulting mixture was washed with saturated brine (200 mL×3). The mixture was dried over anhydrous sodium sulfate. The solids were filtered out. The resulting mixture was concentrated under vacuum. The residue was applied onto a silica gel column and eluted with ethyl acetate/petroleum ether (1:10). The collected fraction was concentrated to give 3.7 g (97.2%) of tert-butyl 2-ethyl-5-formyl-1H-pyrrole-1-carboxylate as yellow oil. MS (ES, m/z) [M+H]⁺: 224.

Step 2. tert-butyl
2-ethyl-5-vinyl-1H-pyrrole-1-carboxylate

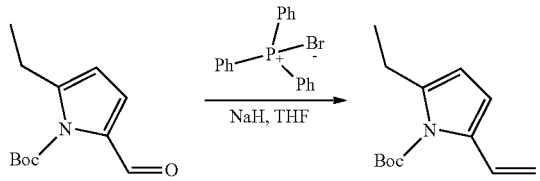

Into a 250-mL 3-necked round-bottom flask purged and maintained with an inert atmosphere of nitrogen, was placed tetrahydrofuran (80 mL). This was followed by the addition of sodium hydride (1.0 g, 41.67 mmol, 1.50 equiv) at 5° C. To this was added methyltriphenylphosphonium bromide (8.9 g, 24.91 mmol, 1.50 equiv) at 5° C. The mixture was stirred for 1.5 hour at 70° C., then cooled to below 35° C., the mixture was added a solution of tert-butyl 2-ethyl-5-formyl-1H-pyrrole-1-carboxylate (3.7 g, 16.57 mmol, 1.00 equiv) in tetrahydrofuran (8 mL). The resulting solution was stirred for 3 h at 70° C. After cooled to room temperature, the solids were filtered out. The residue was applied onto a silica gel column with ethyl acetate/petroleum ether (1/7). This resulted in 2.6 g (71%) of tert-butyl 2-ethenyl-5-ethyl-1H-pyrrole-1-carboxylate as yellow oil. MS (ES, m/z) [M+H]⁺: 222.

Step 3. 1-tert-butyl 4-methyl
2-ethyl-4,5,6,7-tetrahydroindole-1,4-dicarboxylate

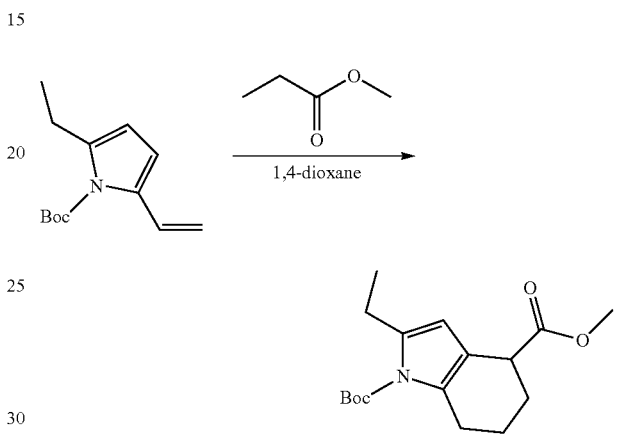

The tert-butyl 2-ethenyl-5-ethyl-1H-pyrrole-1-carboxylate (2.0 g, 9.04 mmol, 1.00 equiv), dioxane (60 mL), methyl prop-2-enoate (3.1 g, 36.01 mmol, 4.00 equiv) was placed into eight 25-mL sealed tube average, purged and maintained with an inert atmosphere of nitrogen. The resulting solution was stirred overnight at 120° C. After cooled to room temperature, the resulting mixture was concentrated under vacuum. This resulted in 500 mg (18%) of 1-tert-butyl 4-methyl 2-ethyl-4,5,6,7-tetrahydro-1H-indole-1,4-dicarboxylate as yellow oil. MS (ES, m/z) [M+H]⁺: 308.

Step 4. methyl
2-ethyl-4,5,6,7-tetrahydro-1H-indole-4-carboxylate

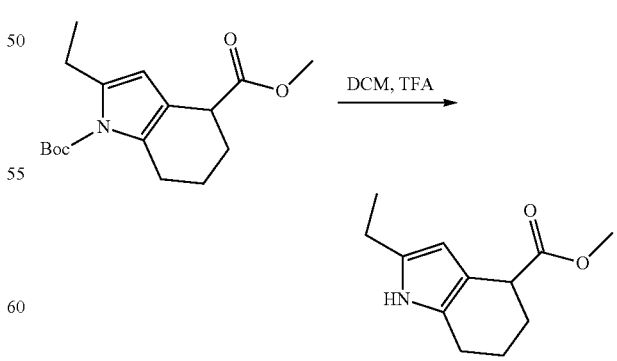

Into a 100-mL round-bottom flask, was placed 1-tert-butyl 4-methyl 2-ethyl-4,5,6,7-tetrahydro-1H-indole-1,4-dicarboxylate (300 mg, 0.98 mmol, 1.00 equiv), dichloromethane (10 g, 117.74 mmol, 120.64 equiv), CF₃COOH (1.5 g, 13.16 mmol, 13.48 equiv). The resulting solution was stirred for 2 h at 25° C. The reaction was then quenched by the addition of water (80 mL). The resulting solution was extracted with dichloromethane (80 mL×2) and the organic layers combined and dried over anhydrous sodium sulfate. The solids were filtered out. The filtrate was concentrated under vacuum. This resulted in 200 mg (99%) of methyl 2-ethyl-4,5,6,7-tetrahydro-1H-indole-4-carboxylate as light yellow crude oil. MS (ES, m/z) [M+H]+: 208.

Step 5.
2-ethyl-4,5,6,7-tetrahydro-1H-indole-4-carboxylic Acid

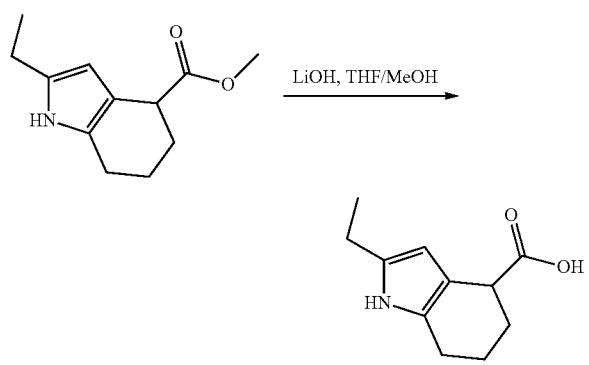

Into a 50-mL round-bottom flask, was placed methyl 2-ethyl-4,5,6,7-tetrahydro-1H-indole-4-carboxylate (200 mg, 0.96 mmol, 1.00 equiv), tetrahydrofuran (8 mL), methanol (4 mL), a solution of LiOH (139.1 mg, 5.81 mmol, 6.00 equiv) in H₂O (3 mL). The resulting solution was stirred overnight at 15° C. The resulting mixture was concentrated under vacuum. The resulting solution was diluted with H₂O (3 mL). The resulting solution was extracted with ethyl acetate (40 mL) and the aqueous layers combined. HCl (1 mol/L) was employed to adjust the pH to 5-6. The resulting solution was extracted with ethyl acetate (80 mL×2) and the organic layers combined and dried over anhydrous sodium sulfate. The solids were filtered out. The resulting mixture was concentrated under vacuum. This resulted in 170 mg (91%) of 2-ethyl-4,5,6,7-tetrahydro-1H-indole-4-carboxylic acid as a red crystal. (ES, m/z) [M+H]+: 194.

Step 6. (3-amino-4,5,6,7-tetrahydroindazol-2-yl)(2-ethyl-4,5,6,7-tetrahydro-1H-indol-4-yl)methanone (82)

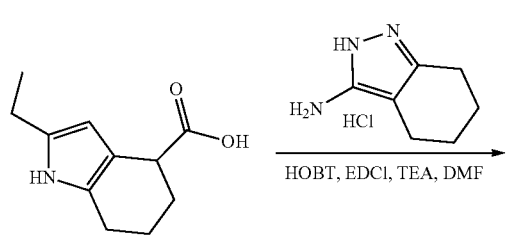

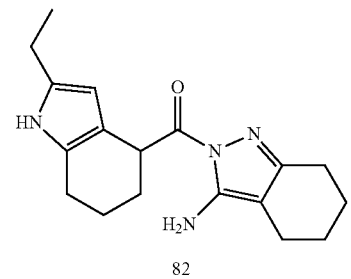

Into a 10-mL vial, was placed 2-ethyl-4,5,6,7-tetrahydro-1H-indole-4-carboxylic acid (30 mg, 0.16 mmol, 1.00 equiv), HOBT (32 mg, 0.24 mmol, 1.50 equiv), EDCI (45 mg, 0.23 mmol, 1.50 equiv), N,N-dimethylformamide (3 mL), TEA (78.6 mg, 0.78 mmol, 5.00 equiv), 4,5,6,7-tetrahydro-2H-indazol-3-amine hydrochloride (40.6 mg, 0.23 mmol, 1.50 equiv). The resulting solution was stirred overnight at 20° C. The reaction was then quenched by the addition of water (15 mL). The resulting solution was extracted with ethyl acetate (40 mL×2) and the organic layers combined and dried over anhydrous sodium sulfate. The solids were filtered out. The crude product was purified by Prep-HPLC with the following conditions: Column, XSelect CSH Prep C18 OBD Column, 5 um, 19×150 mm, mobile phase, water (0.1% FA) and ACN (38.0% ACN up to 75.0% in 7 min), Detector, UV 254 220 nm. The collected fractions were lyophilized to give 5.2 mg (10.4%) of (3-amino-4,5,6,7-tetrahydro-2H-indazol-2-yl)(2-ethyl-4,5,6,7-tetrahydro-1H-indol-4-yl)methanone (82) as a pink solid. Rt: 6.78 min, MS (ES, m/z) [M+H]+: 313, (DMSO-d₆, 400 MHz, ppm): δ 10.09 (s, 1H), 6.30 (s, 2H), 5.28 (d, J=2.4 Hz, 1H), 4.75-4.72 (m, 1H), 2.52-5.48 (m, 4H), 2.46-2.39 (m, 2H), 2.28-2.23 (m, 2H), 2.01-1.92 (m, 3H), 2.71-2.63 (m, 5H), 1.09-1.05 (m, 3H).

Step 7. (S*)-(3-amino-4,5,6,7-tetrahydro-2H-indazol-2-yl)(2-ethyl-4,5,6,7-tetrahydro-1H-indol-4-yl)methanone and (R*)-(3-amino-4,5,6,7-tetrahydro-2H-indazol-2-yl)(2-ethyl-4,5,6,7-tetrahydro-1H-indol-4-yl)methanone

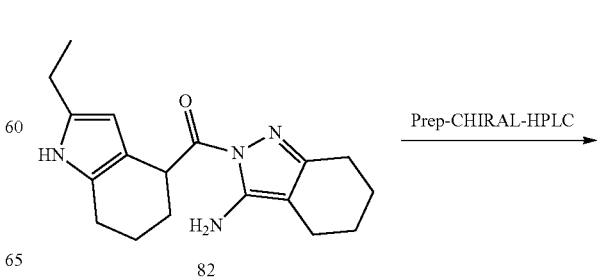

77
-continued

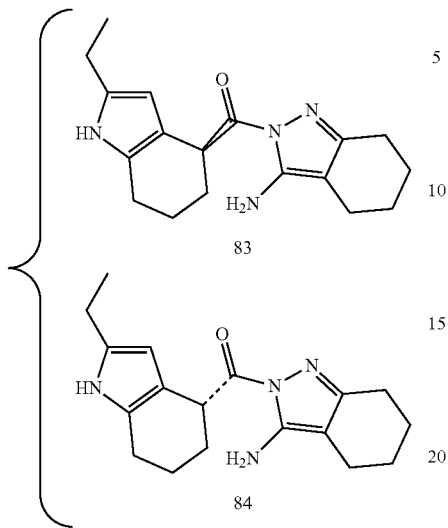

The 2-[(2-ethyl-4,5,6,7-tetrahydro-1H-indol-4-yl)carbonyl]-4,5,6,7-tetrahydro-2H-indazol-3-amine (65 mg, 0.21 mmol, 1.00 equiv) was purified by Prep-Chiral-HPLC: Column: CHIRALPAK IF, 2*25 cm, 5 um, Mobile Phase A: Hex-HPLC, Mobile Phase B: EtOH-HPLC, Flow rate: 20 mL/min, Gradient: 20 B to 20 B in 9 min, 220/254 nm. The resulting mixture was concentrated under vacuum at low temperature.

Enantiomer A: 24.6 mg (38%) of (S*)-(3-amino-4,5,6,7-tetrahydro-2H-indazol-2-yl)(2-ethyl-4,5,6,7-tetrahydro-1H-indol-4-yl)methanone (83) as a pink solid, RT2=7.071 min, MS (ES, m/z) [M+H]$^+$: 313, (DMSO-d$_6$, 400 MHz, ppm): δ 10.10 (s, 1H), 6.31 (s, 2H), 5.27 (s, 1H), 4.74-4.71 (m, 1H), 2.50-2.41 (m, 6H), 2.29-2.24 (m, 2H), 2.01-1.79 (m, 3H), 2.71-2.63 (m, 5H), 1.09-1.04 (m, 3H).

Enantiomer B: 25.4 mg (39%) of (R*)-(3-amino-4,5,6,7-tetrahydro-2H-indazol-2-yl)(2-ethyl-4,5,6,7-tetrahydro-1H-indol-4-yl)methanone (84) as a pink solid, RT1=5.419 min, MS (ES, m/z) [M+H]$^+$: 313, (DMSO-d$_6$, 300 MHz, ppm): δ 10.10 (s, 1H), 6.30 (s, 2H), 5.27 (s, 1H), 4.74-4.70 (m, 1H), 2.48-2.39 (m, 6H), 2.29-2.24 (m, 2H), 2.02-1.95 (m, 1H), 1.93-1.78 (m, 2H), 1.74-1.63 (m, 5H), 1.09- 1.02 (m, 3H).

Example 85: (3-amino-4,5,6,7-tetrahydro-2H-indazol-2-yl)(2-methyl-4,5,6,7-tetrahydrobenzofuran-4-yl)methanone

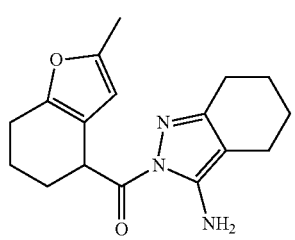

83

78

Step 1. 2-ethenyl-5-methylfuran

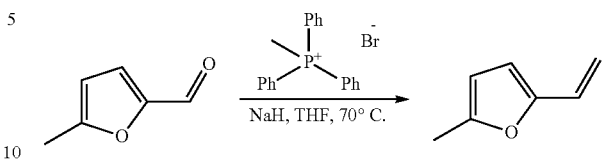

Into a 250-mL round-bottom flask purged and maintained with an inert atmosphere of nitrogen, was placed tetrahydrofuran (30 mL), sodium hydride (2.72 g, 113.5 mmol, 1.50 equiv, 60%) was added at 0° C., (Ph)$_3$PBrMe (22.31 g, 1.40 equiv) was added at 0° C., 5-methylfuran-2-carbaldehyde (5 g, 45.41 mmol, 1.00 equiv). The resulting solution was stirred for 3 h at 70° C. After cooled to room temperature, the reaction was then quenched by the addition of water/ice (30 mL). The resulting solution was extracted with dichloromethane (150 mL×3) and the organic layers combined. The mixture was by distillation at 70° C. This resulted in 4.5 g (92%) of 2-ethenyl-5-methylfuran as yellow oil. MS (ES, m/z) [M+H]$^+$: 112.

Step 2. methyl 2-methyl-4,5,6,7-tetrahydro-1-benzofuran-4-carboxylate

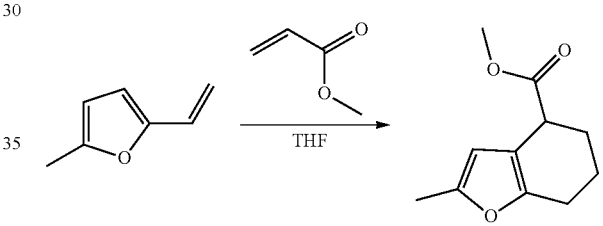

Into a 20-mL sealed tube, was placed 2-ethenyl-5-methylfuran (1 g, 9.25 mmol, 1.00 equiv), methyl prop-2-enoate (3.19 g, 37.05 mmol, 4.00 equiv), tetrahydrofuran (10 mL). The resulting solution was stirred overnight at 120° C. After cooled to room temperature, the resulting mixture was concentrated under vacuum. This resulted in 1 g (56%) of methyl 2-methyl-4,5,6,7-tetrahydro-1-benzofuran-4-carboxylate as yellow oil. MS (ES, m/z) [M+H]$^+$: 195.

Step 3. 2-methyl-4,5,6,7-tetrahydro-1-benzofuran-4-carboxylic

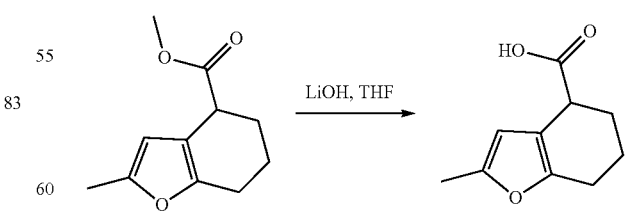

Into a 50-mL round-bottom flask, was placed methyl 2-methyl-4,5,6,7-tetrahydro-1-benzofuran-4-carboxylate (500 mg, 2.57 mmol, 1.00 equiv), LiOH (309 mg, 12.90 mmol, 5.00 equiv), tetrahydrofuran (10 mL), water (2.5 mL), methanol (2.5 mL). The resulting solution was stirred overnight at room temperature. The resulting solution was diluted with H₂O (35 mL). The resulting mixture was washed with DCM (60 mL×2). The pH value of the solution was adjusted to 5-6 with hydrochloric acid (1 mol/L). The resulting solution was extracted with dichloromethane (60 mL×4) and the organic layers combined and concentrated under vacuum. This resulted in 300 mg (65%) of 2-methyl-4,5,6,7-tetrahydro-1-benzofuran-4-carboxylic acid as yellow oil. MS (ES, m/z) [M+H]⁺: 181.

Step 4. (3-amino-4,5,6,7-tetrahydro-2H-indazol-2-yl)(2-methyl-4,5,6,7-tetrahydrobenzofuran-4-yl) methanone (85)

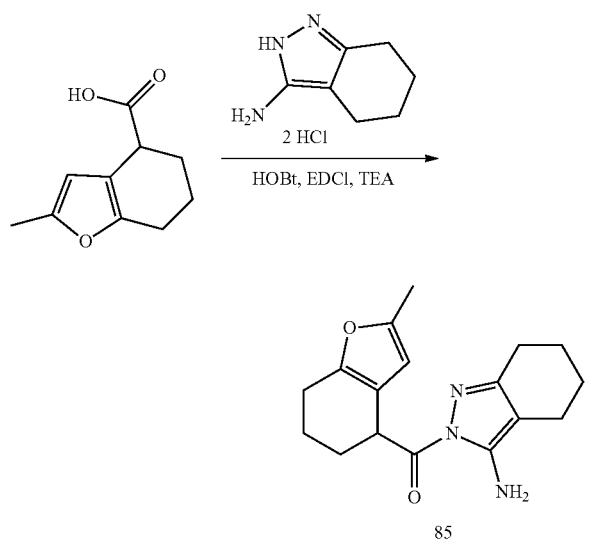

Into a 50-mL round-bottom flask, was placed 2-methyl-4,5,6,7-tetrahydro-1-benzofuran-4-carboxylic acid (50 mg, 0.28 mmol, 1.00 equiv), HOBt (57 mg, 0.42 mmol, 1.50 equiv), EDCI (81 mg, 0.42 mmol, 1.50 equiv), dichloromethane (5 mL), TEA (85 mg, 0.84 mmol, 3.00 equiv). The mixture was stirred for 30 min. 4,5,6,7-tetrahydro-2H-indazol-3-amine dihydrochloride (57.6 mg, 0.33 mmol, 1.20 equiv) was added. The resulting solution was stirred overnight at 25° C. The reaction mixture was diluted with EA (80 mL), washed with H₂O (50 mL×3) and brine (100 mL×2) and dried with Na₂SO₄. After filtration, the filtrate was concentrated under reduced pressure. The crude product was purified by Prep-HPLC with the following conditions: Column, XSelect CSH Prep C18 OBD Column, 5 um, 19×150 mm, mobile phase, water (0.1% FA) and ACN (45.0% ACN up to 80.0% in 7 min), Detector, UV 254 220 nm. The collected fraction was lyophilized to give 14.6 mg (18%) of (3-amino-4,5,6,7-tetrahydro-2H-indazol-2-yl)(2-methyl-4,5,6,7-tetrahydrobenzofuran-4-yl)methanone (85) as a white solid. RT2: 6.62 min, MS (ES, m/z) [M+H]⁺: 300, (300 MHz, DMSO-d₆, ppm): δ 6.34 (s, 2H), 5.72 (s, 1H), 4.68 (s, 1H) 2.50-2.45 (m, 3H), 2.28-2.24 (m, 2H), 2.08 (s, 3H), 1.83-1.79 (m, 2H), 1.77-1.66 (m, 7H).

Example 86: (3-amino-4,5,6,7-tetrahydroindazol-2-yl)(2-methyl-4,5,6,7-tetrahydrobenzo[b]thiophen-4-yl)methanone

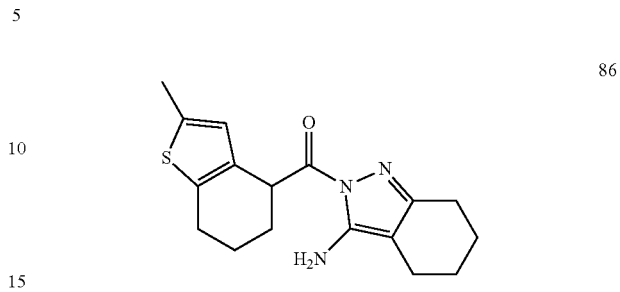

Step 1. 2-methyl-5-vinylthiophene

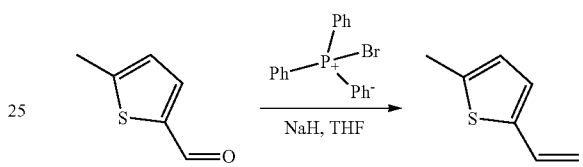

Into a 250-mL round-bottom flask purged and maintained with an inert atmosphere of nitrogen, was placed tetrahydrofuran (80 g, 1.11 mol, 28.00 equiv). This was followed by the addition of sodium hydride (2.06 g, 85.87 mmol, 1.30 equiv, 60%) in several batches at 0° C. To this was added methyltriphenylphosphanium bromide (17 g, 47.59 mmol, 1.20 equiv) in several batches at 5° C. To the mixture was added a solution of 5-methylthiophene-2-carbaldehyde (5 g, 39.63 mmol, 1.00 equiv) in tetrahydrofuran (10 mL) dropwise with stirring at 25° C. The resulting solution was stirred for 4 h at 70° C. After cooled to room temperature, the solids were filtered out. The residue was applied onto a silica gel column with ethyl acetate/petroleum ether (1:10). This resulted in 3.5 g (71%) of 2-ethenyl-5-methylthiophene as colorless oil. MS (ES, m/z) [M+H]⁺: 125.

Step 2. methyl 2-methyl-4,5,6,7-tetrahydrobenzo[b]thiophene-4-carboxylate

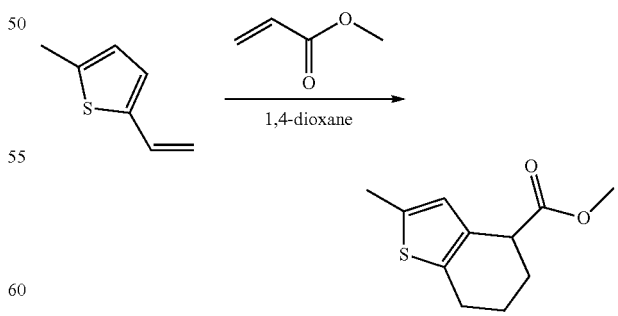

Into a 20-mL pressure tank reactor, was placed 2-ethenyl-5-methylthiophene (200 mg, 1.61 mmol, 1.00 equiv), dioxane (5 mL), methyl prop-2-enoate (554.8 mg, 6.44 mmol, 4.00 equiv). The resulting solution was stirred for 3 h at 120° C. After cooled to room temperature, the resulting mixture was concentrated under vacuum. This resulted in 300 mg (89%) of methyl 2-methyl-4,5,6,7-tetrahydro-1-benzothiophene-4-carboxylate as light yellow crude oil. MS (ES, m/z) [M+H]+: 211.

Step 3. 2-methyl-4,5,6,7-tetrahydrobenzo[b]thiophene-4-carboxylic Acid

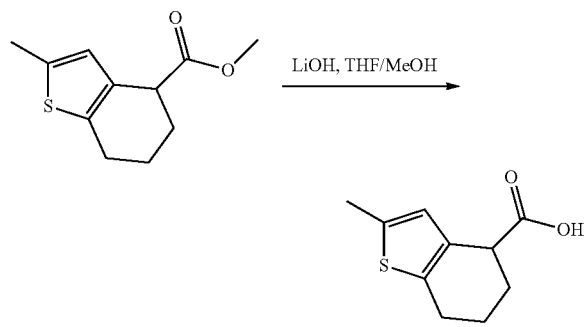

Into a 25-mL round-bottom flask, was placed methyl 2-methyl-4,5,6,7-tetrahydro-1-benzothiophene-4-carboxylate (300 mg, 1.43 mmol, 1.00 equiv). This was followed by the addition of tetrahydrofuran (6 mL) and methanol (4 mL). To this was added LiOH (3 mL, 1 mol/L) The resulting solution was stirred overnight at 25° C. The resulting mixture was concentrated under vacuum. The resulting solution was extracted with ethyl acetate (30 mL) and the aqueous layers combined. Hydrochloric acid (1 mol/L) was employed to adjust the pH to 4. The resulting solution was extracted with ethyl acetate (40 mL×3) and the organic layers combined and dried over anhydrous sodium sulfate. The solids were filtered out. The resulting mixture was concentrated under vacuum. This resulted in 30 mg (11%) of 2-methyl-4,5,6,7-tetrahydro-1-benzothiophene-4-carboxylic acid as a yellow solid. MS (ES, m/z) [M+H]+: 197.

Step 4. (3-amino-4,5,6,7-tetrahydroindazol-2-yl)(2-methyl-4,5,6,7-tetrahydrobenzo[b]thiophen-4-yl)methanone

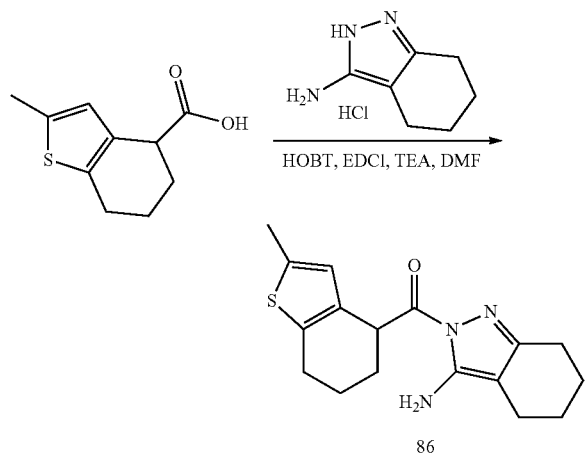

Into a 10-mL vial, was placed 2-methyl-4,5,6,7-tetrahydro-1-benzothiophene-4-carboxylic acid (30 mg, 0.15 mmol, 1.00 equiv), HOBT (31 mg, 0.23 mmol, 1.50 equiv), EDCI (44 mg, 0.23 mmol, 1.50 equiv), N,N-dimethylformamide (3 mL), TEA (77.3 mg, 0.76 mmol, 5.00 equiv), 4,5,6,7-tetrahydro-2H-indazol-3-amine hydrochloride (39.7 mg, 0.23 mmol, 1.50 equiv). The resulting solution was stirred overnight at 25° C. The reaction was then quenched by the addition of water (15 mL). The resulting solution was extracted with ethyl acetate (40 mL×2) and the organic layers combined and dried over anhydrous sodium sulfate. The solids were filtered out. The resulting mixture was concentrated under vacuum. The crude product was purified by Prep-HPLC with the following conditions: Column, XBridge C18 OBD Prep Column, 100 A, 5 um, 19 mm×250 mm, mobile phase: water (0.1% FA) and ACN (55.0% ACN up to 75.0% in 7 min), Detector, UV 254 nm. The collected fractions were lyophilized to give 4.5 mg (9%) of 2-[(2-methyl-4,5,6,7-tetrahydro-1-benzothiophen-4-yl)carbonyl]-4,5,6,7-tetrahydro-2H-indazol-3-amine (86) as a light yellow solid. RT2: 6.58 min, MS (ES, m/z) [M+H]+: 315, (DMSO-d6, 400 MHz, ppm): δ 6.36 (s, 2H), 6.31 (s, 1H), 4.86-4.83 (m, 1H), 2.68-2.65 (m, 2H), 2.49-2.46 (m, 2H), 2.31 (s, 3H), 2.26-2.22 (m, 2H), 2.08-1.83 (m, 3H), 1.79-1.62 (m, 5H).

Example 87: (3-amino-4,5,6,7-tetrahydroindazol-2-yl)(1-methyl-1,2,3,4-tetrahydro-1,8-naphthyridin-4-yl)methanone

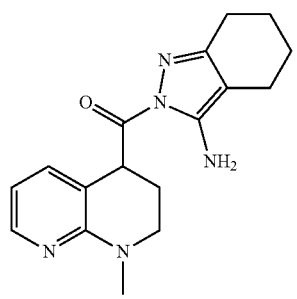

87

Step 1. ethyl 3-(methyl(pyridin-2-yl)amino)propanoate

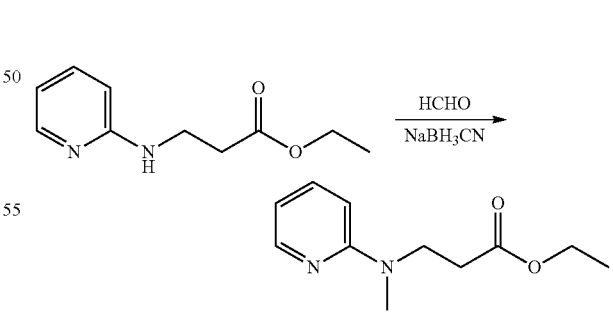

Into a 250-mL 3-necked round-bottom flask, was placed a solution of ethyl 3-[(pyridin-2-yl)amino]propanoate (10 g, 51.49 mmol, 1.00 equiv) in methanol (60 mL), formaldehyde (37% in water, 50.16 g, 618.10 mmol, 12.00 equiv) and acetic acid (20 mL). The resulting solution was stirred for 2.0 h at 30° C. The NaBH3CN (16.24 g, 257.78 mmol, 5.0 equiv) was added in several portions at 0° C. The resulting solution was allowed to react, with stirring, for an additional 18 h at 30° C. The reaction was then poured into saturated aq. Na₂CO₃ (60 mL). The resulting mixture was concentrated under vacuum. The residue was diluted with H₂O (100 mL). The resulting solution was extracted with ethyl acetate (100 mL×3) and the organic layers combined and dried over anhydrous sodium sulfate. The solids were filtered out. The filtrate was concentrated under vacuum. This resulted in 9.0 g (84%) of ethyl 3-[methyl(pyridin-2-yl)amino]propanoate as yellow solid. MS (ES, m/z) [M+H]⁺: 209.

Step 2. 3-(methyl(pyridin-2-yl)amino)propanoic Acid

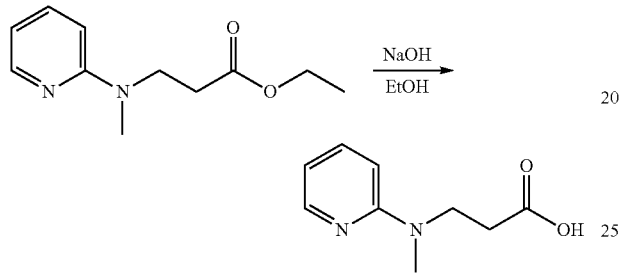

Into a 250-mL 3-necked round-bottom flask, was placed a solution of ethyl 3-[methyl(pyridin-2-yl)amino]propanoate (4.5 g, 21.61 mmol, 1.00 equiv) in ethanol (40 mL), water (40 mL), sodium hydroxide (4.33 g, 108.25 mmol, 5.0 equiv). The resulting solution was stirred for 8.0 h at 30° C. The resulting mixture was concentrated under vacuum. The residue was diluted with H₂O (40 mL). The resulting solution was extracted with ethyl acetate (40 mL) and the aqueous layers combined. The pH value of the solution was adjusted to 7 with hydrochloric acid (6 mol/L). The resulting solution was extracted three times with ethyl acetate (30 mL), washed with water, dried with anhydrous Na₂SO₄ and concentrated under vacuum. The crude product was purified by reversed phase column with the following conditions: Column, C18 silica gel, 120 g, 20-45 um, 100 A, mobile phase, water with 0.05% FA and ACN (1% up to 15% ACN in 20 min), Detector, UV 220/254 nm. This resulted in 3.8 g (97%) of 3-[methyl(pyridin-2-yl)amino]propanoic acid as light yellow solid. MS (ES, m/z) [M+H]⁺: 181.

Step 3. 1-methyl-2,3-dihydro-1,8-naphthyridin-4(1H)-one

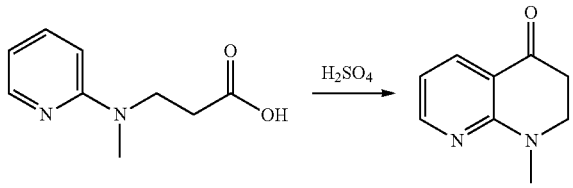

Into a 250-mL 3-necked round-bottom flask, was placed 3-[methyl(pyridin-2-yl)amino]propanoic acid (3.0 g, 16.65 mmol, 1.00 equiv), sulfuric acid (100 mL). The resulting solution was stirred for 15 h at 60° C. The reaction mixture was cooled to 30 degree C. with a water bath. The reaction was then poured into water/ice (1000 mL). The pH value of the solution was adjusted to 12 with sodium hydroxide (6 mol/L). The resulting solution was extracted with ethyl acetate (1000 mL×3) and the organic layers combined and dried over anhydrous sodium sulfate. The solids were filtered out. The filtrate was concentrated under vacuum. The residue was purified by preparative TLC (MeOH:CH₂Cl₂=1:35). This resulted in 661 mg (24%) of 1-methyl-1,2,3,4-tetrahydro-1,8-naphthyridin-4-one as yellow oil. MS (ES, m/z) [M+H]⁺: 163.

Step 4. 1-methyl-4-(trimethylsilyloxy)-1,2,3,4-tetrahydro-1,8-naphthyridine-4-carbonitrile

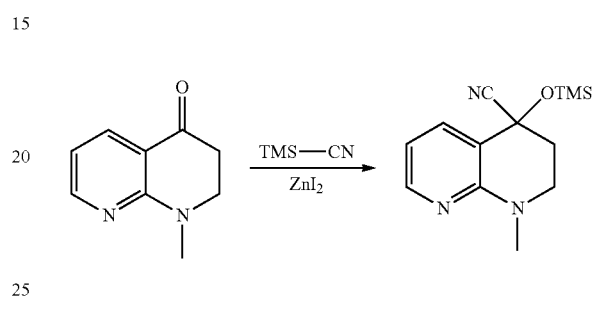

Into a 100-mL round-bottom flask purged and maintained with an inert atmosphere of nitrogen, was placed a solution of 1-methyl-1,2,3,4-tetrahydro-1,8-naphthyridin-4-one (500 mg, 3.08 mmol, 1.00 equiv) in CH₃CN (20 mL), The trimethylsilanecarbonitrile (3.05 g, 30.85 mmol, 10.00 equiv), ZnI₂ (1.0 g, 3.1 mmol, 1.0 equiv) was added. The resulting solution was allowed to react, with stirring, for an additional 15 h at 30° C. The reaction was then poured into water (50 mL). The resulting solution was extracted with ethyl acetate (50 mL×3) and the organic layers combined. The resulting mixture was washed with brine (150 mL×2). The mixture was dried over anhydrous sodium sulfate. The solids were filtered out. The filtrate was concentrated under vacuum. This resulted in 727.5 mg (crude) of 1-methyl-4-[(trimethylsilyl)oxy]-1,2,3,4-tetrahydro-1,8-naphthyridine-4-carbonitrile as a yellow solid. MS (ES, m/z) [M+H]⁺: 262.

Step 5. 1-methyl-1,2,3,4-tetrahydro-1,8-naphthyridine-4-carboxylic Acid

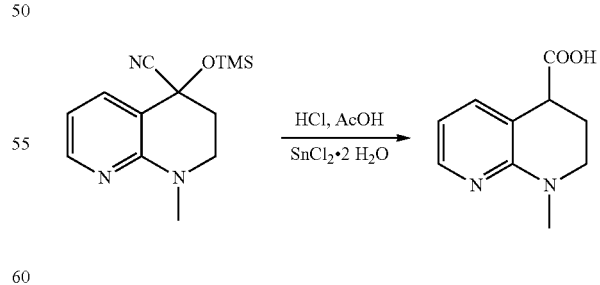

Into a 50-mL round-bottom flask, was placed a solution of 1-methyl-4-[(trimethylsilyl)oxy]-1,2,3,4-tetrahydro-1,8-naphthyridine-4-carbonitrile (420 mg, 1.61 mmol, 1.00 equiv) in hydrogen chloride (5 mL), acetic acid (5 mL), SnCl₂·2H₂O (1.455 g, 6.44 mmol, 4.0 equiv). The resulting solution was stirred for 3.0 h at 115° C. The reaction mixture was cooled to 30° C. with a water bath. The resulting mixture was concentrated under vacuum. The crude product was purified by Prep-HPLC with the following conditions: Column, XBridge C18 OBD Prep Column, 10 μm, 19 mm×250 mm, mobile phase, water (0.1% FA) and ACN (21.0% ACN up to 41.0% in 7 min), Detector, UV 254 nm. This resulted in 306 mg (99%) of 1-methyl-1,2,3,4-tetrahydro-1,8-naphthyridine-4-carboxylic acid as a white solid. MS (ES, m/z) [M+H]$^+$: 193.

Step 6. (3-amino-4,5,6,7-tetrahydroindazol-2-yl)(1-methyl-1,2,3,4-tetrahydro-1,8-naphthyridin-4-yl) methanone

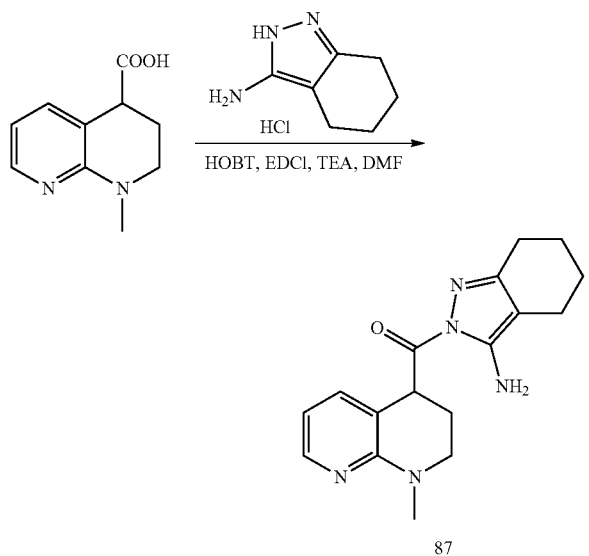

87

Into a 40-mL vial, was placed a solution of 1-methyl-1,2,3,4-tetrahydro-1,8-naphthyridine-4-carboxylic acid (150 mg, 0.78 mmol, 1.00 equiv) in N,N-dimethylformamide (5 mL), HOBT (211 mg, 1.56 mmol, 2.00 equiv), EDCI (298 mg, 1.56 mmol, 2.00 equiv), TEA (394 mg, 3.90 mmol, 5.00 equiv). The resulting solution was stirred for 0.5 h at 30° C. The 4,5,6,7-tetrahydro-2H-indazol-3-amine dihydrochloride (162 mg, 0.94 mmol, 1.20 equiv) was added. The resulting solution was allowed to react, with stirring, for an additional 18 h at 30° C. The reaction was then poured into water (40 mL). The resulting solution was extracted with ethyl acetate (40 mL×3) and the organic layers combined. The resulting mixture was washed with brine (150 mL×2). The mixture was dried over anhydrous sodium sulfate. The solids were filtered out. The filtrate was concentrated under vacuum. The crude product was purified by Prep-HPLC with the following conditions: Column, XSelect CSH Prep C18 OBD Column, 5 um, 19×150 mm, mobile phase, water (0.1% FA) and ACN (hold 5.0% ACN in 6 min, up to 30.0% in 9 min), Detector, UV 254 nm. The collected fraction was lyophilized to give 2.4 mg (1%) of (3-amino-4,5,6,7-tetrahydroindazol-2-yl)(1-methyl-1,2,3,4-tetrahydro-1,8-naphthyridin-4-yl)methanone (87) as a white solid. RT2: 8.56 min, MS (ES, m/z) [M+H]$^+$: 312, (DMSO-$d_6$, 400 MHz, ppm): δ 7.94-7.93 (m, 1H), 7.13 (d, J=6.4 Hz, 1H), 6.48-6.43 (m, 1H), 6.38 (s, 2H), 5.05-5.02 (m, 1H), 3.40-3.35 (m, 2H), 3.04 (s, 3H), 2.50-2.47 (m, 2H), 2.28-2.25 (m, 2H), 2.15-2.10 (m, 2H), 1.70-1.64 (m, 4H).

Example 88: (3-amino-4,5,6,7-tetrahydroindazol-2-yl)(2-methyl-4,5,6,7-tetrahydro-2H-indazol-4-yl) methanone

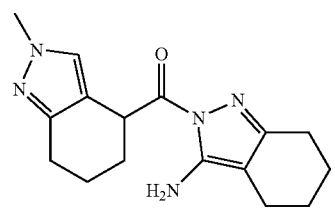

88

Step 1. 4,5,6,7-tetrahydro-2H-indazol-4-one

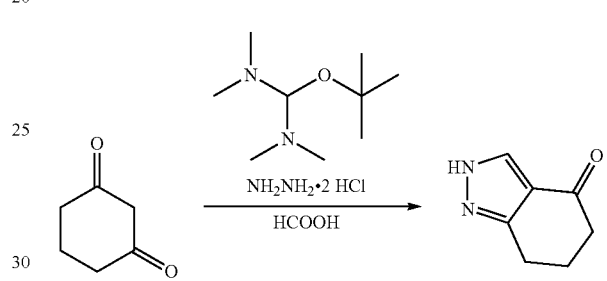

Into a 250-mL round-bottom flask, was placed [(tert-butoxy)(dimethylamino)methyl]dimethylamine (20.55 g, 117.91 mmol, 0.60 equiv), cyclohexane-1,3-dione (22.4 g, 199.77 mmol, 1.00 equiv) and stirred for 5 min, NH$_2$NH$_2$.2HCl (23.1 g, 1.10 equiv) was added and stirred for 1 h, formic acid (50 mL) was added. The resulting solution was stirred for 2 h at 100° C. After cooled to room temperature, the resulting solution was diluted with water (40 mL). The resulting solution was extracted with chloroform/IPA (100 mL×4) and the organic layers combined and dried over anhydrous sodium sulfate. The solids were filtered out. The resulting mixture was concentrated under vacuum. The residue was applied onto a silica gel column with ethyl acetate. This resulted in 1.74 g (6%) of 4,5,6,7-tetrahydro-2H-indazol-4-one as a yellow solid. MS: (ES, m/z) [M+H]$^+$: 137.

Step 2. 2-methyl-4,5,6,7-tetrahydro-2H-indazol-4-one

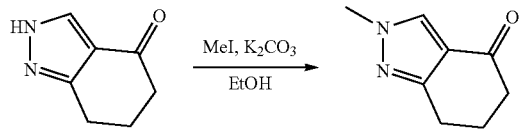

Into a 250-mL round-bottom flask, was placed 4,5,6,7-tetrahydro-2H-indazol-4-one (1.74 g, 12.78 mmol, 1.00 equiv), potassium carbonate (5.3 g, 38.35 mmol, 3.00 equiv), ethanol (25 mL), MeI (2.73 g, 1.50 equiv). The resulting solution was stirred overnight at room temperature. The resulting solution was diluted with H$_2$O (25 mL). The resulting solution was extracted with dichloromethane (150 mL×3) and the organic layers combined and concentrated under vacuum. This resulted in 500 mg (26%) of 2-methyl-4,5,6,7-tetrahydro-2H-indazol-4-one as a yellow solid. MS: (ES, m/z) [M+H]⁺: 151.

Step 3. 2-methyl-6,7-dihydro-2H-indazol-4-yl trifluoromethanesulfonate

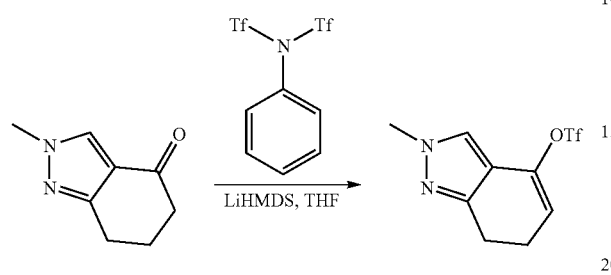

Into a 100-mL 3-necked round-bottom flask purged and maintained with an inert atmosphere of nitrogen, was placed 2-methyl-4,5,6,7-tetrahydro-2H-indazol-4-one (300 mg, 2.00 mmol, 1.00 equiv), tetrahydrofuran (10 mL). This was followed by the addition of LiHMDS (4 mL, 2.00 equiv 1M in tetrahydrofuran) at −78° C. The mixture was stirred for 1 h at −78° C. To this was added 1,1,1-trifluoro-N-phenyl-N-(trifluoromethane)sulfonylmethanesulfonamide (1.36 g, 3.81 mmol, 1.90 equiv) at −78° C. The resulting solution was stirred overnight at 20° C. The reaction was then quenched by the addition of NH₄Cl (10 mL). The resulting solution was extracted with ethyl acetate (30 mL×2) and the organic layers combined. The residue was applied onto a silica gel column with ethyl acetate/petroleum ether (1/3). This resulted in 260 mg (46%) of 2-methyl-6,7-dihydro-2H-indazol-4-yl trifluoromethanesulfonate as yellow oil. MS: (ES, m/z) [M+H]⁺: 283.

Step 4. methyl 2-methyl-6,7-dihydro-2H-indazole-4-carboxylate

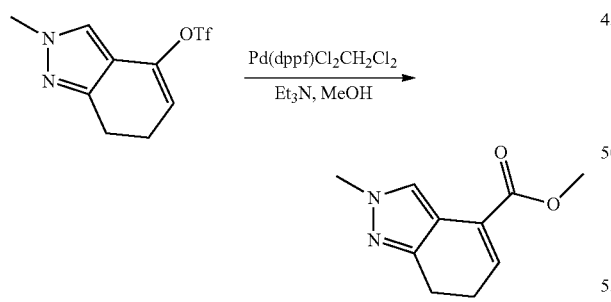

Into a 20-mL pressure tank reactor (60 atm) purged and maintained with an inert atmosphere of CO, was placed 2-methyl-6,7-dihydro-2H-indazol-4-yl trifluoromethanesulfonate (266 mg, 0.94 mmol, 1.00 equiv), Pd(dppf)Cl₂·CH₂Cl₂ (385 mg, 0.50 equiv), TEA (475 mg, 4.69 mmol, 5.00 equiv), methanol (10 mL). The resulting solution was stirred overnight at 120° C. After cooled to room temperature, the solids were filtered out. The resulting mixture was concentrated under vacuum. The residue was applied onto a silica gel column with ethyl acetate/petroleum ether (1/1).

This resulted in 150 mg (83%) of methyl 2-methyl-6,7-dihydro-2H-indazole-4-carboxylate as yellow oil. MS: (ES, m/z) [M+H]⁺: 193.

Step 5. methyl 2-methyl-4,5,6,7-tetrahydro-2H-indazole-4-carboxylate

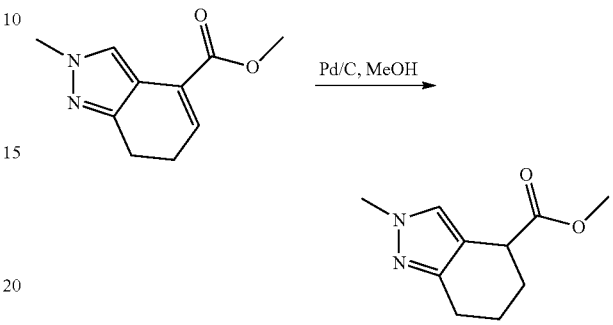

Into a 100-mL round-bottom flask purged and maintained with an inert atmosphere of H₂, was placed methyl 2-methyl-6,7-dihydro-2H-indazole-4-carboxylate (160 mg, 0.83 mmol, 1.00 equiv), Palladium carbon (160 mg), methanol (8 mL), acetic acid (1 mL). The resulting solution was stirred overnight at room temperature. The solids were filtered out. The resulting mixture was concentrated under vacuum. This resulted in 160 mg (99%) of methyl 2-methyl-4,5,6,7-tetrahydro-2H-indazole-4-carboxylate as brown oil. MS: (ES, m/z) [M+H]⁺: 195.

Step 6. 2-methyl-4,5,6,7-tetrahydro-2H-indazole-4-carboxylic

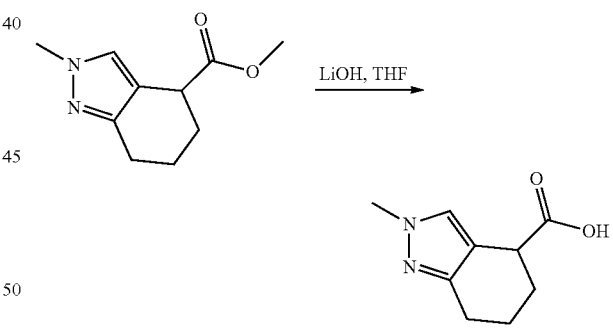

Into a 100-mL round-bottom flask, was placed methyl 2-methyl-4,5,6,7-tetrahydro-2H-indazole-4-carboxylate (160 mg, 0.82 mmol, 1.00 equiv), LiOH (619 mg, 25.85 mmol, 5.00 equiv), water (2.5 mL), methanol (10 mL), tetrahydrofuran (2.5 mL). The resulting solution was stirred overnight at room temperature. The resulting solution was diluted with H₂O (30 mL). The resulting mixture was washed with DCM (60 mL×2). Hydrochloric acid (1 mol/L) was employed to adjust the pH to 5-6. The resulting solution was extracted with dichloromethane (60 mL×4) and the organic layers combined and concentrated under vacuum. This resulted in 110 mg (74%) of 2-methyl-4,5,6,7-tetrahydro-2H-indazole-4-carboxylic acid as brown oil. MS: (ES, m/z) [M+H]⁺: 181.

Step 7. (3-amino-4,5,6,7-tetrahydroindazol-2-yl)(2-methyl-4,5,6,7-tetrahydro-2H-indazol-4-yl)methanone

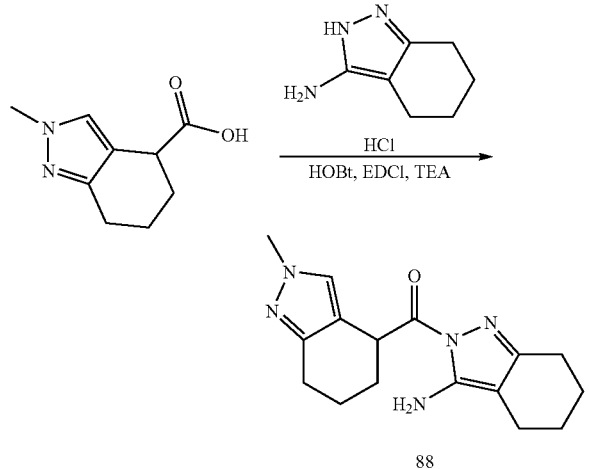

88

Into a 50-mL round-bottom flask, was placed 2-methyl-4,5,6,7-tetrahydro-2H-indazole-4-carboxylic acid (50 mg, 0.28 mmol, 1.00 equiv), HOBt (57 mg, 0.42 mmol, 1.50 equiv), EDCI (81 mg, 0.42 mmol, 1.50 equiv), TEA (85 mg, 0.84 mmol, 3.00 equiv), dichloromethane (5 mL). The mixture was stirred for 30 min. 4,5,6,7-tetrahydro-2H-indazol-3-amine dihydrochloride (57.7 mg, 0.33 mmol, 1.20 equiv) was added. The resulting solution was stirred overnight at 25° C. The reaction mixture was diluted with EA (60 mL), washed with H$_2$O (100 mL×2) and brine (50 mL×3) and dried with Na$_2$SO$_4$. After filtration, the filtrate was concentrated under reduced pressure. The crude product was purified by Prep-HPLC with the following conditions: Column, XSelect CSH Prep C18 OBD Column, 5 um, 19×150 mm, mobile phase, water (0.1% FA) and ACN (15.0% ACN up to 40.0% in 15 min), Detector, UV 254 220 nm. The collected fraction was lyophilized to give 7.3 mg (9%) of (3-amino-4,5,6,7-tetrahydroindazol-2-yl)(2-methyl-4,5,6,7-tetrahydro-2H-indazol-4-yl)methanone (88) as a white solid. RT2: 14.23 min, MS (ES, m/z) [M+H]$^+$: 300. (300 MHz, DMSO-d$_6$, ppm): δ 7.21 (s, 1H), 6.34 (s, 2H), 4.77-4.73 (m, 1H) 3.70 (s, 3H), 2.51-2.50 (m, 2H), 2.49-2.47 (m, 2H), 2.28-2.24 (m, 2H), 1.94-1.66 (m, 8H).

Example 89: (3-amino-4,5,6,7-tetrahydroindazol-2-yl)(2-methyl-4,5,6,7-tetrahydrobenzo[d]thiazol-7-yl)methanone

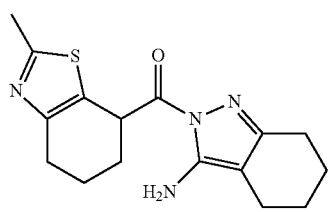

89

Step 1. ethyl 2-bromo-3-oxocyclohexanecarboxylate

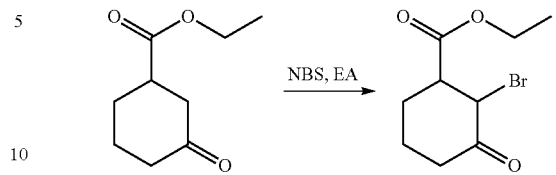

Into a 100-mL round-bottom flask, was placed ethyl 3-oxocyclohexane-1-carboxylate (500 mg, 2.94 mmol, 1.00 equiv), ethyl acetate (10 mL). Then 1-bromopyrrolidine-2,5-dione (572 mg, 3.21 mmol, 1.10 equiv) was added at 0° C. The resulting solution was stirred for 48 h at 25° C. The resulting solution was diluted with EA (10 mL). The resulting mixture was washed with H$_2$O (20 mL×3). The mixture was dried over anhydrous sodium sulfate and concentrated under vacuum. This resulted in 570 mg (78%) of ethyl 2-bromo-3-oxocyclohexane-1-carboxylate as yellow oil. MS (ES, m/z) [M+H]$^+$: 249.

Step 2. ethyl 2-methyl-4,5,6,7-tetrahydrobenzo[d]thiazole-7-carboxylate

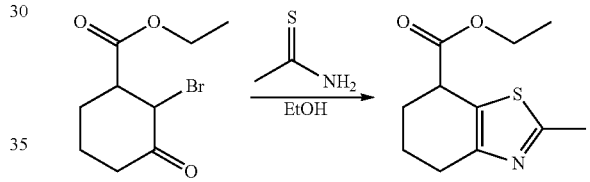

Into a 250-mL round-bottom flask, was placed ethyl 2-bromo-3-oxocyclohexane-1-carboxylate (570 mg, 2.29 mmol, 1.00 equiv), ethanol (20 mL), ethanethioamide (1.38 g, 18.35 mmol, 8.00 equiv). The resulting solution was stirred for 15 h at 80° C. The reaction was cooled to 20 degrees C. The resulting mixture was concentrated under vacuum. The residue was purified by preparative TLC (EA:PE=1:4). This resulted in 350 mg (68%) of ethyl 2-methyl-4,5,6,7-tetrahydro-1,3-benzothiazole-7-carboxylate as yellow oil. MS (ES, m/z) [M+H]$^+$: 226.

Step 3. 2-methyl-4,5,6,7-tetrahydrobenzo[d]thiazole-7-carboxylic Acid

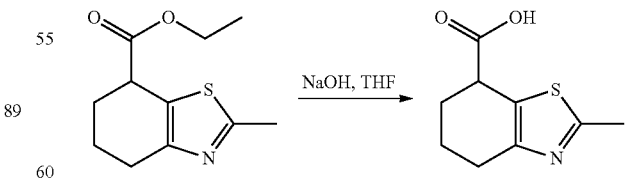

Into a 100-mL round-bottom flask, was placed ethyl 2-methyl-4,5,6,7-tetrahydro-1,3-benzothiazole-7-carboxylate (350 mg, 1.55 mmol, 1.00 equiv), methanol (10 mL), a solution of sodium hydroxide (1238 mg, 31.01 mmol, 20.00 equiv) in water (10 mL). The resulting solution was stirred overnight at 20° C. The resulting solution was extracted with ethyl acetate (20 mL×2) and the aqueous layers were collected. The pH value of the aqueous layers was adjusted to 5-6 with hydrochloric acid (6 mol/L). The resulting solution was extracted with ethyl acetate (50 mL×3) and the organic layers combined and concentrated under vacuum. This resulted in 215 mg (71%) of 2-methyl-4,5,6,7-tetrahydro-1,3-benzothiazole-7-carboxylic acid as a yellow solid. MS (ES, m/z) [M+H]$^+$: 198.

Step 4. (3-amino-4,5,6,7-tetrahydroindazol-2-yl)(2-methyl-4,5,6,7-tetrahydrobenzo[d]thiazol-7-yl)methanone

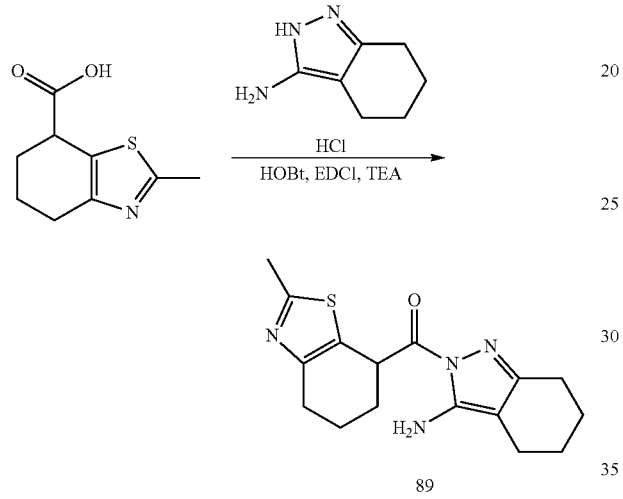

Into a 50-mL round-bottom flask, was placed 2-methyl-4,5,6,7-tetrahydro-1,3-benzothiazole-7-carboxylic acid (40 mg, 0.20 mmol, 1.00 equiv), 4,5,6,7-tetrahydro-2H-indazol-3-amine dihydrochloride (40 mg, 0.67 mmol, 1.00 equiv), HOBT (135 mg, 1.00 mmol, 1.50 equiv), EDCI (190 mg, 0.99 mmol, 1.50 equiv), TEA (200 mg, 1.98 mmol, 3.00 equiv), N,N-dimethylformamide (5 mL). The resulting solution was stirred overnight at room temperature. The reaction was then quenched by the addition of water (40 mL). The resulting solution was extracted with ethyl acetate (50 mL×3) and the organic layers combined. The resulting mixture was washed with brine (100 mL×3). The mixture was dried over anhydrous sodium sulfate. The solids were filtered out. The resulting mixture was concentrated under vacuum. The residue was purified by preparative TLC (DCM:MeOH=10:1). The product was purified by Prep-HPLC with the following conditions: Column: XBridge C18 OBD Prep Column, 100 A, 5 um, 19 mm×250 mm, Mobile Phase A: water (10 MMOL/L NH$_4$HCO$_3$), Mobile Phase B: ACN, Flow rate: 20 mL/min, Gradient: 34% B to 53% B in 7 min, 254 nm. The collected fraction was lyophilized to give 14.8 mg (23%) of 2-[(2-methyl-4,5,6,7-tetrahydro-1,3-benzothiazol-7-yl)carbonyl]-4,5,6,7-tetrahydro-2H-indazol-3-amine (89) as off-white solid. RT2: 7 min, MS (ES, m/z) [M+H]$^+$: 317, (DMSO-d$_6$, 400 MHz, ppm): δ 6.38 (s, 2H), 3.92-3.85 (m, 1H), 3.02-2.96 (m, 1H), 2.91-2.73 (m, 3H), 2.54 (s, 3H), 2.46-2.39 (m, 2H), 2.32-2.24 (m, 2H), 2.21-2.15 (m, 1H), 1.91-1.81 (m, 1H), 1.68-1.62 (m, 4H).

Example 90 & 91: (3-amino-4,5,6,7-tetrahydroindazol-2-yl)(2-methyl-1-(methylsulfonyl)-4,5,6,7-tetrahydro-1H-indol-4-yl)methanone (90) and (3-amino-4,5,6,7-tetrahydroindazol-1-yl)(2-methyl-1-(methylsulfonyl)-4,5,6,7-tetrahydro-1H-indol-4-yl)methanone (91)

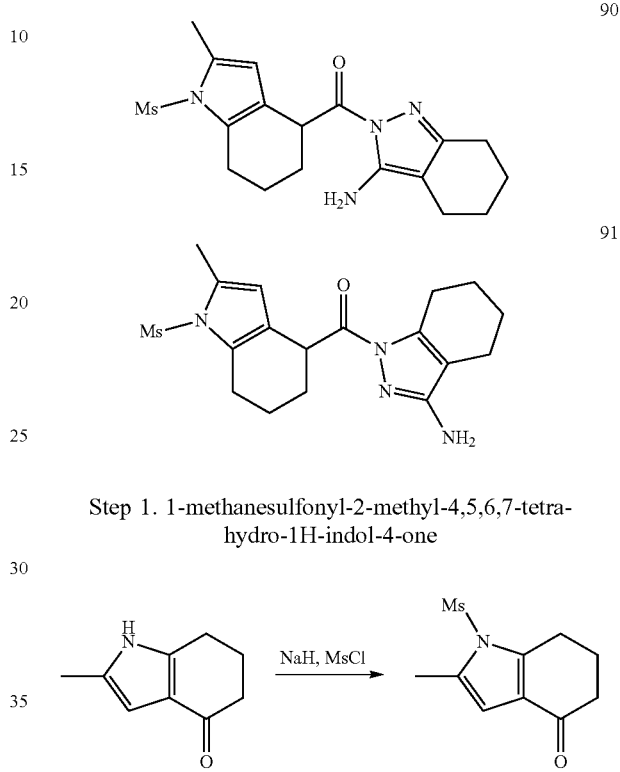

Step 1. 1-methanesulfonyl-2-methyl-4,5,6,7-tetrahydro-1H-indol-4-one

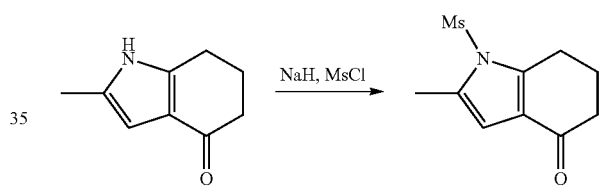

Into a 100-mL 3-necked round-bottom flask purged and maintained with an inert atmosphere of nitrogen, was placed 2-methyl-4,5,6,7-tetrahydro-1H-indol-4-one (3 g, 20.11 mmol, 1.00 equiv), N,N-dimethylformamide (30 mL), sodium hydride (1.2 g, 50.28 mmol, 1.50 equiv, 60%). This was followed by the addition of MsCl (2.75 g, 1.20 equiv), in portions at 0° C. The resulting solution was stirred overnight at 25° C. The reaction was then quenched by the addition of water/ice (40 mL). The resulting solution was extracted with dichloromethane (80 mL×4) and the organic layers combined. The residue was applied onto a silica gel column with ethyl acetate/petroleum ether (3/1). This resulted in 2.7 g (59%) of 1-methanesulfonyl-2-methyl-4,5,6,7-tetrahydro-1H-indol-4-one as a white solid. MS (ES, m/z) [M+1]: 228.

Step 2. 1-methanesulfonyl-2-methyl-4-[(trimethylsilyl)oxy]-4,5,6,7-tetrahydro-1H-indole-4-carbonitrile

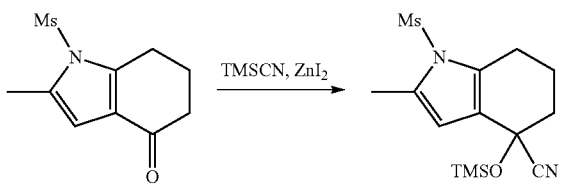

Into a 100-mL round-bottom flask, was placed 1-methanesulfonyl-2-methyl-4,5,6,7-tetrahydro-1H-indol-4-one (1.5 g, 6.60 mmol, 1.00 equiv), ACN (30 mL), TMSCN (6.51 g, 1.20 equiv), ZnI$_2$ (2.52 g, 7.89 mmol, 10.00 equiv). The resulting solution was stirred overnight at 25° C. The resulting solution was diluted with H$_2$O (40 mL). The resulting solution was extracted with ethyl acetate (80 mL×3) and the organic layers combined and concentrated under vacuum. This resulted in 1.5 g (70%) of 1-methanesulfonyl-2-methyl-4-[(trimethylsilyl)oxy]-4,5,6,7-tetrahydro-1H-indole-4-carbonitrile as a brown solid. MS (ES, m/z) [M+H]$^+$: 327.

Step 3. 1-methanesulfonyl-2-methyl-6,7-dihydro-1H-indole-4-carbonitrile

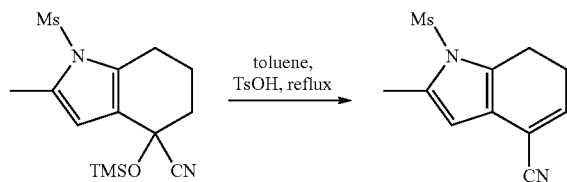

Into a 100-mL round-bottom flask, was placed 1-methanesulfonyl-2-methyl-4-[(trimethylsilyl)oxy]-4,5,6,7-tetrahydro-1H-indole-4-carbonitrile (1.5 g, 4.59 mmol, 1.00 equiv), TsOH (79 mg, 0.46 mmol, 0.10 equiv), methylbenzene (30 mL). The resulting solution was stirred for 1 h at 130° C. The resulting mixture was concentrated under vacuum. The residue was applied onto a silica gel column with ethyl acetate/petroleum ether (1/5). This resulted in 600 mg (55%) of 1-methanesulfonyl-2-methyl-6,7-dihydro-1H-indole-4-carbonitrile as yellow oil. MS (ES, m/z) [M+H]$^+$: 237.

Step 4. 1-methanesulfonyl-2-methyl-4,5,6,7-tetrahydro-1H-indole-4-carbonitrile

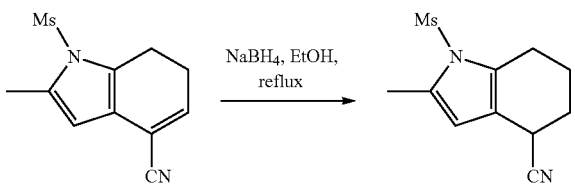 [SMILES: Cc1cc2c(n1S(C)(=O)=O)CCC=C2C#N ; Cc1cc2c(n1S(C)(=O)=O)CCCC2C#N]

Into a 100-mL round-bottom flask, was placed 1-methanesulfonyl-2-methyl-6,7-dihydro-1H-indole-4-carbonitrile (610 mg, 2.58 mmol, 1.00 equiv), ethanol (20 mL), NaBH$_3$ (491 mg, 5.00 equiv) was added at 0° C. The resulting solution was stirred for 4 h at 85° C. The reaction was then quenched by the addition of water (10 mL). The resulting solution was extracted with dichloromethane (80 mL×3) and the organic layers combined. The residue was applied onto a silica gel column with ethyl acetate/petroleum ether (1/1). This resulted in 500 mg (81%) of 1-methanesulfonyl-2-methyl-4,5,6,7-tetrahydro-1H-indole-4-carbonitrile as yellow oil. MS (ES, m/z) [M+H]$^+$: 239.

Step 5. methyl 1-methanesulfonyl-2-methyl-4,5,6,7-tetrahydro-1H-indole-4-carboxylate

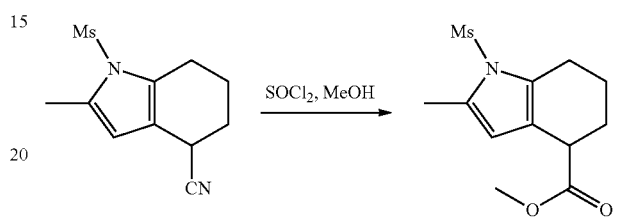

Into a 100-mL round-bottom flask, was placed 1-methanesulfonyl-2-methyl-4,5,6,7-tetrahydro-1H-indole-4-carbonitrile (500 mg, 2.10 mmol, 1.00 equiv), methanol (20 mL). This was followed by the addition of thionyl chloride (10 mL) dropwise with stirring at 0° C. The resulting solution was stirred for 4 h at 85° C. The resulting mixture was concentrated under vacuum. The residue was applied onto a silica gel column with ethyl acetate/petroleum ether (1/2). This resulted in 260 mg (46%) of methyl 1-methanesulfonyl-2-methyl-4,5,6,7-tetrahydro-1H-indole-4-carboxylate as white oil. MS (ES, m/z) [M+H]$^+$: 272.

Step 6. 1-methanesulfonyl-2-methyl-4,5,6,7-tetrahydro-1H-indole-4-carboxylic Acid

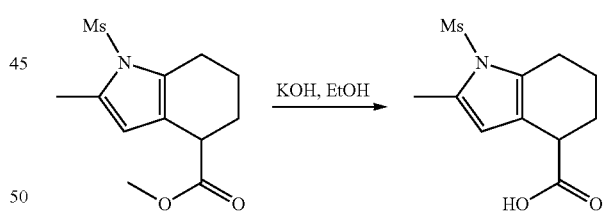

Into a 100-mL round-bottom flask, was placed methyl 1-methanesulfonyl-2-methyl-4,5,6,7-tetrahydro-1H-indole-4-carboxylate (160 mg, 0.59 mmol, 1.00 equiv), methanol (10 mL), water (2.5 mL), potassium hydroxide (330 mg, 5.88 mmol, 10.00 equiv). The resulting solution was stirred for 7 hours at 25° C. The resulting mixture was concentrated under vacuum. The resulting solution was diluted with of H$_2$O (30 mL). The resulting mixture was washed with DCM (80 mL×3). The pH value of the solution was adjusted to 4 with hydrogen chloride (6 mol/L). The resulting solution was extracted with dichloromethane (80 mL×3) and the organic layers combined. The organic phase was dried and concentrated to give 130 mg (86%) of 1-methanesulfonyl-2-methyl-4,5,6,7-tetrahydro-1H-indole-4-carboxylic acid as a pink solid. MS (ES, m/z) [M+H]$^+$: 258.

Step 7. (3-amino-4,5,6,7-tetrahydro-2H-indazol-2-yl)(2-methyl-1-(methylsulfonyl)-4,5,6,7-tetrahydro-1H-indol-4-yl)methanone and (3-amino-4,5,6,7-tetrahydro-1H-indazol-1-yl)(2-methyl-1-(methylsulfonyl)-4,5,6,7-tetrahydro-1H-indol-4-yl)methanone

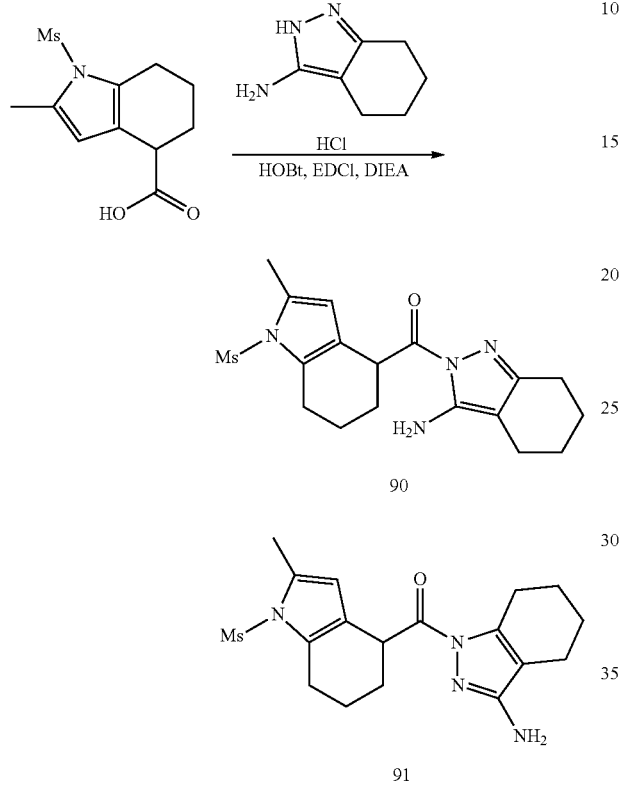

Into a 100-mL round-bottom flask, was placed 1-methanesulfonyl-2-methyl-4,5,6,7-tetrahydro-1H-indole-4-carboxylic acid (50 mg, 0.19 mmol, 1.00 equiv), 4,5,6,7-tetrahydro-2H-indazol-3-amine (60.1 mg, 0.44 mmol, 1.20 equiv), HOBT (39.5 mg, 0.29 mmol, 1.50 equiv), EDCT (56.3 mg, 0.29 mmol, 1.50 equiv), N,N-dimethylformamide (5 mL) and TEA (98.5 mg, 0.97 mmol, 5.00 equiv). The resulting solution was stirred for 12 h at room temperature. The resulting mixture was washed with water (20 mL×2). The resulting solution was extracted with ethyl acetate (50 mL×3) and the organic layers combined and dried over anhydrous sodium sulfate and concentrated under vacuum. The crude product was purified by Prep-HPLC with the following conditions: Column: XBridge C18 OBD Prep Column, 100 Å, 5 μm, 19 mm×250 mm, Mobile Phase A: Water (0.1% FA), Mobile Phase B: ACN, Flow rate: 20 mL/min, Gradient: 20% B to 45% B in 12 min, 254&220 nm. The collected fractions were lyophilized to give 8.9 g (12%) of (3-amino-4,5,6,7-tetrahydro-2H-indazol-2-yl)(2-methyl-1-(methylsulfonyl)-4,5,6,7-tetrahydro-1H-indol-4-yl)methanone (90) as a white solid. RT2: 10.5 min, MS (ES, m/z) [M+H]$^+$: 378, (DMSO-d$_6$, 400 MHz, ppm): δ 6.34 (s, 2H), 5.71 (s, 1H), 4.72-4.71 (m, 1H), 3.37-3.29 (m, 3H), 2.85 (s, 2H), 2.56-2.45 (m, 2H), 2.32-2.24 (m, 5H), 2.16-1.89 (m, 2H), 1.81-1.79 (m, 1H), 1.71-1.59 (m, 5H). And 3.3 g (5%) of (3-amino-4,5,6,7-tetrahydro-1H-indazol-1-yl)(2-methyl-1-(methylsulfonyl)-4,5,6,7-tetrahydro-1H-indol-4-yl)methanone (91) as a white solid. RT1: 7 min, MS (ES, m/z) [M+H]$^+$: 378, (DMSO-d$_6$, 400 MHz, ppm): δ 5.71 (s, 1H), 5.50 (s, 2H), 4.62 (s, 1H), 3.38-3.29 (m, 3H), 2.79-2.72 (m, 2H), 2.67 (s, 2H), 2.32-2.27 (m, 3H), 2.39-2.23 (m, 2H), 1.95-1.90 (m, 2H), 1.80-1.78 (d, 1H), 1.76 (d, 5H).

Examples 92, 93, 94 and 95: (3-amino-4,5,6,7-tetrahydroindazol-2-yl)(4,5,6,7-tetrahydro-1H-indol-4-yl)methanone (92) and (3-amino-4,5,6,7-tetrahydroindazol-1-yl)(4,5,6,7-tetrahydro-1H-indol-4-yl)methanone (93) and (S*)-(3-amino-4,5,6,7-tetrahydroindazol-2-yl)(4,5,6,7-tetrahydro-1H-indol-4-yl)methanone (94) and (R*)-(3-amino-4,5,6,7-tetrahydroindazol-2-yl)(4,5,6,7-tetrahydro-1H-indol-4-yl)methanone (95)

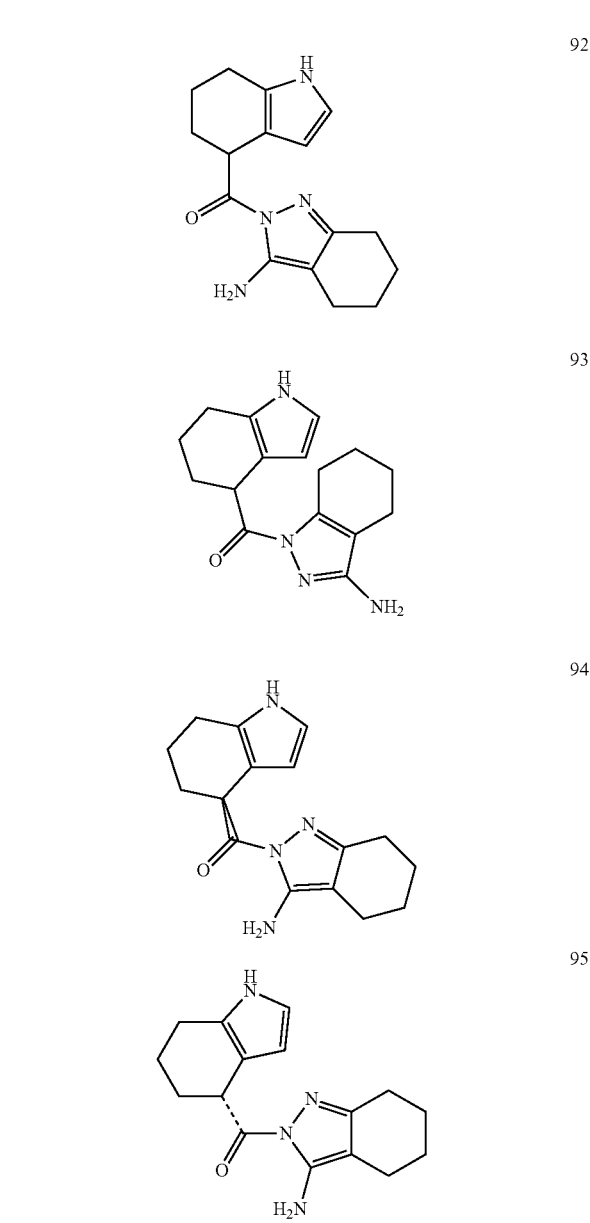

Step 1. (3-amino-4,5,6,7-tetrahydroindazol-2-yl)(4,5,6,7-tetrahydro-1H-indol-4-yl)methanone and (3-amino-4,5,6,7-tetrahydroindazol-1-yl)(4,5,6,7-tetrahydro-1H-indol-4-yl)methanone Step 2. (S*)-(3-amino-4,5,6,7-tetrahydroindazol-2-yl)(4,5,6,7-tetrahydro-1H-indol-4-yl)methanone (94) and (R*)-(3-amino-4,5,6,7-tetrahydroindazol-2-yl)(4,5,6,7-tetrahydro-1H-indol-4-yl)methanone (95)

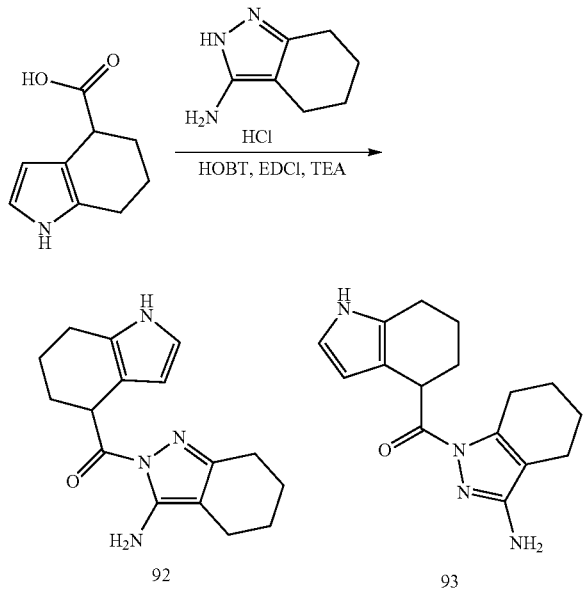

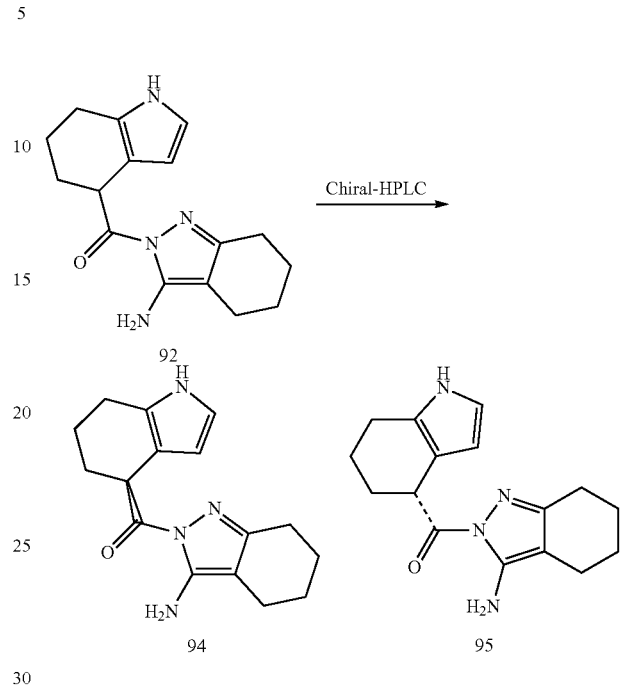

Into a 40-mL vial, was placed a solution of 4,5,6,7-tetrahydro-1H-indole-4-carboxylic acid (80 mg, 0.48 mmol, 1.00 equiv) in N,N-dimethylformamide (10 mL), 4,5,6,7-tetrahydro-2H-indazol-3-amine dihydrochloride (100 mg, 0.58 mmol, 1.20 equiv), HOBT (98 mg, 0.73 mmol, 1.50 equiv), EDCI (139 mg, 0.73 mmol, 1.50 equiv), TEA (245 mg, 2.43 mmol, 5.00 equiv). The resulting solution was stirred for 18 h at 25° C. The resulting solution was diluted with H$_2$O (50 mL). The resulting solution was extracted with ethyl acetate (50 mL×4) and the organic layers combined. The resulting mixture was washed with brine (200 mL×2). The mixture was dried over anhydrous sodium sulfate. The solids were filtered out. The filtrate was concentrated under vacuum. The crude product was purified by Prep-HPLC with the following conditions: Column, XSelect CSH Prep C18 OBD Column, 5 um, 19×150 mm, mobile phase, water (0.1% FA) and ACN (35.0% ACN up to 60.0% in 7 min), Detector, UV 254 220 nm. The collected fractions were lyophilized to give 3.4 mg (2%) of (3-amino-4,5,6,7-tetrahydroindazol-2-yl)(4,5,6,7-tetrahydro-1H-indol-4-yl)methanone (92) as an off-white solid. RT2: 6.85 min, MS (ES, m/z) [M+H]$^+$: 285, (DMSO-d$_6$, 400 MHz, ppm): δ 10.36 (s, 1H), 6.46-6.45 (m, 1H), 6.30 (s, 2H), 5.59-5.58 (m, 1H), 4.79-4.75 (m, 1H), 2.50-2.46 (m, 4H), 2.28-2.25 (m, 2H), 2.02-1.81 (m, 3H), 1.70 (s, 5H). And 12.8 mg (9%) of (3-amino-4,5,6,7-tetrahydroindazol-1-yl)(4,5,6,7-tetrahydro-1H-indol-4-yl)methanone (93) as an off-white solid. RT1: 5.25 min, MS (ES, m/z) [M+H]$^+$: 285, (DMSO-d$_6$, 400 MHz, ppm): δ 10.31 (s, 1H), 6.45-6.44 (m, 1H), 5.60-5.59 (m, 1H), 5.43 (s, 2H), 4.71-4.68 (m, 1H), 2.79-2.73 (m, 2H), 2.50 (s, 2H), 2.24 (s, 2H), 2.01-1.97 (m, 1H), 1.92-1.78 (m, 2H), 1.67-1.66 (m, 5H).

2-[(4,5,6,7-tetrahydro-1H-indol-4-yl)carbonyl]-4,5,6,7-tetrahydro-2H-indazol-3-amine was separated by Chiral-Prep-HPLC with the following conditions: Column. CHIRALPAK-IB, 20×250 mm, mobile phase, Hex and EtOH (hold 36% EtOH in 16.5 min), Detector, UV 220/254 nm.

Enantiomer A: 13.9 mg (10%) of (S*)-(3-amino-4,5,6,7-tetrahydroindazol-2-yl)(4,5,6,7-tetrahydro-1H-indol-4-yl)methanone (94) as an off-white solid. RT2: 13.25 min, MS (ES, m/z) [M+H]$^+$: 285, (DMSO-d$_6$, 400 MHz, ppm): δ 10.36 (s, 1H), 6.46-6.45 (m, 1H), 6.30 (s, 2H), 5.59-5.58 (m, 1H), 4.79-4.75 (m, 1H), 2.51-2.46 (m, 4H), 2.28-2.25 (m, 2H), 2.02-1.81 (m, 3H), 1.70 (s, 5H).

Enantiomer B: 16.0 mg (12%) of (R*)-(3-amino-4,5,6,7-tetrahydroindazol-2-yl)(4,5,6,7-tetrahydro-1H-indol-4-yl)methanone (95) as an off-white solid. RT1: 9.24 min, MS (ES, m/z) [M+H]$^+$: 285, (DMSO-d$_6$, 400 MHz, ppm): δ 10.36 (s, 1H), 6.46-6.45 (m, 1H), 6.30 (s, 2H), 5.59-5.58 (m, 1H), 4.79-4.76 (m, 1H), 2.50-2.46 (m, 4H), 2.28-2.25 (m, 2H), 2.02-1.85 (m, 3H), 1.70 (s, 5H).

Example 96, 97 and 98: (3-amino-4,5,6,7-tetrahydroindazol-2-yl)(1-methyl-4,5,6,7-tetrahydro-1H-indol-4-yl)methanone (96) and (S*)-(3-amino-4,5,6,7-tetrahydroindazol-2-yl)(1-methyl-4,5,6,7-tetrahydro-1H-indol-4-yl)methanone (97) and (R*)-(3-amino-4,5,6,7-tetrahydroindazol-2-yl)(1-methyl-4,5,6,7-tetrahydro-1H-indol-4-yl)methanone (98)

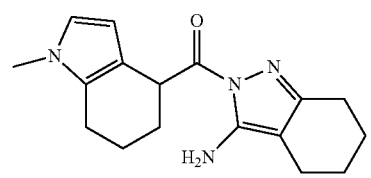

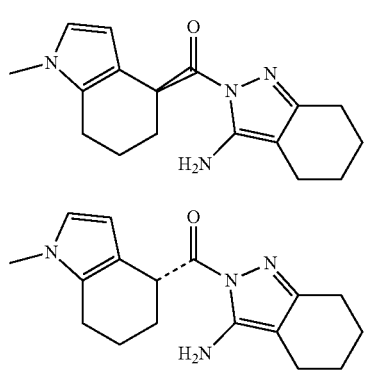

97

98

Step 1. tert-butyl 2-formyl-1H-pyrrole-1-carboxylate

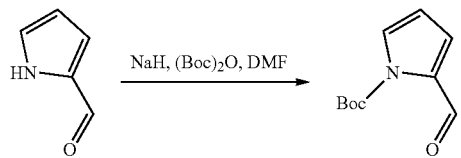

Into a 100-mL 3-necked round-bottom flask, was placed 1H-pyrrole-2-carbaldehyde (2.5 g, 26.29 mmol, 1.00 equiv), N,N-dimethylformamide (50 mL). This was followed by the addition of sodium hydride (1.58 g, 65.72 mmol, 1.50 equiv, 60% in oil) at 5° C. After 10 min, a solution of (Boc)$_2$O (6.3 g, 28.87 mmol, 1.10 equiv) in N,N-dimethylformamide (10 mL) was added with dropwise. The resulting solution was stirred overnight at 20° C. The reaction mixture was then poured into water/ice (150 mL). The resulting solution was extracted with ethyl acetate (100 mL×3) and the organic layers combined. The resulting mixture was washed with brine (200 mL×3), dried over anhydrous sodium sulfate and concentrated to give in 4.0 g (78%) of tert-butyl 2-formyl-1H-pyrrole-1-carboxylate as a yellow solid. MS: (ES, m/z) [M+H]+:196.

Step 2. tert-butyl 2-vinyl-1H-pyrrole-1-carboxylate

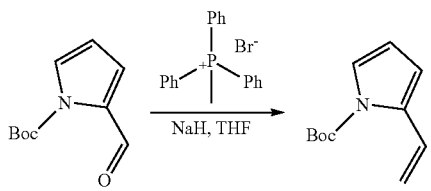

Into a 100-mL 3-necked round-bottom flask, was placed sodium hydride (742 mg, 30.90 mmol, 1.20 equiv, 60% in oil) in dry THF (20 mL), methyltriphenyl bromide phosphanium (5.5 g, 15.45 mmol, 1.0 equiv). The resulting mixture was heated to 70° C. for 1 h. To the above was added a solution of tert-butyl 2-formyl-1H-pyrrole-1-carboxylate (3.0 g, 15.37 mmol, 1.0 equiv) in dry THF (10 ml) at 35° C. The resulting mixture was heated to 70° C. for 3 h. The reaction mixture was cooled to room temperature and filtered, and the clear yellow filtrate was concentrated under vacuum to give a light yellow semi-solid residue which is taken up in petroleum ether and filtered through a cake of diatomaceous earth on neutral alumina. This resulted in 2.5 g (84%) of tert-butyl 2-ethenyl-1H-pyrrole-1-carboxylate as reddish crude oil. MS: (ES, m/z) [M+H]+:194.

Step 3. 1-tert-butyl 4-methyl 4,5,6,7-tetrahydroindole-1,4-dicarboxylate

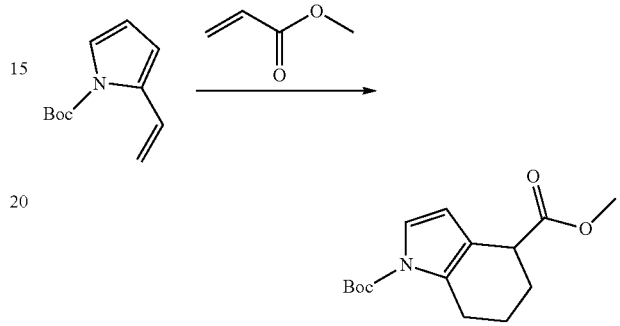

Into a 100-mL round-bottom flask, was placed tert-butyl 2-ethenyl-1H-pyrrole-1-carboxylate (8.41 g, 43.52 mmol, 1.00 equiv), methyl prop-2-enoate (7.49 g, 87.00 mmol, 2.00 equiv). The resulting solution was stirred for 3.0 h at 80° C. The reaction mixture was cooled to 25° C. and then concentrated under vacuum. The residue was applied onto a silica gel column and eluted with ethyl acetate/petroleum ether (0-4%). The collected fraction was concentrated to give 0.902 g (7.4%) of 1-tert-butyl 4-methyl 4,5,6,7-tetrahydro-1H-indole-1,4-dicarboxylate as light yellow oil. MS: (ES, m/z) [M+H]+:280.

Step 4. Methyl 4,5,6,7-tetrahydro-1H-indole-4-carboxylate

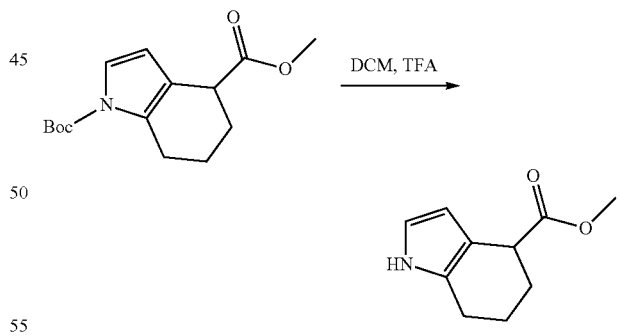

Into a 50-mL round-bottom flask, was placed a solution of 1-tert-butyl 4-methyl 4,5,6,7-tetrahydro-1H-indole-1,4-dicarboxylate (600 mg, 2.15 mmol, 1.00 equiv) in dichloromethane (15 mL) and CF$_3$COOH (3 mL). The resulting solution was stirred for 1.5 h at 25° C. The reaction was then poured into 50 mL of sat. NaHCO$_3$. The resulting solution was extracted with dichloromethane (50 mL×3) and the organic layers combined. The resulting mixture was washed with brine (200 mL), dried over anhydrous sodium sulfate and concentrated under vacuum. The residue was applied onto a silica gel column and eluted with MeOH/CH$_2$Cl$_2$ (0-5%). The collected fraction was concentrated to give 100 mg (26%) of methyl 4,5,6,7-tetrahydro-1H-indole-4-carboxylate as light yellow oil. MS: (ES, m/z) [M+H]+: 180.

Step 5. methyl 1-methyl-4,5,6,7-tetrahydro-1H-indole-4-carboxylate

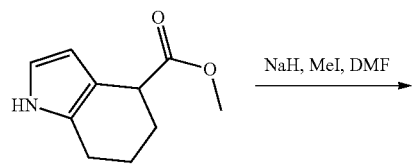

Into a 50-mL round-bottom flask purged and maintained with an inert atmosphere of nitrogen, was placed methyl 4,5,6,7-tetrahydro-1H-indole-4-carboxylate (70 mg, 0.39 mmol, 1.00 equiv), N,N-dimethylformamide (4 mL), sodium hydride (18.0 mg, 0.78 mmol, 1.20 equiv, 60% in oil). This was followed by the addition of MeI (61 mg, 1.10 equiv) dropwise with stirring at 0° C. The resulting solution was stirred for 4 h at 25° C. The reaction was then quenched by the addition of water/ice (15 mL). The resulting solution was extracted with ethyl acetate (30 mL×2) and the organic layers combined. The resulting mixture was washed with saturated brine (60 mL×2). The mixture was dried over anhydrous sodium sulfate. The solids were filtered out. This resulted in 65 mg (86%) of methyl 1-methyl-4,5,6,7-tetrahydro-1H-indole-4-carboxylate as yellow oil. (ES, m/z) [M+H]+: 194.

Step 6. 1-methyl-4,5,6,7-tetrahydro-1H-indole-4-carboxylic Acid

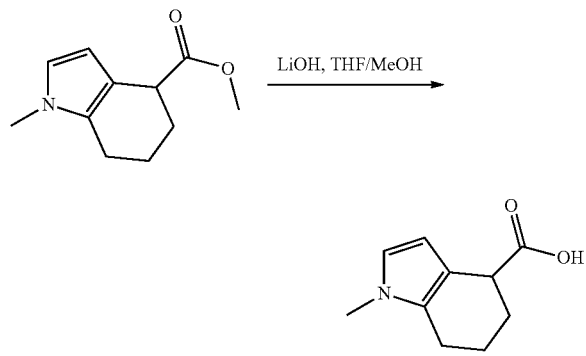

Into a 50-mL round-bottom flask, was placed methyl 1-methyl-4,5,6,7-tetrahydro-1H-indole-4-carboxylate (65 mg, 0.34 mmol, 1.00 equiv), methanol (2 mL), tetrahydrofuran (8 mL), a solution of LiOH (48.5 mg, 2.03 mmol, 6.00 equiv) in H$_2$O (3 mL). The resulting solution was stirred overnight at 20° C. The resulting mixture was concentrated under vacuum. The resulting solution was extracted with ethyl acetate (30 mL) and the aqueous layers combined. Hydrochloric acid (1 mol/L) was employed to adjust the pH to 6. The resulting solution was extracted with ethyl acetate (40 mL×2) and the organic layers combined and dried over anhydrous sodium sulfate. The solids were filtered out. This resulted in 45 mg (75%) of 1-methyl-4,5,6,7-tetrahydro-1H-indole-4-carboxylic acid as a light yellow solid. (ES, m/z) [M+H]+: 180.

Step 7. (3-amino-4,5,6,7-tetrahydroindazol-2-yl)(1-methyl-4,5,6,7-tetrahydro-1H-indol-4-yl)methanone

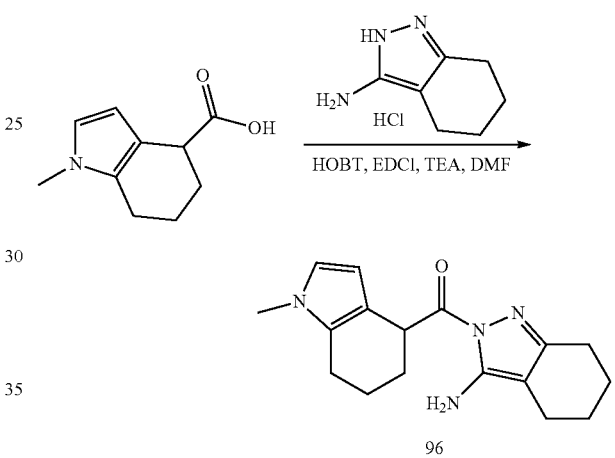

Into a 10-mL vial, was placed 1-methyl-4,5,6,7-tetrahydro-1H-indole-4-carboxylic acid (45 mg, 0.25 mmol, 1.00 equiv), HOBT (50.9 mg, 0.38 mmol, 1.50 equiv), N,N-dimethylformamide (4 mL), EDCI (72.4 mg, 0.38 mmol, 1.50 equiv), TEA (126.9 mg, 1.25 mmol, 5.00 equiv), 4,5,6,7-tetrahydro-2H-indazol-3-amine hydrochloride (65.2 mg, 0.38 mmol, 1.50 equiv). The resulting solution was stirred overnight at 20° C. The resulting solution was diluted with EA (80 mL). The resulting mixture was washed with saturated brine (120 mL×2). The mixture was dried over anhydrous sodium sulfate. The solids were filtered out. The filtrate was concentrated under vacuum. The crude product was purified by Prep-HPLC with the following conditions: Column, XBridge Shield RP18 OBD Column, 5 um, 19×150 mm, mobile phase, water (0.1% FA) and ACN (40.0% ACN up to 65.0% in 7 min), Detector, UV 254 nm. The collected fractions were lyophilized to give 10 mg (13%) of (3-amino-4,5,6,7-tetrahydroindazol-2-yl)(1-methyl-4,5,6,7-tetrahydro-1H-indol-4-yl)methanone (96) as a pink solid. RT2: 6.8 min, MS (ES, m/z) [M+H]+: 299, (CDCL$_3$, 400 MHz, ppm): δ 6.49 (s, 1H), 5.85 (s, 1H), 4.96-4.91 (m, 1H), 3.47 (s, 3H), 2.68-2.65 (m, 2H), 2.59-2.49 (m, 2H), 2.31-2.27 (m, 2H), 2.19-2.11 (m, 1H), 2.09-1.98 (m, 2H), 1.91- 1.84 (m, 1H), 1.80-1.74 (m, 4H).

Step 4. (S*)-(3-amino-4,5,6,7-tetrahydroindazol-2-yl)(1-methyl-4,5,6,7-tetrahydro-1H-indol-4-yl)methanone and (R*)-(3-amino-4,5,6,7-tetrahydroindazol-2-yl)(1-methyl-4,5,6,7-tetrahydro-1H-indol-4-yl)methanone

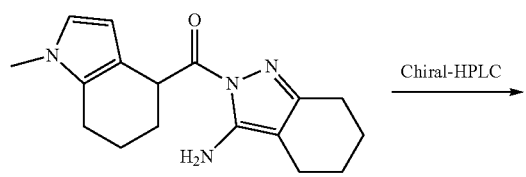

96

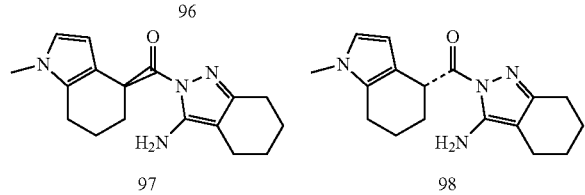

97    98

Into a 100-mL round-bottom flask, was placed 2-[(1-methyl-4,5,6,7-tetrahydro-1H-indol-4-yl)carbonyl]-4,5,6,7-tetrahydro-2H-indazol-3-amine (10 mg, 0.03 mmol, 1.00 equiv). Prep-CHIRAL-HPLC: Column: Chiralpak IB, 2×25 cm, 5 um, Mobile Phase A: Hex-HPLC, Mobile Phase B: EtOH-HPLC, Flow rate: 20 mL/min, Gradient: 30 B to 30 B in 12.5 min, 220/254 nm, The collected fractions were concentrated under vacuum at low temperature.

Enantiomer A: 4.3 mg (43%) of (S*)-(3-amino-4,5,6,7-tetrahydroindazol-2-yl)(1-methyl-4,5,6,7-tetrahydro-1H-indol-4-yl)methanone (97) as a pink solid. RT2: 10.83 min, (ES, m/z) [M+H]$^+$: 299, (CDCL$_3$, 400 MHz, ppm): δ 6.49 (s, 1H), 5.85 (s, 1H), 4.96-4.91 (m, 1H), 3.47 (s, 3H), 2.68-2.65 (m, 2H), 2.59-2.49 (m, 2H), 2.31-2.27 (m, 2H), 2.19-2.11 (m, 1H), 2.09-1.98 (m, 2H), 1.91-1.84 (m, 1H), 1.80-1.74 (m, 4H).

Enantiomer B: 3.8 mg (38%) of (R*)-(3-amino-4,5,6,7-tetrahydroindazol-2-yl)(1-methyl-4,5,6,7-tetrahydro-1H-indol-4-yl)methanone (98) as a pink solid. RT1: 6.43 min, MS (ES, m/z) [M+H]$^+$: 299, (CDCL$_3$, 400 MHz, ppm): δ 6.49 (s, 1H), 5.85 (s, 1H), 4.96-4.91 (m, 1H), 3.47 (s, 3H), 2.68-2.65 (m, 2H), 2.59-2.49 (m, 2H), 2.31-2.27 (m, 2H), 2.19-2.11 (m, 1H), 2.09-1.98 (m, 2H), 1.90-1.83 (m, 1H), 1.80-1.74 (m, 4H).

Example 99 and 100: (3-amino-4,5,6,7-tetrahydroindazol-2-yl)(1-(methylsulfonyl)-1,2,3,4-tetrahydroquinolin-4-yl)methanone and (3-amino-4,5,6,7-tetrahydroindazol-1-yl)(1-(methylsulfonyl)-1,2,3,4-tetrahydroquinolin-4-yl)methanone

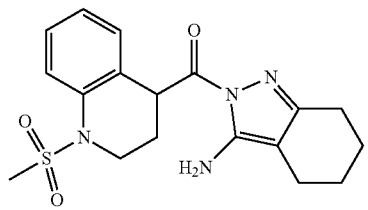

99

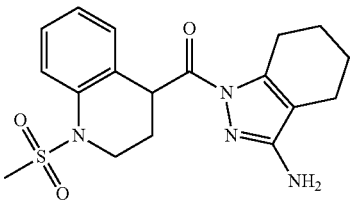

100

Step 1. Methyl quinoline-4-carboxylate

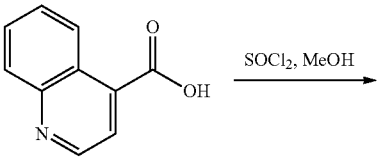

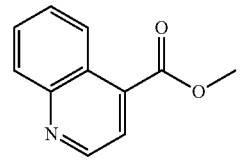

Into a 100-mL round-bottom flask purged and maintained with an inert atmosphere of nitrogen, was placed quinoline-4-carboxylic acid (1 g, 5.77 mmol, 1.00 equiv), methanol (25 mL), thionyl chloride (1.38 g, 2.00 equiv) was added at 0° C. The resulting solution was stirred overnight at 60° C. After cooled to room temperature, the resulting mixture was concentrated under vacuum. This resulted in 1 g (93%) of methyl quinoline-4-carboxylate as yellow oil. MS: (ES, m/z) [M+H]$^+$: 188.

Step 2. Methyl 1,2,3,4-tetrahydroquinoline-4-carboxylate

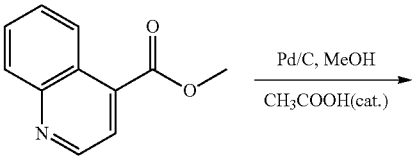

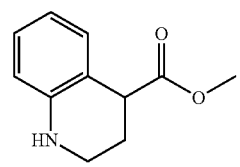

Into a 100-mL round-bottom flask purged and maintained with an inert atmosphere of H$_2$, was placed methyl quinoline-4-carboxylate (2 g, 10.68 mmol, 1.00 equiv), Palladium carbon (2 g), methanol (15 mL), acetic acid (5 mL). The resulting solution was stirred for 1 h at room temperature. The solids were filtered out. The resulting mixture was concentrated under vacuum. This resulted in 2 g (98%) of methyl 1,2,3,4-tetrahydroquinoline-4-carboxylate as yellow oil. MS (ES, m/z) [M+H]$^+$: 180.

Step 3. Methyl 1-methanesulfonyl-1,2,3,4-tetrahydroquinoline-4-carboxylate

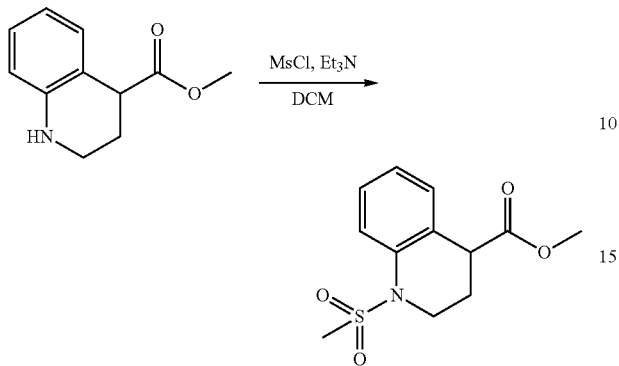

Into a 100-mL round-bottom flask, was placed methyl 1,2,3,4-tetrahydroquinoline-4-carboxylate (1.4 g, 7.32 mmol, 1.00 equiv), dichloromethane (18 mL), TEA (2.22 g, 21.94 mmol, 3.00 equiv), MsCl (1 g, 1.20 equiv) was added at 0° C. The resulting solution was stirred for 3 h at room temperature. The resulting solution was diluted with H$_2$O (20 mL). The resulting solution was extracted with dichloromethane (150 mL×2) and the organic layers combined and concentrated under vacuum. The residue was applied onto a silica gel column with ethyl acetate/petroleum ether (1/2). This resulted in 400 mg (20%) of methyl 1-methanesulfonyl-1,2,3,4-tetrahydroquinoline-4-carboxylate as yellow oil. MS (ES, m/z) [M+H]$^+$: 270.

Step 4. 1-methanesulfonyl-1,2,3,4-tetrahydroquinoline-4-carboxylic Acid

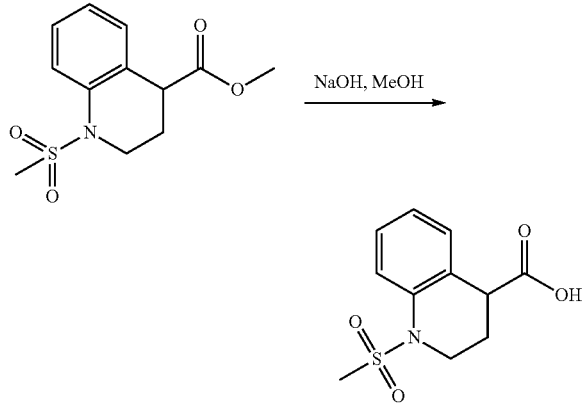

Into a 100-mL round-bottom flask, was placed methyl 1-methanesulfonyl-1,2,3,4-tetrahydroquinoline-4-carboxylate (240 mg, 0.89 mmol, 1.00 equiv), LiOH (107 mg, 4.47 mmol, 5.00 equiv), tetrahydrofuran (2.5 mL), methanol (2.5 mL), tetrahydrofuran (10 mL). The resulting solution was stirred overnight at room temperature (20° C.). The resulting solution was diluted with H$_2$O (30 mL). The resulting mixture was washed with DCM (60 mL×2). The pH value of the solution was adjusted to 5-6 with hydrogen chloride (1 mol/L). The resulting solution was extracted with dichloromethane (60 mL×4) and the organic layers combined and dried over anhydrous sodium sulfate. The solids were filtered out. The resulting mixture was concentrated under vacuum. This resulted in 200 mg (88%) of 1-methanesulfonyl-1,2,3,4-tetrahydroquinoline-4-carboxylic acid as yellow oil. MS: (ES, m/z): 256 [M+H]$^+$.

Step 5. (3-amino-4,5,6,7-tetrahydroindazol-2-yl)(1-(methylsulfonyl)-1,2,3,4-tetrahydroquinolin-4-yl)methanone and (3-amino-4,5,6,7-tetrahydroindazol-1-yl)(1-(methylsulfonyl)-1,2,3,4-tetrahydroquinolin-4-yl)methanone

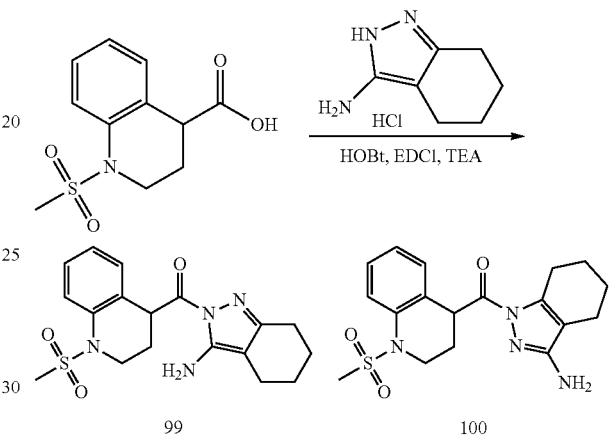

Into a 50-mL round-bottom flask, was placed 1-methanesulfonyl-1,2,3,4-tetrahydroquinoline-4-carboxylic acid (75 mg, 0.29 mmol, 1.00 equiv), HOBt (57 mg, 0.42 mmol, 1.50 equiv), EDCI (81 mg, 0.42 mmol, 1.50 equiv), dichloromethane (5 mL), TEA (85 mg, 0.84 mmol, 3.00 equiv). The mixture was stirred for 30 min. 4,5,6,7-tetrahydro-2H-indazol-3-amine hydrochloride (60.6 mg, 0.35 mmol, 1.20 equiv) was added. The resulting solution was stirred overnight at room temperature. The resulting solution was stirred overnight at 25° C. The reaction mixture was diluted with DCM (80 mL), washed with H$_2$O (50 mL×3) and brine (50 mL×3) and dried with Na$_2$SO$_4$. After filtration, the filtrate was concentrated under reduced pressure. The crude product was purified by Prep-HPLC with the following conditions: Column, XSelect CSH Prep C18 OBD Column, 5 um, 19×150 mm, mobile phase, water (0.1% FA) and ACN (35.0% ACN up to 70.0% in 7 min), Detector, UV 254 220 nm. The collected fractions were lyophilized to give 15.4 mg (14%) of (3-amino-4,5,6,7-tetrahydroindazol-2-yl)(1-(methylsulfonyl)-1,2,3,4-tetrahydroquinolin-4-yl)methanone (99) as a white solid. RT2: 6.59 min, MS (ES, m/z) [M+H]$^+$: 375, (300 MHz, DMSO-d$_6$, ppm): δ 7.63 (d, J=8.1 Hz, 1H), 7.26-7.25 (m, 1H), 7.10-7.08 (m, 2H) 6.41 (s, 2H), 5.23-5.21 (m, 1H), 3.80-3.76 (m, 2H), 3.08 (s, 3H), 2.51-2.50 (m, 2H), 2.27-2.20 (m, 4H), 1.67-1.65 (m, 4H). And 32.4 mg (29%) of (3-amino-4,5,6,7-tetrahydroindazol-1-yl)(1-(methylsulfonyl)-1,2,3,4-tetrahydroquinolin-4-yl)methanone (100) as a white solid. RT1: 5.87 min, MS (ES, m/z) [M+H]$^+$: 375, (300 MHz, DMSO-d$_6$, ppm): δ 7.62 (d, J=8.1 Hz, 1H), 7.24-7.23 (m, 1H), 7.09-7.07 (m, 2H), 5.62 (s, 2H), 5.15-5.11 (m, 1H), 3.80-3.75 (m, 2H), 3.08 (s, 3H), 2.80 (s, 2H), 2.52-2.18 (m, 4H), 1.67-1.66 (m, 4H).

Example 101 and 102: (3-amino-4,5,6,7-tetrahydroindazol-2-yl)(7-methyl-1,2,3,4-tetrahydroquinolin-4-yl)methanone (101) and (3-amino-4,5,6,7-tetrahydroindazol-1-yl)(7-methyl-1,2,3,4-tetrahydroquinolin-4-yl)methanone (102)

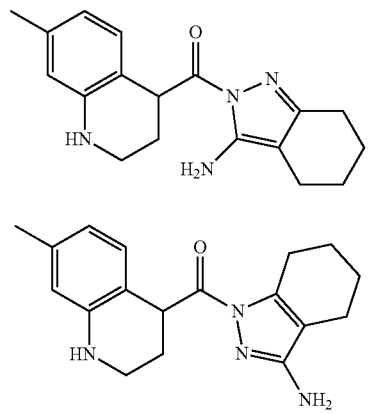

Step 1. Methyl 7-hydroxyquinoline-4-carboxylate

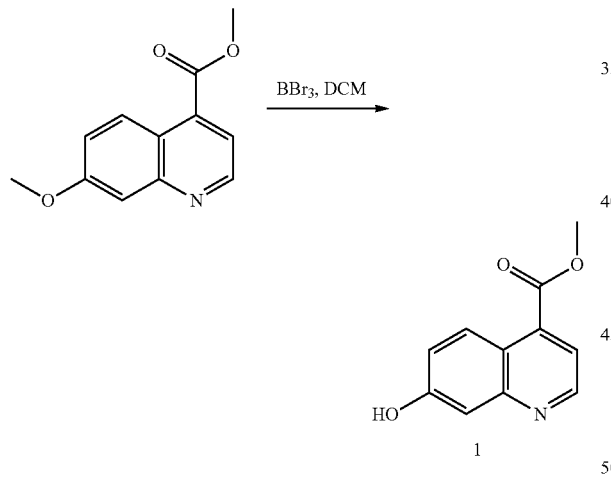

Into a 250-mL 3-necked round-bottom flask purged and maintained with an inert atmosphere of nitrogen, was placed methyl 7-methoxyquinoline-4-carboxylate (1.5 g, 6.91 mmol, 1.00 equiv), dichloromethane (30 mL). This was followed by the addition of BBr$_3$ in DCM (1M) (34.56 mL, 5.00 equiv) dropwise with stirring at 0° C. The resulting solution was stirred for 16 h at 25° C. The reaction progress was monitored by LCMS. The reaction was then quenched by the addition of water/ice (100 mL). The pH value of the solution was adjusted to 7-8 with hydrochloric acid (1 mol/L). The resulting solution was extracted with dichloromethane (50 mL×3), dried over anhydrous sodium sulfate and concentrated under vacuum. This resulted in 200 mg (14%) of methyl 7-hydroxyquinoline-4-carboxylate as an off-white solid. MS (ES, m/z) [M+H]$^+$: 204.

Step 2. Methyl 7-(trifluoromethylsulfonyloxy)quinoline-4-carboxylate

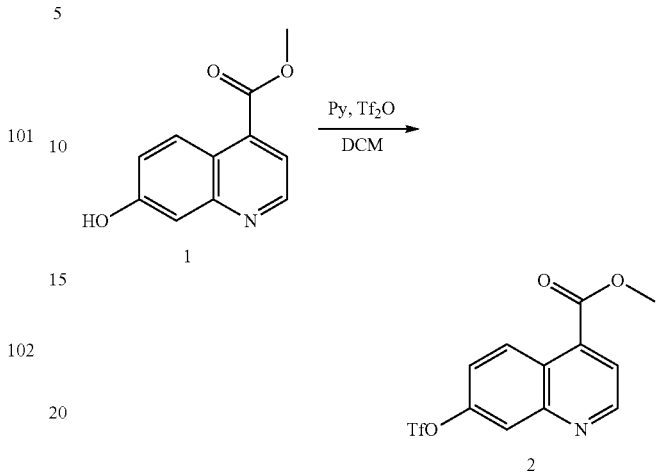

Into a 50-mL 3-necked round-bottom flask purged and maintained with an inert atmosphere of nitrogen, was placed methyl 7-hydroxyquinoline-4-carboxylate (200 mg, 0.98 mmol, 1.00 equiv), pyridine (5 mL), triethylamine (497.5 mg, 4.92 mmol, 5.00 equiv), 4-dimethylaminopyridine (2 mg, 0.02 mmol, 0.01 equiv). This was followed by the addition of (Tf)$_2$O (416.7 mg, 1.50 equiv) dropwise with stirring at 0° C. The resulting solution was stirred for 16 h at 25° C. The reaction progress was monitored by LCMS. The resulting mixture was concentrated under vacuum. The residue was applied onto a silica gel column with ethyl acetate/petroleum ether (1:4). This resulted in 225 mg (68%) of methyl 7-[(trifluoromethane)sulfonyloxy]quinoline-4-carboxylate as a light yellow solid. MS (ES, m/z) [M+H]$^+$: 336.

Step 3. Methyl 7-methylquinoline-4-carboxylate

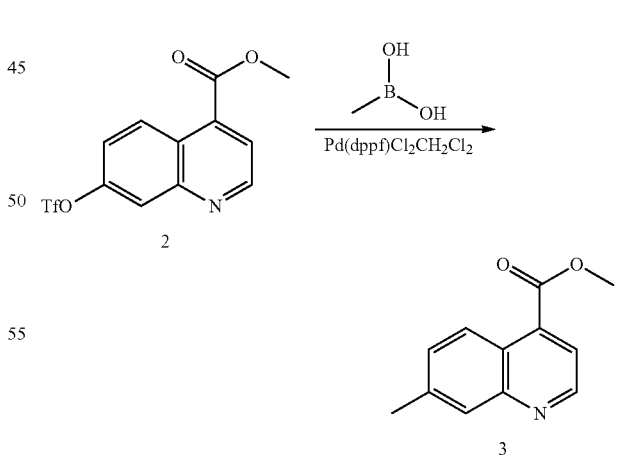

Into a 50-mL round-bottom flask purged and maintained with an inert atmosphere of nitrogen, was placed methyl 7-[(trifluoromethane)sulfonyloxy]quinoline-4-carboxylate (393 mg, 1.17 mmol, 1.00 equiv), 1,4-dioxane:H$_2$O=4:1 (5 mL), methylboronic acid (105.6 mg, 1.76 mmol, 1.50 equiv), potassium carbonate (485.7 mg, 3.51 mmol, 3.00 equiv), Pd(dppf)Cl$_2$.CH$_2$Cl$_2$ (95.8 mg, 0.10 equiv). The resulting solution was stirred for 16 h at 80° C. The reaction progress was monitored by LCMS. The reaction mixture was cooled to 25 degree C. with a water bath. The solids were filtered out. The resulting mixture was concentrated under vacuum. The residue was applied onto a silica gel column with ethyl acetate/petroleum ether (1:3). This resulted in 143 mg (61%) of methyl 7-methylquinoline-4-carboxylate as a light yellow solid. MS (ES, m/z) [M+H]$^+$: 202.

Step 4. Methyl 7-methyl-1,2,3,4-tetrahydroquinoline-4-carboxylate

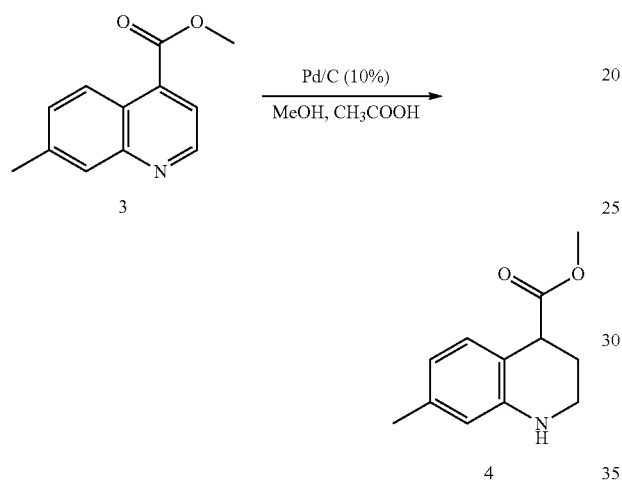

Into a 25-mL round-bottom flask, was placed methyl 7-methylquinoline-4-carboxylate (143 mg, 0.71 mmol, 1.00 equiv), methanol:HOAc=10:1 (3.3 mL), Palladium carbon (10%) (14 mg). H$_2$ (g) was introduced in. The resulting solution was stirred for 16 h at 25° C. The reaction progress was monitored by LCMS. The resulting solution was diluted with methanol (20 mL). The solids were filtered out. The resulting mixture was concentrated under vacuum. This resulted in 140 mg (crude) of methyl 7-methyl-1,2,3,4-tetrahydroquinoline-4-carboxylate as light yellow oil. MS (ES, m/z) [M+H]$^+$: 206.

Step 5. 7-methyl-1,2,3,4-tetrahydroquinoline-4-carboxylic Acid

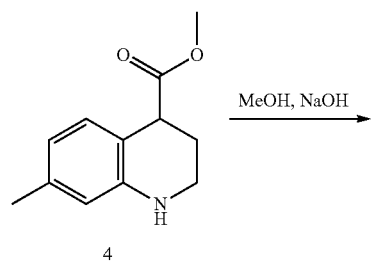

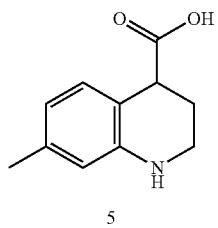

Into a 25-mL round-bottom flask, was placed methyl 7-methyl-1,2,3,4-tetrahydroquinoline-4-carboxylate (140 mg, 0.70 mmol, 1.00 equiv), methanol (10 mL), LiOH (290 mg, 7.02 mmol, 10.00 equiv) and H$_2$O (2 mL). The resulting solution was stirred for 2 h at 25° C. The reaction progress was monitored by LCMS. The pH value of the solution was adjusted to 6 with hydrochloric acid (1 mol/L). The resulting mixture was concentrated under vacuum. The residue was dispersed in MeOH:DCM=1:10 (100 mL) and stirred for 10 mins. The solids were filtered out. The filtrate was concentrated under vacuum. This resulted in 210 mg (72%) of 7-methy-1,2,3,4-tetrahydroquinoline-4-carboxylic acid as off-white crude solid. MS (ES, m/z) [M+H]$^+$: 191.

Step 6. (3-amino-4,5,6,7-tetrahydroindazol-2-yl)(7-methyl-1,2,3,4-tetrahydroquinolin-4-yl)methanone and (3-amino-4,5,6,7-tetrahydroindazol-1-yl)(7-methyl-1,2,3,4-tetrahydroquinolin-4-yl)methanone

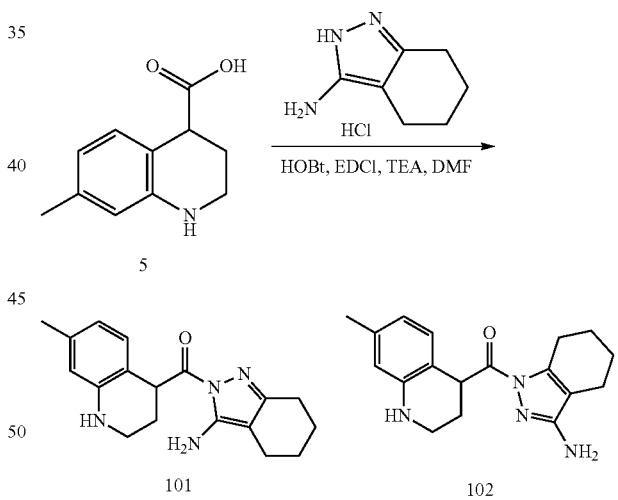

Into a 50-mL round-bottom flask, was placed 7-methyl-1,2,3,4-tetrahydroquinoline-4-carboxylic acid (50 mg, 0.26 mmol, 1.00 equiv), 4,5,6,7-tetrahydro-2H-indazol-3-amine dihydrochloride (55 mg, 0.26 mmol, 1.00 equiv), HOBT (53 mg, 0.39 mmol, 1.50 equiv), EDCI (75 mg, 0.39 mmol, 1.50 equiv), TEA (80 mg, 0.79 mmol, 3.00 equiv), N,N-dimethylformamide (5 mL). The resulting solution was stirred overnight at room temperature. The reaction was then quenched by the addition of water (40 mL). The resulting solution was extracted with ethyl acetate (40 mL×3) and the organic layers combined and concentrated under vacuum.

The crude product was purified by Prep-HPLC with the following conditions: Column: XSelect CSH Prep C18 OBD Column, 5 um, 19×150 mm, Mobile Phase A: water (0.1% FA), Mobile Phase B: ACN, Flow rate: 20 mL/min, Gradient: 40% B to 75% B in 7 min, 254 nm. The collected fraction was lyophilized to give 2.8 mg (3%) of (3-amino-4,5,6,7-tetrahydroindazol-2-yl)(7-methyl-1,2,3,4-tetrahydroquinolin-4-yl)methanone (101) as an off-white solid. RT2: 6.68 min, MS (ES, m/z) [M+H]$^+$: 311, (DMSO-d$_6$, 300 MHz, ppm): δ 6.63 (d, J=7.8 Hz, 1H), 6.32 (d, J=7.8 Hz, 1H), 6.31 (s, 2H), 6.22-6.20 (m, 1H), 5.73 (s, 1H), 5.00-4.98 (m, 1H), 3.27-3.26 (m, 1H), 3.16-3.12 (m, 1H), 2.46-2.43 (m, 2H), 2.28-2.24 (m, 2H), 2.11 (s, 3H), 2.01-1.99 (m, 2H), 1.68-1.66 (m, 4H). And 1.9 mg (2%) of (3-amino-4,5,6,7-tetrahydroindazol-1-yl)(7-methyl-1,2,3,4-tetrahydroquinolin-4-yl)methanone (102) as an off-white solid. RT1: 6 min, MS (ES, m/z) [M+H]$^+$: 311, (DMSO-d$_6$, 300 MHz, ppm): δ 6.63 (d, J=7.8 Hz, 1H), 6.20 (d, J=8.1 Hz, 1H), 6.18-6.12 (m, 1H), 5.68 (s, 1H), 5.55 (s, 2H), 4.96-4.91 (m, 1H), 3.29-3.26 (m, 1H), 3.13-3.09 (m, 1H), 2.78-2.73 (m, 2H), 2.27-2.24 (m, 2H), 2.03 (s, 3H), 1.98-1.90 (m, 2H), 1.67-1.64 (m, 4H).

Example 103 and 104: (3-amino-4,5,6,7-tetrahydroindazol-2-yl)(7-chloro-1,2,3,4-tetrahydroquinolin-4-yl)methanone (103) and (3-amino-4,5,6,7-tetrahydroindazol-1-yl)(7-chloro-1,2,3,4-tetrahydroquinolin-4-yl)methanone (104)

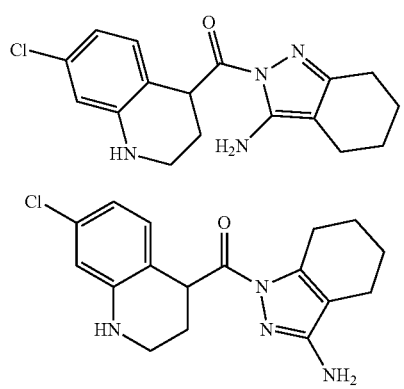

Step 1. 7-chloro-4-iodoquinoline

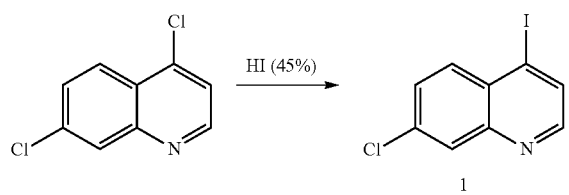 [SMILES: Clc1ccc2c(Cl)ccnc2c1 ; "HI (45%)" ; Clc1ccc2c(I)ccnc2c1]

Into a 250-mL round-bottom flask, was placed 4,7-dichloroquinoline (5 g, 25.25 mmol, 1.00 equiv), HI (45%) (50 mL). The resulting solution was stirred for 16 h at 125° C. The reaction progress was monitored by LCMS. The reaction mixture was cooled to 10° C. with an ice/salt bath. The solids were collected by filtration. The resulting solution was diluted with H$_2$O (100 mL). The pH value of the solution was adjusted to 7-8 with sat. Na$_2$CO$_3$/H$_2$O. The resulting solution was extracted with ethyl acetate (50 mL×3) and the organic layers combined and dried over anhydrous sodium sulfate and concentrated under vacuum. This resulted in 5.5 g (75%) of 7-chloro-4-iodoquinoline as an off-white solid. MS (ES, m/z) [M+H]$^+$: 290 and 292.

Step 2. 7-chloroquinoline-4-carbonitrile

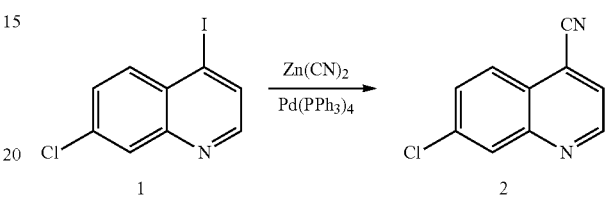

Into a 100-mL round-bottom flask, was placed 7-chloro-4-iodoquinoline (1 g, 3.45 mmol, 1.00 equiv), Zn(CN)$_2$ (200 mg, 1.72 mmol, 0.50 equiv), Pd(PPh$_3$)$_4$ (800 mg, 0.69 mmol, 0.20 equiv), N,N-dimethylformamide (10 mL). The resulting solution was stirred overnight at 120° C. The reaction progress was monitored by LCMS. The reaction mixture was cooled to room temperature. The solids were filtered out. The mixture was diluted with water (50 mL) and extracted with EA (40 mL×3) and the organic layers combined and concentrated under vacuum. The residue was applied onto a silica gel column with ethyl acetate/petroleum ether (0-10%). This resulted in 250 mg (38%) of 7-chloroquinoline-4-carbonitrile as a yellow solid.

Step 3. 7-chloroquinoline-4-carboxylic Acid

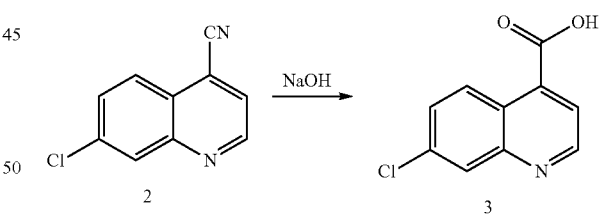

Into a 100-mL round-bottom flask, was placed 7-chloroquinoline-4-carbonitrile (250 mg, 1.33 mmol, 1.00 equiv), sodium hydroxide (4N) (2 mL), methanol (10 mL). The resulting solution was stirred overnight at 68° C. The reaction mixture was cooled to 10° C. The resulting mixture was concentrated under vacuum. The resulting solution was diluted with H$_2$O (50 mL). The resulting solution was extracted with ethyl acetate (50 mL×3) and the aqueous layers combined. The pH value of the solution was adjusted to 6 with hydrochloric acid (3 mol/L). The solids were collected by filtration. This resulted in 165 mg (60%) of 7-chloroquinoline-4-carboxylic acid as a gray solid. MS (ES, m/z) [M+H]$^+$: 208.

Step 4.
7-chloro-1,2,3,4-tetrahydroquinoline-4-carboxylic Acid

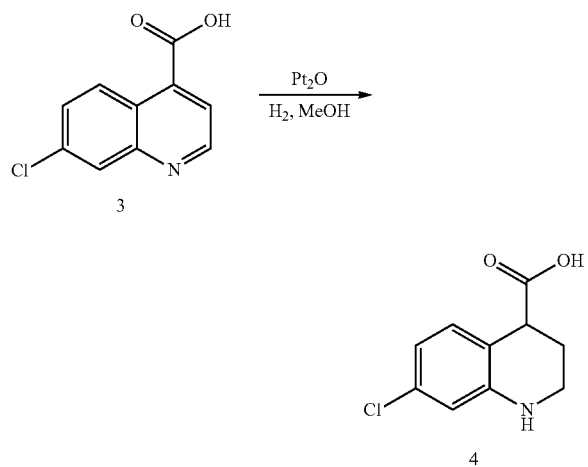

Into a 50-mL round-bottom flask, was placed 6-chloronaphthalene-1-carboxylic acid (400 mg, 1.94 mmol, 1.00 equiv), PtO$_2$ (400 mg), methanol (10 mL). To the above hydrogen was introduced in. The resulting solution was stirred for 30 min at room temperature. The solids were filtered out. The resulting mixture was concentrated under vacuum. The crude product was purified by Prep-HPLC with the following conditions: Column: XBridge Shield RP18 OBD Column, 5 um, 19×150 mm, Mobile Phase A: water (0.1% FA), Mobile Phase B: ACN, Flow rate: 20 mL/min, Gradient: 25% B to 50% B in 7 min, 254 nm, Rt: 6 min. The collected fraction was concentrated under vacuum. This resulted in 120 mg (29%) of 6-chloro-1,2,3,4-tetrahydronaphthalene-1-carboxylic acid as a yellow solid. MS (ES, m/z) [M+H]$^+$: 212 and 214.

Step 5. (3-amino-4,5,6,7-tetrahydroindazol-2-yl)(7-chloro-1,2,3,4-tetrahydroquinolin-4-yl)methanone (103) and (3-amino-4,5,6,7-tetrahydroindazol-1-yl)(7-chloro-1,2,3,4-tetrahydroquinolin-4-yl)methanone (104)

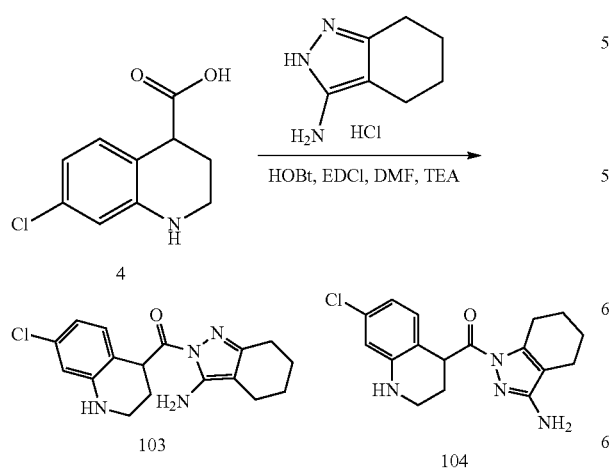

Into a 50-mL round-bottom flask, was placed 7-chloro-1,2,3,4-tetrahydroquinoline-4-carboxylic acid (50 mg, 0.24 mmol, 1.00 equiv), 4,5,6,7-tetrahydro-2H-indazol-3-amine dihydrochloride (41 mg, 0.24 mmol, 1.00 equiv), HOBT (48 mg, 0.36 mmol, 1.50 equiv), EDCI (68 mg, 0.35 mmol, 1.50 equiv), TEA (75 mg, 0.74 mmol, 3.00 equiv), N,N-dimethylformamide (5 mL). The resulting solution was stirred overnight at room temperature. The reaction was then quenched by the addition of water (30 mL). The resulting solution was extracted with ethyl acetate (30 mL×3) and the organic layers combined. The resulting mixture was washed with Brine (60 mL×2). The resulting mixture was concentrated under vacuum. The product was purified by reversed phase column with the following conditions: Column: XSelect CSH Prep C18 OBD Column, 5 um, 19×150 mm, Mobile Phase A: water (0.1% FA), Mobile Phase B: ACN, Flow rate: 20 mL/min, Gradient: 40% B to 75% B in 7 min, 254 nm. The collected fraction was lyophilized to give 4.7 mg (6%) of (3-amino-4,5,6,7-tetrahydroindazol-2-yl)(7-chloro-1,2,3,4-tetrahydroquinolin-4-yl)methanone (103) as an off-white solid. Rt: 6.80 min, MS (ES, m/z) [M+H]$^+$: 331 and 333, (DMSO-d$_6$, 300 MHz, ppm): δ 6.78 (d, J=8.1 Hz, 1H), 6.55-6.54 (m, 1H), 6.45-6.42 (m, 1H), 5.03-5.01 (m, 1H), 3.38-3.35 (m, 1H), 3.31-3.25 (m, 1H), 2.59-2.55 (m, 2H), 2.35-2.31 (m, 2H), 2.16-2.07 (m, 2H), 1.81-1.76 (m, 4H). And 2.2 mg (3%) of (3-amino-4,5,6,7-tetrahydroindazol-1-yl)(7-chloro-1,2,3,4-tetrahydroquinolin-4-yl)methanone (104) as an off-white solid. Rt: 6 min, MS (ES, m/z) [M+1]: 331 and 333, (DMSO-d$_6$, 300 MHz, ppm): δ 6.78 (d, J=8.1 Hz, 1H), 6.54-6.53 (m, 1H), 6.42 (d, J=8.1 Hz, 1H), 5.01-4.98 (m, 1H), 3.38-3.35 (m, 1H), 3.31-3.25 (m, 1H), 2.89-2.86 (m, 2H), 2.35-2.32 (m, 2H), 2.12-2.09 (m, 2H), 1.77-1.29 (m, 4H).

Example 105: (3-amino-4,5,6,7-tetrahydro-2H-indazol-2-yl)(7-(trifluoromethyl)-1,2,3,4-tetrahydroquinolin-4-yl)methanone

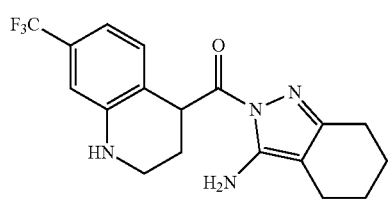

Step 1. 7-(trifluoromethyl)quinolin-4-yl trifluoromethanesulfonate

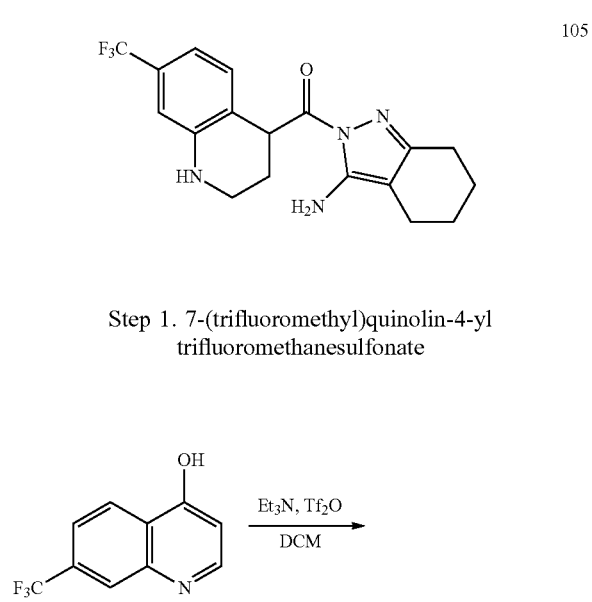

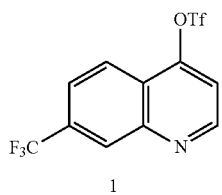

Into a 100-mL 3-necked round-bottom flask purged and maintained with an inert atmosphere of nitrogen, was placed 7-(trifluoromethyl)quinolin-4-ol (1 g, 4.69 mmol, 1.00 equiv), dichloromethane (25 mL), TEA (1.42 g, 14.03 mmol, 3.00 equiv), 4-dimethylaminopyridine (100 mg, 0.82 mmol, 0.17 equiv), (Tf)$_2$O (1.83 g, 1.50 equiv) was added at 0° C. The resulting solution was stirred overnight at room temperature. The resulting mixture was concentrated under vacuum. The residue was diluted with H$_2$O (100 mL). The resulting solution was extracted with ethyl acetate (100 mL×3) and, dried over anhydrous sodium sulfate and concentrated under vacuum. The residue was applied onto a silica gel column and eluted with ethyl acetate/petroleum ether (1/8). The collected fraction was concentrated to give 1 g (62%) of 7-(trifluoromethyl)quinolin-4-yl trifluoromethanesulfonate as a white solid. MS (ES, m/z) [M+H]$^+$: 346.

Step 2. 7-(trifluoromethyl)quinoline-4-carboxylate

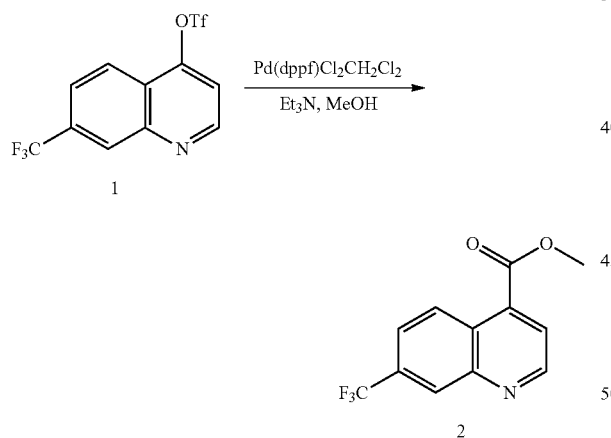

Into a 30-mL pressure tank reactor (60 atm) purged and maintained with an inert atmosphere of CO, was placed 7-(trifluoromethyl)quinolin-4-yl trifluoromethanesulfonate (360 mg, 1.04 mmol, 1.00 equiv), Pd(dppf)Cl$_2$CH$_2$Cl$_2$ (426 mg, 0.50 equiv), TEA (526 mg, 5.20 mmol, 5.00 equiv), methanol (10 mL). The resulting solution was stirred overnight at 120° C. After cooled to room temperature, the solids were filtered out. The resulting mixture was concentrated under vacuum. The residue was applied onto a silica gel column with ethyl acetate/petroleum ether (1/3). This resulted in 50 mg (19%) of methyl 7-(trifluoromethyl) quinoline-4-carboxylate as yellow oil. MS (ES, m/z) [M+H]$^+$: 256.

Step 3. 7-(trifluoromethyl)-1,2,3,4-tetrahydroquinoline-4-carboxylate

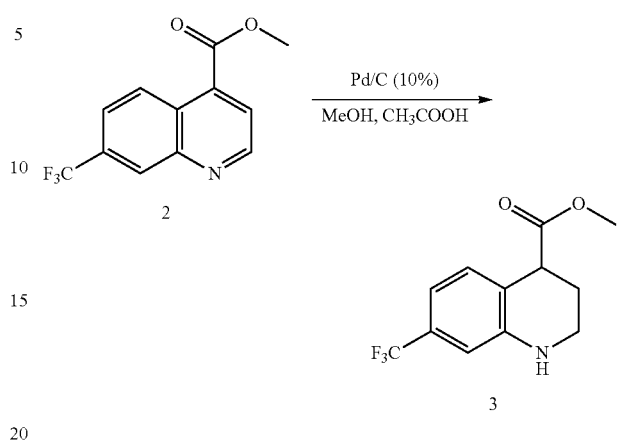

Into a 100-mL round-bottom flask purged and maintained with an inert atmosphere of H2, was placed methyl 7-(trifluoromethyl)quinoline-4-carboxylate (50 mg, 0.20 mmol, 1.00 equiv), Palladium carbon (50 mg), methanol (9 mL), acetic acid (3 mL). The resulting solution was stirred for 3 h at room temperature. The solids were filtered out. The resulting mixture was concentrated under vacuum. This resulted in 50 mg (98%) of methyl 7-(trifluoromethyl)-1,2,3,4-tetrahydroquinoline-4-carboxylate as yellow oil. MS (ES, m/z) [M+H]$^+$: 260.

Step 4. 7-(trifluoromethyl)-1,2,3,4-tetrahydroquinoline-4-carboxylic Acid

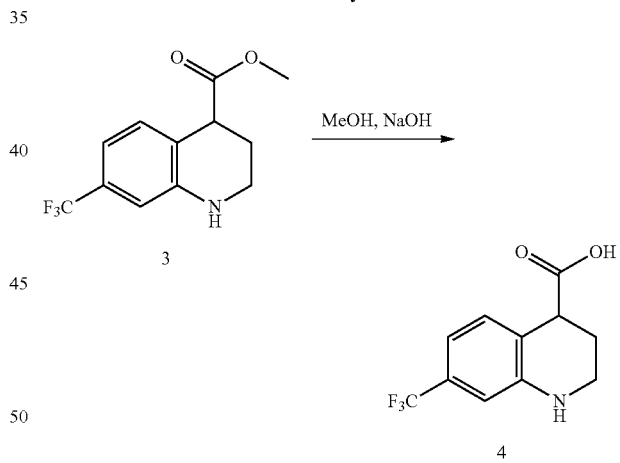

Into a 10-mL round-bottom flask, was placed methyl 7-(trifluoromethyl)-1,2,3,4-tetrahydroquinoline-4-carboxylate (50 mg, 0.19 mmol, 1.00 equiv), LiOH (23 mg, 0.96 mmol, 5.00 equiv), water (1 mL), methanol (4 mL) and tetrahydrofuran (1 mL). The resulting solution was stirred overnight at room temperature. The resulting solution was diluted with H$_2$O (10 mL). The resulting mixture was washed with DCM (60 mL×2). Hydrochloric acid (1 mol/L) was employed to adjust the pH to 5-6. The resulting solution was extracted with dichloromethane (60 mL×2) and the organic layers combined and concentrated under vacuum. This resulted in 45 mg (95%) of 7-(trifluoromethyl)-1,2,3,4-tetrahydroquinoline-4-carboxylic acid as yellow oil. MS: (ES, m/z) [M+H]$^+$: 268.

117

Step 5. (3-amino-4,5,6,7-tetrahydro-2H-indazol-2-yl)(7-(trifluoromethyl)-1,2,3,4-tetrahydroquinolin-4-yl)methanone

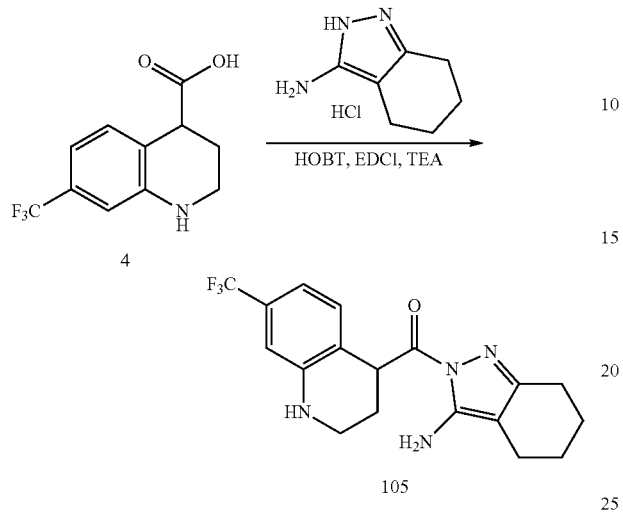

Into a 50-mL round-bottom flask, was placed 7-methyl-1,2,3,4-tetrahydroquinoline-4-carboxylic acid (45 mg, 0.24 mmol, 1.00 equiv), dichloromethane (5 mL), 4,5,6,7-tetrahydro-2H-indazol-3-amine dihydrochloride (46 mg, 0.22 mmol, 1.20 equiv), HOBt (38 mg, 0.28 mmol, 1.50 equiv), EDCI (54 mg, 0.28 mmol, 1.50 equiv), TEA (56 mg, 0.55 mmol, 3.00 equiv). The resulting solution was stirred overnight at 25° C. The reaction mixture was diluted with DCM (80 mL), washed with H$_2$O (50 mL×3) and brine (50 mL×3) and dried with Na$_2$SO$_4$. After filtration, the filtrate was concentrated under reduced pressure. The crude product was purified by Prep-HPLC with the following conditions: Column, XBridge Prep Phenyl OBD Column, 19×150 mm, 5 um 13 nm, mobile phase, water (0.1% FA) and ACN (40.0% ACN up to 80.0% in 7 min), Detector, UV 254 nm. The collected fraction was lyophilized to give 10.2 mg (14%) of (3-amino-4,5,6,7-tetrahydro-2H-indazol-2-yl)(7-(trifluoromethyl)-1,2,3,4-tetrahydroquinolin-4-yl)methanone (105) as a white solid. RT: 6.58 min, MS (ES, m/z) [M+H]$^+$: 365. (400 MHz, DMSO-d$_6$, ppm): δ 6.83 (d, J=7.6 Hz, 1H), 6.81 (s, 1H), 6.67 (d, J=8.0 Hz, 1H), 6.39 (s, 1H), 6.38 (s, 2H), 5.08-5.06 (m, 1H), 3.27-3.25 (m, 2H), 2.50-2.48 (m, 2H), 2.28-2.25 (m, 2H), 2.12-2.01 (m, 2H), 2.00-1.66 (m, 4H).

Example 106 and 107: (S*)-(3-amino-4,5,6,7-tetrahydro-2H-indazol-2-yl)(2-chloro-4,5,6,7-tetrahydro-1H-indol-4-yl)methanone (106) and (R*)-(3-amino-4,5,6,7-tetrahydro-2H-indazol-2-yl)(2-chloro-4,5,6,7-tetrahydro-1H-indol-4-yl)methanone (107)

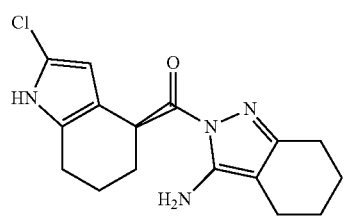

118

-continued

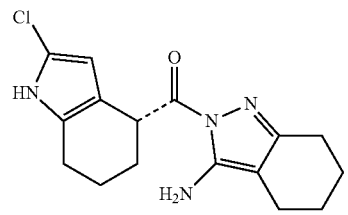

Step 1. 1-[(4-methylbenzene)sulfonyl]-4,5,6,7-tetrahydro-1H-indol-4-one

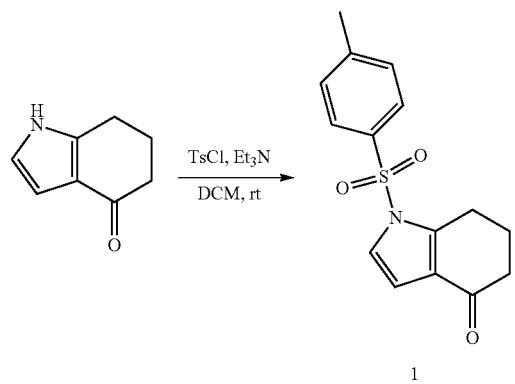

Into a 5000-mL round-bottom flask, was placed a solution of 4,5,6,7-tetrahydro-1H-indol-4-one (200 g, 1.48 mol, 1.00 equiv) in dichloromethane (3000 mL), 4-methylbenzene-1-sulfonyl chloride (290 g, 1.52 mol, 1.03 equiv), TEA (600 mL), 4-dimethylaminopyridine (18 g, 147.34 mmol, 0.10 equiv). The resulting solution was stirred for 16 h at 25° C. The reaction was then quenched by the addition of water. The resulting solution was extracted with ethyl acetate (4000 ml). The organic layer was washed with brine (1000 mL×4) and concentrated under vacuum. The isolated solid was collected and purified by crystallization with PE/EA. This resulted in 130 g (30%) of 1-[(4-methylbenzene)sulfonyl]-4,5,6,7-tetrahydro-1H-indol-4-one as a white solid. MS [M+H]$^+$ (ES, m/z): 290.

Step 2. 1-[(4-methylbenzene)sulfonyl]-4-[(trimethylsilyl)oxy]-4,5,6,7-tetrahydro-1H-indole-4-carbonitrile

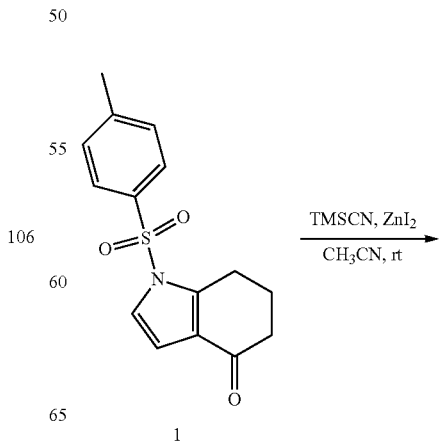

-continued

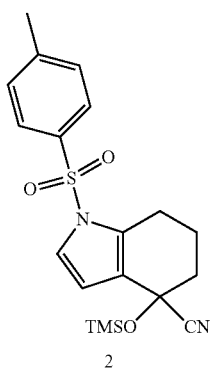

2

Into a 2000-mL round-bottom flask purged and maintained with an inert atmosphere of nitrogen, was placed a solution of 1-[(4-methylbenzene)sulfonyl]-4,5,6,7-tetrahydro-1H-indol-4-one (130 g, 449.28 mmol, 1.00 equiv) in CH₃CN (1000 mL), TMSCN (120 mL), ZnI₂ (13 g, 40.72 mmol, 0.09 equiv). The resulting solution was stirred for 3 h at 25° C. The reaction was then quenched by the addition of water. The resulting solution was extracted with ethyl acetate (4000 mL). The resulting mixture was washed with brine (1000 mL×4). The mixture was dried over anhydrous sodium sulfate. The solids were filtered out. The resulting mixture was concentrated. This resulted in 170 g of 1-[(4-methylbenzene)sulfonyl]-4-[(trimethylsilyl)oxy]-4,5,6,7-tetrahydro-1H-indole-4-carbonitrile as yellow oil. MS [M+H]⁺ (ES, m/z): 389.

Step 3. 1-[(4-methylbenzene)sulfonyl]-6,7-dihydro-1H-indole-4-carbonitrile

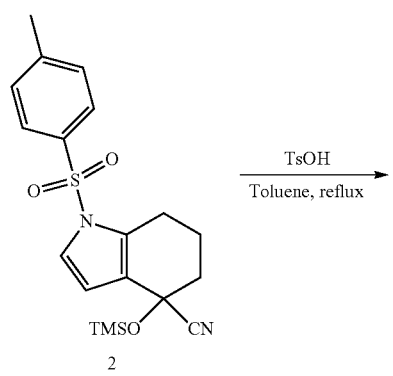

Into a 3000-mL round-bottom flask, was placed a solution of 1-[(4-methylbenzene)sulfonyl]-4-[(trimethylsilyl)oxy]-4,5,6,7-tetrahydro-1H-indole-4-carbonitrile (170 g, crude) in toluene (2000 mL), 4-methylbenzene-1-sulfonic acid (5 g). The resulting solution was stirred for 5 h at 110° C. The reaction was then quenched by the addition of water. The resulting solution was extracted with ethyl acetate (4000 mL). The resulting mixture was washed with brine (1000 mL×4). The mixture was dried over anhydrous sodium sulfate. The solids were filtered out. The resulting mixture was concentrated. The isolated solid was collected and purified by crystallization with PE/EA. This resulted in 110 g (crude) of 1-[(4-methylbenzene)sulfonyl]-6,7-dihydro-1H-indole-4-carbonitrile as a yellow solid. MS [M+H]⁺ (ES, m/z):

Step 4. 1-[(4-methylbenzene)sulfonyl]-4,5,6,7-tetrahydro-1H-indole-4-carbonitrile

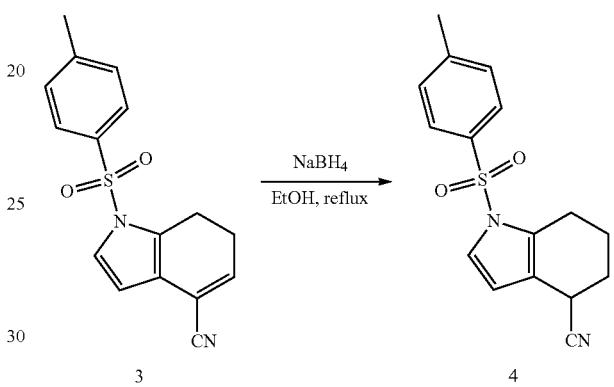

Into a 2000-mL round-bottom flask, was placed a solution of 1-[(4-methylbenzene)sulfonyl]-6,7-dihydro-1H-indole-4-carbonitrile (110 g, crude) in ethanol (1000 mL), borane sodium (45 g, 1.22 mol). The resulting solution was stirred for 6 h at 80° C. The reaction was then quenched by the addition of water/ice. The resulting solution was extracted with ethyl acetate (4000 mL). The organic layer was washed with brine (1000 mL×4) and dried over anhydrous sodium sulfate. The solids were filtered out and concentrated under vacuum. The isolated solid was collected and purified by crystallization with PE/EA. This resulted in 89 g of 1-[(4-methylbenzene)sulfonyl]-4,5,6,7-tetrahydro-1H-indole-4-carbonitrile as a white solid. MS [M+H]⁺ (ES, m/z): 301.

Step 5. 1-[(4-methylbenzene)sulfonyl]-4,5,6,7-tetrahydro-1H-indole-4-carboxylate

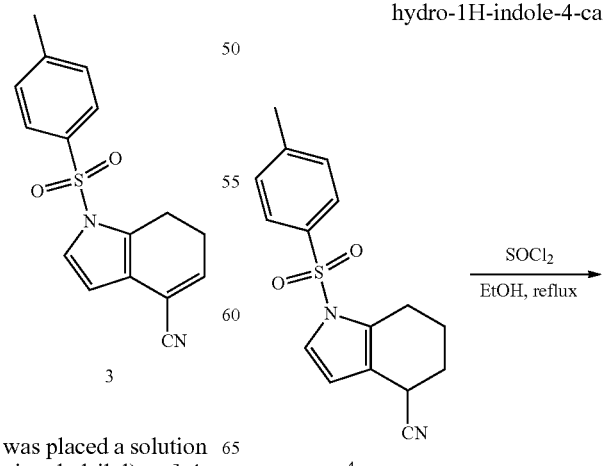

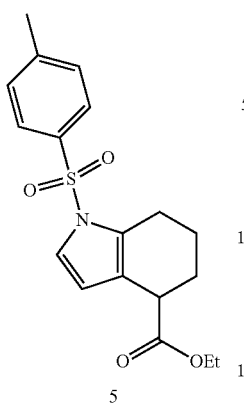

5

Into a 2000-mL round-bottom flask, was placed a solution of 1-[(4-methylbenzene)sulfonyl]-4,5,6,7-tetrahydro-1H-indole-4-carbonitrile (89 g, 296.30 mmol, 1.00 equiv) in ethanol (1000 mL), sulfurooyl dichloride (350 g, 2.94 mol, 9.93 equiv). The resulting solution was stirred for 16 h at 90° C. The reaction was then quenched by the addition of water/ice. The resulting solution was extracted with of ethyl acetate (4000 mL). The resulting mixture was washed with brine (1000 mL×4). The resulting mixture was concentrated under vacuum. The residue was applied onto a silica gel column (PE/EA) to afford 70 g (68%) of ethyl 1-[(4-methylbenzene)sulfonyl]-4,5,6,7-tetrahydro-1H-indole-4-carboxylate as a white solid. MS [M+H]⁺ (ES, m/z): 348.

Step 6. 4,5,6,7-tetrahydro-1H-indole-4-carboxylic Acid

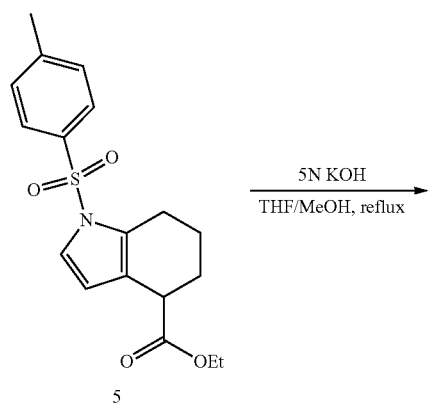

Into a 2000-mL round-bottom flask, was placed ethyl 1-[(4-methylbenzene)sulfonyl]-4,5,6,7-tetrahydro-1H-indole-4-carboxylate (60 g, 172.70 mmol, 1.00 equiv), methanol (240 mL), tetrahydrofuran (240 mL), potassium hydroxide (5N) (420 mL). The resulting solution was stirred for 26 h at 85° C. The resulting mixture was concentrated under vacuum to remove the MeOH and THF. The resulting solution was extracted with of ethyl acetate (1000 mL×3). The PH value of the aqueous phase was adjusted to 6 with HCl (1 N). The resulting mixture was washed with brine (1000 mL×4) and dried over anhydrous sodium sulfate. The solids were filtered out and concentrated under vacuum. The isolated solid was collected and purified by crystallization with PE/EA. This resulted in 26 g (91%) of 4,5,6,7-tetrahydro-1H-indole-4-carboxylic acid as a white solid. MS [M+H]⁺ (ES, m/z): 166.

Step 7. 2-chloro-4,5,6,7-tetrahydro-1H-indole-4-carboxylic Acid

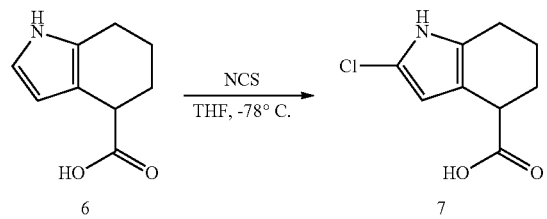 [SMILES: O=C(O)C1CCCc2[nH]ccc21 ; "NCS" ; "THF, -78° C." ; O=C(O)C1CCCc2[nH]c(Cl)cc21]

Into a 500-mL round-bottom flask purged and maintained with an inert atmosphere of nitrogen, was placed a solution of 4,5,6,7-tetrahydro-1H-indole-4-carboxylic acid (7.5 g, 45.40 mmol, 1.00 equiv) in tetrahydrofuran (210 mL). This was followed by the addition of 1-chloropyrrolidine-2,5-dione (6.6 g, 49.43 mmol, 1.09 equiv) in THF (20 mL) dropwise with stirring at −78° C. The resulting solution was stirred for 3 h at −78° C. The reaction was then quenched by the addition of water. The resulting solution was extracted with ethyl acetate (800 mL×3) and the organic layers combined and dried over anhydrous sodium sulfate. The solids were filtered out. The resulting solution was diluted with DMF (150 ml). The resulting mixture was concentrated under vacuum (out of EA). This resulted in 9 g (conversion) of 2-chloro-4,5,6,7-tetrahydro-1H-indole-4-carboxylic acid. MS [M+H]⁺ (ES, m/z): 200 and 202.

Step 8. (S*)-(3-amino-4,5,6,7-tetrahydro-2H-indazol-2-yl)(2-choro-4,5,6,7-tetrahydro-1H-indol-4-yl)methanone and (R*)-(3-amino-4,5,6,7-tetrahydro-2H-indazol-2-yl)(2-chloro-4,5,6,7-tetrahydro-1H-indol-4-yl)methanone

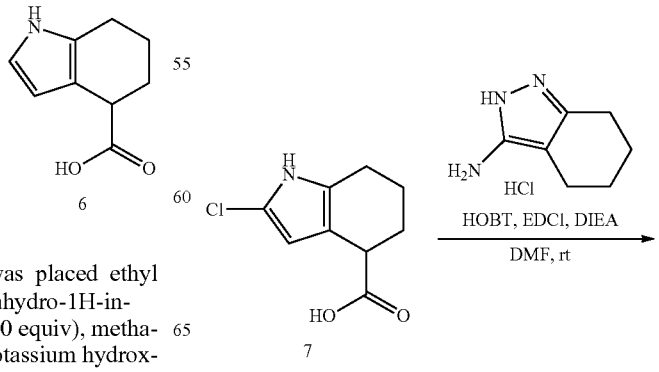

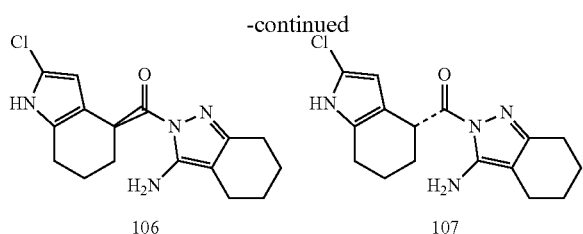

106 107

Into a 2000-mL round-bottom flask, was placed a solution of 2-chloro-4,5,6,7-tetrahydro-1H-indole-4-carboxylic acid (40 g, 201 mmol, 1.00 equiv) in N,N-dimethylformamide (500 mL), 4,5,6,7-tetrahydro-2H-indazol-3-amine hydrochloride (40 g, 231 mmol, 1.15 equiv), HOBt (40 g, 296.03 mmol, 1.48 equiv), EDCI (60 g, 312.99 mmol, 1.56 equiv), TEA (120 mL). The resulting solution was stirred for 16 h at 25° C. The reaction was then quenched by the addition of water/ice (3500 mL). The resulting solution was extracted with ethyl acetate (1000 mL×4) and the organic layers combined and concentrated under vacuum. The residue was applied onto a silica gel column (PE/EA, 50:1-1:1) to afford 15 g of mixture. Column: CHIRALPAK AD-H SFC, 5*25 cm, 5 um, Mobile Phase A: CO$_2$:50, Mobile Phase B: MeOH-Preparative: 50, Flow rate: 150 mL/min, 240 nm.

Enantiomer A: 5.5151 g (9%) of (S*)-(3-amino-4,5,6,7-tetrahydro-2H-indazol-2-yl)(2-chloro-4,5,6,7-tetrahydro-1H-indol-4-yl)methanone (106) as a white solid RT2: 5.84 min, MS [M+H]$^+$ (ES, m/z): 319 and 321, (DMSO-d$_6$, 400 MHz, ppm) δ 11.07 (s, 1H), 6.32 (s, 2H), 5.54 (d, J=2.4 Hz, 1H), 4.70 (m, 1H), 2.41-2.51 (m, 4H), 2.22-2.33 (m, 2H), 1.78-2.03 (m, 3H), 1.59-1.75 (m, 5H).

Enantiomer B: 6.7178 g (11%) of (R*)-(3-amino-4,5,6,7-tetrahydro-2H-indazol-2-yl)(2-chloro-4,5,6,7-tetrahydro-1H-indol-4-yl)methanone (107) as a pink solid. RT1: 4.27 min, MS [M+H]$^+$ (ES, m/z): 319 and 321, (DMSO-d$_6$ 400 MHz, ppm) δ 11.07 (s, 1H), 6.32 (s, 2H), 5.54 (d, J=2.4 Hz, 1H), 4.70 (m, 1H), 2.41-2.51 (m, 4H), 2.22-2.33 (m, 2H), 1.78-2.03 (m, 3H), 1.59-1.75 (m, 5H).

Example 108 and 109: (S*)-(3-amino-4,5,6,7-tetrahydroindazol-2-yl)(2-bromo-4,5,6,7-tetrahydro-1H-indol-4-yl)methanone (108) and (R*)-(3-amino-4,5,6,7-tetrahydroindazol-2-yl)(2-bromo-4,5,6,7-tetrahydro-1H-indol-4-yl)methanone (109)

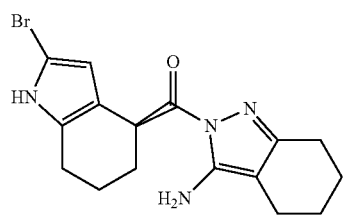

108

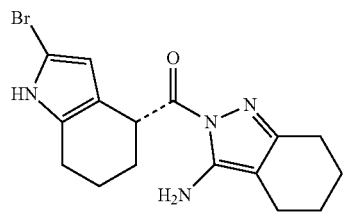

109

Step 1.
2-bromo-4,5,6,7-tetrahydro-1H-indole-4-carboxylic Acid

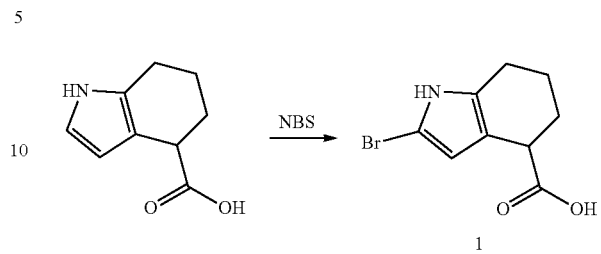

1

Into a 100-mL 3-necked round-bottom flask purged and maintained with an inert atmosphere of nitrogen, was placed 4,5,6,7-tetrahydro-1H-indole-4-carboxylic acid (240 mg, 1.45 mmol, 1.00 equiv), tetrahydrofuran (10 mL). This was followed by the addition of a solution of NBS (209 mg, 1.17 mmol, 0.80 equiv) in tetrahydrofuran (5 mL) dropwise with stirring at −78° C. The resulting solution was stirred for 1 h at −78° C. The reaction was then quenched by the addition of brine (50 mL). The resulting solution was extracted with ethyl acetate (50 mL×3) and the organic layers combined and dried over anhydrous sodium sulfate. The solids were filtered out. The resulting mixture was concentrated under vacuum. This resulted in 150 mg (42%) of 2-bromo-4,5,6,7-tetrahydro-1H-indole-4-carboxylic acid as yellow oil. MS (ES, m/z) [M+1]: 244 and 246.

Step 2. (3-amino-4,5,6,7-tetrahydroindazol-2-yl)(2-bromo-4,5,6,7-tetrahydro-1H-indol-4-yl)methanone

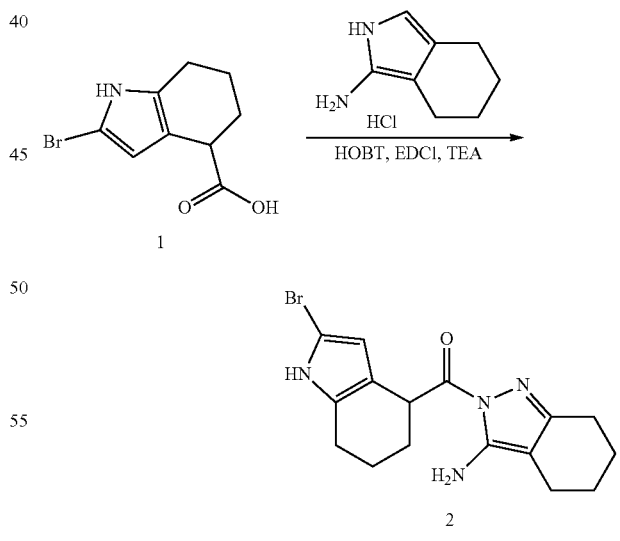

1

2

Into a 50-mL round-bottom flask, was placed 2-bromo-4,5,6,7-tetrahydro-1H-indole-4-carboxylic acid (150 mg, 0.61 mmol, 1.00 equiv), 4,5,6,7-tetrahydro-2H-indazol-3-amine dihydrochloride (130 mg, 0.62 mmol, 1.00 equiv), HOBT (125 mg, 0.93 mmol, 1.50 equiv), EDCI (180 mg, 0.94 mmol, 1.50 equiv), TEA (190 mg, 1.88 mmol, 3.00 equiv), N,N-dimethylformamide (5 mL). The resulting solution was stirred overnight at room temperature. The reaction was then quenched by the addition of Brine (40 mL). The resulting solution was extracted with ethyl acetate (50 mL×3) and the organic layers combined and dried over anhydrous sodium sulfate. The solids were filtered out. The resulting mixture was concentrated under vacuum. The crude product was purified by Pre-TLC with MeOH/DCM (1:50~1:20). This resulted in 95 mg (43%) of 2-[(2-bromo-4,5,6,7-tetrahydro-1H-indol-4-yl)carbonyl]-4,5,6,7-tetrahydro-2H-indazol-3-amine as a pink solid. MS (ES, m/z) [M+1]: 363 and 365.

Step 3. (S*)-(3-amino-4,5,6,7-tetrahydroindazol-2-yl)(2-bromo-4,5,6,7-tetrahydro-1H-indol-4-yl)methanone and (R*)-(3-amino-4,5,6,7-tetrahydroindazol-2-yl)(2-bromo-4,5,6,7-tetrahydro-1H-indol-4-yl)methanone

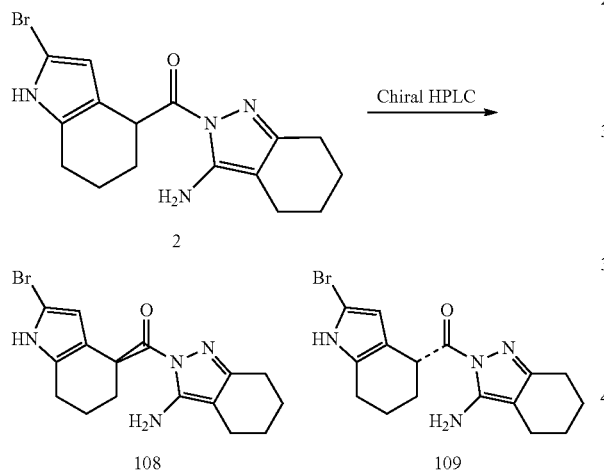

2-[(2-bromo-4,5,6,7-tetrahydro-1H-indol-4-yl)carbonyl]-4,5,6,7-tetrahydro-2H-indazol-3-amine (95 mg) was separated by Prep-chiral-HPLC with the following conditions: Column: CHIRAL ART Cellulose-SB, 2×25 cm, 5 um, Mobile Phase A: Hex-HPLC, Mobile Phase B: EtOH-HPLC, Flow rate: 20 mL/min, Gradient: 20 B to 20 B in 11 min, 220/254 nm, Enantiomer A: 27.2 mg (29%) of (S*)-(3-amino-4,5,6,7-tetrahydroindazol-2-yl)(2-bromo-4,5,6,7-tetrahydro-1H-indol-4-yl)methanone (108) as a pink solid. RT2: 9.192 min, MS (ES, m/z) [M+H]+: 363 and 365, (DMSO-$d_6$, 300 MHz, ppm): δ 11.05 (s, 1H), 6.30 (s, 2H), 5.60 (s, 1H), 4.71-4.68 (m, 1H), 2.48-2.46 (m, 4H), 2.45-2.43 (m, 2H), 1.92-1.77 (m, 3H), 1.66-1.64 (m, 5H).

Enantiomer B: 30.6 mg (32%) of (R*)-(3-amino-4,5,6,7-tetrahydroindazol-2-yl)(2-bromo-4,5,6,7-tetrahydro-1H-indol-4-yl)methanone (109) as a pink solid. RT1: 6.259 min, MS (ES, m/z) [M+1]:363 and 365, (DMSO-$d_6$, 300 MHz, ppm): δ 11.05 (s, 1H), 6.30 (s, 2H), 5.60 (s, 1H), 4.71-4.67 (m, 1H), 2.49-2.45 (m, 4H), 2.45-2.44 (m, 2H), 1.92-1.81 (m, 3H), 1.65-1.64 (m, 5H).

Example 110 & 111: (3-amino-4,5,6,7-tetrahydroindazol-2-yl)(7-methoxy-1,2,3,4-tetrahydroquinolin-4-yl)methanone (110) and (3-amino-4,5,6,7-tetrahydroindazol-1-yl)(7-methoxy-1,2,3,4-tetrahydroquinolin-4-yl)methanone (111)

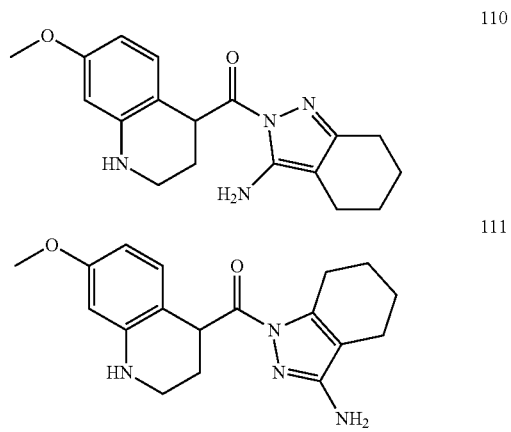

Step 1. 7-methoxyquinolin-4-yl trifluoromethanesulfonate

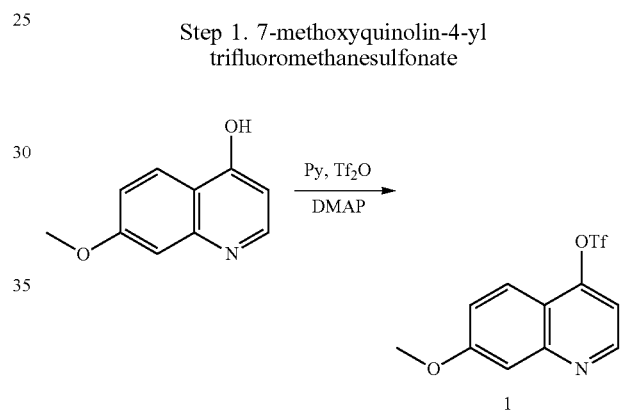

Into a 50-mL 3-necked round-bottom flask, was placed 7-methoxyquinolin-4-ol (1.0 g, 5.71 mmol, 1.00 equiv), pyridine (20 mL), 4-dimethylaminopyridine (10 mg, 0.08 mmol, 0.01 equiv), DCM (50 mL). This was followed by the addition of Tf$_2$O (2.42 g, 1.50 equiv) dropwise with stirring at 0° C. The resulting solution was stirred for 16 h at 25° C. The resulting mixture was concentrated under vacuum. The residue was diluted with H$_2$O (100 mL). The resulting solution was extracted with ethyl acetate (100 mL×3) and, dried over anhydrous sodium sulfate and concentrated under vacuum. The residue was applied onto a silica gel column and eluted with ethyl acetate/petroleum ether (0-30%). The collected fraction was concentrated to give 1.28 g (73%) of 7-methoxyquinolin-4-yl trifluoromethanesulfonate as yellow oil. MS (ES, m/z) [M+H]+: 308.

Step 2. Methyl 7-methoxyquinoline-4-carboxylate

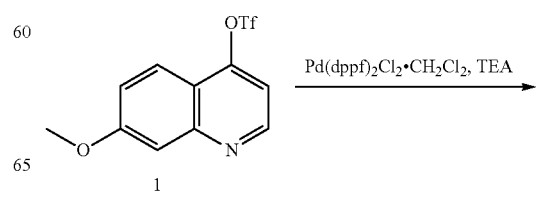

127

-continued

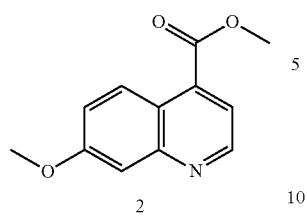

Into a 150-mL pressure tank reactor (90 atm), was placed 7-methoxyquinolin-4-yl trifluoromethanesulfonate (7.7 g, 25.06 mmol, 1.00 equiv), methanol (70 mL), triethylamine (12.67 g, 125.21 mmol, 5.00 equiv), Pd(dppf)Cl$_2$.CH$_2$Cl$_2$ (4.09 g, 0.20 equiv), CO (gas. 50 atm). The resulting solution was stirred for 16 h at 80° C. The reaction was cooled to 20° C. The solids were filtered out. The resulting mixture was concentrated under vacuum. The residue was applied onto a silica gel column with ethyl acetate/petroleum ether (1:4). This resulted in 3.1 g (57%) of methyl 7-methoxyquinoline-4-carboxylate as off-white solid. MS (ES, m/z) [M+H]$^+$: 218.

Step 3. Methyl 7-methoxy-1,2,3,4-tetrahydroquinoline-4-carboxylate

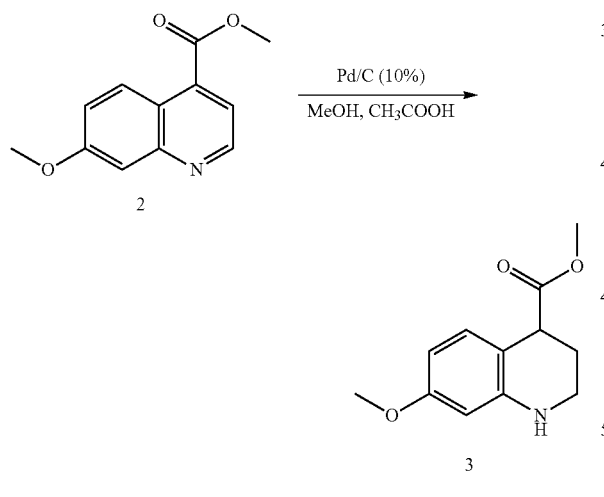

Into a 100-mL round-bottom flask, was placed methyl 7-methoxyquinoline-4-carboxylate (150 mg, 0.69 mmol, 1.00 equiv), methanol:acetic acid=10:1 (5.5 mL), Palladium carbon (10%) (15 mg). The flask was evacuated and flushed three times with nitrogen, followed by flushing with hydrogen. The resulting solution was stirred for 16 h at 25° C. The reaction progress was monitored by LC-MS. The solids were filtered out. The resulting mixture was concentrated under vacuum. This resulted in 120 mg (79%) of methyl 7-methoxy-1,2,3,4-tetrahydroquinoline-4-carboxylate as off-white solid. MS (ES, m/z) [M+H]$^+$: 222.

128

Step 4. 7-methoxy-1,2,3,4-tetrahydroquinoline-4-carboxylic Acid

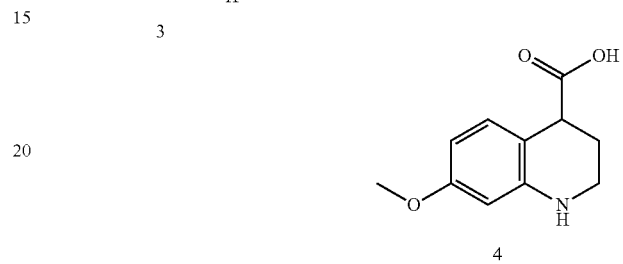

Into a 50-mL round-bottom flask, was placed methyl 7-methoxy-1,2,3,4-tetrahydroquinoline-4-carboxylate (120 mg, 0.54 mmol, 1.00 equiv), methanol (5 mL), LiOH (228 mg, 5.43 mmol, 10.00 equiv) and water (1 mL). The resulting solution was stirred for 2 h at 25° C. The reaction progress was monitored by LCMS. The pH value of the solution was adjusted to 5-6 with HCl (1 mol/L). The resulting solution was extracted with ethyl acetate (10 mL×3), dried over anhydrous sodium sulfate and concentrated under vacuum. This resulted in 75 mg (67%) of 7-methoxy-1,2,3,4-tetrahydroquinoline-4-carboxylic acid as off-white solid. MS (ES, m/z) [M+H]$^+$: 208.

Step 5. (3-amino-4,5,6,7-tetrahydroindazol-2-yl)(7-methoxy-1,2,3,4-tetrahydroquinolin-4-yl)methanone and (3-amino-4,5,6,7-tetrahydroindazol-1-yl)(7-methoxy-1,2,3,4-tetrahydroquinolin-4-yl)methanone

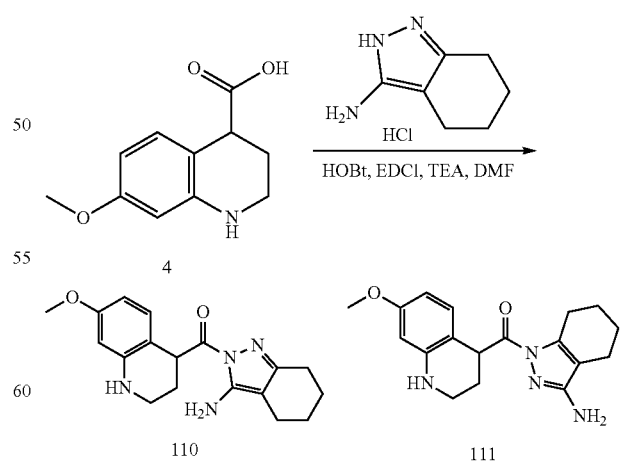

Into a 8-mL vial, was placed 7-methoxy-1,2,3,4-tetrahydroquinoline-4-carboxylic acid (75 mg, 0.36 mmol, 1.00 equiv), N,N-dimethylformamide (3 mL), HOBT (73.4 mg, 0.54 mmol, 1.50 equiv), triethylamine (182.97 mg, 1.81 mmol, 5.00 equiv), EDCI (104.3 mg, 0.54 mmol, 1.50 equiv), 4,5,6,7-tetrahydro-2H-indazol-3-amine (63.04 mg, 0.46 mmol, 1.00 equiv). The resulting solution was stirred for 2 h at 25° C. The reaction progress was monitored by LCMS. The resulting solution was diluted with H$_2$O (40 mL). The resulting solution was extracted with ethyl acetate (50 mL×3) and the organic layers combined and dried over anhydrous sodium sulfate and concentrated under vacuum. The crude product was purified by Prep-HPLC with the following conditions: Column, XBridge Shield RP18 OBD Column, 5 um, 19×150 mm, mobile phase, water (10 MMOL/L NH$_4$HCO$_3$) and ACN (5.0% ACN up to 60.0% in 7 min), Detector, UV 254 nm. The collected fractions were lyophilized to give 3 mg (3%) of (3-amino-4,5,6,7-tetrahydroindazol-2-yl)(7-methoxy-1,2,3,4-tetrahydroquinolin-4-yl)methanone (110) as an off-white solid. RT: 6.89 min, MS (ES, m/z) [M+H]$^+$: 327, (DMSO-d$_6$, 300 MHz, ppm): δ 6.68-6.65 (m, 1H), 6.52 (s, 2H), 6.39 (s, 1H), 6.07-5.98 (m, 1H), 5.85 (s, 1H), 4.97-4.93 (m, 1H), 3.62 (s, 3H), 3.32-3.25 (m, 1H), 3.24-3.18 (m, 1H), 2.46-2.43 (m, 2H), 2.27-2.24 (m, 2H), 2.01-1.93 (m, 2H), 1.68-1.66 (m, 4H). And 4 mg (3%) of (3-amino-4,5,6,7-tetrahydroindazol-1-yl)(7-methoxy-1,2,3,4-tetrahydroquinolin-4-yl)methanone (111) as off-white solid. RT: 6.0 min, MS (ES, m/z) [M+H]$^+$: 327, (DMSO-d$_6$, 300 MHz, ppm): δ 6.65 (d, J=8.4 Hz, 1H), 6.59-6.01 (m, 1H), 5.99 (d, J=8.4 Hz, 1H), 5.81 (s, 1H), 5.51 (s, 2H), 4.89-4.85 (m, 1H), 3.62 (s, 3H), 3.32-3.30 (m, 1H), 3.15-3.08 (m, 1H), 2.84-2.79 (m, 2H), 2.27-2.24 (m, 2H), 1.97-1.85 (m, 2H), 1.66-1.64 (m, 4H).

Example 112: (3-amino-4,5,6,7-tetrahydroindazol-2-yl)(2-chloro-1-methyl-4,5,6,7-tetrahydro-1H-indol-4-yl)methanone

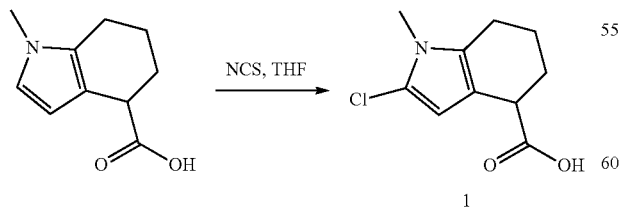

112

Step 1. 2-chloro-1-methyl-4,5,6,7-tetrahydro-1H-indole-4-carboxylic Acid

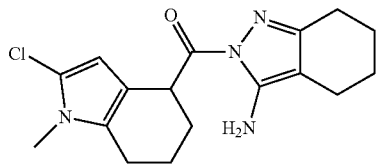

Into a 50-mL 3-necked round-bottom flask purged and maintained with an inert atmosphere of nitrogen, was placed 1-methyl-4,5,6,7-tetrahydro-1H-indole-4-carboxylic acid (50 mg, 0.28 mmol, 1.00 equiv), tetrahydrofuran (5 mL), a solution of NCS (37.4 mg, 0.28 mmol, 1.10 equiv) in tetrahydrofuran (2 mL). The resulting solution was stirred for 30 min at −78° C. The reaction was then quenched by the addition of saturated brine (25 mL). The resulting solution was extracted with ethyl acetate (80 mL×2) and the organic layers combined and dried over anhydrous sodium sulfate. The solids were filtered out. The resulting mixture was concentrated under vacuum. This resulted in 50 mg (84%) of 2-chloro-1-methyl-4,5,6,7-tetrahydro-1H-indole-4-carboxylic acid as a dark green crude solid. MS (ES, m/z) [M+H]$^+$: 214.

Step 2. (3-amino-4,5,6,7-tetrahydroindazol-2-yl)(2-chloro-1-methyl-4,5,6,7-tetrahydro-1H-indol-4-yl)methanone

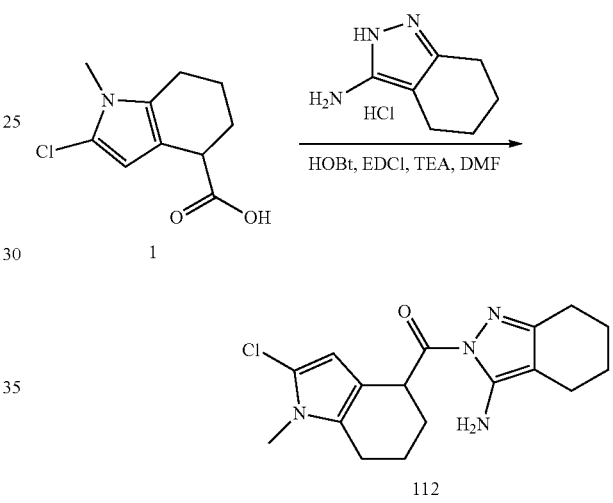

Into a 10-mL round-bottom flask, was placed 2-chloro-1-methyl-4,5,6,7-tetrahydro-1H-indole-4-carboxylic acid (50 mg, 0.23 mmol, 1.00 equiv), HOBT (47.3 mg, 0.35 mmol, 1.50 equiv), EDCI (67.3 mg, 0.35 mmol, 1.50 equiv), N,N-dimethylformamide (3 mL), TEA (118 mg, 1.17 mmol, 5.00 equiv), 4,5,6,7-tetrahydro-2H-indazol-3-amine hydrochloride (48.8 mg, 0.28 mmol, 1.20 equiv). The resulting solution was stirred overnight at 25° C. The resulting solution was diluted with EA (80 mL). The resulting mixture was washed with saturated brine (60 mL×3). The mixture was dried over anhydrous sodium sulfate. The solids were filtered out. The resulting mixture was concentrated under vacuum. The residue was purified by preparative TLC (EA:PE=1:1). The crude product was purified by Prep-HPLC with the following conditions Column: XBridge Shield RP18 OBD Column, 5 um, 19×150 mm, Mobile Phase A: water (0.1% FA), Mobile Phase B: ACN, Flow rate: 20 mL/min, Gradient: 25% B to 85% B in 7 min, 254 nm, The collected fraction was lyophilized to give 8.0 mg (10%) of (3-amino-4,5,6,7-tetrahydroindazol-2-yl)(2-chloro-1-methyl-4,5,6,7-tetrahydro-1H-indol-4-yl)methanone (112) as a pink solid. RT: 6.66 min, MS (ES, m/z) [M+H]$^+$: 333, (DMSO-d$_6$, 400 MHz, ppm): δ 6.32 (s, 2H), 5.66 (s, 1H), 4.73-4.68 (m, 1H), 3.37 (s, 3H), 2.48-2.43 (m, 4H), 2.28-2.22 (m, 2H), 2.03-1.62 (m, 8H).

Example 113 and 114: (3-amino-4,5,6,7-tetrahydro-2H-indazol-2-yl)(2-ethyl-1H-pyrrolo[2,3-b]pyridin-4-yl)methanone (113) and (3-amino-4,5,6,7-tetrahydro-1H-indazol-1-yl)(2-ethyl-1H-pyrrolo[2,3-b]pyridin-4-yl)methanone (114)

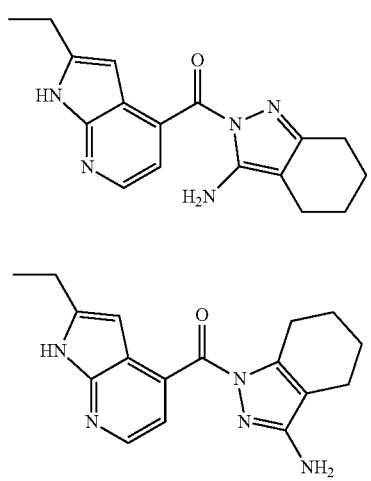

Step 1. 4-chloro-1-tosyl-1H-pyrrolo[2,3-b]pyridine

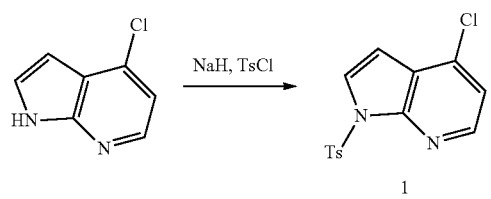 [SMILES: Clc1ccnc2[nH]ccc12 ; Cc1ccc(S(=O)(=O)n2ccc3c(Cl)ccnc32)cc1]

Into a 250-mL 3-necked round-bottom flask purged and maintained with an inert atmosphere of nitrogen, was placed 4-chloro-1H-pyrrolo[2,3-b]pyridine (10 g, 65.54 mmol, 1.00 equiv), tetrahydrofuran (150 mL), sodium hydride (3.9 g, 162.50 mmol, 1.50 equiv, 60%) was added at 0° C. The mixture was stirred for 30 min. TsCl (18.8 g, 98.61 mmol, 1.50 equiv) was added at 0° C. The resulting solution was stirred overnight at room temperature (25° C.). The reaction was then quenched by the addition water/ice (30 mL). The resulting solution was extracted dichloromethane (100 mL×3) and the organic layers combined. The combined organic phase was dried with anhydrous Na$_2$SO$_4$ and concentrated under vacuum. The residue was applied onto a silica gel column with ethyl acetate/petroleum ether (1/3). This resulted in 18 g (90%) of 4-chloro-1-[(4-methylbenzene)sulfonyl]-1H-pyrrolo[2,3-b]pyridine as a white solid. MS: (ES, m/z) [M+H]$^+$: 307 and 309.

Step 2. 4-chloro-2-ethyl-1-tosyl-1H-pyrrolo[2,3-b]pyridine

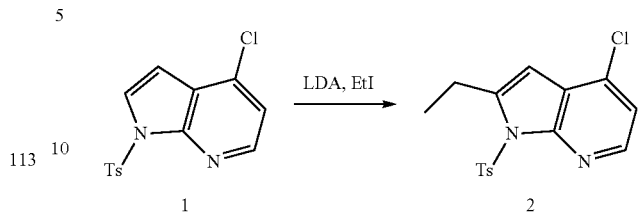

Into a 100-mL 3-necked round-bottom flask purged and maintained with an inert atmosphere of nitrogen, was placed 4-chloro-1-[(4-methylbenzene)sulfonyl]-1H-pyrrolo[2,3-b]pyridine (3 g, 9.78 mmol, 1.00 equiv), tetrahydrofuran (20 mL). This was followed by the addition of LDA (7.4 mL, 1.50 equiv, 2M) was added at −78° C. The mixture was stirred for 40 min at −78° C. To this was added EtI (3.06 g, 2.00 equiv) at −78° C. The resulting solution was stirred overnight at room temperature (20° C.). The reaction was then quenched by the addition sat. NH$_4$Cl (15 mL). The resulting solution was extracted with dichloromethane (100 mL×3) and the organic layers combined. The combined organic phase was dried with anhydrous Na$_2$SO$_4$ and concentrated under vacuum. The residue was applied onto a silica gel column with ethyl acetate/petroleum ether (1/4). This resulted in 2 g (61%) of 4-chloro-2-ethyl-1-tosyl-1H-pyrrolo[2,3-b]pyridine as a yellow solid. MS: (ES, m/z) [M+H]$^+$: 335 and 337.

Step 3. Methyl 2-ethyl-1-tosyl-1H-pyrrolo[2,3-b]pyridine-4-carboxylate

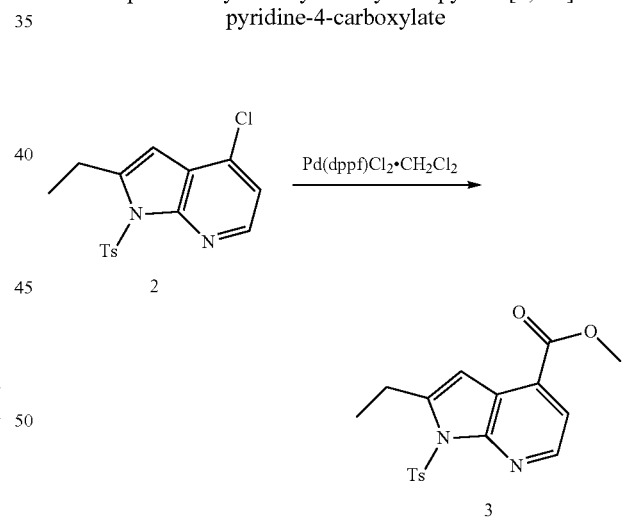

Into a 30-mL pressure tank reactor (60 atm) purged and maintained with an inert atmosphere of CO, was placed 4-chloro-2-ethyl-1-[(4-methylbenzene)sulfonyl]-1H-pyrrolo[2,3-b]pyridine (1 g, 2.99 mmol, 1.00 equiv), Pd(dppf)Cl$_2$.CH$_2$Cl$_2$ (1.2 g, 0.50 equiv), TEA (1.52 g, 15.02 mmol, 5.00 equiv), methanol (20 mL). The resulting solution was stirred overnight at 120° C. The resulting mixture was concentrated under vacuum. The residue was applied onto a silica gel column with ethyl acetate/petroleum ether (1/5). This resulted in 880 mg (82%) of methyl 2-ethyl-1-tosyl-1H-pyrrolo[2,3-b]pyridine-4-carboxylate as a yellow solid. MS: (ES, m/z) [M+H]$^+$: 359.

Step 4. 2-ethyl-1-tosyl-1H-pyrrolo[2,3-b]pyridine-4-carboxylic Acid

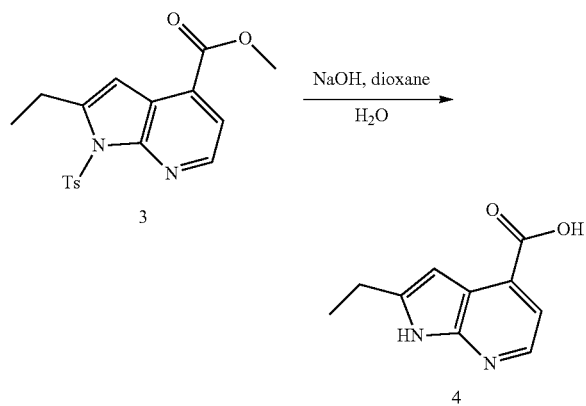

Into a 100-mL round-bottom flask, was placed methyl 2-ethyl-1-[(4-methylbenzene)sulfonyl]-1H-pyrrolo[2,3-b]pyridine-4-carboxylate (440 mg, 1.23 mmol, 1.00 equiv), methanol (25 mL), water (5 mL), sodium hydroxide (492 mg, 12.30 mmol, 10.00 equiv). The resulting solution was stirred for 2 days at 75° C. The resulting solution was diluted with H$_2$O (15 mL). The resulting mixture was washed with DCM (100 mL×3). The pH value of the solution was adjusted to 3-4 with hydrogen chloride (1 mol/L). The solids were collected by filtration. This resulted in 150 mg (64%) of 2-ethyl-1-tosyl-1H-pyrrolo[2,3-b]pyridine-4-carboxylic acid as a yellow solid. MS: (ES, m/z) [M+H]$^+$: 345.

Step 5. (3-amino-4,5,6,7-tetrahydro-2H-indazol-2-yl)(2-ethyl-1H-pyrrolo[2,3-b]pyridin-4-yl)methanone and (3-amino-4,5,6,7-tetrahydro-1H-indazol-1-yl)(2-ethyl-1H-pyrrolo[2,3-b]pyridin-4-yl)methanone

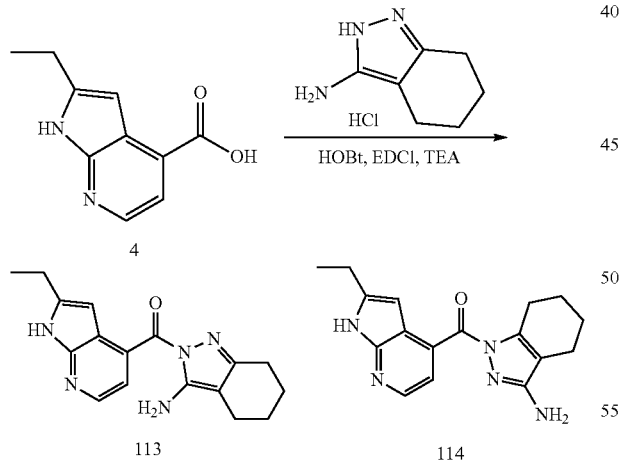

Into a 50-mL round-bottom flask, was placed 2-ethyl-1H-pyrrolo[2,3-b]pyridine-4-carboxylic acid (60 mg, 0.32 mmol, 1.00 equiv), 4,5,6,7-tetrahydro-2H-indazol-3-amine dihydrochloride (65.6 mg, 0.38 mmol, 1.20 equiv), HOBt (64 mg, 0.47 mmol, 1.50 equiv), EDCI (91 mg, 0.47 mmol, 1.50 equiv), N,N-dimethylformamide (3 mL), TEA (159 mg, 1.57 mmol, 5.00 equiv). The resulting solution was stirred overnight at 25° C. The resulting solution was stirred overnight at 25° C. The resulting solution was diluted with EA (100 mL). The resulting mixture was washed with brine (60 mL×3). The mixture was dried over anhydrous sodium sulfate. The solids were filtered out. The resulting mixture was concentrated under vacuum. The crude product was purified by Prep-HPLC with the following conditions: Column, XSelect CSH Prep C18 OBD Column, 5 um, 19×150 mm, mobile phase, water (0.1% FA) and ACN (45.0% ACN up to 65.0% in 7 min), Detector, UV 254 nm. The collected fractions were lyophilized to give 7.8 mg (8%) of (3-amino-4,5,6,7-tetrahydro-2H-indazol-2-yl)(2-ethyl-1H-pyrrolo[2,3-b]pyridin-4-yl)methanone (113) as a white solid. RT: 6.89 min, MS (ES, m/z )[M+H]$^+$: 310, (DMSO-d$_6$, 400 MHz, ppm): δ 11.78 (s, 1H), 8.19 (d, J=5.2 Hz, 1H), 7.37 (d, J=5.2 Hz, 1H), 6.49 (s, 2H), 6.18 (s, 1H), 2.79-2.74 (m, 2H), 2.36-2.31 (m, 4H), 1.65 (s, 4H), 1.29-1.25 (m, 3H). And 8.1 mg (8%) of (3-amino-4,5,6,7-tetrahydro-1H-indazol-1-yl)(2-ethyl-1H-pyrrolo[2,3-b]pyridin-4-yl)methanone (114) as a white solid. RT: 6.14 min, MS (ES, m/z) [M+H]$^+$: 310, (DMSO-d$_6$, 400 MHz, ppm): δ 11.70 (s, 1H), 8.16 (d, J=4.8 Hz, 1H), 7.26 (d, J=5.2 Hz, 1H), 6.12 (s, 1H), 5.49 (s, 2H), 2.97 (s, 2H), 2.76-2.74 (m, 2H), 2.26 (s, 2H), 1.81-1.59 (m, 4H), 1.28-1.24 (m, 3H).

Example 115 and 116: (3-amino-4,5,6,7-tetrahydroindazol-2-yl)(7-fluoro-1,2,3,4-tetrahydroquinolin-4-yl)methanone (115) and (3-amino-4,5,6,7-tetrahydroindazol-1-yl)(7-fluoro-1,2,3,4-tetrahydroquinolin-4-yl)methanone (116)

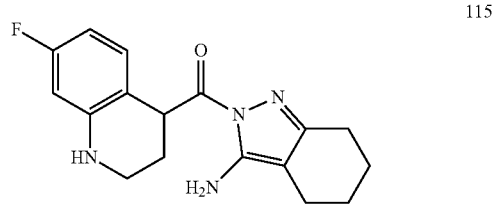

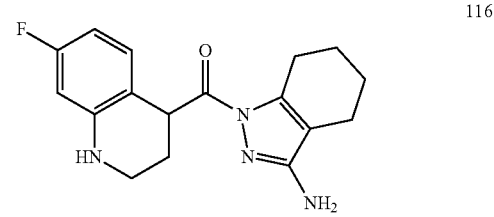

Step 1. 7-fluoro-1,2,3,4-tetrahydroquinoline-4-carboxylic Acid

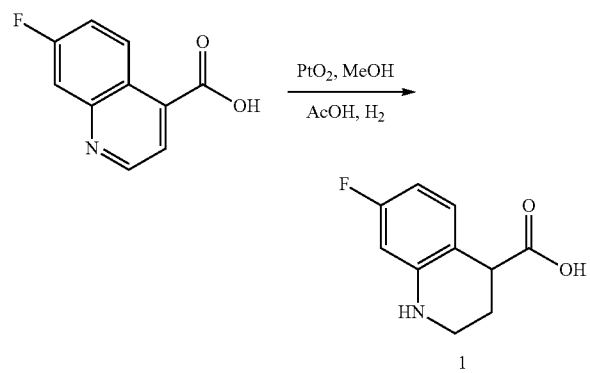

Into a 100-mL round-bottom flask, was placed 7-fluoroquinoline-4-carboxylic acid (100 mg, 0.52 mmol, 1.00 equiv), methanol (10 mL), PtO$_2$ (100 mg). To the above hydrogen was introduced in. The resulting solution was stirred for 2 h at room temperature. The solids were filtered out. The resulting mixture was concentrated under vacuum. This resulted in 90 mg (88%) of 7-fluoro-1,2,3,4-tetrahydroquinoline-4-carboxylic acid as a red solid. MS (ES, m/z) [M+H]$^+$: 196.

Step 2. (3-amino-4,5,6,7-tetrahydroindazol-2-yl)(7-fluoro-1,2,3,4-tetrahydroquinolin-4-yl)methanone and (3-amino-4,5,6,7-tetrahydroindazol-1-yl)(7-fluoro-1,2,3,4-tetrahydroquinolin-4-yl)methanone

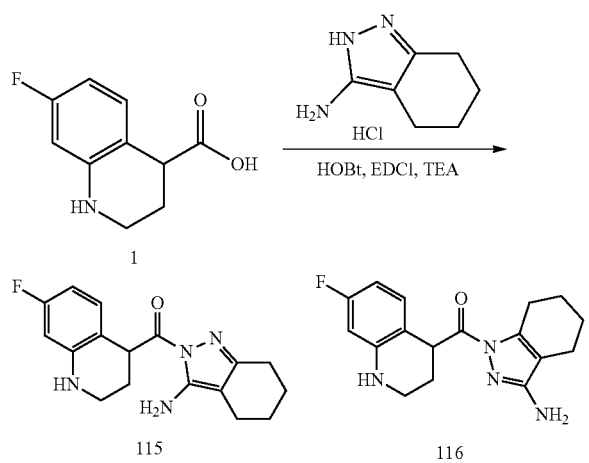

Into a 50-mL round-bottom flask, was placed 7-fluoro-1,2,3,4-tetrahydroquinoline-4-carboxylic acid (40 mg, 0.20 mmol, 1.00 equiv), 4,5,6,7-tetrahydro-2H-indazol-3-amine dihydrochloride (44 mg, 0.21 mmol, 1.00 equiv), HOBT (42 mg, 0.31 mmol, 1.50 equiv), EDCI (60 mg, 0.31 mmol, 1.50 equiv), TEA (62 mg, 0.61 mmol, 3.00 equiv), N,N-dimethylformamide (5 mL). The resulting solution was stirred overnight at room temperature. The reaction was then quenched by the addition of water (30 mL). The resulting solution was extracted with ethyl acetate (30 mL×3) and the organic layers combined. The resulting mixture was washed with Brine (60 mL×2). The resulting mixture was concentrated under vacuum. The crude product was purified by Prep-HPLC with the following conditions: Column: XSelect CSH Prep C18 OBD Column, 5 um, 19×150 mm, Mobile Phase A: water (0.1% FA), Mobile Phase B: ACN, Flow rate: 20 mL/min, Gradient: 40% B to 70% B in 7 min, 254 nm. The collected fraction was lyophilized to give 5.7 mg (9%) of (3-amino-4,5,6,7-tetrahydroindazol-2-yl)(7-fluoro-1,2,3,4-tetrahydroquinolin-4-yl)methanone (115) as off-white solid. Rt: 6.85 min, MS (ES, m/z) [M+H]$^+$: 315, (DMSO-d$_6$, 300 MHz, ppm): δ 6.81-6.76 (m, 1H), 6.35 (s, 2H), 6.29-6.24 (m, 1H), 6.19-6.13 (m, 2H), 4.99-4.96 (m, 1H), 3.28-3.18 (m, 2H), 2.48-2.47 (m, 2H), 2.27-2.24 (m, 2H), 2.07-1.95 (m, 2H), 1.68- 1.66 (m, 4H). And 1.7 mg (3%) of (3-amino-4,5,6,7-tetrahydroindazol-1-yl)(7-fluoro-1,2,3,4-tetrahydroquinolin-4-yl)methanone (116) as off-white solid. Rt: 6 min, MS (ES, m/z) [M+H]$^+$: 315, (DMSO-d$_6$, 300 MHz, ppm): δ 6.80-6.75 (m, 1H), 6.27-6.22 (m, 1H), 6.18-6.12 (m, 2H), 5.48 (s, 2H), 4.92-4.88 (m, 1H), 3.29-3.14 (m, 1H), 3.18-3.13 (m, 1H), 2.79-2.71 (m, 2H), 2.24-2.22 (m, 2H), 2.08- 1.93 (m, 2H), 1.66-1.64 (m, 4H).

Example 117 and 118: (3-amino-5-(benzyloxy)-4,5,6,7-tetrahydroindazol-2-yl)(2-methyl-1H-indol-4-yl)methanone (117) and (3-amino-5-(benzyloxy)-4,5,6,7-tetrahydroindazol-1-yl)(2-methyl-1H-indol-4-yl)methanone (118)

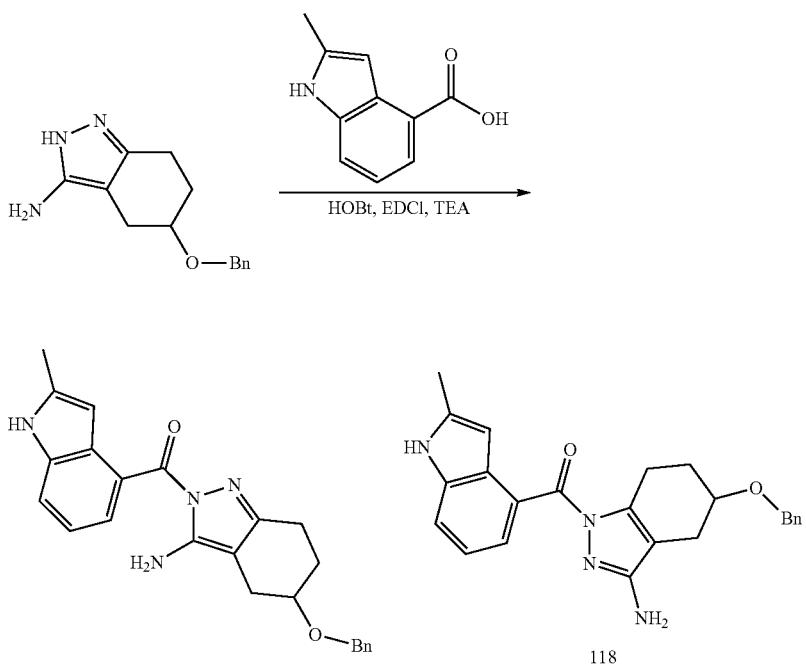

Into a 40-mL vial, was placed 2-methyl-1H-indole-4-carboxylic acid (40 mg, 0.23 mmol, 1.00 equiv), N,N-dimethylformamide (5 mL), HOBT (46.28 mg, 0.34 mmol, 1.50 equiv), EDCI (65.48 mg, 0.34 mmol, 1.50 equiv), TEA (115.39 mg, 1.14 mmol, 5.00 equiv), The resulting solution was stirred for 10 min at 25° C. Then added 5-(benzyloxy)-4,5,6,7-tetrahydro-2H-indazol-3-amine (66.65 mg, 0.27 mmol, 1.20 equiv). The resulting solution was allowed to react, with stirring, for an additional overnight at 25° C. The resulting solution was diluted with water (20 ml), and extracted with EA (20 mL×3) and the organic layers combined. The resulting mixture was washed with Brine (50 mL×3). The mixture was dried over anhydrous sodium sulfate and concentrated under vacuum. The residue was purified by preparative TLC (DCM:MeOH=30:1). The crude product was purified by Prep-HPLC with the following conditions: Column: XBridge Shield RP18 OBD Column, 5 um, 19×150 mm, Mobile Phase A: water (0.1% FA), Mobile Phase B: ACN, Flow rate: 20 mL/min, Gradient: 25% B to 50% B in 7 min, 254 nm. The collected fractions were combined and lyophilization to give 8.2 mg (9%) of (3-amino-5-(benzyloxy)-4,5,6,7-tetrahydroindazol-2-yl)(2-methyl-1H-indol-4-yl)methanone (117) as a yellow solid. RT: 6.56 min, MS (ES, m/z) [M+H]$^+$: 401, (DMSO, ppm): 11.19 (s, 1H), 7.55 (d, J=8.1 Hz, 1H), 7.46 (d, J=8.1 Hz, 1H), 7.35 (d, J=4.2 Hz, 5H), 7.07-7.02 (m, 1H), 6.40 (s, 2H), 6.27 (s, 1H), 4.56 (d, J=2.4 Hz, 2H), 3.82 (s, 1H), 2.73 (s, 1H), 2.66 (d, J=4.8 Hz, 1H), 2.44-2.36 (m, 5H), 1.91-1.87 (m, 2H). and 4.9 mg (5%) of (3-amino-5-(benzyloxy)-4,5,6,7-tetrahydroindazol-1-yl)(2-methyl-1H-indol-4-yl)methanone (118) as an off white solid. RT: 5.5 min, MS (ES, m/z) [M+H]$^+$: 401, (DMSO, ppm): 11.10 (s, 1H), 7.42-7.35 (m, 7H), 7.04-6.99 (m, 1H), 6.19 (s, 1H), 5.35 (s, 2H), 4.59 (d, J=3.3 Hz, 2H), 3.89 (d, J=4.8 Hz, 1H), 3.06-2.98 (m, 2H), 2.73-2.68 (m, 1H), 2.50-2.38 (m, 4H), 1.98-1.94 (m, 2H).

Example 119 and 120: (3-amino-5-methoxy-4,5,6,7-tetrahydro-2H-indazol-2-yl)(2-methyl-1H-indol-4-yl)methanone (119) and (3-amino-5-methoxy-4,5,6,7-tetrahydro-2H-indazol-1-yl)(2-methyl-1H-indol-4-yl)methanone (120)

119

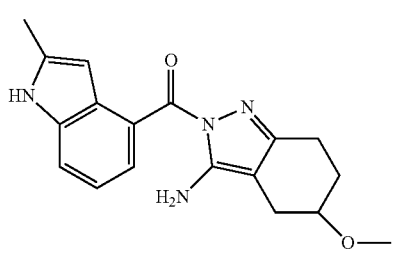

120

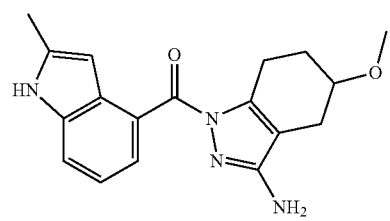

Step 1.
5-methoxy-2-oxocyclohexane-1-carbaldehyde

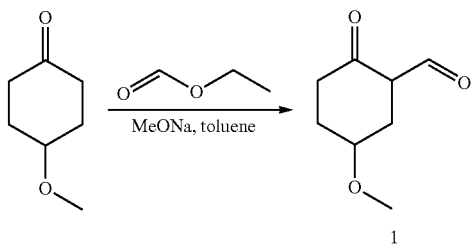

1

Into a 250-mL 3-necked round-bottom flask, was placed a solution of 4-methoxycyclohexan-1-one (5 g, 39.01 mmol, 1.00 equiv) in toluene (100 mL), methoxysodium (6.3 g, 116.62 mmol, 3.00 equiv). This was followed by the addition of ethyl formate (17.2 g, 232.19 mmol, 6.00 equiv) dropwise with stirring at 0° C. The resulting solution was stirred overnight at room temperature. The resulting mixture was concentrated under vacuum. The pH value of the solution was adjusted to 6 with HCl (1 mol/L). The resulting solution was extracted with ethyl acetate (500 mL×3) and the organic layers combined and dried over anhydrous sodium sulfate and concentrated under vacuum. This resulted in 4.88 g (crude) of 5-methoxy-2-oxocyclohexane-1-carbaldehyde as black oil. MS (ES, m/z) [M+H]$^+$: 157.

Step 2. 2-[(1Z)-(hydroxyimino)methyl]-4-methoxy-cyclohexan-1-one

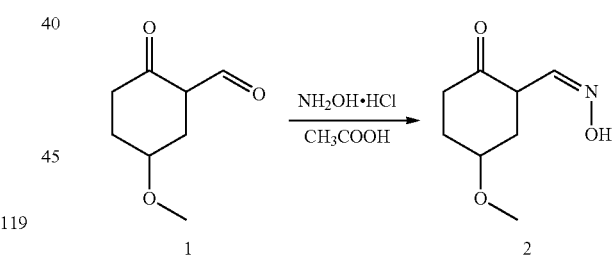

1                                                  2

Into a 100-mL round-bottom flask, was placed 5-methoxy-2-oxocyclohexane-1-carbaldehyde (4.88 g, 31.25 mmol, 1.00 equiv), hydroxylamine hydrochloride (2.37 g, 34.11 mmol, 1.10 equiv), acetic acid (50 mL). The resulting solution was stirred for 3 h at 100° C. The resulting mixture was concentrated under vacuum. The pH value of the solution was adjusted to 7-8 with sat. Na$_2$CO$_3$ aqueous solution. The resulting solution was extracted with dichloromethane (200 mL×3) and the organic layers combined and dried over anhydrous sodium sulfate and concentrated under vacuum. This resulted in 3.3 g (crude) of 2-[(1Z)-(hydroxyimino)methyl]-4-methoxycyclohexan-1-one as black oil. MS (ES, m/z) [M+H]$^+$: 172.

Step 3. 5-methoxy-2-oxocyclohexane-1-carbonitrile

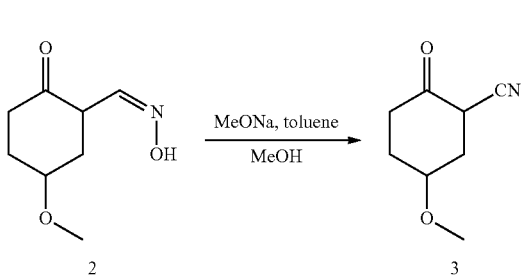

Into a 100-mL round-bottom flask, was placed 2-[(1Z)-(hydroxyimino)methyl]-4-methoxycyclohexan-1-one (3.3 g, 19.28 mmol, 1.00 equiv), MeONa (2.08 g, 38.52 mmol, 2.00 equiv), toluene (60 mL), methanol (5 mL). The resulting solution was stirred overnight at room temperature. The pH value of the solution was adjusted to 5 with HCl (1 mol/L). The resulting solution was extracted with dichloromethane (200 mL×3) and the organic layers combined and concentrated under vacuum. This resulted in 2.3 g (crude) of 5-methoxy-2-oxocyclohexane-1-carbonitrile as black oil. MS (ES, m/z) [M+H]⁺: 154.

Step 4. 5-methoxy-4,5,6,7-tetrahydro-2H-indazol-3-amine

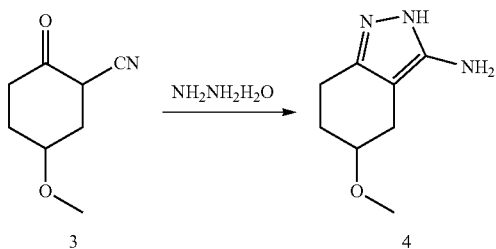

Into a 100-mL round-bottom flask, was placed a solution of 5-methoxy-2-oxocyclohexane-1-carbonitrile (2.3 g, 15.02 mmol, 1.00 equiv) in ethanol (3 mL), hydrazine hydrate (3 mL). The resulting solution was stirred overnight at room temperature. The resulting mixture was concentrated under vacuum. The residue was applied onto a silica gel column with dichloromethane/methanol (100-90%). This resulted in 0.7 g (28%) of 5-methoxy-4,5,6,7-tetrahydro-2H-indazol-3-amine as yellow oil. MS (ES, m/z) [M+H]⁺: 168.

Step 5. (3-amino-5-methoxy-4,5,6,7-tetrahydro-2H-indazol-2-yl)(2-methyl-1H-indol-4-yl)methanone and (3-amino-5-methoxy-4,5,6,7-tetrahydro-2H-indazol-1-yl)(2-methyl-1H-indol-4-yl)methanone

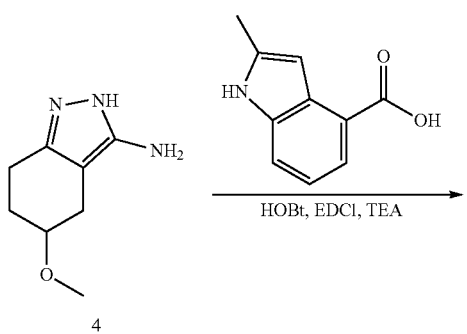

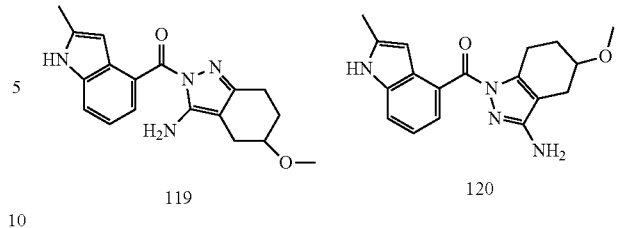

Into a 100-mL round-bottom flask, was placed 5-methoxy-4,5,6,7-tetrahydro-2H-indazol-3-amine (70 mg, 0.42 mmol, 1.00 equiv), 2-methyl-3H-indole-4-carboxylic acid (73.35 mg, 0.42 mmol, 1.20 equiv), HOBT (85 mg, 0.63 mmol, 1.50 equiv), EDCT (121 mg, 0.63 mmol, 1.50 equiv), N,N-dimethylformamide (20 mL), TEA (212 mg, 2.10 mmol, 5.00 equiv). The resulting solution was stirred for 12 min at room temperature. The resulting mixture was washed with water (40 mL). The resulting solution was extracted with ethyl acetate (40 mL×2) and the organic layers combined and dried over anhydrous sodium sulfate and concentrated under vacuum. The crude product was purified by Flash-Prep-HPLC with the following conditions: Column: XSelect CSH Prep C18 OBD Column, 5 um, 19*150 mm, Mobile Phase A: Water (0.1% FA), Mobile Phase B: ACN, Flow rate: 20 mL/min, Gradient: 35% B to 70% B in 7 min, 254 nm. The collected fractions were lyophilizaied to give 7.5 mg (5.5%) of (3-amino-5-methoxy-4,5,6,7-tetrahydro-2H-indazol-2-yl)(2-methyl-1H-indol-4-yl)methanone (119) as a white solid. RT2: 6.9 min MS (ES, m/z) [M+H]⁺: 325, (DMSO-d₆, 400 MHz, ppm): δ 7.61-7.62 (m, 1H), 7.45 (d, J=8.0 Hz, 1H), 7.06-7.02 (m, 1H), 6.42 (m, 2H), 6.26 (s, 1H), 3.59 (s, 1H), 3.35-3.28 (m, 3H), 2.67-2.60 (m, 1H), 2.50-2.40 (m, 3H), 2.38-2.32 (m, 4H), 2.29-2.28 (m, 2H), 1.86-1.85 (m, 1H), 1.79-1.77 (m, 1H). And 7.9 mg (5.8%) of (3-amino-5-methoxy-4,5,6,7-tetrahydro-2H-indazol-1-yl)(2-methyl-1H-indol-4-yl)methanone (120) as a white solid. RT: 6 min, MS (ES, m/z) [M+H]⁺: 325, (DMSO-d₆, 400 MHz, ppm): δ 11.10 (s, 1H), 7.43-7.39 (m, 2H), 7.03-6.99 (m, 1H), 6.18 (m, 1H), 5.34 (s, 2H), 3.67-3.65 (m, 1H), 3.32-3.29 (m, 3H), 3.08-2.92 (m, 2H), 2.67-2.57 (m, 1H), 2.40 (s, 3H), 2.32- 2.24 (m, 1H), 1.95-1.93 (m, 1H), 1.86-1.81 (m, 1H).

Example 121 and 122: (3-amino-5,5-difluoro-4,5,6,7-tetrahydro-2H-indazol-2-yl)(2-methyl-1H-indol-4-yl)methanone (121) and (3-amino-5,5-difluoro-4,5,6,7-tetrahydro-2H-indazol-1-yl)(2-methyl-1H-indol-4-yl)methanone (122)

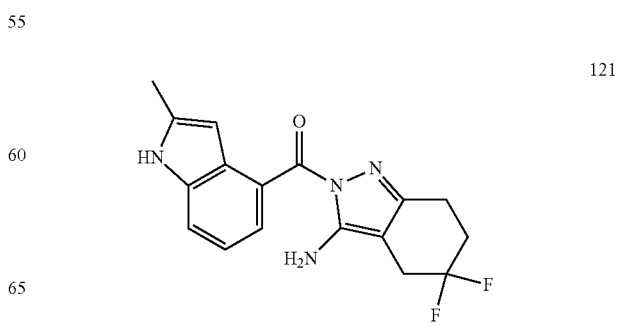

-continued

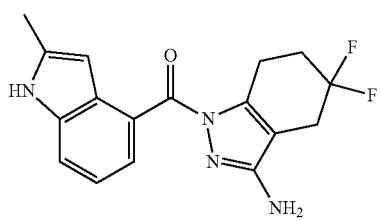

122

Step 1.
5,5-difluoro-2-oxocyclohexane-1-carbaldehyde

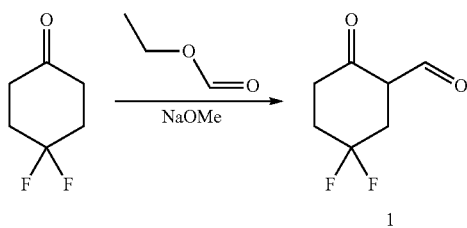

1

Into a 250-mL 3-necked round-bottom flask, was placed 4,4-difluorocyclohexan-1-one (10 g, 74.56 mmol, 1.00 equiv), toluene (80 mL). This was followed by the addition of MeONa (12 g, 222.22 mmol, 3.00 equiv) in several batches at 0° C. To this was added ethyl formate (33 g, 445.47 mmol, 6.00 equiv) dropwise with stirring at 0° C. The resulting solution was stirred overnight at room temperature. The resulting solution was diluted with $H_2O$ (100 mL). The pH value of the solution was adjusted to 5 with HCl (1 mol/L). The resulting solution was extracted with dichloromethane (200 mL×3) and the organic layers combined and concentrated under vacuum. This resulted in 13 g (crude) of 5,5-difluoro-2-oxocyclohexane-1-carbaldehyde as black oil. MS (ES, m/z) $[M+H]^+$: 163.

Step 2. 4,4-difluoro-2-[(1E)-(hydroxyimino)methyl]cyclohexan-1-one

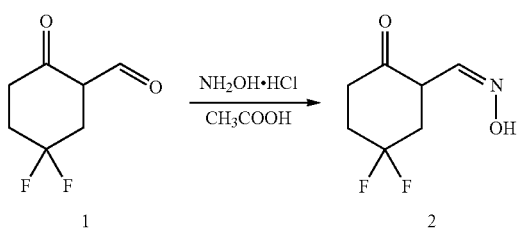

Into a 250-mL round-bottom flask, was placed 5,5-difluoro-2-oxocyclohexane-1-carbaldehyde (12 g, 74.01 mmol, 1.00 equiv), acetic acid (100 mL), $NH_2OH \cdot HCl$ (5.6 g, 81.16 mmol, 1.10 equiv). The resulting solution was stirred overnight at 100° C. The resulting mixture was concentrated under vacuum. The resulting solution was diluted with $H_2O$ (100 mL). The pH value of the solution was adjusted to 7-8 with sat. $Na_2CO_3$ aqueous solution. The resulting solution was extracted with ethyl acetate (200 mL×4) and the organic layers combined and dried over anhydrous sodium sulfate. The solids were filtered out. The resulting mixture was concentrated under vacuum. This resulted in 12 g (crude) of 4,4-difluoro-2-[(1E)-(hydroxyimino)methyl]cyclohexan-1-one as black oil. MS (ES, m/z) $[M+H]^+$: 178.

Step 3.
5,5-difluoro-2-oxocyclohexane-1-carbonitrile

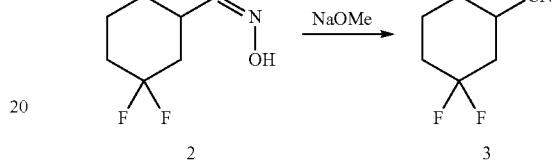

Into a 250-mL round-bottom flask, was placed 4,4-difluoro-2-[(1E)-(hydroxyimino)methyl]cyclohexan-1-one (12 g, 67.74 mmol, 1.00 equiv), toluene (100 mL), methanol (20 mL), MeONa (4.4 g, 81.48 mmol, 1.20 equiv). The resulting solution was stirred overnight at room temperature. The resulting mixture was concentrated under vacuum. The resulting solution was diluted with water (100 mL). The pH value of the solution was adjusted to 4 with HCl (1 mol/L). The resulting solution was extracted with ethyl acetate (200 mL×4) and the organic layers combined. The resulting mixture was filtered and concentrated under vacuum. This resulted in 10 g (crude) of 5,5-difluoro-2-oxocyclohexane-1-carbonitrile as black oil. MS (ES, m/z) $[M+H]^+$: 160.

Step 4.
5,5-difluoro-4,5,6,7-tetrahydro-2H-indazol-3-amine

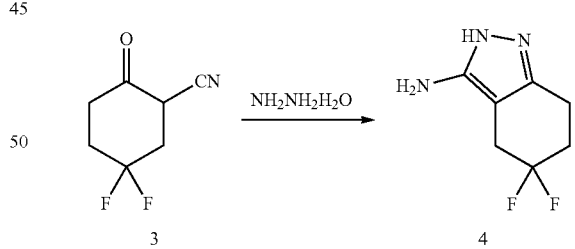

Into a 250-mL round-bottom flask, was placed a solution of 5,5-difluoro-2-oxocyclohexane-1-carbonitrile (8.0 g, 50.27 mmol, 1.00 equiv) in ethanol (50 mL), hydrazine hydrate (10 mL). The resulting solution was stirred overnight at room temperature. The resulting mixture was concentrated under vacuum. The residue was applied onto a silica gel column with dichloromethane/methanol (100-90%). The crude product was further purified by Pre-TLC with dichloromethane/methanol (20:1). This resulted in 374 mg (4%) of 5,5-difluoro-4,5,6,7-tetrahydro-2H-indazol-3-amine as a yellow solid. MS (ES, m/z) $[M+H]^+$: 174.

Step 5. (3-amino-5,5-difluoro-4,5,6,7-tetrahydro-2H-indazol-2-yl)(2-methyl-1H-indol-4-yl)methanone and (3-amino-5,5-difluoro-4,5,6,7-tetrahydro-2H-indazol-1-yl)(2-methyl-1H-indol-4-yl)methanone

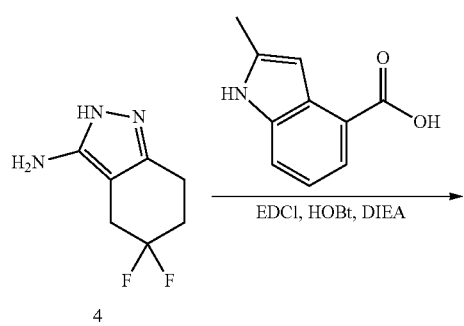

4

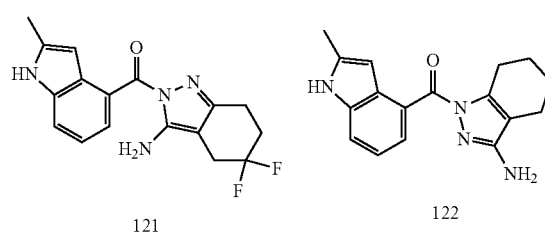

121      122

Into a 100-mL round-bottom flask, was placed 5,5-difluoro-4,5,6,7-tetrahydro-2H-indazol-3-amine (40 mg, 0.23 mmol, 1.00 equiv), 2-methyl-1H-indole-4-carboxylic acid (40.5 mg, 0.23 mmol, 1.00 equiv), EDCI (66 mg, 0.34 mmol, 1.50 equiv), HOBt (46.6 mg, 0.34 mmol, 1.50 equiv), TEA (101 mg, 1.00 mmol, 5.00 equiv), N,N-dimethylformamide (10 mL). The resulting solution was stirred for 3 h at room temperature. The resulting mixture was washed with H₂O (40 mL). The resulting solution was extracted with of ethyl acetate (40 mL×2) and the organic layers combined and concentrated under vacuum. The crude product was purified by Prep-HPLC with the following conditions: Column: XSelect CSH Prep C18 OBD Column, 5 um, 19*150 mm, Mobile Phase A: Water (0.1% FA), Mobile Phase B: ACN, Flow rate: 20 mL/min, Gradient: 45% B to 48% B in 7 min, 254/220 nm. The collected fraction s were lyophilized to give 1.9 mg (2%) of (3-amino-5,5-difluoro-4,5,6,7-tetrahydro-2H-indazol-2-yl)(2-methyl-1H-indol-4-yl)methanone (121) as a yellow solid. RT2: 5.95 min, MS (ES, m/z) [M+1]: 331, (DMSO-d₆, 400 MHz, ppm): δ 11.21 (s, 1H), 7.57 (d, J=7.6 Hz, 1H), 7.47 (d, J=8.0 Hz, 1H), 7.06 (d, J=7.6 Hz, 1H), 6.59 (s, 2H), 6.28 (s, 1H), 2.95-2.88 (m, 2H), 2.62-2.59 (m, 2H), 2.40 (s, 3H), 2.22 (s, 2H). And 3.2 mg (4.2%) of (3-amino-5,5-difluoro-4,5,6,7-tetrahydro-2H-indazol-1-yl)(2-methyl-1H-indol-4-yl)methanone (122) as a yellow solid. RT1: 4.90 min, MS (ES, m/z) [M+1]: 331, (DMSO-d₆, 400 MHz, ppm): δ 11.13 (s, 1H), 7.48-7.41 (m, 2H), 7.05-7.01 (m, 1H), 6.22 (s, 1H), 5.47 (s, 2H), 3.18-3.15 (m, 2H), 2.94-2.87 (m, 2H), 2.60-2.50 (m, 1H), 2.38 (s, 3H), 2.30-2.26 (m, 1H).

Example 123 and 124: (3-amino-4,5,6,7-tetrahydro-2H-indazol-2-yl)(7-chloroquinolin-4-yl)methanone (123) and (3-amino-4,5,6,7-tetrahydro-2H-indazol-1-yl)(7-chloroquinolin-4-yl)methanone (124)

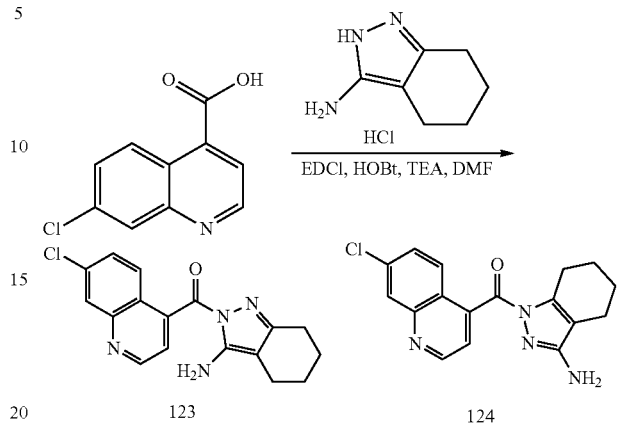

123      124

Into a 50-mL round-bottom flask, was placed 7-chloroquinoline-4-carboxylic acid (50 mg, 0.24 mmol, 1.00 equiv) (prepared as in example 103) 4,5,6,7-tetrahydro-2H-indazol-3-amine (40.5 mg, 0.24 mmol, 1.00 equiv), HOBT (48 mg, 0.36 mmol, 1.50 equiv), EDCI (68 mg, 0.35 mmol, 1.50 equiv), TEA (75 mg, 0.74 mmol, 3.00 equiv), N,N-dimethylformamide (5.0 mL). The resulting solution was stirred overnight at 20° C. The reaction was then quenched by the addition of 100 mL of water. The resulting solution was extracted with ethyl acetate (50 mL×3) and the organic layers combined. The resulting mixture was washed with brine (150 mL×2). The mixture was dried over anhydrous sodium sulfate. The solids were filtered out. The filtrate was concentrated under vacuum. The crude product was purified by Prep-HPLC with the following conditions (2#-AnalyseHPLC-SHIMADZU (HPLC-10)): Column, XBridge Shield RP18 OBD Column, 5 um, 19*150 mm, mobile phase, water (0.1% FA) and ACN (24.0% ACN up to 54.0% in 7 min), Detector, UV 254 nm. After lyophilization to collected 4.2 mg (5%) of (3-amino-4,5,6,7-tetrahydroindazol-2-yl)(7-chloroquinolin-4-yl)methanone (123) as a white solid. RT: 6.58 min, MS (ES, m/z) [M+H]⁺: 327, (DMSO-d₆, 400 MHz, ppm): δ 9.05 (d, J=4.4 Hz, 1H), 8.19 (s, 1H), 7.76-7.67 (m, 3H), 6.63 (s, 2H), 2.31 (s, 2H), 2.24 (s, 2H), 1.61 (s, 4H). And 5.2 mg (6%) of (3-amino-4,5,6,7-tetrahydroindazol-1-yl)(7-chloroquinolin-4-yl)methanone (124) as a white solid. RT1: 5.26 min, MS (ES, m/z) [M+H]⁺: 327, (DMSO-d₆, 400 MHz, ppm): δ 9.03 (d, J=4.4 Hz, 1H), 8.16 (s, 1H), 7.75-7.64 (m, 3H), 5.62 (s, 2H), 3.06 (s, 2H), 2.27 (d, J=5.6 Hz, 2H), 1.82-1.70 (m, 4H).

Example 125 and 126: ((5R*)-3-amino-5-hydroxy-4,5,6,7-tetrahydroindazol-2-yl)((4R*)-2-chloro-4,5,6,7-tetrahydro-1H-indol-4-yl)methanone (125) and ((5R*)-3-amino-5-hydroxy-4,5,6,7-tetrahydroindazol-2-yl)((4S*)-2-chloro-4,5,6,7-tetrahydro-1H-indol-4-yl)methanone (126)

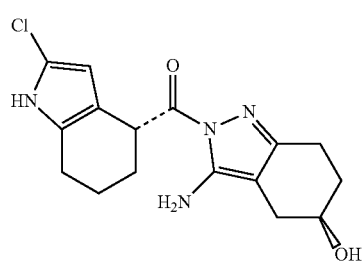

125

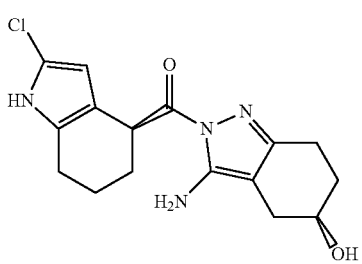

126

Step 1. 8-(benzyloxy)-1,4-dioxaspiro[4.5]decane

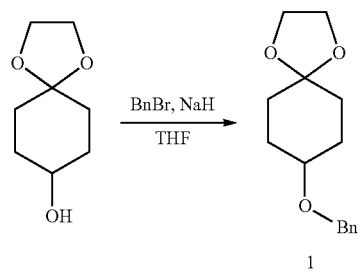

Into a 500-mL 3-necked round-bottom flask purged and maintained with an inert atmosphere of nitrogen, was placed 1,4-dioxaspiro[4.5]decan-8-ol (20 g, 126.43 mmol, 1.00 equiv), oxolane (150 mL), sodium hydride (6.1 g, 253.86 mmol, 1.20 equiv, 60%) with stirring for 5 min at 0° C. A solution of (bromomethyl)benzene (33.5 g, 195.87 mmol, 1.50 equiv) was added slowly at 0° C. The temperature was increased to room temperature naturally. The resulting solution was stirred for 15 h at room temperature. The reaction was then quenched by the addition of water/ice (200 mL). The resulting solution was extracted with ethyl acetate (200 mL×3) and the organic layers combined and dried over anhydrous sodium sulfate and concentrated under vacuum. This resulted in 40 g (crude) of 8-(benzyloxy)-1,4-dioxaspiro[4.5]decane as brown oil. MS (ES, m/z) [M+H]$^+$: 249.

Step 2. 4-(benzyloxy)cyclohexan-1-one

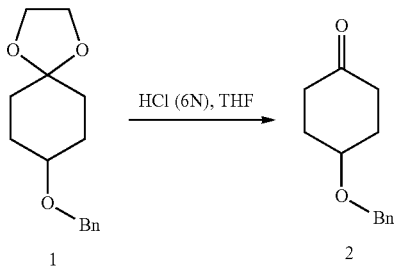 [SMILES: c1ccc(COC2CCC3(CC2)OCCO3)cc1 ; "HCl (6N), THF" ; O=C1CCC(OCc2ccccc2)CC1]

Into a 1-L round-bottom flask, was placed 8-(benzyloxy)-1,4-dioxaspiro[4.5]decane (40 g, 161.08 mmol, 1.00 equiv), HCl (6N, 400 mL, 2.50 equiv), tetrahydrofuran (300 mL). The resulting solution was stirred for 18 h at room temperature. The resulting solution was extracted with ethyl acetate (200 mL×3) and the organic layers combined and concentrated under vacuum. The residue was applied onto a silica gel column with ethyl acetate/hexane (1:10). This resulted in 19.2 g (58%) of 4-(benzyloxy)cyclohexan-1-one as yellow oil. MS (ES, m/z) [M+H]$^+$: 205.

Step 3. 5-(benzyloxy)-2-oxocyclohexane-1-carbaldehyde

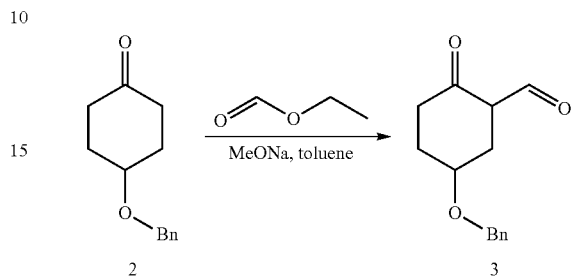

Into a 500-mL 3-necked round-bottom flask purged and maintained with an inert atmosphere of nitrogen, was placed 4-(benzyloxy)cyclohexan-1-one (19 g, 93.02 mmol, 1.00 equiv), toluene (150 mL), MeONa (15.1 g, 3.00 equiv) was added with stirring at 0° C. The above mixture was stirred for 5 min at 0° C. A solution of ethyl formate (41.4 g, 558.87 mmol, 6.00 equiv) was added slowly at 0° C. The temperature was increased to room temperature naturally. The resulting solution was stirred for 12 h at room temperature. The reaction was then quenched by the addition of water/ice (300 mL). The pH value of the solution was adjusted to 4 with hydrogen chloride (1 mol/L). The resulting solution was extracted with ethyl acetate (300 mL×3) and the organic layers combined, dried over anhydrous sodium sulfate and concentrated under vacuum. This resulted in 25 g (crude) of 5-(benzyloxy)-2-oxocyclohexane-1-carbaldehyde as yellow oil. MS (ES, m/z) [M+H]$^+$: 233.

Step 4. 4-(benzyloxy)-2-[(1Z)-(hydroxyimino)methyl]cyclohexan-1-one

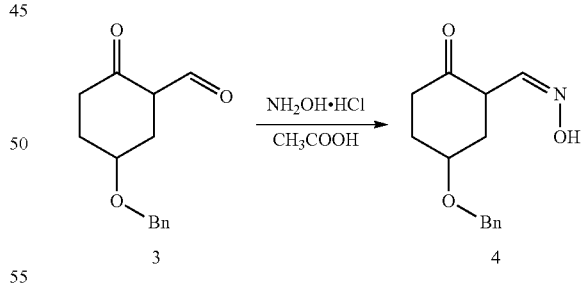

Into a 500-mL round-bottom flask, were placed 5-(benzyloxy)-2-oxocyclohexane-1-carbaldehyde (25 g, 107.63 mmol, 1.00 equiv), hydroxylamine hydrochloride (8.25 g, 118.72 mmol, 1.10 equiv) and acetic acid (150 mL). The resulting solution was stirred for 3.5 h at 100° C. The pH value of the solution was adjusted to 7 with sodium bicarbonate. The resulting solution was extracted with dichloromethane (300 mL×3, dried over anhydrous sodium sulfate and concentrated under vacuum. This resulted in 27.7 g (crude) of 4-(benzyloxy)-2-[(1Z)-(hydroxyimino)methyl]cyclohexan-1-one as yellow oil. MS (ES, m/z) [M+H]$^+$: 248.

Step 5.
5-(benzyloxy)-2-oxocyclohexane-1-carbonitrile

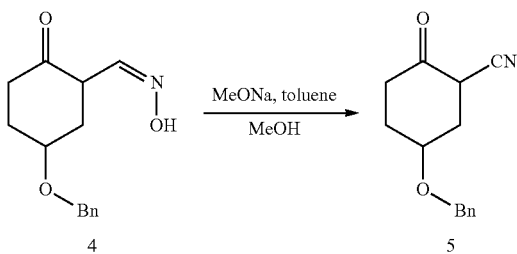 [SMILES: "MeOH" ; O=C1CCC(OCc2ccccc2)CC1/C=N\O ; "MeONa, toluene" ; N#CC1CC(OCc2ccccc2)CCC1=O]

Into a 500-mL round-bottom flask, was placed 4-(benzyloxy)-2-[(1E)-(hydroxyimino)methyl]cyclohexan-1-one (27.7 g, 112.01 mmol, 1.00 equiv), methylbenzene (200 mL), methoxysodium (7.7 g, 142.53 mmol, 1.30 equiv), methanol (15 mL). The resulting solution was stirred for 15 h at room temperature. The reaction was then quenched by the addition of water (200 mL). The pH value of the solution was adjusted to 4 with HCl (1 mol/L). The resulting solution was extracted with ethyl acetate (300 mL×3) and the resulted solution was concentrated to give 20 g (crude) of 5-(benzyloxy)-2-oxocyclohexane-1-carbonitrile as yellow oil. MS (ES, m/z) [M+H]$^+$: 230.

Step 6. 5-(benzyloxy)-4,5,6,7-tetrahydro-2H-indazol-3-amine

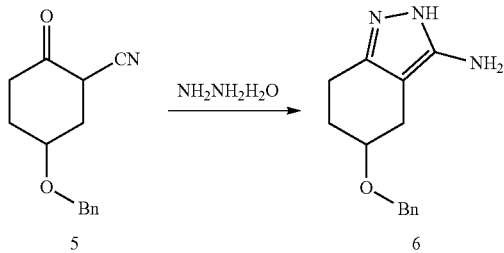 [SMILES: N#CC1CC(OCc2ccccc2)CCC1=O ; "NH2NH2H2O" ; Nc1[nH]nc2c1CC(OCc1ccccc1)CC2]

Into a 500-mL round-bottom flask, was placed 5-(benzyloxy)-2-oxocyclohexane-1-carbonitrile (20 g, 87.23 mmol, 1.00 equiv), hydrazine hydrate (200 mL), ethanol (20 mL). The resulting solution was stirred for 15 h at room temperature. The resulting solution was concentrated under vacuum. The residue was applied onto a silica gel column with dichloromethane/methanol (10:1). This resulted in 3.8 g (18%) of 5-(benzyloxy)-4,5,6,7-tetrahydro-2H-indazol-3-amine as yellow oil. MS (ES, m/z) [M+H]$^+$: 244.

Step 7. 3-amino-4,5,6,7-tetrahydro-2H-indazol-5-ol

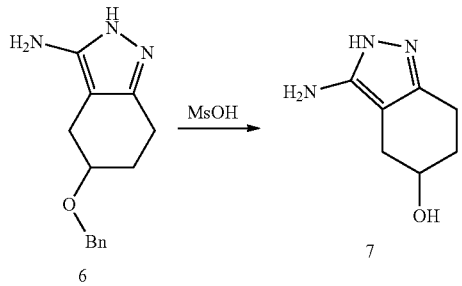 [SMILES: "MsOH" ; Nc1[nH]nc2c1CC(OCc1ccccc1)CC2 ; Nc1[nH]nc2c1CC(O)CC2]

Into a 250-mL round-bottom flask, was placed 5-(benzyloxy)-4,5,6,7-tetrahydro-2H-indazol-3-amine (3.6 g, 14.80 mmol, 1.00 equiv), dichloromethane (150 mL), methanesulfonic acid (2.13 g, 22.16 mmol, 1.50 equiv). The resulting solution was stirred for 15 h at room temperature and then concentrated under vacuum. The residue was applied onto a silica gel column with dichloromethane/methanol (5:1). This resulted in 1.1 g (49%) of 3-amino-4,5,6,7-tetrahydro-2H-indazol-5-ol as a yellow solid. MS (ES, m/z) [M+H]$^+$: 154.

Step 8. (5R*)-3-amino-4,5,6,7-tetrahydro-2H-indazol-5-ol (125i) and (5S*)-3-amino-4,5,6,7-tetrahydro-2H-indazol-5-ol (127i)

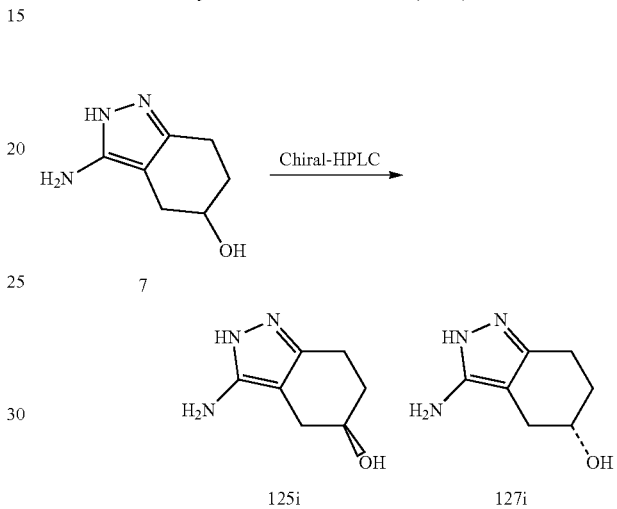

3-amino-4,5,6,7-tetrahydro-2H-indazol-5-ol (1.1 g) was purified by Chiral-Prep-HPLC with the following conditions (Prep-HPLC-009): Column: Chiralpak IC, 2*25 cm, 5 um, Mobile Phase A: Hex (0.1% DEA)-HPLC, Mobile Phase B: EtOH-HPLC, Flow rate: 20 mL/min, Gradient: 30 B to 30 B in 15.5 min, 220/254 nm. This resulted in 330 mg (30%) of (5R*)-3-amino-4,5,6,7-tetrahydro-2H-indazol-5-ol (125i) as a white solid, RT2: 12.84 min, MS (ES, m/z) [M+1]: 154. And 299 mg (30%) of (5S*)-3-amino-4,5,6,7-tetrahydro-2H-indazol-5-ol (127i) as a white solid. RT1: 9.96 min, MS (ES, m/z) [M+1]: 154.

Step 9. ((5R*)-3-amino-5-hydroxy-4,5,6,7-tetrahydroindazol-2-yl)(R/S)(2-chloro-4,5,6,7-tetrahydro-1H-indol-4-yl)methanone

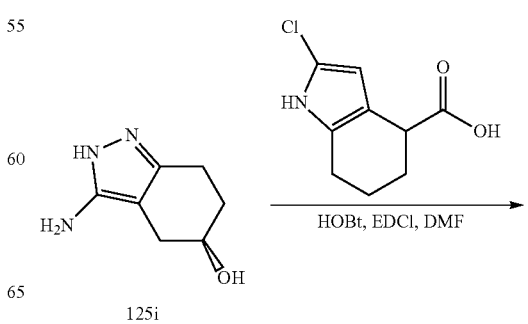

149

-continued

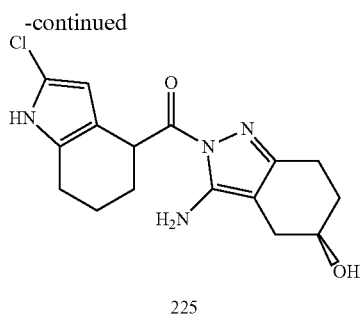

225

Into a 50-mL round-bottom flask, was placed 3-amino-4,5,6,7-tetrahydro-2H-indazol-5-ol (Enantiomer B) (130 mg, 0.85 mmol, 1.00 equiv), 2-chloro-4,5,6,7-tetrahydro-1H-indole-4-carboxylic acid (240 mg, 1.20 mmol, 0.90 equiv), HOBT (170 mg, 1.26 mmol, 1.50 equiv), EDCI (240 mg, 1.25 mmol, 1.50 equiv), TEA (255 mg, 2.52 mmol, 3.00 equiv), N,N-dimethylformamide (5 mL). The resulting solution was stirred for 5 h at room temperature. The reaction was then quenched by the addition of water (30 mL). The resulting solution was extracted with ethyl acetate (30 mL×3) and the organic layers combined. The resulting mixture was washed with Brine (100 mL×2). The resulting mixture was concentrated under vacuum. The crude product was purified by Prep-HPLC with the following conditions: Column: XBridge C18 OBD Prep Column 10 μm, 19 mm×250 mm, Mobile Phase A: water (0.1% FA), Mobile Phase B: ACN, Flow rate: 20 mL/min, Gradient: 15% B to 35% B in 7 min, 254 nm, RT2: 7 min. The collected fraction was lyophilized to give 35 mg ((5R*)-3-amino-5-hydroxy-4,5,6,7-tetrahydroindazol-2-yl)(R/S)(2-chloro-4,5,6,7-tetrahydro-1H-indol-4-yl)methanone as a pink solid. MS (ES, m/z) [M+H]⁺: 335 and 337.

Step 10. ((5R*)-3-amino-5-hydroxy-4,5,6,7-tetrahydroindazol-2-yl)((4R*)-2-chloro-4,5,6,7-tetrahydro-1H-indol-4-yl)methanone (125) and ((5R*)-3-amino-5-hydroxy-4,5,6,7-tetrahydroindazol-2-yl)((4S*)-2-chloro-4,5,6,7-tetrahydro-1H-indol-4-yl)methanone (126)

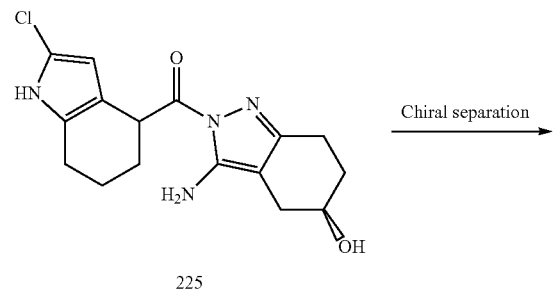

225

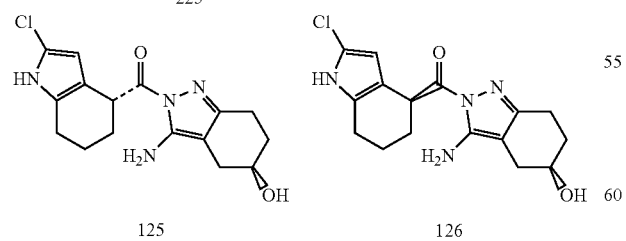

125        126

(5R)-3-amino-2-[[2-chloro-4,5,6,7-tetrahydro-1H-indol-4-yl]carbonyl]-4,5,6,7-tetrahydro-2H-indazol-5-ol (35 mg) was separated by CHIRAL-HPLC with the following conditions: Column: Phenomenex Lux 5u Cellulose-AXIA Packed, 2.12×25 cm, 5 um, Mobile Phase A: Hex-HPLC,

150

Mobile Phase B: EtOH-HPLC, Flow rate: 20 mL/min, Gradient: 30 B to 30 B in 13.5 min, 220/254 nm.

Enantiomer A: The collected fraction was concentrated under vacuum to give 10.9 mg (4%) of ((5R*)-3-amino-5-hydroxy-4,5,6,7-tetrahydroindazol-2-yl)((4R*)-2-chloro-4,5,6,7-tetrahydro-1H-indol-4-yl)methanone (125) as off-white solid. RT2:10.38 min, MS (ES, m/z) [M+H]⁺: 335 and 337, (DMSO-d₆, 400 MHz, ppm): δ 11.06 (s, 1H), 6.33 (s, 2H), 5.54 (s, 1H), 4.79-4.78 (m, 1H), 4.69-4.67 (m, 1H), 3.87-3.86 (m, 1H), 2.63-2.55 (m, 1H), 2.47-2.41 (m, 4H), 2.16-2.10 (m, 1H), 1.95-1.91 (m, 2H), 1.84-1.80 (m, 2H), 1.72-1.68 (m, 2H).

Enantiomer B: 9.6 mg (3%) of ((5R*)-3-amino-5-hydroxy-4,5,6,7-tetrahydroindazol-2-yl)((4S*)-2-chloro-4,5,6,7-tetrahydro-1H-indol-4-yl)methanone (126) as a pink solid. RT1:7.38 min, MS (ES, m/z) [M+H]⁺: 335 and 337, (DMSO-d₆, 400 MHz, ppm): δ 11.06 (s, 1H), 6.33 (s, 2H), 5.53 (s, 1H), 4.78-4.76 (m, 1H), 4.69-4.67 (m, 1H), 3.89-3.78 (m, 1H), 2.67-2.56 (m, 1H), 2.47-2.29 (m, 4H), 2.15-2.07 (m, 1H), 1.95-1.89 (m, 2H), 1.86-1.80 (m, 2H), 1.72-1.61 (m, 2H).

Example 127 and 128: ((5S*)-3-amino-5-hydroxy-4,5,6,7-tetrahydroindazol-2-yl)((4S*)-2-chloro-4,5,6,7-tetrahydro-1H-indol-4-yl)methanone (127) and ((5S*)-3-amino-5-hydroxy-4,5,6,7-tetrahydroindazol-2-yl)((4R*)-2-chloro-4,5,6,7-tetrahydro-H-indol-4-yl)methanone (128)

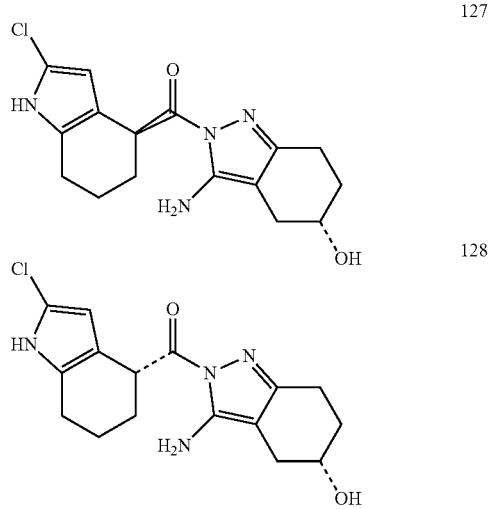

127

128

Step 1. ((5S*)-3-amino-5-hydroxy-4,5,6,7-tetrahydroindazol-2-yl)((4R/S)(2-chloro-4,5,6,7-tetrahydro-1H-indol-4-yl))methanone

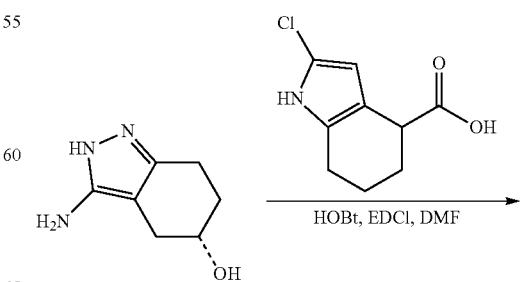

127i

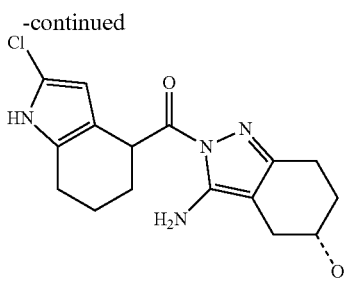

1

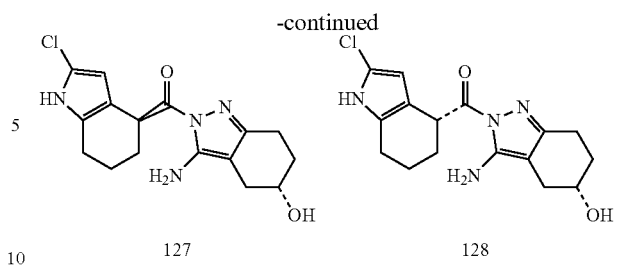

127    128

Into a 50-mL round-bottom flask, was placed (5S)-3-amino-4,5,6,7-tetrahydro-2H-indazol-5-ol (assumed) (70 mg, 0.46 mmol, 1.00 equiv), 2-chloro-4,5,6,7-tetrahydro-1H-indole-4-carboxylic acid (114 mg, 0.57 mmol, 0.90 equiv), HOBT (116 mg, 0.86 mmol, 1.50 equiv), EDCI (164 mg, 0.86 mmol, 1.50 equiv), TEA (173 mg, 1.72 mmol, 3.00 equiv), N,N-dimethylformamide (5 mL). The resulting solution was stirred for 5 h at room temperature. The reaction was then quenched by the addition of water (30 mL). The resulting solution was extracted with ethyl acetate (30 mL×3) and the organic layers combined. The resulting mixture was washed with brine (100 mL×2). The resulting mixture was concentrated under vacuum. The crude product was purified by Prep-HPLC with the following conditions: Column: XBridge C18 OBD Prep Column 10 μm, 19 mm×250 mm, Mobile Phase A: water (0.1% FA), Mobile Phase B: ACN, Flow rate: 20 mL/min, Gradient: 24% B to 40% B in 7 min, 254 nm, RT2: 7 min. The collected fraction was lyophilized to give 13 mg ((5S*)-3-amino-5-hydroxy-4,5,6,7-tetrahydroindazol-2-yl)((4S/R)-2-chloro-4,5,6,7-tetrahydro-1H-indol-4-yl)methanone as a pink solid. MS (ES, m/z) [M+H]+: 335 and 337.

Step 2. ((5S*)-3-amino-5-hydroxy-4,5,6,7-tetrahydroindazol-2-yl)((4S*)-2-choro-4,5,6,7-tetrahydro-1H-indol-4-yl)methanone and ((5S*)-3-amino-5-hydroxy-4,5,6,7-tetrahydroindazol-2-yl)((4R*)-2-chloro-4,5,6,7-tetrahydro-1H-indol-4-yl)methanone

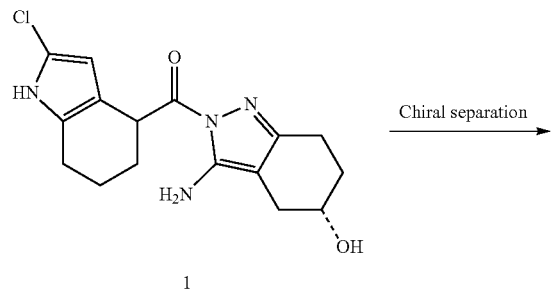

1 → Chiral separation ((5S*)-3-amino-5-hydroxy-4,5,6,7-tetrahydroindazol-2-yl)((4 S/R)-2-chloro-4,5,6,7-tetrahydro-1H-indol-4-yl) methanone (13 mg) was separated by CHIRAL-HPLC with the following conditions: Column: Phenomenex Lux 5u Cellulose-AXIA Packed, 2.12×25 cm, 5 um, Mobile Phase A: Hex-HPLC, Mobile Phase B: EtOH-HPLC, Flow rate: 20 mL/min, Gradient: 30 B to 30 B in 13.5 min, 220/254 nm.

Enantiomer A: The collected fraction was concentrated under vacuum to give 2.5 mg (4%) of ((5S*)-3-amino-5-hydroxy-4,5,6,7-tetrahydroindazol-2-yl)((4S*)-2-chloro-4,5,6,7-tetrahydro-1H-indol-4-yl)methanone (127) as off-white solid. RT2:10.38, MS (ES, m/z) [M+H]+: 335 and 337, (DMSO-$d_6$, 400 MHz, ppm): δ 11.06 (s, 1H), 6.32 (s, 2H), 5.53 (s, 1H), 4.78-4.77 (m, 1H), 4.69-4.67 (m, 1H), 3.91-3.86 (m, 1H), 2.63-2.54 (m, 1H), 2.46-2.41 (m, 4H), 2.16-2.10 (m, 1H), 1.95-1.91 (m, 2H), 1.84-1.81 (m, 2H), 1.71-1.61 (m, 2H)

Enantiomer B: 3.1 mg (3%) of ((5S*)-3-amino-5-hydroxy-4,5,6,7-tetrahydroindazol-2-yl)((4R*)-2-chloro-4,5,6,7-tetrahydro-1H-indol-4-yl)methanone (128) as a pink solid. RT1:7.38 min, MS (ES, m/z) [M+H]+: 335 and 337, (DMSO-$d_6$, 400 MHz, ppm): δ 11.05 (s, 1H), 6.32 (s, 2H), 5.54 (s, 1H), 4.77-4.76 (m, 1H), 4.69-4.67 (m, 1H), 3.89-3.87 (m, 1H), 2.62-2.55 (m, 1H), 2.49-2.45 (m, 4H), 2.15-2.09 (m, 1H), 1.95-1.80 (m, 4H), 1.70-1.66 (m, 2H).

Examples 129-132: ((5R*)-3-amino-5-hydroxy-4,5,6,7-tetrahydro-2H-indazol-2-yl)(4(S*)-6-fluoro-1,2,3,4-tetrahydroquinolin-4-yl)methanone (129); ((5R*)-3-amino-5-hydroxy-4,5,6,7-tetrahydro-2H-indazol-2-yl)(4(R*)-6-fluoro-1,2,3,4-tetrahydroquinolin-4-yl)methanone (130); ((5R*)-3-amino-5-hydroxy-4,5,6,7-tetrahydro-2H-indazol-1-yl)((4S*)-6-fluoro-1,2,3,4-tetrahydroquinolin-4-yl)methanone (131) and ((5R*)-3-amino-5-hydroxy-4,5,6,7-tetrahydro-2H-indazol-1-yl)((4R*)-6-fluoro-1,2,3,4-tetrahydroquinolin-4-yl)methanone (132)

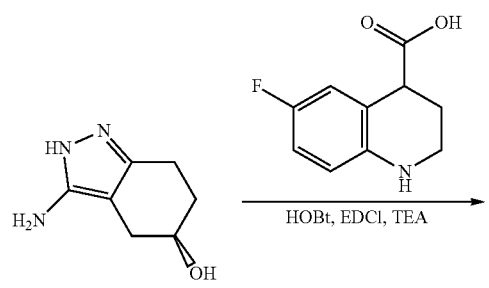

125i

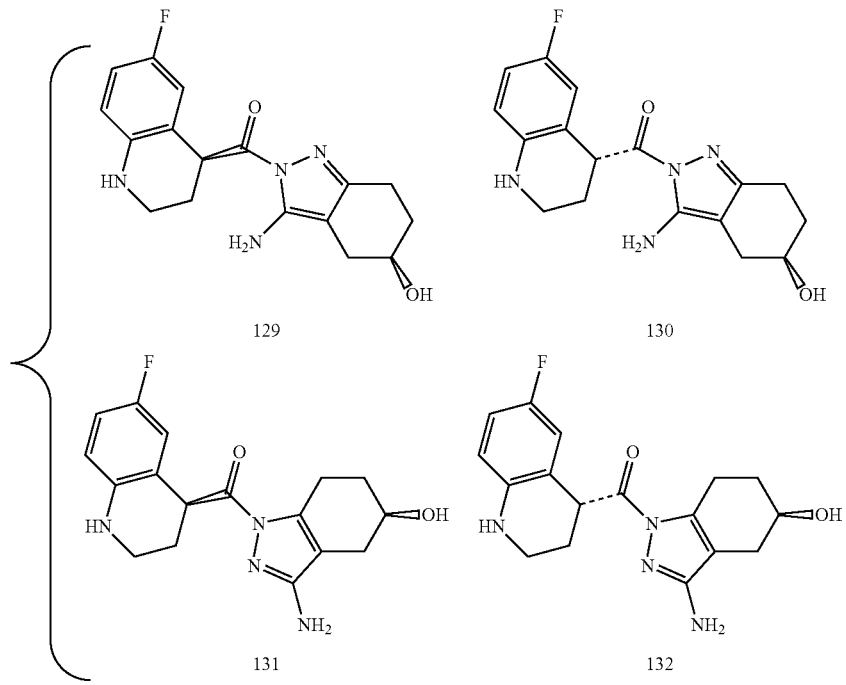

Into a 40-mL vial, was placed a solution of 6-fluoro-1,2,3,4-tetrahydroquinoline-4-carboxylic acid (81.6 mg, 0.42 mmol, 1.00 equiv) in N,N-dimethylformamide (5 mL), HOBT (85 mg, 0.63 mmol, 1.50 equiv), EDCI (120 mg, 0.63 mmol, 1.50 equiv), TEA (211 mg, 2.09 mmol, 5.00 equiv). The resulting solution was stirred for 10 min at 25° C. Then (5R*)-3-amino-4,5,6,7-tetrahydro-2H-indazol-5-ol (125i, 64 mg, 0.42 mmol, 1.00 equiv) was added. The resulting solution was allowed to react, with stirring, for an additional 1.5 h at 25° C. The reaction was then poured into 30 mL of water. The resulting solution was extracted with ethyl acetate (30 mL×3) and the organic layers combined. The resulting mixture was washed with brine (100 mL×2). The mixture was dried over anhydrous sodium sulfate. The solids were filtered out. The filtrate was concentrated under vacuum. The crude product was purified by Prep-HPLC with the following conditions: Column, XBridge C18 OBD Prep Column, 100 A, 10 um, 19 mm×250 mm, mobile phase: water (10 mmoL/L $NH_4HCO_3$) and ACN (22.0% ACN up to 23.0% in 20 min), Detector, UV 254 nm.

Enantiomer A: The collected fraction was lyophilized to give 3.2 mg (2.3%) of ((5R*)-3-amino-5-hydroxy-4,5,6,7-tetrahydroindazol-2-yl)((4S*)-6-fluoro-1,2,3,4-tetrahydroquinolin-4-yl)methanone (129) as a white solid. RT4: 15.6 min, MS (ES, m/z) [M+H]$^+$: 331, (DMSO-$d_6$, 400 MHz, ppm): δ 6.80-6.75 (m, 1H), 6.66-6.63 (m, 1H), 6.52-6.48 (m, 1H), 6.37 (s, 2H), 5.78 (s, 1H), 4.99-4.97 (m, 1H), 4.78 (s 1H), 3.89 (s, 1H), 3.26-3.15 (m, 2H), 2.64-2.51 (m, 2H), 2.16-1.98 (m, 4H), 1.85-1.82 (m, 1H), 1.70- 1.65 (m, 1H).

Enantiomer B: The collected fraction was lyophilized to give 5.1 mg (4%) of ((5R*)-3-amino-5-hydroxy-4,5,6,7-tetrahydroindazol-2-yl)((4R*)-6-fluoro-1,2,3,4-tetrahydroquinolin-4-yl)methanone (130) as a white solid. RT3: 11.6 min, MS (ES, m/z) [M+H]$^+$: 331, (DMSO-$d_6$, 400 MHz, ppm): δ 6.80-6.75 (m, 1H), 6.66-6.63 (m, 1H), 6.52-6.48 (m, 1H), 6.38 (s, 2H), 5.78 (s, 1H), 4.99-4.97 (m, 1H), 4.79 (d, J=3.6 Hz, 1H), 3.89 (s, 1H), 3.26-3.16 (m, 2H), 2.67-2.60 (m, 1H), 2.56-2.51 (m, 1H), 2.17-1.98 (m, 4H), 1.84-1.81 (m, 1H), 1.71-1.66 (m, 1H).

Enantiomer C: The collected fraction was lyophilized to give 4.2 mg (3%) of ((5R*)-3-amino-5-hydroxy-4,5,6,7-tetrahydroindazol-1-yl)((4S*)-6-fluoro-1,2,3,4-tetrahydrquinolin-4-yl)methanone (131) as a white solid. RT2:10.1 min, MS (ES, m/z) [M+H]$^+$: 331, (DMSO-$d_6$, 400 MHz, ppm): δ 6.78-6.73 (m, 1H), 6.66-6.63 (m, 1H), 6.50-6.45 (m, 1H), 5.74 (s, 1H), 5.56 (s, 2H), 4.93-4.90 (m, 1H), 4.79 (d, J=4.0 Hz, 1H), 3.90 (s, 1H), 3.29-3.24 (m, 2H), 3.13-3.12 (m, 1H), 2.95-2.89 (m, 1H), 2.81-2.79 (m, 1H), 2.17-2.11 (m, 1H), 2.03-1.91 (m, 2H), 1.81-1.79 (m, 1H), 1.69-1.65 (m, 1H).

Enantiomer D: The collected fraction was lyophilized to give 4.0 mg (2.9%) of ((5R*)-3-amino-5-hydroxy-4,5,6,7-tetrahydroindazol-1-yl)((4R*)-6-fluoro-1,2,3,4-tetrahydroquinolin-4-yl)methanone (132) as a light yellow solid. RT1: 8.96 min, MS (ES, m/z) [M+H]$^+$: 331, (DMSO-$d_6$, 400 MHz, ppm): δ 6.78-6.73 (m, 1H), 6.65-6.62 (m, 1H), 6.50-6.47 (m, 1H), 5.74 (s, 1H), 5.58 (s, 2H), 4.93-4.90 (m, 1H), 4.79 (d, J=4.0 Hz, 1H), 3.92-3.91 (m, 1H), 3.29-3.23 (m, 1H), 3.14-3.11 (m, 1H), 2.94-2.89 (m, 1H), 2.82-2.79 (m, 1H), 2.54-2.51 (m, 1H), 2.16-2.10 (m, 1H), 2.02-1.94 (m, 2H), 1.81-1.78 (m, 1H), 1.68-1.63 (m, 1H).

Examples 133-136: ((5S*)-3-amino-5-hydroxy-4,5,6,7-tetrahydroindazol-2-yl)((4S*)-6-fluoro-1,2,3,4-tetrahydroquinolin-4-yl)methanone (133); ((5S*)-3-amino-5-hydroxy-4,5,6,7-tetrahydroindazol-2-yl)((4R*)-6-fluoro-1,2,3,4-tetrahydroquinolin-4-yl)methanone (134); ((5S*)-3-amino-5-hydroxy-4,5,6,7-tetrahydro-1H-indazol-1-yl)((4S*)-6-fluoro-1,2,3,4-tetrahydroquinolin-4-yl)methanone (135) and ((5S*)-3-amino-5-hydroxy-4,5,6,7-tetrahydroindazol-1-yl)((4R*)-6-fluoro-1,2,3,4-tetrahydroquinolin-4-yl)methanone (136)

Phase B: ACN, Flow rate: 20 mL/min, Gradient: 23% B to 24% B in 16 min, 254/220 nm.

Enantiomer A: The collected fraction was lyophilized to give 11 mg (6%) of ((5S*)-3-amino-5-hydroxy-4,5,6,7-tetrahydroindazol-2-yl)((4S*)-6-fluoro-1,2,3,4-tetrahydroquinolin-4-yl)methanone (133). RT4: 13.18 min, MS (ES, m/z) [M+H]$^+$: 331, (DMSO-$d_6$, 300 MHz, ppm): δ 6.81-6.80 (m, 1H) 6.78-6.77 (m, 1H), 6.76-6.74 (m, 1H), 6.38 (s, 2H), 6.06 (s, 1H), 5.78 (s, 1H), 5.00-4.96 (m, 1H), 3.91-3.88 (m, 1H), 3.30-3.16 (m, 4H), 2.65-2.59 (m, 1H), 2.45-1.98 (m, 3H), 1.96-1.45 (m, 2H).

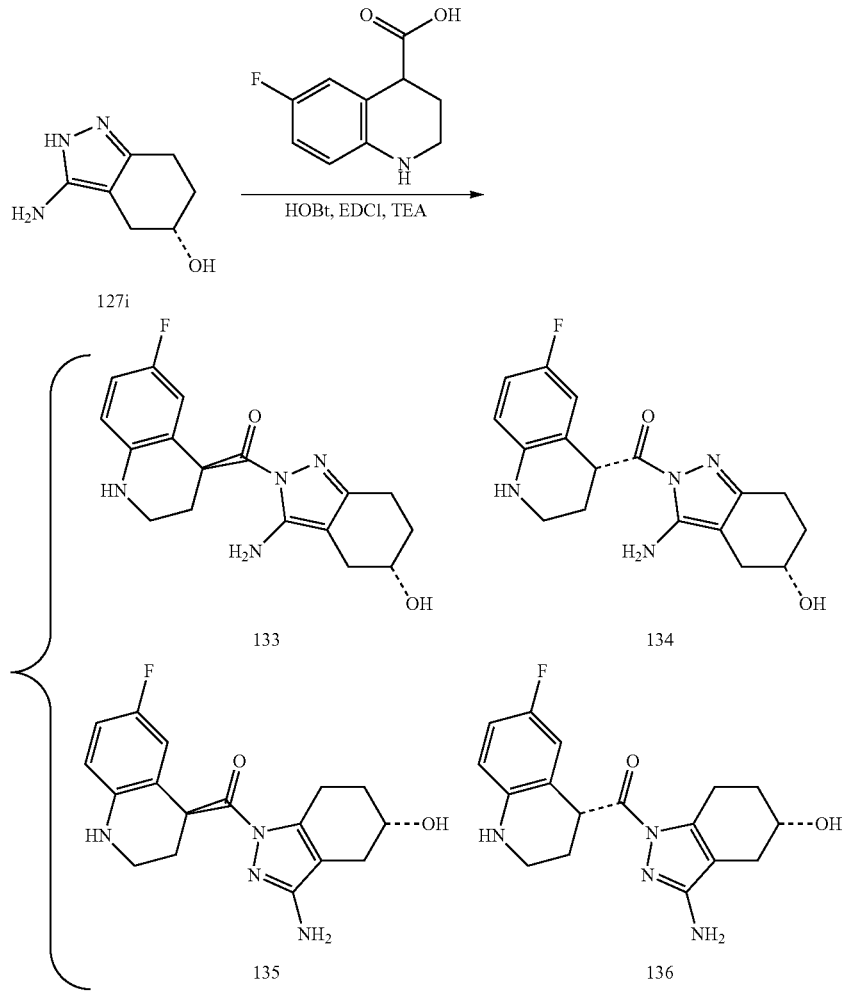

Into a 50-mL round-bottom flask, was placed (5S*)-3-amino-4,5,6,7-tetrahydro-2H-indazol-5-ol (127i, 80 mg, 0.52 mmol, 1.00 equiv), 6-fluoro-1,2,3,4-tetrahydroquinoline-4-carboxylic acid (122 mg, 0.63 mmol, 1.20 equiv), HOBT (105 mg, 0.78 mmol, 1.50 equiv), EDCI (150 mg, 0.78 mmol, 1.50 equiv), N,N-dimethylformamide (5 mL), TEA (158 mg, 1.56 mmol, 3.00 equiv). The resulting solution was stirred for 1 h at 25° C. The reaction mixture was diluted with DCM (80 mL), washed with H$_2$O (50 mL×3) and brine (50 mL×3) and dried with Na$_2$SO$_4$. After filtration, the filtrate was concentrated under reduced pressure. The crude product was purified by Prep-HPLC with the following conditions (Analyse HPLC-SHIMADZU): Column: XBridge Shield RP18 OBD Column, 5 um, 19×150 mm, Mobile Phase A: water (10 mmol/L NH$_4$HCO$_3$), Mobile Enantiomer B: The collected fraction was lyophilized to give 19 mg (10%) of ((5S*)-3-amino-5-hydroxy-4,5,6,7-tetrahydroindazol-2-yl)((4R*)-6-fluoro-1,2,3,4-tetrahydroquinolin-4-yl)methanone (134). RT3: 12.07 min, MS (ES, m/z) [M+H]$^+$: 331, (DMSO-$d_6$, 300 MHz, ppm): δ 6.81-6.80 (m, 1H) 6.79-6.78 (m, 1H), 6.76-6.71 (m, 1H), 6.38 (s, 2H), 6.05 (s, 3H), 5.78 (s, 1H), 5.00-4.96 (m, 1H), 3.90-3.81 (m, 1H), 3.27-3.16 (m, 2H), 2.66-2.58 (m, 1H), 2.45-1.98 (m, 3H), 1.96-1.45 (m, 2H).

Enantiomer C: The collected fraction was lyophilized to give 5 mg (2.7%) of ((5S*)-3-amino-5-hydroxy-4,5,6,7-tetrahydroindazol-1-yl)((4S*)-6-fluoro-1,2,3,4-tetrahydroquinolin-4-yl)methanone (135). RT2: 10.30 min, MS (ES, m/z) [M+H]$^+$: 331, (DMSO-$d_6$, 300 MHz, ppm): δ 6.79-6.75 (m, 1H) 6.75-6.73 (m, 1H), 6.66-6.61 (m, 1H), 5.75 (s, 1H), 5.59 (s, 2H), 4.93-4.89 (m, 1H), 4.81 (s, 1H), 3.94-3.88 (m, 1H), 3.33-3.23 (m, 1H), 3.14-3.05 (m, 1H), 2.89-2.75 (m, 2H), 2.16-1.89 (m, 4H), 1.88-1.69 (m, 2H).

Enantiomer D: The collected fraction was lyophilized to give 5 mg (2.7%) of ((5S*)-3-amino-5-hydroxy-4,5,6,7-tetrahydroindazol-1-yl)((4R*)-6-fluoro-1,2,3,4-tetrahydroquinolin-4-yl)methanone (136). RT1: 9.40 min, MS (ES, m/z) [M+H]$^+$: 331, (DMSO-d$_6$, 300 MHz, ppm): δ 6.77-6.76 (m, 1H), 6.67-6.66 (m, 1H), 6.51-6.46 (m, 1H), 5.75 (s, 1H), 5.59 (s, 2H), 4.91-4.79 (m, 1H), 4.81-4.78 (s, 1H), 3.94-3.88 (m, 1H), 3.33-3.30 (m, 2H), 3.14-3.05 (m, 1H), 2.89-2.75 (m, 2H), 2.18-1.79 (m, 3H), 1.78-1.69 (m, 2H).

Example 137-139 ((5R*)-3-amino-5-fluoro-4,5,6,7-tetrahydroindazol-2-yl)((4S*)-6-fluoro-1,2,3,4-tetrahydroquinolin-4-yl)methanone (137); ((5R*)-3-amino-5-fluoro-4,5,6,7-tetrahydroindazol-2-yl)((4R*)-6-fluoro-1,2,3,4-tetrahydroquinolin-4-yl)methanone (138) and ((5R*)-3-amino-5-fluoro-4,5,6,7-tetrahydroindazol-1-yl)((4RS)-6-fluoro-1,2,3,4-tetrahydroquinolin-4-yl)methanone (139)

Step 1. 5-fluoro-2-oxocyclohexane-1-carbaldehyde

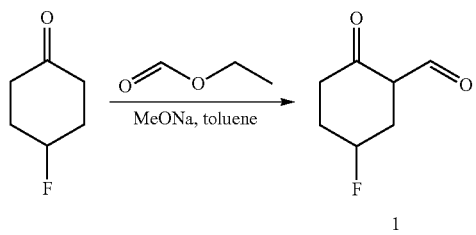

Into a 100-mL 3-necked round-bottom flask, was placed 4-fluorocyclohexane-1-one (1 g, 8.61 mmol, 1.00 equiv), toluene (20 mL), MeONa (1.4 g, 25.93 mmol, 3.00 equiv). This was followed by the addition of ethyl formate (3.83 g, 51.70 mmol, 6.00 equiv) dropwise with stirring at 0° C. The resulting solution was stirred overnight at room temperature. The pH value of the solution was adjusted to 4 with HCl (1 mol/L). The resulting solution was extracted with ethyl acetate (300 mL×3) and the organic layers combined and concentrated under vacuum. This resulted in 1.0 g (crude) of 5-fluoro-2-oxocyclohexane-1-carbaldehyde as black oil. MS (ES, m/z) [M+H]$^+$: 145.

Step 2. 4-fluoro-2-[(1Z)-(hydroxyimino)methyl]cyclohexan-1-one

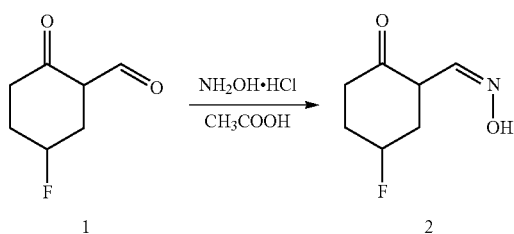

Into a 100-mL round-bottom flask, was placed 5-fluoro-2-oxocyclohexane-1-carbaldehyde (1.0 g, 6.94 mmol, 1.00 equiv), hydroxylamine hydrochloride (481 mg, 6.92 mmol, 1.10 equiv), acetic acid (20 mL). The resulting solution was stirred overnight at 100° C. The resulting mixture was concentrated under vacuum. The pH value of the solution was adjusted to 7-8 with sat. sodium bicarbonate. The resulting solution was extracted ethyl acetate with (100 mL×4), dried over anhydrous sodium sulfate and concentrated under vacuum. This resulted in 0.8 g (crude) of 4-fluoro-2-[(1Z)-(hydroxyimino)methyl]cyclohexan-1-one as black oil. MS (ES, m/z) [M+H]$^+$: 160.

Step 3. 5-fluoro-2-oxocyclohexane-1-carbonitrile

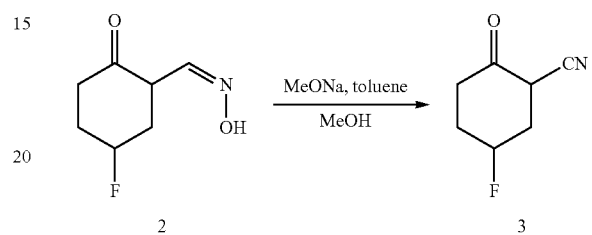

Into a 100-mL round-bottom flask, was placed 4-fluoro-2-[(1Z)-(hydroxyimino)methyl]cyclohexan-1-one (800 mg, 5.03 mmol, 1.00 equiv), MeONa (299 mg, 5.54 mmol, 1.10 equiv), toluene (20 mL), methanol (2 mL). The resulting solution was stirred overnight at room temperature. The pH value of the solution was adjusted to 5 with HCl (1 mol/L). The resulting solution was extracted with ethyl with acetate (100 mL×4) dried over anhydrous sodium sulfate and concentrated under vacuum. This resulted in 0.6 g (crude) of 5-fluoro-2-oxocyclohexane-1-carbonitrile as black oil. MS (ES, m/z) [M+H]$^+$: 142.

Step 4. (5R*)-5-fluoro-4,5,6,7-tetrahydro-2H-indazol-3-amine (137i) and (5S)-5-fluoro-4,5,6,7-tetrahydro-2H-indazol-3-amine (140i)

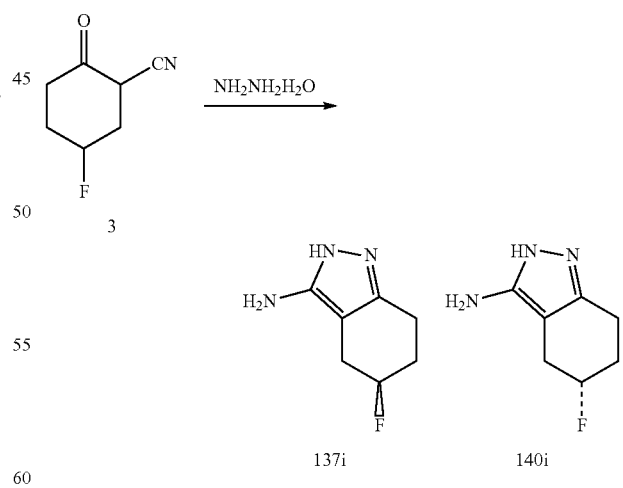

Into a 100-mL round-bottom flask, was placed a solution of 5-fluoro-2-oxocyclohexane-1-carbonitrile (600 mg, 4.25 mmol, 1.00 equiv) in ethanol (20 mL), hydrazine hydrate (2 mL). The resulting solution was stirred overnight at room temperature. The resulting mixture was concentrated under vacuum. The residue was purified by Pre-TLC with dichloromethane/methanol (20:1). The racemic 5-fluoro-4,5,6,7-tetrahydro-2H-indazol-3-amine (120 mg) was separated by Chiral-Prep-HPLC with the following conditions (Prep-HPLC-004): Column: CHIRALPAK IC, 2*25 cm, 5 um, Mobile Phase A: Hex, Mobile Phase B: EtOH, Flow rate: 20 mL/min, Gradient: 30 B to 30 B in 13 min, 220/254 nm. The first eluting isomer (Rt1=8.512 min) was collected and concentrated to give 36 mg (5%) of (5S)-5-fluoro-4,5,6,7-tetrahydro-2H-indazol-3-amine (140i) as yellow oil. MS (ES, m/z) [M+H]+: 156. The second eluting isomer (Rt2=10.72 min) was collection and concentrated to give 53 mg (8%) of (5R*)-5-fluoro-4,5,6,7-tetrahydro-2H-indazol-3-amine (137i) as yellow oil. MS (ES, m/z) [M+H]+: 156.

Step 5. ((5R*)-3-amino-5-fluoro-4,5,6,7-tetrahydroindazol-2-yl)(4R/S)(6-fluoro-1,2,3,4-tetrahydroquinolin-4-yl)methanone (Ex 237) and ((5R*)-3-amino-5-fluoro-4,5,6,7-tetrahydroindazol-1-yl)(4R/S)(6-fluoro-1,2,3,4-tetrahydroquinolin-4-yl) methanone (Ex 139)

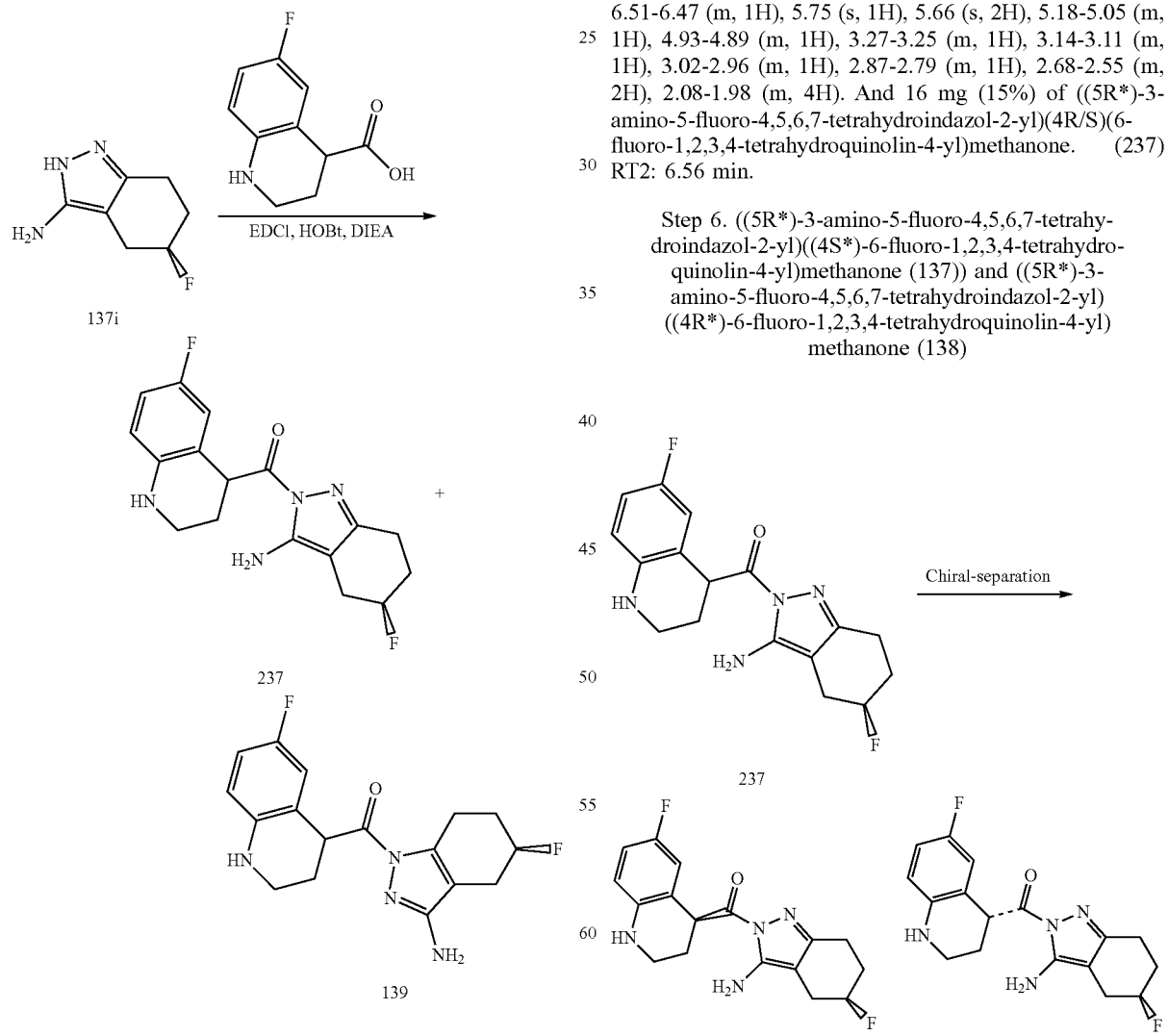

Into a 40-mL vial, was placed a solution of 6-fluoro-1,2,3,4-tetrahydroquinoline-4-carboxylic acid (70.5 mg, 0.36 mmol, 1.00 equiv) in N,N-dimethylformamide (8 mL), HOBT (73 mg, 0.54 mmol, 1.50 equiv), EDCI (104 mg, 0.54 mmol, 1.50 equiv), TEA (182.3 mg, 1.80 mmol, 5.00 equiv). The resulting solution was stirred for 20 min at 25° C. Then 5-fluoro-4,5,6,7-tetrahydro-2H-indazol-3-amine (assumed) (56 mg, 0.36 mmol, 1.00 equiv) was added. The resulting solution was allowed to react, with stirring, for an additional 2.0 h at 25° C. The reaction was then poured into 40 mL of water. The resulting solution was extracted with ethyl acetate (40 mL×3) and the organic layers combined. The resulting mixture was washed with brine (100 mL×2). The mixture was dried over anhydrous sodium sulfate. The solids were filtered out. The filtrate was concentrated under vacuum. The crude product was purified by Prep-HPLC with the following conditions: Column, XBridge C18 OBD Prep Column, 5 μm, 19 mm×250 mm, mobile phase, water (10 mmol/L, NH$_4$HCO$_3$) and ACN (20.0% ACN up to 40.0% in 7 min), Detector, UV 254/220 nm. The collected fraction was lyophilized to give 10.1 mg (9%) of ((5R*)-3-amino-5-fluoro-4,5,6,7-tetrahydroindazol-1-yl)(4R/S)(6-fluoro-1,2,3,4-tetrahydroquinolin-4-yl)methanone (139) as a white solid. RT1: 5.75 min, MS (ES, m/z) [M+H]+: 333, (DMSO-d$_6$, 400 MHz, ppm): δ 6.79-6.74 (m, 1H), 6.67-6.63 (m, 1H), 6.51-6.47 (m, 1H), 5.75 (s, 1H), 5.66 (s, 2H), 5.18-5.05 (m, 1H), 4.93-4.89 (m, 1H), 3.27-3.25 (m, 1H), 3.14-3.11 (m, 1H), 3.02-2.96 (m, 1H), 2.87-2.79 (m, 1H), 2.68-2.55 (m, 2H), 2.08-1.98 (m, 4H). And 16 mg (15%) of ((5R*)-3-amino-5-fluoro-4,5,6,7-tetrahydroindazol-2-yl)(4R/S)(6-fluoro-1,2,3,4-tetrahydroquinolin-4-yl)methanone. (237) RT2: 6.56 min.

Step 6. ((5R*)-3-amino-5-fluoro-4,5,6,7-tetrahydroindazol-2-yl)((4S*)-6-fluoro-1,2,3,4-tetrahydroquinolin-4-yl)methanone (137)) and ((5R*)-3-amino-5-fluoro-4,5,6,7-tetrahydroindazol-2-yl)((4R*)-6-fluoro-1,2,3,4-tetrahydroquinolin-4-yl) methanone (138)

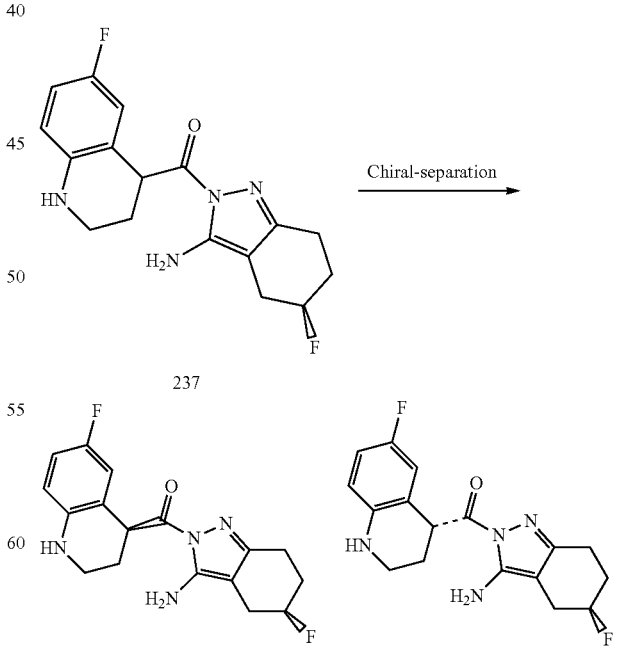

The racemic product (16 mg) was separated by Chiral-HPLC with the following conditions: Column: CHIRAL-PAK IA, 2×25 cm, 5 um, Mobile Phase A: Hex, Mobile Phase B: EtOH, Flow rate: 20 mL/min, Gradient: 15 B to 15 B in 16 min, 254/220 nm, Enantiomer A: The collected fraction was lyophilized to give 3.9 mg (49%) of ((5R*)-3-amino-5-fluoro-4,5,6,7-tetrahydroindazol-2-yl)((4S*)-6-fluoro-1,2,3,4-tetrahydroquinolin-4-yl)methanone (137) as a white solid. RT2:13.112 min, MS (ES, m/z) [M+H]+: 333, (DMSO-d6, 400 MHz, ppm): δ 6.82-6.77 (m, 1H), 6.67-6.64 (m, 1H), 6.54-6.50 (m, 3H), 5.83 (s, 1H), 5.19-5.02 (m, 1H), 5.00-4.99 (m, 1H), 3.28-3.15 (m, 2H), 2.70-2.51 (m, 4H), 2.12-1.92 (m, 4H).

Enantiomer B: The collected fraction was lyophilized to give 5.4 mg (67.5%) of ((5R*)-3-amino-5-fluoro-4,5,6,7-tetrahydroindazol-2-yl)((4R*)-6-fluoro-1,2,3,4-tetrahydroquinolin-4-yl)methanone (138) as a white solid. RT1:10.758 min, MS (ES, m/z) [M+H]+: 333, (DMSO-d6, 400 MHz, ppm): δ 6.82-6.76 (m, 1H), 6.69-6.66 (m, 1H), 6.53-6.50 (m, 3H), 5.79 (s, 1H), 5.18-5.05 (m, 1H), 5.00-4.98 (m, 1H), 3.26-3.14 (m, 2H), 2.73-2.51 (m, 4H), 2.15-1.88 (m, 4H).

Examples 140-142: ((5S*)-3-amino-5-fluoro-4,5,6,7-tetrahydroindazol-2-yl)((4S*)-6-fluoro-1,2,3,4-tetrahydroquinolin-4-yl)methanone (140); ((5S*)-3-amino-5-fluoro-4,5,6,7-tetrahydroindazol-2-yl)((4R*)-6-fluoro-1,2,3,4-tetrahydroquinolin-4-yl)methanone (141) and ((5S*)-3-amino-5-fluoro-4,5,6,7-tetrahydroindazol-1-yl)((4R/S)-6-fluoro-1,2,3,4-tetrahydroquinolin-4-yl)methanone (142)

Step 1: ((5S*)-3-amino-5-fluoro-4,5,6,7-tetrahydroindazol-2-yl)(4R/S)(6-fluoro-1,2,3,4-tetrahydroquinolin-4-yl)methanone (240) and ((5S*)-3-amino-5-fluoro-4,5,6,7-tetrahydroindazol-1-yl)(4R/S)(6-fluoro-1,2,3,4-tetrahydroquinolin-4-yl)methanone (142)

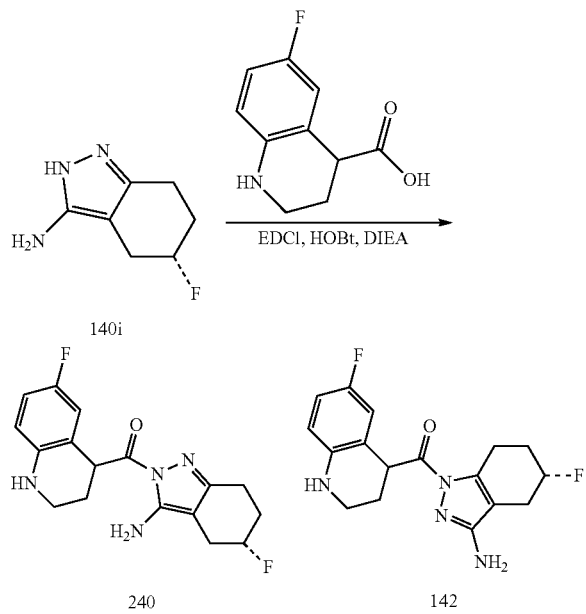

Into a 50-mL round-bottom flask, was placed 6-fluoro-1,2,3,4-tetrahydroquinoline-4-carboxylic acid (54 mg, 0.28 mmol, 1.20 equiv), (5S*)-5-fluoro-4,5,6,7-tetrahydro-2H-indazol-3-amine (140i) (36 mg, 0.23 mmol, 1.00 equiv), HOBT (47 mg, 0.35 mmol, 1.50 equiv), EDCI (67 mg, 0.35 mmol, 1.50 equiv), N,N-dimethylformamide (5 mL), TEA (71 mg, 0.70 mmol, 3.00 equiv). The resulting solution was stirred for 3 h at 25° C. The reaction mixture was diluted with DCM (80 mL), washed with H2O (50 mL×3) and brine (50 mL×3) and dried with Na2SO4. After filtration, the filtrate was concentrated under reduced pressure. The crude product was purified by Prep-HPLC with the following conditions: Column: XBridge Prep C18 OBD Column 19×150 mm 5 um, Mobile Phase A: water (10 mmoL/L NH4HCO3), Mobile Phase B: ACN, Flow rate: 30 mL/min, Gradient: 33% B to 45% B in 8 min, 254.220 nm, The collected fraction was lyophilized to give 4.1 mg (5.4%) of ((5S*)-3-amino-5-fluoro-4,5,6,7-tetrahydroindazol-1-yl)(4R/S)(6-fluoro-1,2,3,4-tetrahydroquinolin-4-yl)methanone (142) as a white solid. RT1: 6.2 min, MS (ES, m/z) [M+H]+: 333, (DMSO-d6, 400 MHz, ppm): δ 6.79-6.74 (m, 1H), 6.68-6.63 (m, 1H), 6.51-6.48 (m, 1H), 5.77 (s, 1H), 5.68 (s, 2H), 5.18-5.01 (m, 1H), 4.92-4.90 (m, 1H), 3.27-3.14 (m, 2H), 2.97-2.54 (m, 4H), 2.16-1.81 (m, 4H). And 5 mg (6.5%) of ((5S*)-3-amino-5-fluoro-4,5,6,7-tetrahydroindazol-2-yl)(R/S)(6-fluoro-1,2,3,4-tetrahydroquinolin-4-yl)methanone (240). RT2: 6.85 min.

Step 2. ((5S*)-3-amino-5-fluoro-4,5,6,7-tetrahydroindazol-2-yl)((4S*)-6-fluoro-1,2,3,4-tetrahydroquinolin-4-yl)methanone (140) and ((5S*)-3-amino-5-fluoro-4,5,6,7-tetrahydroindazol-2-yl)(4(R*)-6-fluoro-1,2,3,4-tetrahydroquinolin-4-yl)methanone (141)

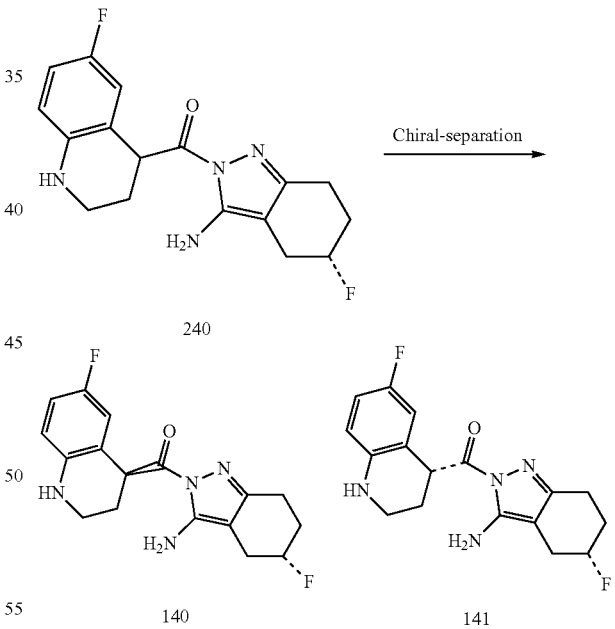

The racemic product 240 (5 mg) was separated by Chiral-Prep-HPLC with the following conditions (Prep-HPLC-032): Column, CHIRALPAK IA, 2×25 cm, 5 um, mobile phase A: Hex, mobile phase B: Ethanol (hold 20.0% ethanol in 24 min), Detector, UV 254/220 nm.

Enantiomer A: The collected fraction was lyophilized to give 1.6 mg (64%) of ((5S*)-3-amino-5-fluoro-4,5,6,7-tetrahydroindazol-2-yl)((4S*)-6-fluoro-1,2,3,4-tetrahydroquinolin-4-yl)methanone (140) as a white solid. RT2: 15.6 min, MS (ES, m/z) [M+H]+: 333, (DMSO-d6, 400 MHz, ppm): δ 6.81-6.78 (m, 1H), 6.77-6.52 (m, 1H), 6.52-6.49 (m, 3H), 5.80 (s, 1H), 5.17-5.04 (m, 1H), 4.99-4.96 (m, 1H), 3.21-3.16 (m, 2H), 2.59-2.51 (m, 4H), 2.14-1.91 (m, 4H).

Enantiomer B: The collected fraction was lyophilized to 1.6 mg (64%) of ((5S*)-3-amino-5-fluoro-4,5,6,7-tetrahydroindazol-2-yl)((4R*)-6-fluoro-1,2,3,4-tetrahydroquinolin-4-yl)methanone (141) as a white solid. RT1: 11.3 min, MS (ES, m/z) [M+H]$^+$: 333, (DMSO-$d_6$, 400 MHz, ppm): δ 6.81-6.78 (m, 1H), 6.77-6.52 (m, 1H), 6.52-6.49 (m, 3H), 5.81 (s, 1H), 5.18-5.05 (m, 1H), 5.00-4.97 (m, 1H), 3.27-3.14 (m, 2H), 2.68-2.61 (m, 4H), 2.16-1.81 (m, 4H).

Examples 143-146: ((5S*)-3-amino-5-hydroxy-4,5,6,7-tetrahydroindazol-2-yl)(4S*)-6-chloro-1,2,3,4-tetrahydroquinolin-4-yl)methanone (143); ((5S*)-3-amino-5-hydroxy-4,5,6,7-tetrahydroindazol-2-yl)((4R*)-6-chloro-1,2,3,4-tetrahydroquinolin-4-yl)methanone (144); ((5S*)-3-amino-5-hydroxy-4,5,6,7-tetrahydroindazol-1-yl)((4R*)-6-chloro-1,2,3,4-tetrahydroquinolin-4-yl)methanone (145); and ((5S*)-3-amino-5-hydroxy-4,5,6,7-tetrahydroindazol-1-yl)((4S*)-6-chloro-1,2,3,4-tetrahydroquinolin-4-yl)methanone (146)

HOBT (135 mg, 1.00 mmol, 1.50 equiv), EDCI (190 mg, 0.99 mmol, 1.50 equiv), TEA (200 mg, 1.98 mmol, 3.00 equiv), N,N-dimethylformamide (5 mL). The resulting solution was stirred for 2.5 h at room temperature. The reaction was then quenched by the addition of water (30 mL). The resulting solution was extracted with ethyl acetate (30 mL×3) and the organic layers combined and concentrated under vacuum. The crude product was purified by Prep-HPLC with the following conditions: Column: XBridge Prep OBD C18 Column 30×150 mm 5 um, Mobile Phase A: water (10 mmol/L NH$_4$HCO$_3$), Mobile Phase B: ACN, Flow rate: 60 mL/min, Gradient: 10% B to 35% B in 17 min, 220 nm.

Enantiomer A: The collected fraction was lyophilized to give 12.4 mg (5%) of ((5S*)-3-amino-5-hydroxy-4,5,6,7-tetrahydroindazol-2-yl)((4S*)-6-chloro-1,2,3,4-tetrahydroquinolin-4-yl)methanone (143) as a white solid. RT3: 16.13 min, MS (ES, m/z) [M+H]$^+$: 347 and 349, (DMSO-$d_6$, 300 MHz, ppm): δ 6.95-6.91 (m, 1H), 6.82-6.81 (m, 1H), 6.53-6.50 (m, 1H), 6.38 (s, 2H), 6.07 (s, 1H), 5.00-4.96 (m, 1H), 4.79-4.78 (m, 1H), 3.92-3.88 (m, 1H), 3.24-3.17 (m, 2H),

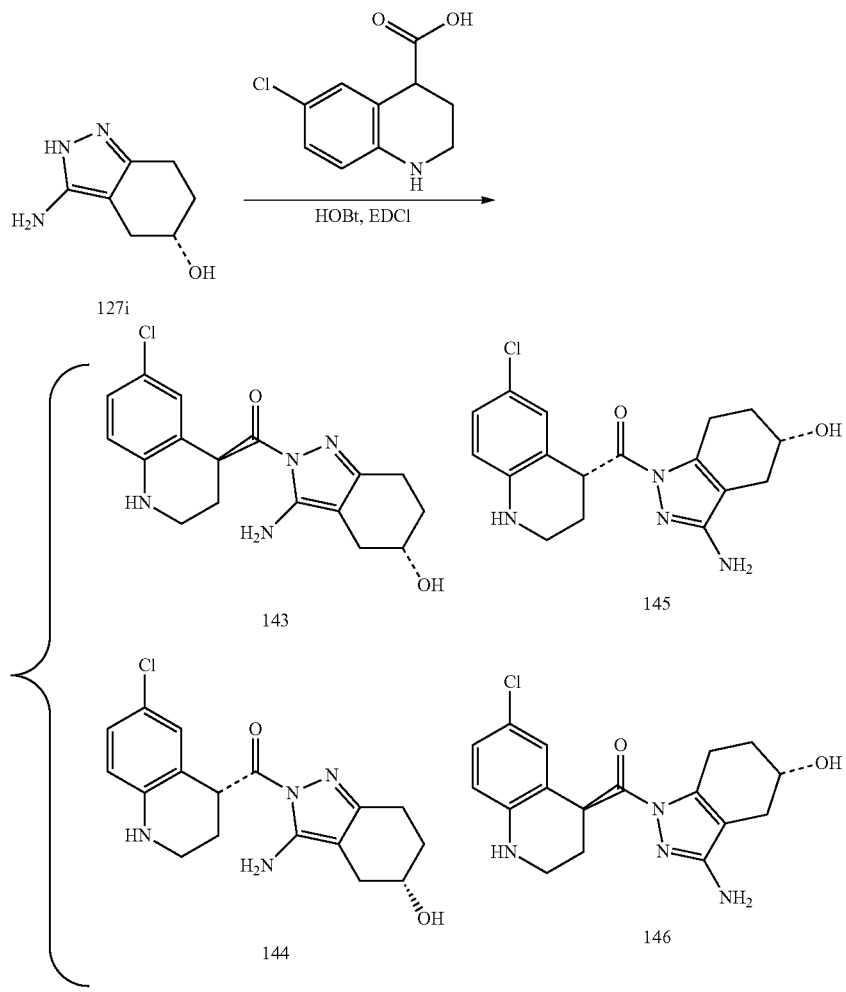

Into a 50-mL round-bottom flask, was placed (5S*)-3-amino-4,5,6,7-tetrahydro-2H-indazol-5-ol (assumed) (100 mg, 0.65 mmol, 1.00 equiv), 6-chloro-1,2,3,4-tetrahydroquinoline-4-carboxylic acid (170 mg, 0.80 mmol, 1.10 equiv), 2.66-2.51 (m, 2H), 2.47- 2.43 (m, 1H), 2.18-1.96 (m, 3H), 1.85-1.81 (m, 1H), 1.72-1.65 (m, 1H).

Enantiomer B: 9.6 mg (4%) of ((5S*)-3-amino-5-hydroxy-4,5,6,7-tetrahydroindazol-2-yl)((4R*)-6-chloro-1,2, 3,4-tetrahydroquinolin-4-yl)methanone (144) as a white solid. RT4: 15.42 min, MS (ES, m/z) [M+H]⁺: 347 and 349, (DMSO-d₆, 300 MHz, ppm): δ 6.95-6.91 (m, 1H), 6.81-6.80 (m, 1H), 6.53-6.50 (m, 1H), 6.38 (s, 2H), 6.07 (s, 1H), 5.00-4.96 (m, 1H), 4.79-4.77 (m, 1H), 3.90-3.88 (m, 1H), 3.28-3.20 (m, 2H), 2.65-2.51 (m, 2H), 2.46-2.43 (m, 1H), 2.17-1.96 (m, 3H), 1.88-1.83 (m, 1H), 1.73- 1.64 (m, 1H).

Enantiomer C: 5.4 mg (2%) of ((5S*)-3-amino-5-hydroxy-4,5,6,7-tetrahydroindazol-1-yl)((4R*)-6-chloro-1,2,3,4-tetrahydroquinolin-4-yl)methanone (145) as a white solid. RT1: 14.65 min, MS (ES, m/z) [M+H]⁺: 347 and 349, (DMSO-d₆, 300 MHz, ppm): δ 6.93-6.89 (m, 1H), 6.82-6.81 (m, 1H), 6.52-6.49 (m, 1H), 6.04 (s, 1H), 5.58 (s, 2H), 4.93-4.89 (m, 1H), 4.79-4.78 (m, 1H), 3.91-3.89 (m, 1H), 3.27-3.18 (m, 2H), 2.90-2.83 (m, 2H), 2.55-2.54 (m, 1H), 2.16-1.93 (m, 3H), 1.80-1.79 (m, 1H), 1.69- 1.66 (m, 1H).

Examples 147-150: ((5R*)-3-amino-5-hydroxy-4,5,6,7-tetrahydroindazol-2-yl)((4R*)-6-chloro-1,2,3,4-tetrahydroquinolin-4-yl)methanone (147); ((5R*)-3-amino-5-hydroxy-4,5,6,7-tetrahydroindazol-2-yl)((4S*)-6-chloro-1,2,3,4-tetrahydroquinolin-4-yl)methanone (148); ((5R*)-3-amino-5-hydroxy-4,5,6,7-tetrahydroindazol-1-yl)((4R*)-6-chloro-1,2,3,4-tetrahydroquinolin-4-yl)methanone (149); and ((5R*)-3-amino-5-hydroxy-4,5,6,7-tetrahydroindazol-1-yl)((4S*)-6-chloro-1,2,3,4-tetrahydroquinolin-4-yl)methanone

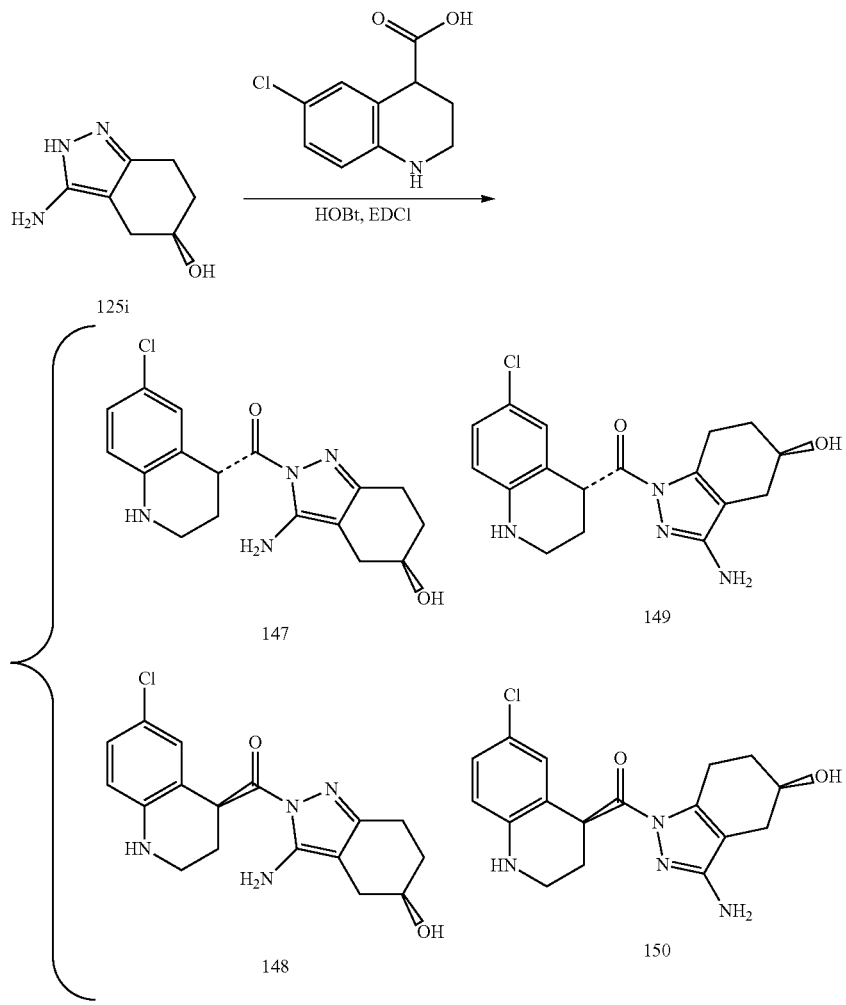

3.26-3.17 (m, 2H), 2.89-2.79 (m, 2H), 2.47-2.46 (m, 1H), 2.17-2.13 (m, 1H), 2.09-1.89 (m, 2H), 1.78- 1.65 (m, 2H).

Enantiomer D: 7.1 mg (3%) of ((5S*)-3-amino-5-hydroxy-4,5,6,7-tetrahydroindazol-1-yl)((4S*)-6-chloro-1,2,3,4-tetrahydroquinolin-4-yl)methanone (146) as a white solid. RT2: 13.9 min, MS (ES, m/z) [M+H]⁺: 347 and 349, (DMSO-d₆, 300 MHz, ppm): δ 6.93-6.89 (m, 1H), 6.81-6.80 (m, 1H), 6.52-6.49 (m, 1H), 6.04 (s, 1H), 5.58 (s, 2H), 4.93-4.89 (m, 1H), 4.80-4.78 (m, 1H), 3.92-3.89 (m, 1H), Into a 50-mL round-bottom flask, was placed 6-chloro-1,2,3,4-tetrahydroquinoline-4-carboxylic acid (140 mg, 0.66 mmol, 1.00 equiv), (5R*)-3-amino-4,5,6,7-tetrahydro-2H-indazol-5-ol (assumed) (100 mg, 0.65 mmol, 1.00 equiv), HOBT (135 mg, 1.00 mmol, 1.50 equiv), EDCI (190 mg, 0.99 mmol, 1.50 equiv), TEA (200 mg, 1.98 mmol, 2.00 equiv), N,N-dimethylformamide (5 mL). The resulting solution was stirred for 2.5 h at room temperature. The reaction was then quenched by the addition of water (30 mL). The resulting solution was extracted with ethyl acetate (30 mL×3) and the organic layers combined and concentrated under vacuum. The crude product was purified by Prep-HPLC with the following conditions: Column: XBridge Prep C18 OBD Column, 5 um, 19×150 mm, Mobile Phase A: water (10 mmoL/L NH₄HCO₃), Mobile Phase B: ACN, Flow rate: 20 mL/min, Gradient: 15% B to 28% B in 15 min, 254 nm.

Enantiomer A: The collected fraction was lyophilized to give 13.8 mg (6%) of ((5R*)-3-amino-5-hydroxy-4,5,6,7-tetrahydroindazol-2-yl)((4S*)-6-chloro-1,2,3,4-tetrahydroquinolin-4-yl)methanone (148) as a white solid. RT4: 23.58 min, MS (ES, m/z) [M+H]$^+$: 347 and 349, (DMSO-d₆, 400 MHz, ppm): δ 6.94-6.92 (m, 1H), 6.81-6.80 (m, 1H), 6.53-6.50 (m, 1H), 6.38 (s, 2H), 6.07 (s, 1H), 4.99-4.97 (m, 1H), 4.79-4.78 (m, 1H), 3.92-3.90 (m, 1H), 3.26-3.20 (m, 2H), 2.67-2.56 (m, 2H), 2.46- 2.45 (m, 1H), 2.16-1.93 (m, 3H), 1.85-1.82 (m, 1H), 1.72-1.62 (m, 1H).

Enantiomer B: 15.9 mg (7%) of ((5R*)-3-amino-5-hydroxy-4,5,6,7-tetrahydroindazol-2-yl)((4R*)-6-chloro-1,2,3,4-tetrahydroquinolin-4-yl)methanone (147) as a white solid. RT3: 21.23 min, MS (ES, m/z) [M+H]$^+$: 347 and 349, (DMSO-d₆, 400 MHz, ppm): δ 6.95-6.92 (m, 1H), 6.82-6.81 (m, 1H), 6.53-6.51 (m, 1H), 6.38 (s, 2H), 6.07 (s, 1H), 4.99-4.96 (m, 1H), 4.79-4.78 (m, 1H), 3.91-3.89 (m, 1H), 3.26-3.20 (m, 2H), 2.67-2.54 (m, 2H), 2.47-2.44 (m, 1H), 2.17-2.11 (m, 1H), 2.08-1.94 (m, 2H), 1.84- 1.79 (m, 1H), 1.71-1.68 (m, 1H).

Enantiomer C: 2.1 mg (1%) of ((5R*)-3-amino-5-hydroxy-4,5,6,7-tetrahydroindazol-1-yl)((4R*)-6-chloro-1,2,3,4-tetrahydroquinolin-4-yl)methanone (149) as a white solid. RT1: 19.42 min, MS (ES, m/z) [M+H]$^+$: 347 and 349, (DMSO-d₆, 400 MHz, ppm): δ 6.93-6.90 (m, 1H), 6.82-6.81 (m, 1H), 6.51-6.49 (m, 1H), 6.04 (s, 1H), 5.59 (s, 2H), 4.93-4.89 (m, 1H), 4.80-4.79 (m, 1H), 3.90-3.89 (m, 1H), 3.29-3.25 (m, 1H), 3.16-3.12 (m, 1H), 2.95-2.89 (m, 1H), 2.83-2.76 (m, 1H), 2.56-2.55 (m, 1H), 2.17-2.11 (m, 1H), 2.05-2.00 (m, 1H), 1.96-1.93 (m, 1H), 1.88-1.78 (m, 1H), 1.72-1.65 (m, 1H).

Enantiomer D: 2.9 mg (1%) of ((5R*)-3-amino-5-hydroxy-4,5,6,7-tetrahydroindazol-1-yl)((4S*)-6-chloro-1,2,3,4-tetrahydroquinolin-4-yl)methanone (150) as a white solid. RT2: 17.75 min, MS (ES, m/z) [M+H]$^+$: 347 and 349, (DMSO-d₆, 400 MHz, ppm): δ 6.93-6.90 (m, 1H), 6.81-6.80 (m, 1H), 6.51-6.49 (m, 1H), 6.04 (s, 1H), 5.59 (s, 2H), 4.92-4.89 (m, 1H), 4.80-4.79 (m, 1H), 3.90-3.89 (m, 1H), 3.30-3.24 (m, 1H), 3.17-3.14 (m, 1H), 2.94-2.76 (m, 2H), 2.54-2.53 (m, 1H), 2.15-2.10 (m, 1H), 2.06- 1.90 (m, 2H), 1.85-1.81 (m, 1H), 1.71-1.62 (m, 1H).

Table 2: The following compounds in Table 2 (Examples 152-164) were prepared by procedures similar to those described above and well known to those skilled in the art.

TABLE 2

| | | |
|---|---|---|
| Example 152 | 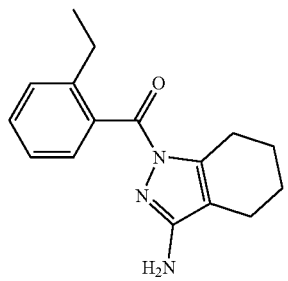 [SMILES: CCc1ccccc1C(=O)n1nc(N)c2c1CCCC2] | (DMSO-d₆, 400 MHz, ppm): δ 7.38-7.20 (m, 4H), 4.50-6.10 (s, 2H), 2.93-2.89 (m, 2H), 2.52 (s, 1H), 2.48 (s, 1H), 2.33-2.22 (m, 2H), 1.75-1.55 (m, 4H), 1.11-1.04 (m, 3H). |
| Example 154 | 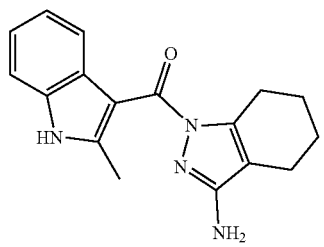 [SMILES: Cc1[nH]c2ccccc2c1C(=O)n1nc(N)c2c1CCCC2] | (DMSO-d₆, 300 MHz, ppm): δ 11.63 (s, 1H), 7.46 (d, J = 7.5 Hz, 1H), 7.32 (d, J = 7.5 Hz, 1H), 7.07-7.00 (m, 2H), 5.19 (s, 2H), 2.89 (s, 2H), 2.44 (s, 3H), 2.27 (s, 2H), 1.71 (d, J = 4.5 Hz, 4H). |
| Example 155 | 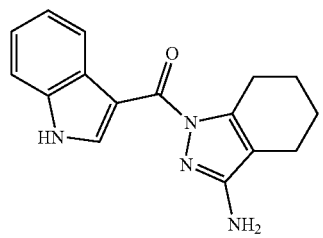 [SMILES: Nc1nn(C(=O)c2c[nH]c3ccccc23)c2c1CCCC2] | (DMSO-d₆, 400 MHz, ppm): δ 11.95 (s, 1H), 8.87 (d, J = 2.8 Hz, 1H), 8.28 (d, J = 7.2 Hz, 1H), 7.48 (d, J = 7.2 Hz, 1H), 7.23-7.15 (m, 2H), 5.36 (s, 2H), 2.99-2.96 (m, 2H), 2.29-2.26 (m, 2H), 1.74-1.67 (m, 4H). |

TABLE 2-continued

| Example 156 | | (DMSO-d₆, 400 MHz, ppm): δ 7.66 (d, J = 8.4 Hz, 1H), 7.34 (d, J = 7.2 Hz, 1H), 7.05-7.01 (m, 1H), 6.18 (s, 1H), 4.97-5.79 (m, 2H), 4.75-4.68 (m, 1H), 2.94-2.91 (m, 2H), 2.41 (s, 3H), 2.26-2.24 (m, 2H), 1.74-1.67 (m, 4H), 1.53 (d, J = 7.2 Hz, 6H). |
|---|---|---|
| Example 157 | | (DMSO-d₆, 400 MHz, ppm): δ 13.26 (s, 1H), 8.03 (s, 1H), 7.73-7.67 (m, 2H), 7.44-7.40 (m, 1H), 5.46 (s, 2H), 2.99-2.97 (m, 2H), 2.30-2.28 (m, 2H), 1.77-1.70 (m, 4H). |
| Example 158 | | (DMSO-d₆, 400 MHz, ppm): δ 9.01 (d, J = 4.4 Hz, 1H), 8.12 (d, J = 8.8 Hz, 1H), 7.85-7.81 (m, 1H), 7.71-7.63 (m, 3H), 6.64 (s, 2H), 2.32 (s, 2H), 2.24 (s, 2H), 1.61 (m, 4H). |
| Example 159 | | (DMSO, 400 MHz, ppm): δ 11.32 (s, 1H), 8.17 (s, 1H), 7.66 (d, J = 7.2 Hz, 1H), 7.54 (d, J = 8.0 Hz, 1H), 7.12-7.09 (m, 1H), 6.35 (s, 1H). 2.64-2.58 (m, 4H), 2.42 (s, 3H), 1.79-1.68 (m, 4H). |
| Example 160 | | (CD3OD, 400 MHz, ppm): δ 7.5-7.47 (m, 3H), 7.12-7.06 (m, 1H), 6.25 (s, 1H), 3.04-2.98 (m, 2H), 2.61-2.56 (m, 2H), 2.45 (s, 3H), 1.90-1.85 (m, 2H), 1.84-1.80 (m, 2H). |
| Example 161 | | (DMSO-d₆, 400 MHz, ppm): δ 11.20 (s, 1H), 7.56-7.54 (m, 2H), 7.07-7.03 (m, 1H), 6.38 (s, 2H), 6.27 (s, 1H), 4.79 (s, 1H), 3.89 (s, 1H), 2.42-2.33 (m, 5H), 2.42-2.33 (m, 1H), 2.42-2.33 (m, 1H), 2.21-2.15 (m, 1H), 1.83-1.79 (m, 1H), 1.79-1.68 (m, 1H). |
| Example 162 | | (DMSO-d6, 400 MHz, ppm): δ 11.11 (s, 1H), 7.43-7.40 (m, 2H), 7.04-7.02 (m, 1H), 6.19 (s, 1H), 5.34 (s, 2H), 4.85 (s, 1H), 3.89 (s, 1H), 2.42-2.33 (m, 5H), 2.42-2.33 (m, 1H), 2.42-2.33 (m, 1H), 2.21-2.15 (m, 1H), 1.83-1.79 (m, 1H), 1.79-1.68 (m, 1H). |

TABLE 2-continued

| | | |
|---|---|---|
| Example 163 | 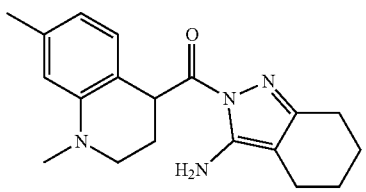 [SMILES: Cc1ccc2c(c1)N(C)CCC2C(=O)n1nc2c(c1N)CCCC2] | (DMSO-d$_6$, 300 MHz, ppm): δ 6.68 (d, J = 7.8 Hz, 1H), 6.46 (d, J = 8.1 Hz, 1H), 6.34-6.30 (m, 3H), 5.03-4.99 (m, 1H), 3.29-3.25 (m, 1H), 3.18-3.14 (m, 1H), 2.84 (s, 3H), 2.48-2.44 (m, 2H), 2.26-2.21 (m, 2H), 2.19 (s, 3H), 2.10-2.08 (m, 2H), 1.68-1.66 (m, 4H). |
| Example 164 | 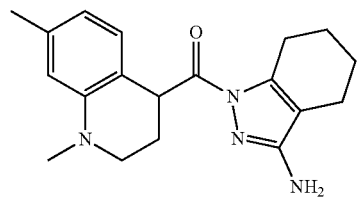 [SMILES: Cc1ccc2c(c1)N(C)CCC2C(=O)n1nc(N)c2c1CCCC2] | (DMSO-d6, 300 MHz, ppm): δ 6.68 (d, J = 7.5 Hz, 1H), 6.45-6.42 (m, 1H), 6.35-6.32 (m, 1H), 5.52 (s, 2H), 4.98-4.96 (m, 1H), 3.29-3.26 (m, 1H), 3.15-3.09 (m, 1H), 2.83 (s, 3H), 2.80-2.77 (m, 2H), 2.24-2.22 (m, 2H), 2.19 (s, 3H), 2.07-2.05 (m, 2H), 1.67-1.65 (m, 4H) |

Example 165-168: ((5R*)-3-amino-5-hydroxy-4,5,6,7-tetrahydroindazol-2-yl)((4S*)-1,2,3,4-tetrahydroquinolin-4-yl)methanone (165); ((5R*)-3-amino-5-hydroxy-4,5,6,7-tetrahydroindazol-2-yl)((4R*)-1,2,3,4-tetrahydroquinolin-4-yl)methanone (166); ((5R*)-3-amino-5-hydroxy-4,5,6,7-tetrahydroindazol-1-yl)((4S*)-1,2,3,4-tetrahydroquinolin-4-yl)methanone (167); and ((5R*)-3-amino-5-hydroxy-4,5,6,7-tetrahydroindazol-1-yl)((4R*))-1,2,3,4-tetrahydroquinolin-4-yl)methanone (168)

Into a 50-mL round-bottom flask, was placed 1,2,3,4-tetrahydroquinoline-4-carboxylic acid (135 mg, 0.76 mmol, 1.20 equiv), (5R*)-3-amino-4,5,6,7-tetrahydro-2H-indazol-5-ol (96 mg, 0.63 mmol, 1.00 equiv), HOBT (130 mg, 0.96 mmol, 1.50 equiv), EDCI (180 mg, 0.94 mmol, 1.50 equiv), TEA (190 mg, 1.88 mmol, 3.00 equiv), N,N-dimethylformamide (7 mL). The resulting solution was stirred for overnight at room temperature. The reaction was then quenched by the addition water (30 mL). The resulting solution was extracted with 3×30 mL of ethyl acetate and the

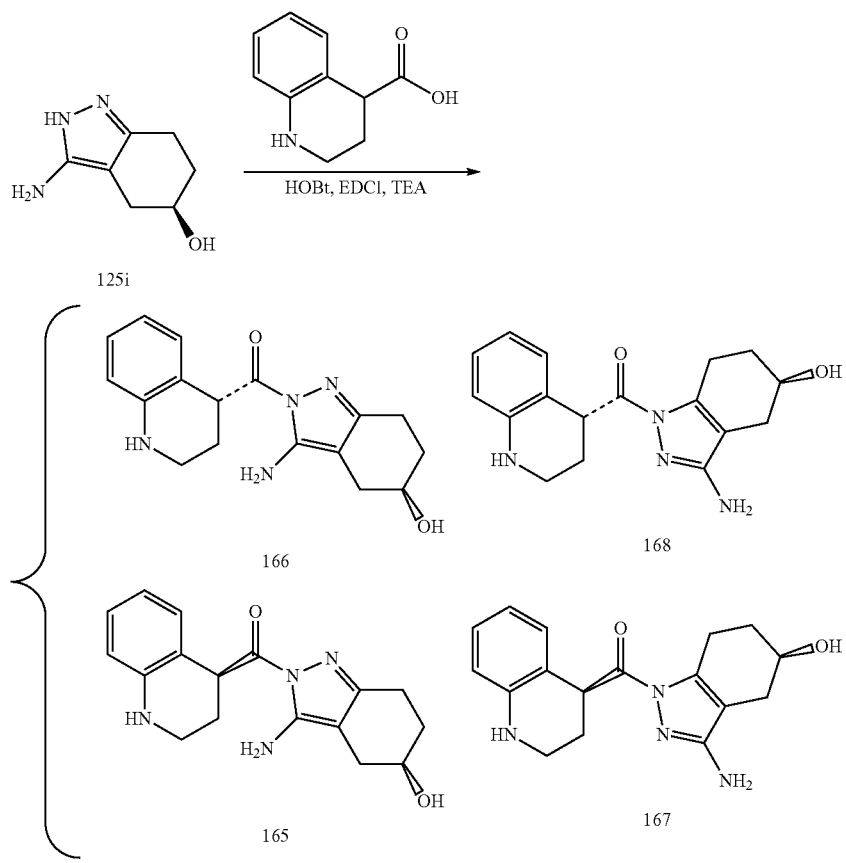

organic layers combined. The resulting mixture was washed with 2×60 mL of Brine. The solid was dried in an oven under reduced pressure. The solids were filtered out. The resulting mixture was concentrated under vacuum. The crude product was purified by Prep-HPLC with the following conditions: Column: XBridge Prep C18 OBD Column 19×150 mm, 5 um, Mobile Phase A: water (10 mmol/L NH$_4$HCO$_3$), Mobile Phase B: ACN, Flow rate: 20 mL/min, Gradient: 5% B to 35% B in 15 min, 254 nm.

Enantiomer A: The collected fraction was lyophilized to give 20.3 mg (10%) of ((5R*)-3-amino-5-hydroxy-4,5,6,7-tetrahydroindazol-2-yl)((4S*)-1,2,3,4-tetrahydroquinolin-4-yl)methanone (Ex. 165) as off-white solid. RT4: 14 min, MS (ES, m/z) [M+H]$^+$: 313, (DMSO-d$_6$, 300 MHz, ppm): δ 6.92-6.87 (m, 1H), 6.75 (d, J=7.2 Hz, 1H), 6.59 (d, J=7.8 Hz, 1H), 6.40-6.36 (m, 3H), 5.82 (s, 1H), 5.03-4.99 (m, 1H), 4.78-4.77 (m, 1H), 3.92-3.89 (m, 1H), 3.27-3.22 (m, 1H), 3.18-3.16 (m, 1H), 2.61-2.56 (m, 2H), 2.49-2.48 (m, 1H), 2.17-2.02 (m, 3H), 1.88-1.81 (m, 1H), 1.75-1.68 (m, 1H).

Enantiomer B: 21.6 mg (11%) of ((5R*)-3-amino-5-hydroxy-4,5,6,7-tetrahydroindazol-2-yl)((4R*)-1,2,3,4-tetrahydroquinolin-4-yl)methanone (166) as off-white solid. RT3: 13.1 min, MS (ES, m/z) [M+H]$^+$: 313, (DMSO-d$_6$, 300 MHz, ppm): δ 6.89-6.88 (m, 1H), 6.76 (d, J=7.2 Hz, 1H), 6.50 (d, J=6.9 Hz, 1H), 6.41-6.36 (m, 3H), 5.82 (s, 1H), 5.03-5.00 (m, 1H), 4.80-4.78 (m, 1H), 3.89-3.87 (m, 1H), 3.28-3.25 (m, 1H), 3.18-3.14 (m, 1H), 2.67-2.55 (m, 2H), 2.49-2.43 (m, 1H), 2.18-2.10 (m, 1H), 2.03-1.97 (m, 2H), 1.84-1.81 (m, 1H), 1.71-1.67 (m, 1H).

Enantiomer C: 10.7 mg (5%) of ((5R*)-3-amino-5-hydroxy-4,5,6,7-tetrahydroindazol-1-yl)((4S*)-1,2,3,4-tetrahydroquinolin-4-yl)methanone (167) as off-white solid. RT2: 11.6 min, MS (ES, m/z) [M+H]$^+$: 313, (DMSO-d$_6$, 300 MHz, ppm): δ 6.90-6.85 (m, 1H), 6.74 (d, J=7.5 Hz, 1H), 6.47 (d, J=7.2 Hz, 1H), 6.39-6.34 (m, 1H), 5.78 (s, 1H), 5.53 (s, 2H), 4.96-4.92 (m, 1H), 4.79-4.78 (m, 1H), 3.92-3.90 (m, 1H), 3.29-3.26 (m, 1H), 3.16-3.14 (m, 1H), 2.92-2.90 (m, 1H), 2.83-2.72 (m, 1H), 2.51-2.50 (m, 1H), 2.16-1.92 (m, 3H), 1.82-1.64 (m, 2H).

Enantiomer D: 9.3 mg (6%) of ((5R*)-3-amino-5-hydroxy-4,5,6,7-tetrahydroindazol-1-yl)((4R*)-1,2,3,4-tetrahydroquinolin-4-yl)methanone (168) as off-white solid. RT1: 10.5 min, MS (ES, m/z) [M+H]$^+$: 313, (DMSO-d$_6$, 300 MHz, ppm): δ 6.90-6.85 (m, 1H), 6.75 (d, J=7.2 Hz, 1H), 6.48 (d, J=7.2 Hz, 1H), 6.40-6.35 (m, 1H), 5.78 (s, 1H), 5.53 (s, 2H), 4.97-4.93 (m, 1H), 4.80-4.77 (m, 1H), 3.90-3.88 (m, 1H), 3.30-3.26 (m, 1H), 3.16-3.14 (m, 1H), 2.90-2.78 (m, 1H), 2.51-2.50 (m, 1H), 2.14-1.97 (m, 3H), 1.82-1.62 (m, 2H).

Example 169-172: ((5S*)-3-amino-5-hydroxy-4,5,6,7-tetrahydroindazol-2-yl)((4R*)-1,2,3,4-tetrahydroquinolin-4-yl)methanone (169); ((5S*)-3-amino-5-hydroxy-4,5,6,7-tetrahydroindazol-2-yl)((4S*)-1,2,3,4-tetrahydroquinolin-4-yl)methanone (170); ((5S*)-3-amino-5-hydroxy-4,5,6,7-tetrahydroindazol-1-yl)((4S*)-1,2,3,4-tetrahydroquinolin-4-yl)methanone (171); ((5S*)-3-amino-5-hydroxy-4,5,6,7-tetrahydroindazol-1-yl)((4R*)-1,2,3,4-tetrahydroquinolin-4-yl)methanone (172)

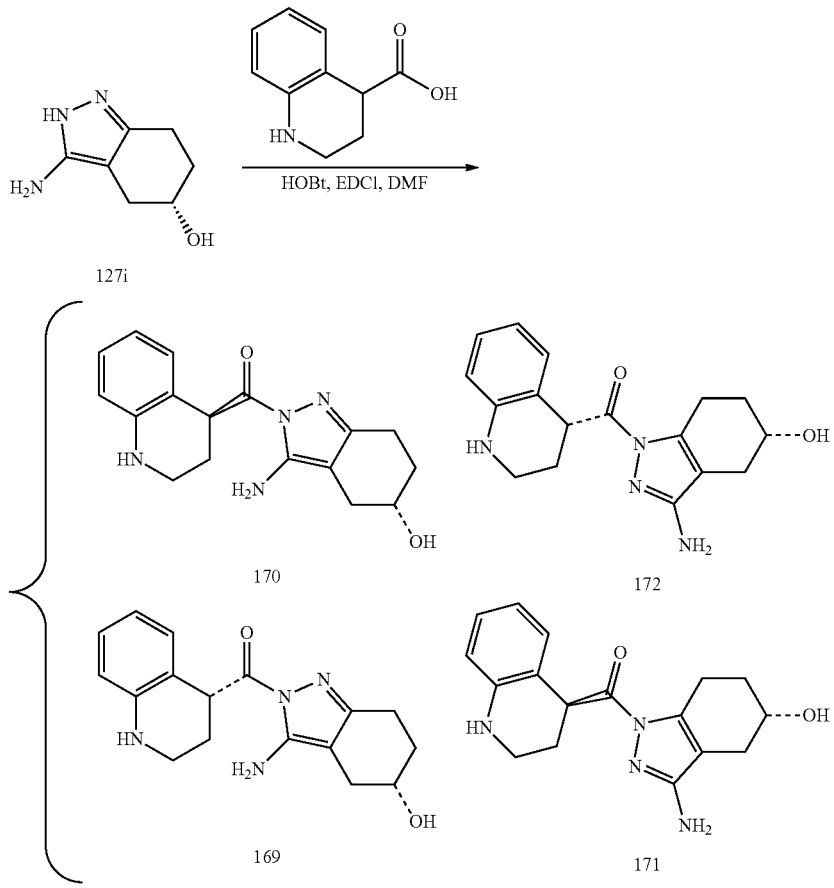

Into a 50-mL round-bottom flask, was placed (5S*)-3-amino-4,5,6,7-tetrahydro-2H-indazol-5-ol (85 mg, 0.55 mmol, 1.00 equiv), N,N-dimethylformamide (5 mL), 1,2,3,4-tetrahydroquinoline-4-carboxylic acid (118 mg, 0.67 mmol, 1.20 equiv), HOBT (113 mg, 0.84 mmol, 1.50 equiv), EDCI (160 mg, 0.83 mmol, 1.50 equiv), TEA (281 mg, 2.78 mmol, 5.00 equiv). The resulting solution was stirred for 16 h at room temperature. The reaction was then quenched by the addition of water (30 mL). The resulting solution was extracted with ethyl acetate (30 mL×3) and the organic layers combined. The resulting mixture was washed with of Brine (100 mL×3). The mixture was concentrated under vacuum. The residue was purified by Pre-TLC with EtOAc. The crude product was purified by Prep-HPLC with the following conditions: Column, XSelect CSH Prep C18 OBD Column, 5 um, 19×150 mm, mobile phase, water (0.1% FA) and ACN (5.0% ACN up to 25.0% in 12 min), Detector, 254 nm.

Enantiomer A: 14.1 mg (8%) of ((5S*)-3-amino-5-hydroxy-4,5,6,7-tetrahydroindazol-2-yl)((4R*)-1,2,3,4-tetrahydroquinolin-4-yl)methanone (169) as a white solid. RT4: 11 min, MS (ES, m/z): [M+H]$^+$:313, (DMSO-d$_6$, 300 MHz, ppm): δ 6.97-6.86 (m, 1H), 6.75 (d, J=7.5 Hz, 1H), 6.50 (d, J=7.2 Hz, 1H), 6.41-3.63 (m, 3H), 5.82 (s, 1H), 5.03-5.00 (m, 1H), 4.77 (d, J=3.9 Hz, 1H), 3.90 (s, 1H), 3.32-3.19 (m, 1H), 3.15 (s, 1H), 2.73-2.49 (m, 3H), 2.28-1.97 (m, 3H), 1.85-1.82 (m, 1H), 1.70-1.61 (m, 1H)

Enantiomer B: 13.1 mg (8%) of ((5S*)-3-amino-5-hydroxy-4,5,6,7-tetrahydroindazol-2-yl)((4S*)-1,2,3,4-tetrahydroquinolin-4-yl)methanone (170) as a white solid. RT3: 10.3 min, MS (ES, m/z): [M+H]+:313, (DMSO-d$_6$, 300 MHz, ppm): δ 6.92-6.90 (m, 1H), 6.87-6.86 (m, 1H), 6.76 (d, J=7.2 Hz, 1H), 6.51-6.48 (m, 3H), 5.82 (s, 1H), 5.03-5.00 (m, 1H), 4.78 (d, J=3.9 Hz, 1H), 3.89 (s, 1H), 3.31-3.25 (m, 1H), 3.18 (s, 1H), 2.60-2.51 (m, 2H), 2.51-2.47 (m, 1H), 2.21-2.00 (m, 3H), 1.89-1.80 (m, 1H), 1.79-1.62 (m, 1H).

Enantiomer C: 9.1 mg (9%) of ((5S*)-3-amino-5-hydroxy-4,5,6,7-tetrahydroindazol-1-yl)((4S*)-1,2,3,4-tetrahydroquinolin-4-yl)methanone (171) as a white solid. RT2: 9.1 min, MS (ES, m/z): [M+H]+:313, (DMSO-d$_6$, 300 MHz, ppm): δ 6.90-6.89 (m, 1H), 6.75 (d, J=7.2 Hz, 1H), 6.37 (d, J=0.9 Hz, 1H), 6.34-6.33 (m, 1H), 5.78 (s, 1H), 5.53 (s, 2H), 4.94-4.90 (m, 1H), 4.78 (d, J=4.2 Hz, 1H), 3.90 (s, 1H), 3.31-3.16 (m, 1H), 3.12 (s, 1H), 2.96-2.73 (m, 2H), 2.49 (s, 1H), 2.17-1.99 (m, 3H), 1.97-1.78 (m, 1H), 1.78-1.77 (m, 1H).

Enantiomer D: 8.5 mg (8%) of ((5S*)-3-amino-5-hydroxy-4,5,6,7-tetrahydroindazol-1-yl)((4R*)-1,2,3,4-tetrahydroquinolin-4-yl)methanone (172) as a white solid. RT1: 8.0 min, MS (ES, m/z): [M+H]+:313, (DMSO-d6, 400 MHz, ppm): δ 6.90-6.89 (m, 1H), 7.76 (d, J=7.6 Hz, 1H), 6.48 (d, J=8.0 Hz, 1H), 6.45-6.37 (m, 1H), 5.79 (s, 1H), 5.55 (s, 2H), 4.94-4.90 (m, 1H), 4.79 (d, J=4.0 Hz, 1H), 3.89 (s, 1H), 3.32-3.14 (m, 1H), 3.12 (s, 1H), 2.93-2.77 (m, 2H), 2.50 (s, 1H), 2.33-2.32 (m, 1H), 2.12-1.99 (m, 2H), 1.98-1.96 (m, 1H), 1.96-1.95 (m, 1H).

Examples 173-175: (S*)-(3-amino-5,5-difluoro-4,5,6,7-tetrahydroindazol-2-yl)(6-fluoro-1,2,3,4-tetrahydroquinolin-4-yl)methanone (173); (R*)-(3-amino-5,5-difluoro-4,5,6,7-tetrahydroindazol-2-yl)(6-fluoro-1,2,3,4-tetrahydroquinolin-4-yl)methanone (174) and (3-amino-5,5-difluoro-4,5,6,7-tetrahydroindazol-1-yl)(6-fluoro-1,2,3,4-tetrahydroquinolin-4-yl)methanone (175)

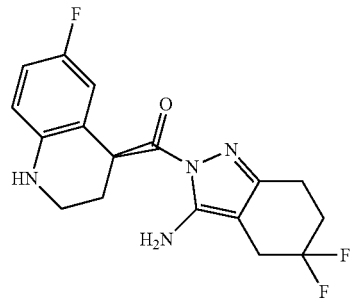

173

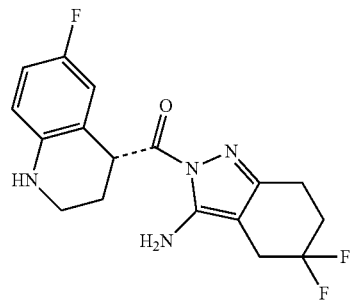

174

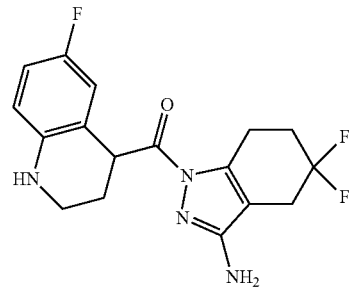

175

Step 1. (3-amino-5,5-difluoro-4,5,6,7-tetrahydroindazol-2-yl)(6-fluoro-1,2,3,4-tetrahydroquinolin-4-yl)methanone

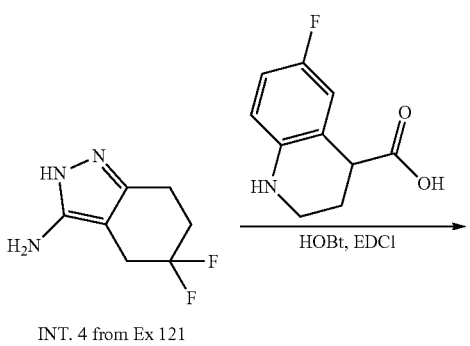

INT. 4 from Ex 121

-continued

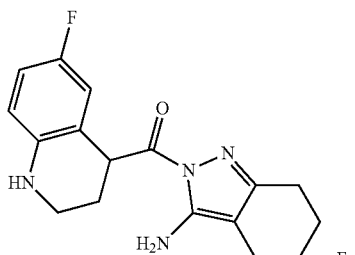

275

175
PH-RU1-AT-916

Step 2. (S*)-(3-amino-5,5-difluoro-4,5,6,7-tetrahydroindazol-2-yl)(6-fluoro-1,2,3,4-tetrahydroquinolin-4-yl)methanone (173) and (R*)-(3-amino-5,5-difluoro-4,5,6,7-tetrahydroindazol-2-yl)(6-fluoro-1,2,3,4-tetrahydroquinolin-4-yl)methanone (174)

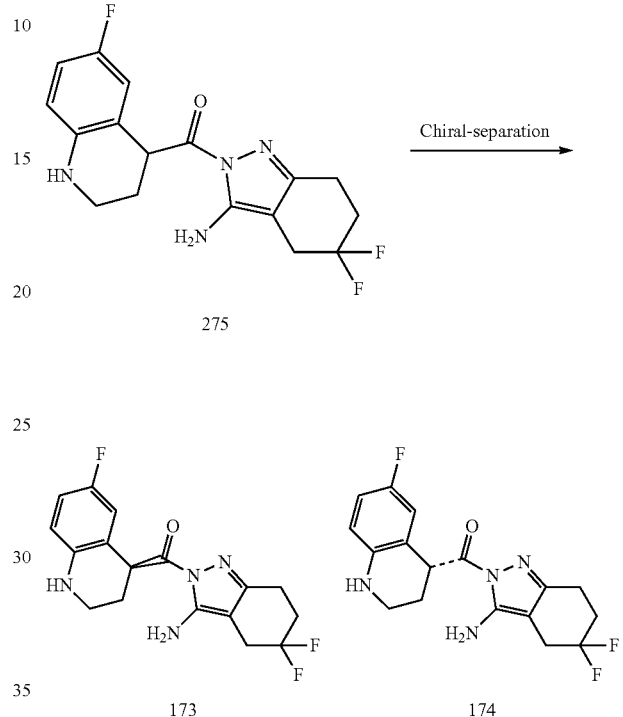

275

173     174

Into a 100-mL round-bottom flask, was placed 5,5-difluoro-4,5,6,7-tetrahydro-2H-indazol-3-amine (88.7 mg, 0.51 mmol, 1.00 equiv), 6-fluoro-1,2,3,4-tetrahydroquinoline-4-carboxylic acid (100 mg, 0.51 mmol, 1.00 equiv), HOBt (104 mg, 0.77 mmol, 1.50 equiv), EDCI (147.8 mg, 0.77 mmol, 1.50 equiv), TEA (260 mg, 2.57 mmol, 5.00 equiv), N,N-dimethylformamide (10 mL). The resulting solution was stirred for 3 h at room temperature. The resulting mixture was washed with $H_2O$ (60 mL). The resulting solution was extracted with ethyl acetate (60 mL×3) and the organic layers combined and concentrated under vacuum. The crude product was purified by Prep-HPLC with the following conditions: Column: XSelect CSH Prep C18 OBD Column, 5 um, 19*150 mm, Mobile Phase A: water (0.1% FA), Mobile Phase B: ACN, Flow rate: 20 mL/min, Gradient: 30% B to 60% B in 8 min, 254 nm. 7 mg of (3-amino-5,5-difluoro-4,5,6,7-tetrahydroindazol-2-yl)(6-fluoro-1,2,3,4-tetrahydroquinolin-4-yl)methanone (275). RT2: 7.30 min. And 4.8 mg (3%) of (3-amino-5,5-difluoro-4,5,6,7-tetrahydroindazol-1-yl)(6-fluoro-1,2,3,4-tetrahydroquinolin-4-yl)methanone (175) as a white solid. Rt: 5.97 min, MS (ES, m/z) [M+H]$^+$: 351, (DMSO-d$_6$, 300 MHz, ppm): δ 6.76 (s, 1H), 6.70-6.64 (m, 1H), 6.51-6.48 (m, 1H), 5.76 (d, J=8.4 Hz, 2H), 4.90 (s, 1H), 3.32 (s, 1H), 3.30-2.88 (m, 6H), 2.30-2.18 (m, 2H), 2.10-1.90 (m, 2H).

The racemic (3-amino-5,5-difluoro-4,5,6,7-tetrahydroindazol-2-yl)(6-fluoro-1,2,3,4-tetrahydroquinolin-4-yl)methanone was separated by Chiral-Prep-HPLC with the following conditions (Prep-HPLC-009): Column: CHIRAL ART Cellulose-SB, 2*25 cm, 5 um, Mobile Phase A: Hex-HPLC, Mobile Phase B: EtOH-HPLC, Flow rate: 20 mL/min, Gradient: 50 B to 50 B in 10 min, 220/254 nm.

Enantiomer A: 1.3 mg (37%) of (S*)-(3-amino-5,5-difluoro-4,5,6,7-tetrahydroindazol-2-yl)(6-fluoro-1,2,3,4-tetrahydroquinolin-4-yl)methanone (173) as a white solid. RT2: 8.54, MS (ES, m/z) [M+H]$^+$: 351, (DMSO-d$_6$, 300 MHz, ppm): δ 6.87-6.80 (m, 1H), 6.74-6.70 (m, 1H), 6.61-6.57 (m, 1H), 4.99 (s, 1H), 3.20 (d, J=4.8 Hz, 2H), 3.90-2.80 (m, 2H), 2.73-2.72 (m, 2H), 2.38-2.20 (m, 3H), 2.14-1.98 (m, 2H), 1.23-1.18 (m, 2H).

Enantiomer B: 3.3 mg (94%) of (R*)-(3-amino-5,5-difluoro-4,5,6,7-tetrahydroindazol-2-yl)(6-fluoro-1,2,3,4-tetrahydroquinolin-4-yl)methanone (174) as a white solid. RT1: 6.73 min, MS (ES, m/z) [M+H]$^+$: 351, (DMSO-d$_6$, 300 MHz, ppm): δ 6.82-6.75 (m, 1H), 6.68-6.61 (m, 3H), 6.52-6.48 (m, 1H), 5.80 (s, 1H), 4.98-4.95 (m, 1H), 3.32-3.17 (m, 2H), 2.93-2.82 (m, 2H), 2.74-2.69 (m, 2H), 2.30- 2.22 (m, 2H), 2.07-1.99 (m, 2H).

Example 176-178: ((5S*)-3-amino-5-methoxy-4,5,6,7-tetrahydroindazol-2-yl)((4R*)-6-fluoro-1,2,3,4-tetrahydroquinolin-4-yl)methanone (176); ((5S*)-3-amino-5-methoxy-4,5,6,7-tetrahydroindazol-2-yl)((4S*)-6-fluoro-1,2,3,4-tetrahydroquinolin-4-yl)methanone (177) and ((5S*)-3-amino-5-methoxy-4,5,6,7-tetrahydroindazol-1-yl)((4R/S)-6-fluoro-1,2,3,4-tetrahydroquinolin-4-yl)methanone (178)

176
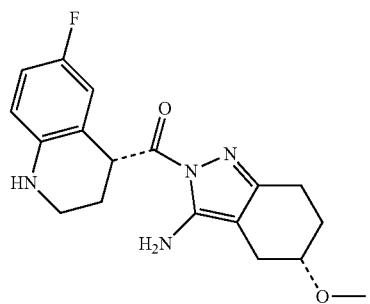

177
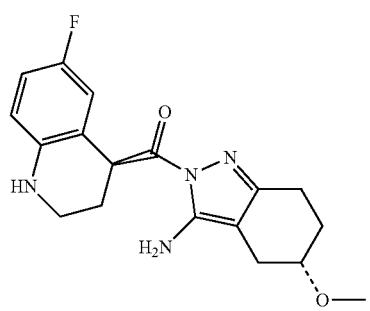

178
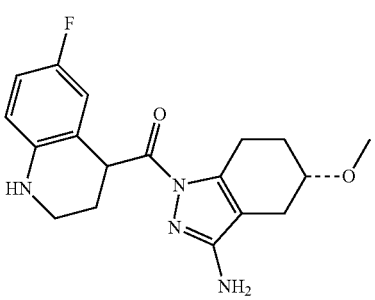

Step 1. (5R*)-5-methoxy-4,5,6,7-tetrahydro-2H-indazol-3-amine and (5S*)-5-methoxy-4,5,6,7-tetrahydro-2H-indazol-3-amine

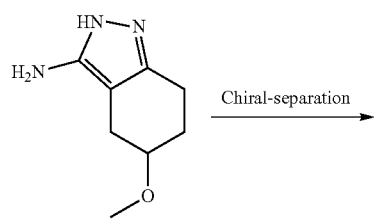

INT. 4 from Ex. 119

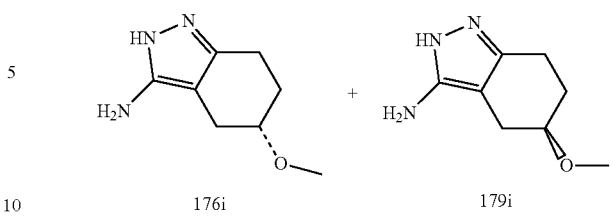

176i 179i

Into a 100-mL round-bottom flask, was placed a solution of 5-methoxy-4,5,6,7-tetrahydro-2H-indazol-3-amine (700 mg, 4.19 mmol, 1.00 equiv) was separated by prep-Chiral-HPLC with following condition. Column: CHIRALPAK IC, 2×25 cm, 5 um, Mobile Phase A: Hex (0.1% DEA) HPLC, Mobile Phase B: EtOH, Flow rate: 20 mL/min, Gradient: 30 B to 30 B in 18 min, 254/220 nm. This resulted in 249 mg (36%) of (5S*)-5-methoxy-4,5,6,7-tetrahydro-2H-indazol-3-amine (176i) as a yellow solid. RT1: 10.096 min. And 250 mg (36%) of (5R*)-5-methoxy-4,5,6,7-tetrahydro-2H-indazol-3-amine (179i) as yellow oil. RT2: 13.279 min.

Step 2. ((5S*)-3-amino-5-methoxy-4,5,6,7-tetrahydroindazol-2-yl)((4R/S)-6-fluoro-1,2,3,4-tetrahydroquinolin-4-yl)methanone (276) and ((5S*)-3-amino-5-methoxy-4,5,6,7-tetrahydroindazol-1-yl)((4R/S)-6-fluoro-1,2,3,4-tetrahydroquinolin-4-yl)methanone (178)

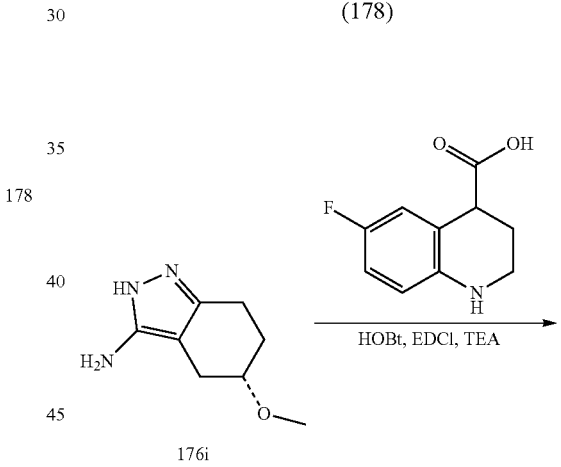

176i

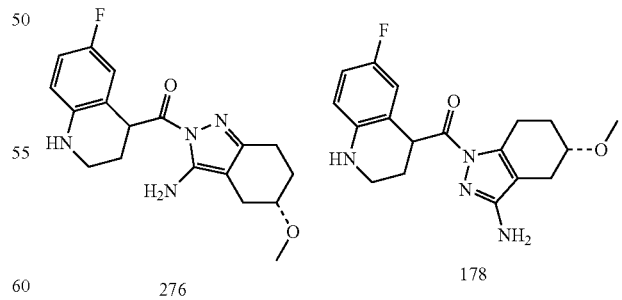

276 178

Into a 100-mL round-bottom flask, was placed (5S)-5-methoxy-4,5,6,7-tetrahydro-2H-indazol-3-amine (240 mg, 1.44 mmol, 1.00 equiv), 6-fluoro-1,2,3,4-tetrahydroquinoline-4-carboxylic acid (309 mg, 1.58 mmol, 1.10 equiv), HOBt (294 mg, 2.18 mmol, 1.50 equiv), EDCI (415 mg, 2.16 mmol, 1.50 equiv). The resulting solution was stirred for 2 h at room temperature. The resulting mixture was washed with H$_2$O (60 mL). The resulting solution was extracted with ethyl acetate (60 mL×3) and the organic layers combined and concentrated under vacuum. The crude product was purified by Prep-HPLC with the following conditions: Column: XBridge Shield RP18 OBD Column, 5 um, 19*150 mm, Mobile Phase A: water (0.1% FA), Mobile Phase B: ACN, Flow rate: 20 mL/min, Gradient: 20% B to 50% B in 10 min, 254/220 nm. This resulted in 23.9 mg (5%) of ((S*)-3-amino-5-methoxy-4,5,6,7-tetrahydroindazol-1-yl)((4RS)-6-fluoro-1,2,3,4-tetrahydroquinolin-4-yl)methanone (178) as a white solid. RT1: 7.98 min, MS (ES, m/z) [M+H]$^+$: 345, (DMSO-d$_6$, 300 MHz, ppm): δ 6.79-6.72 (m, 1H), 6.67-6.61 (m, 1H), 6.51-6.46 (m, 1H), 5.74 (s, 1H), 5.60 (s, 2H), 4.92-4.89 (m, 1H), 3.64-3.61 (m, 1H), 3.32-3.28 (m, 3H), 3.25-3.23 (m, 1H), 3.14-3.10 (m, 1H), 2.80 (s, 2H), 2.60-2.49 (m, 1H), 2.29-2.27 (m, 1H), 2.07-1.77 (m, 4H). And 150.0 mg (30%) of ((S*)-3-amino-5-methoxy-4,5,6,7-tetrahydroindazol-2-yl)((4RS)-6-fluoro-1,2,3,4-tetrahydroquinolin-4-yl)methanone (276). RT2: 9.73 min.

Step 2. ((5S*)-3-amino-5-methoxy-4,5,6,7-tetrahydroindazol-2-yl)((4R*)-6-fluoro-1,2,3,4-tetrahydroquinolin-4-yl)methanone (176) and ((5S*)-3-amino-5-methoxy-4,5,6,7-tetrahydroindazol-2-yl)((4S*)-6-fluoro-1,2,3,4-tetrahydroquinolin-4-yl)methanone (177)

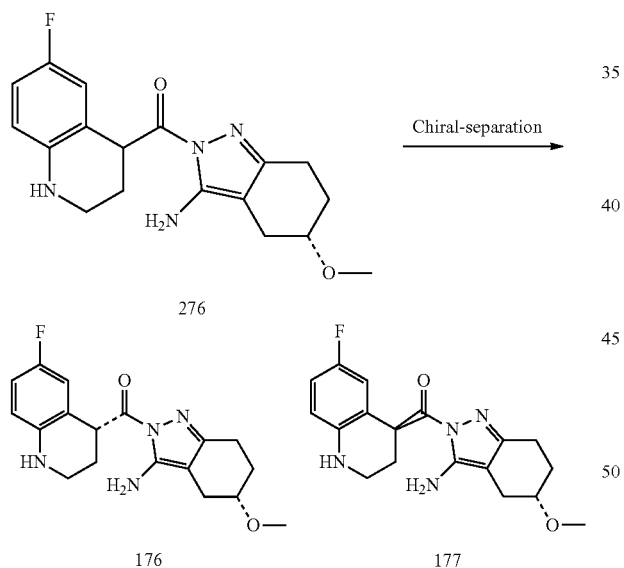

((S)-3-amino-5-methoxy-4,5,6,7-tetrahydroindazol-2-yl)(6-fluoro-1,2,3,4-tetrahydroquinolin-4-yl)methanone (assumed) was separated by Chiral-Prep-HPLC with the following conditions (Prep-HPLC-009): Column: CHIRALPAK IA, 2.12*15 cm, 5 um, Mobile Phase A: Hex, Mobile Phase B: IPA, Flow rate: 20 mL/min, Gradient: 25 B to 25 B in 14.5 min, 220/254 nm.

Enantiomer A: 58.8 mg (78.4%) of ((5S*)-3-amino-5-methoxy-4,5,6,7-tetrahydroindazol-2-yl)((4R*)-6-fluoro-1,2,3,4-tetrahydroquinolin-4-yl)methanone (176) as a white solid. RT2: 11.66 min, MS (ES, m/z) [M+H]$^+$: 345, (DMSO-d$_6$, 300 MHz, ppm): δ 6.81-6.75 (m, 1H), 6.68-6.64 (m, 1H), 6.53-6.48 (m, 1H), 6.40 (s, 2H), 5.82 (s, 1H), 4.99-4.95 (m, 1H), 3.60 (d, J=3.6 Hz, 1H), 2.28 (d, J=7.6 Hz, 3H), 2.23-2.12 (m, 2H), 2.62-2.49 (m, 2H), 2.44 (s, 1H), 2.32-2.24 (m, 1H), 2.07-1.79 (m, 4H).

Enantiomer B: 60.3 mg (80.4%) of ((5S*)-3-amino-5-methoxy-4,5,6,7-tetrahydroindazol-2-yl)((4S*)-6-fluoro-1,2,3,4-tetrahydroquinolin-4-yl)methanone (177) as a white solid. RT1: 9.35 min, MS (ES, m/z) [M+H]$^+$: 345, (DMSO-d$_6$, 300 MHz, ppm): δ 6.81-6.75 (m, 1H), 6.68-6.64 (m, 1H), 6.53-6.48 (m, 1H), 6.40 (s, 2H), 5.82 (s, 1H), 4.99-4.95 (m, 1H), 3.60 (d, J=3.6 Hz, 1H), 2.28 (d, J=7.6 Hz, 3H), 2.23-2.12 (m, 2H), 2.62-2.49 (m, 2H), 2.44 (s, 1H), 2.32-2.24 (m, 1H), 2.07-1.80 (m, 4H).

Example 179-181: ((5R*)-3-amino-5-methoxy-4,5,6,7-tetrahydroindazol-2-yl)((4S*)-6-fluoro-1,2,3,4-tetrahydroquinolin-4-yl)methanone (179); ((5R*)-3-amino-5-methoxy-4,5,6,7-tetrahydroindazol-2-yl)((4R*)-6-fluoro-1,2,3,4-tetrahydroquinolin-4-yl)methanone (180) and ((5R*)-3-amino-5-methoxy-4,5,6,7-tetrahydroindazol-1-yl)((4RS)-6-fluoro-1,2,3,4-tetrahydroquinolin-4-yl)methanone (181)

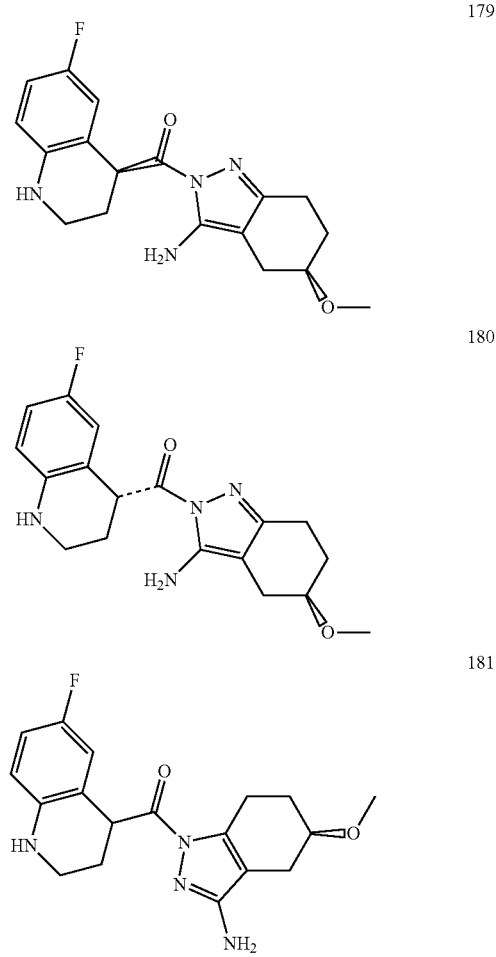

Step 1. ((5R*)-3-amino-5-methoxy-4,5,6,7-tetrahydroindazol-1-yl)((4RS)-6-fluoro-1,2,3,4-tetrahydroquinolin-4-yl)methanone (181) and ((5R*)-3-amino-5-methoxy-4,5,6,7-tetrahydroindazol-2-yl)((4RS)-6-fluoro-1,2,3,4-tetrahydroquinolin-4-yl)methanone (279)

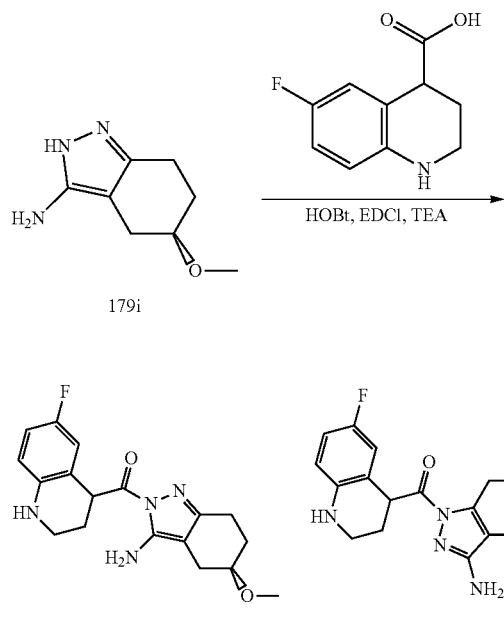

Into a 50-mL round-bottom flask, was placed (5R*)-5-methoxy-4,5,6,7-tetrahydro-2H-indazol-3-amine (130 mg, 0.78 mmol, 1.10 equiv), 6-fluoro-1,2,3,4-tetrahydroquinoline-4-carboxylic acid (100 mg, 0.51 mmol, 1.00 equiv), HOBT (120 mg, 0.89 mmol, 1.50 equiv), EDCI (170 mg, 0.89 mmol, 1.50 equiv), TEA (180 mg, 1.78 mmol, 3.00 equiv), N,N-dimethylformamide (5 mL). The resulting solution was stirred for 2 h at room temperature. The reaction was then quenched by the addition of water (30 mL). The resulting solution was extracted with ethyl acetate (30 mL×3) and the organic layers combined and concentrated under vacuum. The crude product was purified by Flash-Prep-HPLC with the following conditions (IntelFlash-1): Column, C18 silica gel, Mobile Phase A: water (0.1% FA), Mobile Phase B: ACN, Flow rate: 40 mL/min, Gradient: 20% B to 47% B in 10 min, 254 nm. The collected fractions were lyophilized to give 50 mg (28%) of ((5R*)-3-amino-5-methoxy-4,5,6,7-tetrahydroindazol-2-yl)((4R/S)-6-fluoro-1,2,3,4-tetrahydroquinolin-4-yl) methanone (279) as a white solid. RT2: 9.5 min, MS (ES, m/z) [M+H]$^+$: 345. And 12.7 mg (7%) of ((5R*)-3-amino-5-methoxy-4,5,6,7-tetrahydroindazol-1-yl)((4R/S)-6-fluoro-1,2,3,4-tetrahydroquinolin-4-yl)methanone (181) as a white solid. RT1: 8.56 min, MS (ES, m/z) [M+H]$^+$: 345, (DMSO-d$_6$, 400 MHz, ppm): δ 6.79-6.75 (m, 1H), 6.67-6.62 (m, 1H), 6.51-6.47 (m, 1H), 5.76 (s, 1H), 5.60 (s, 2H), 4.91-4.89 (m, 1H), 3.62-3.61 (m, 1H), 3.28 (s, 3H), 3.26-3.23 (m, 1H), 3.14-3.11 (m, 1H), 2.89-2.84 (m, 2H), 2.59-2.55 (m, 1H), 2.33-2.24 (m, 1H), 2.05-1.79 (m, 4H).

Step 2. ((5R*)-3-amino-5-methoxy-4,5,6,7-tetrahydroindazol-2-yl)((4S*)-6-fluoro-1,2,3,4-tetrahydroquinolin-4-yl)methanone (179) and ((5R*)-3-amino-5-methoxy-4,5,6,7-tetrahydroindazol-2-yl)((4R*)-6-fluoro-1,2,3,4-tetrahydroquinolin-4-yl)methanone (180)

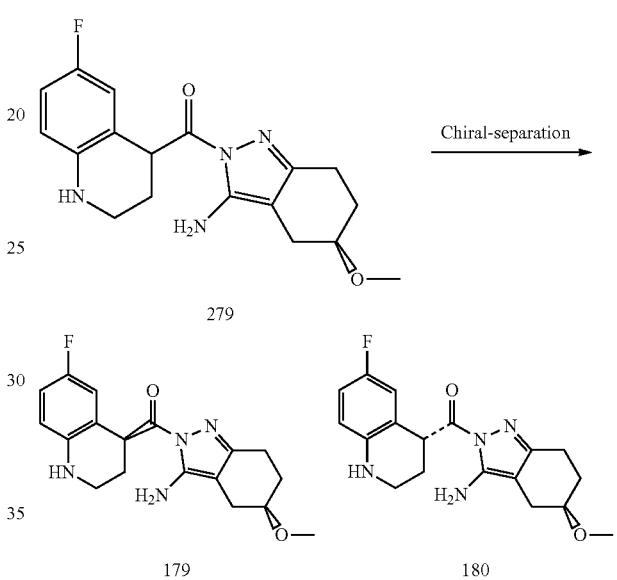

The ((5R*)-3-amino-5-methoxy-4,5,6,7-tetrahydroindazol-2-yl)((4R/S)-6-fluoro-1,2,3,4-tetrahydroquinolin-4-yl)methanone (279) (50 mg, 0.15 mmol, 1.00 equiv) was separated by Prep-chiral-HPLC with the following conditions: Column: CHIRALPAK ID-03, 2.0 cm×25 cm, 5 um, Mobile Phase A: Hex Mobile Phase B: EtOH, Flow rate: 20 mL/min, Gradient: 20 B to 20 B in 20 min, 254/220 nm. The collected fraction was concentrated under vacuum.

Enantiomer A: 15.5 mg (62%) of ((5R*)-3-amino-5-methoxy-4,5,6,7-tetrahydroindazol-2-yl)((4S*)-6-fluoro-1,2,3,4-tetrahydroquinolin-4-yl)methanone (179) as a white solid. RT2: 16.828 min, MS (ES, m/z) [M+H]$^+$: 345, (DMSO-d$_6$, 300 MHz, ppm): δ 6.82-6.75 (m, 1H), 6.67-6.63 (m, 1H), 6.53-6.48 (m, 1H), 6.41 (s, 2H), 5.82 (s, 1H), 4.99-4.96 (m, 1H), 3.63-3.61 (m, 1H), 3.30 (s, 3H), 3.28-3.15 (m, 2H), 2.61-2.51 (m, 2H), 2.50-2.49 (m, 1H), 2.31-2.26 (m, 1H), 2.01-1.79 (m, 4H).

Enantiomer B: 17.3 mg (69.2%) of ((5R*)-3-amino-5-methoxy-4,5,6,7-tetrahydroindazol-2-yl)((4R*)-6-fluoro-1,2,3,4-tetrahydroquinolin-4-yl)methanone (180) as a white solid. RT1: 12.092 min, MS (ES, m/z) [M+H]$^+$: 345, (DMSO-d$_6$, 300 MHz, ppm): δ 6.88-6.81 (m, 1H), 6.74-6.70 (m, 1H), 6.62-6.58 (m, 1H), 6.41 (s, 2H), 5.82 (s, 1H), 4.99-4.95 (m, 1H), 3.62-3.60 (m, 1H), 3.29 (s, 3H), 3.27-3.15 (m, 2H), 2.63-2.54 (m, 2H), 2.48-2.45 (m, 1H), 2.32-2.26 (m, 1H), 2.11-2.02 (m, 2H), 1.91-1.79 (m, 2H).

Example 182 & 183. ((6S*)-3-amino-6-hydroxy-4,5,6,7-tetrahydroindazol-2-yl)((4R*)-6-fluoro-1,2,3,4-tetrahydroquinolin-4-yl)methanone and ((6S*)-3-amino-6-hydroxy-4,5,6,7-tetrahydroindazol-2-yl)((4S*)-6-fluoro-1,2,3,4-tetrahydroquinolin-4-yl)methanone

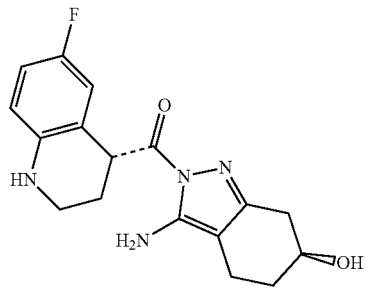

182

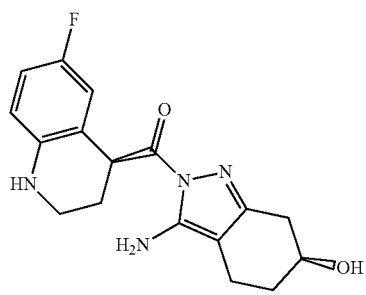

183

Step 1. 4-ethoxy-2-oxocyclohex-3-enecarbaldehyde

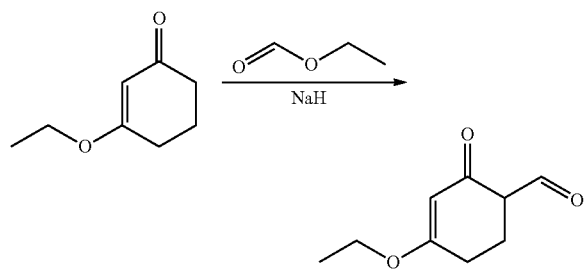

Into a 500-mL 3-necked round-bottom flask purged and maintained with an inert atmosphere of nitrogen, was placed ether, 300 ml), sodium hydride (11.52 g, 288.00 mmol, 1.60 equiv, 60%), ethanol (1.32 g, 28.65 mmol, 0.16 equiv). The mixture was stirred for 20 min, 3-ethoxycyclohex-2-en-1-one (25 g, 178.34 mmol, 1.00 equiv) and ethyl formate (26.64 g, 359.62 mmol, 2.00 equiv) was added. The resulting solution was stirred overnight at 35° C. The resulting mixture was concentrated under vacuum. The resulting solution was diluted with water (200 mL). The pH value of the solution was adjusted to 4-5 with HCl (1 mol/L). The resulting solution was extracted with dichloromethane (200 mL×3) and concentrated under vacuum. The residue was applied onto a silica gel column and eluted with ethyl acetate/petroleum ether (1/10). This resulted in 17 g (57%) of 4-ethoxy-2-oxocyclohex-3-ene-1-carbaldehyde as a white solid. MS (ES, m/z) [M+H]⁺: 169.

Step 2. 4,5-dihydrobenzo[d]isoxazol-6(7H)-one

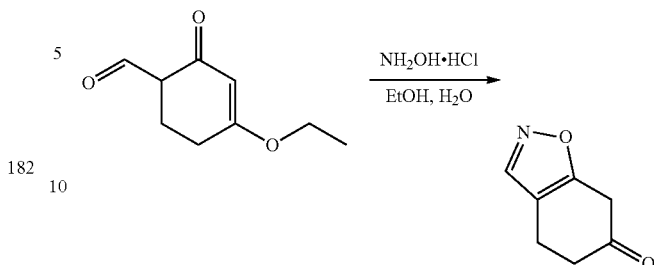

Into a 250-mL round-bottom flask, was placed 4-ethoxy-2-oxocyclohex-3-ene-1-carbaldehyde (5 g, 29.73 mmol, 1.00 equiv), NH₂OH.HCl (2.05 g, 29.71 mmol, 1.00 equiv), water (45 mL), ethanol (45 mL). The resulting solution was stirred overnight at 90° C. The mixture was cooled to room temperature (25° C.). The resulting mixture was concentrated under vacuum to remove the ethanol. The residue was extracted with dichloromethane (80 mL×3) and concentrated under vacuum. The residue was applied onto a silica gel column and eluted with ethyl acetate/petroleum ether (1/1). This resulted in 2.8 g (69%) of 4,5-dihydrobenzo[d]isoxazol-6(7H)-one as a yellow liquid. MS (ES, m/z) [M+H]⁺: 138.

Step 3. 4,5,6,7-tetrahydrobenzo[d]isoxazol-6-ol

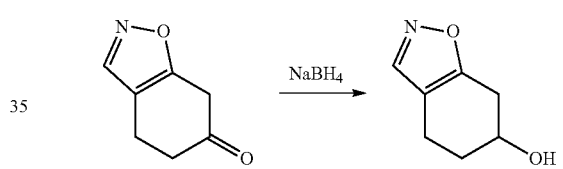

Into a 250-mL round-bottom flask, was placed 4,5,6,7-tetrahydro-1,2-benzoxazol-6-one (2.53 g, 18.45 mmol, 1.00 equiv), methanol (50 mL). This was followed by the addition of NaBH₄ (1.38 g, 2.00 equiv), in portions at 20° C. The resulting solution was stirred for 1 h at 25° C. The resulting mixture was concentrated under vacuum. The resulting solution was diluted with water (80 mL). The resulting solution was extracted with dichloromethane (100 mL×6) and the organic layers combined and concentrated under vacuum. This resulted in 1.8 g (70%) of 4,5,6,7-tetrahydro-1,2-benzoxazol-6-ol as yellow oil. MS (ES, m/z) [M+H]⁺: 140.

Step 4. 6-(tert-butyldiphenylsilyloxy)-4,5,6,7-tetrahydrobenzo[d]isoxazole

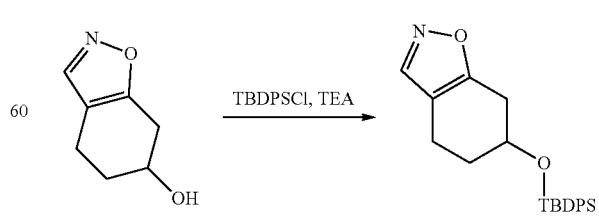

Into a 250-mL round-bottom flask, was placed 4,5,6,7-tetrahydro-1,2-benzoxazol-6-ol (1.8 g, 12.94 mmol, 1.00 equiv), dichloromethane (30 mL), TEA (3.92 g, 38.74 mmol, 3.00 equiv), TBDPSCl (7.1 g, 25.91 mmol, 2.00 equiv). The resulting solution was stirred overnight at 25° C. The resulting mixture was concentrated under vacuum. The residue was applied onto a silica gel column with ethyl acetate/petroleum ether (1/20). This resulted in 4 g (82%) of 6-(tert-butyldiphenylsilyloxy)-4,5,6,7-tetrahydrobenzo[d]isoxazole as yellow oil. MS (ES, m/z) [M+H]⁺: 378.

Step 5. 4-(tert-butyldiphenylsilyloxy)-2-oxocyclohexanecarbonitrile

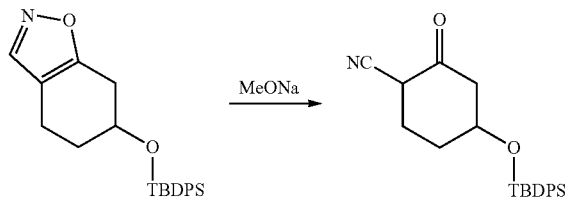

Into a 250-mL 3-necked round-bottom flask, was placed 6-[(tert-butyldiphenylsilyl)oxy]-4,5,6,7-tetrahydro-1,2-benzoxazole (4 g, 10.59 mmol, 1.00 equiv), ether (50 mL), methanol (30 mL) and NaOMe (3.44 g, 63.70 mmol, 6.00 equiv). The resulting solution was stirred overnight at room temperature (25° C.). The resulting mixture was concentrated under vacuum. The resulting solution was diluted with water (40 mL). The PH value was adjusted to 5 with HCl (1 mol/L). The resulting solution was extracted with dichloromethane (100 mL×5) and concentrated under vacuum. The residue was applied onto a silica gel column and eluted with ethyl acetate/petroleum ether (1/5). This resulted in 1.8 g (45%) of 4-(tert-butyldiphenylsilyloxy)-2-oxocyclohexanecarbonitrile as yellow oil. MS (ES, m/z) [M+H]⁺: 378

Step 6. 6-(tert-butyldiphenylsilyloxy)-4,5,6,7-tetrahydro-2H-indazol-3-amine

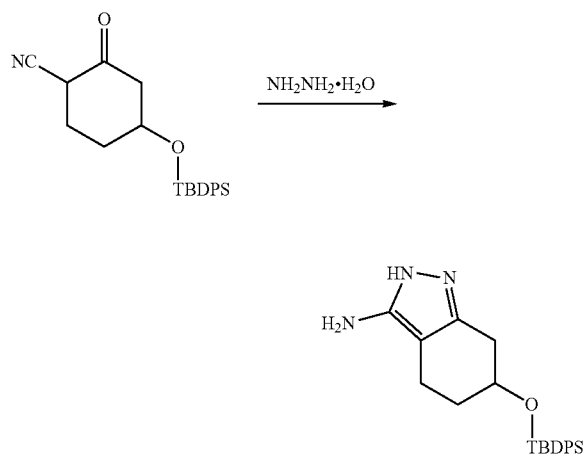

Into a 100-mL round-bottom flask, was placed 4-[(tert-butyldiphenylsilyl)oxy]-2-oxocyclohexane-1-carbonitrile (1.7 g, 4.50 mmol, 1.00 equiv), ethanol (20 mL), NH₂NH₂·H₂O (8 mL). The resulting solution was stirred for 2 days at room temperature (25° C.). The resulting mixture was concentrated under vacuum. This resulted in 1.7 g (96%) of 6-(tert-butyldiphenylsilyloxy)-4,5,6,7-tetrahydro-2H-indazol-3-amine as yellow oil. MS (ES, m/z) [M+H]⁺: 392.

Step 7. (R*)-3-amino-4,5,6,7-tetrahydro-2H-indazol-6-ol and (S*)-3-amino-4,5,6,7-tetrahydro-2H-indazol-6-ol

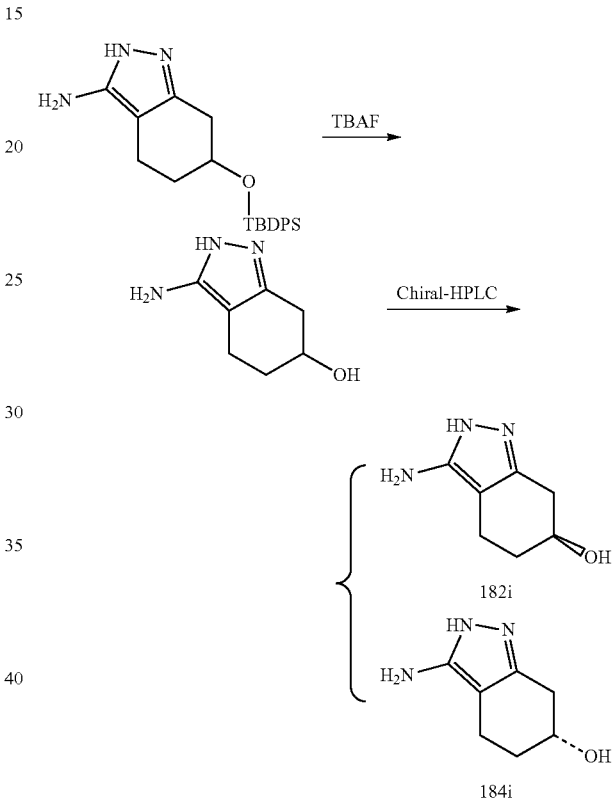

Into a 250-mL round-bottom flask, was placed 6-[(tert-butyldiphenylsilyl)oxy]-4,5,6,7-tetrahydro-2H-indazol-3-amine (1.7 g, 4.34 mmol, 1.00 equiv), tetrahydrofuran (20 mL), TBAF (2.85 g, 9.02 mmol, 2.00 equiv). The resulting solution was stirred overnight at 35° C. The resulting mixture was concentrated under vacuum. The residue was applied onto a silica gel column and eluted with dichloromethane/methanol (10/1). This resulted in 450 mg (68%) of 3-amino-4,5,6,7-tetrahydro-2H-indazol-6-ol as a yellow solid. The racemic product was separated by Prep-Chiral-HPLC with the following conditions (Analyse HPLC-SHIMADZU): Column: CHIRALPAK IG, 20×250 mm, 5 um; Mobile Phase A: Hex, Mobile Phase B: EtOH; Flow rate: 20 mL/min; Gradient: 20 B to 20 B in 25 min; 220/254 nm. The resulting mixture was concentrated under vacuum. The first eluting isomer (RT1:16.5 min) was collected and concentrated to give 200 mg (89%) of (R*)-3-amino-4,5,6,7-tetrahydro-2H-indazol-6-ol. (ES, m/z): 154 [M+H]⁺. The second eluting isomer (RT2:19 min) was collected and concentrated to give 200 mg (89%) of (S*)-3-amino-4,5,6,7-tetrahydro-2H-indazol-6-ol. (ES, m/z): 154 [M+H]⁺.

Step 8. ((6S*)-3-amino-6-hydroxy-4,5,6,7-tetrahydroindazol-2-yl)((4R*)-6-fluoro-1,2,3,4-tetrahydroquinolin-4-yl)methanone and ((6S*)-3-amino-6-hydroxy-4,5,6,7-tetrahydroindazol-2-yl)((4S*)-6-fluoro-1,2,3,4-tetrahydroquinolin-4-yl)methanone Example 184 & 185. ((6R*)-3-amino-6-hydroxy-4,5,6,7-tetrahydroindazol-2-yl)((4R*)-6-fluoro-1,2,3,4-tetrahydroquinolin-4-yl)methanone and ((6R*)-3-amino-6-hydroxy-4,5,6,7-tetrahydroindazol-2-yl)((4S*)-6-fluoro-1,2,3,4-tetrahydroquinolin-4-yl)methanone

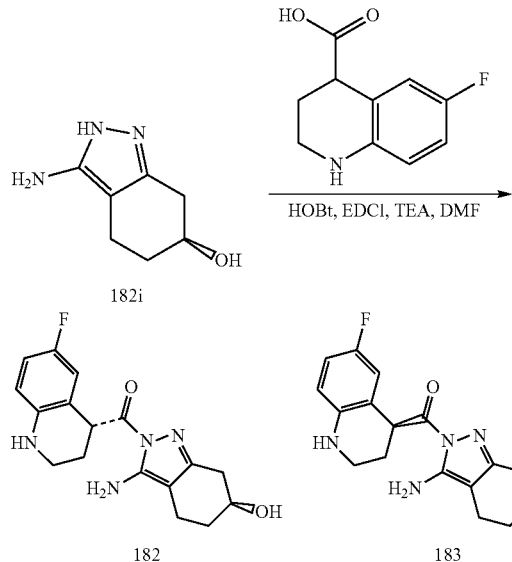
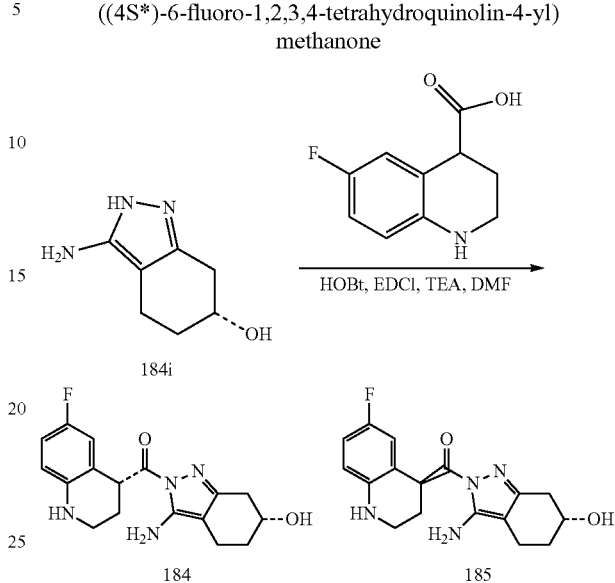

Into a 100-mL round-bottom flask, was placed (S*)-3-amino-4,5,6,7-tetrahydro-2H-indazol-6-ol (180 mg, 1.18 mmol, 1.00 equiv), 6-fluoro-1,2,3,4-tetrahydroquinoline-4-carboxylic acid (275 mg, 1.41 mmol, 1.20 equiv), HOBT (239 mg, 1.77 mmol, 1.50 equiv), EDCI (340 mg, 1.77 mmol, 1.50 equiv), N,N-dimethylformamide (8 mL), TEA (357 mg, 3.53 mmol, 3.00 equiv). The resulting solution was stirred for 2 h at room temperature (25° C.). The reaction mixture was diluted with DCM (80 mL), washed with water (50 mL×3) and brine (50 mL×3) and dried with $Na_2SO_4$. After filtration, the filtrate was concentrated under reduced pressure. The crude product was purified by Prep-HPLC with the following conditions (Analyse HPLC-SHIMADZU): Column: XSelect CSH Prep C18 OBD Column, 5 um, 19×150 mm; Mobile Phase A: water (0.1% FA), Mobile Phase B: ACN; Flow rate: 20 mL/min; Gradient: 3% B to 33% B in 8.9 min; 254 nm;

Enantiomer A (182): The collected fraction was lyophilized to give 12.8 mg (3%) of ((6S*)-3-amino-6-hydroxy-4,5,6,7-tetrahydroindazol-2-yl)((4R*)-6-fluoro-1,2,3,4-tetrahydroquinolin-4-yl)methanone as a white solid. RT4: 8.78 min; MS (ES, m/z) [M+H]$^+$: 331; (300 MHz, DMSO-$d_6$, ppm): δ 6.81-6.78 (m, 1H), 6.77-6.74 (m, 1H), 6.66-6.62 (m, 1H), 6.38 (s, 2H), 5.79 (s, 1H), 4.99-4.97 (m, 1H), 4.83-4.82 (m, 1H), 3.96-3.92 (m, 1H), 3.32-3.19 (m, 2H), 2.76-2.69 (m, 1H), 2.51-1.92 (m, 5H), 1.89- 1.55 (m, 2H).

Enantiomer B (183): The collected fraction was lyophilized to give 12.8 mg (3%) of ((6S*)-3-amino-6-hydroxy-4,5,6,7-tetrahydroindazol-2-yl)((4S*)-6-fluoro-1,2,3,4-tetrahydroquinolin-4-yl)methanone as a white solid. RT3: 8.27 min; MS (ES, m/z) [M+H]$^+$: 331; (300 MHz, DMSO-$d_6$, ppm): δ 6.82-6.78 (m, 1H), 6.76-6.73 (m, 1H), 6.66-6.63 (m, 1H), 6.38 (s, 2H), 5.78 (s, 1H), 4.99-4.97 (m, 1H), 4.83-4.79 (m, 1H), 3.96-3.94 (m, 1H), 3.23-3.19 (m, 2H), 2.74-2.69 (m, 1H), 2.51-1.92 (m, 5H), 1.81- 1.61 (m, 2H).

Into a 100-mL round-bottom flask, was placed (6R)-3-amino-4,5,6,7-tetrahydro-2H-indazol-6-ol (180 mg, 1.18 mmol, 1.00 equiv), EDCI (334 mg, 1.74 mmol, 1.50 equiv), TEA (238 mg, 2.35 mmol, 3.00 equiv), 1H-1,2,3-benzotriazol-1-ol (339 mg, 2.51 mmol, 1.50 equiv), 6-fluoro-1,2,3,4-tetrahydroquinoline-4-carboxylic acid (356 mg, 1.82 mmol, 1.50 equiv), DMF (10 ml). The resulting solution was stirred for 1 h at room temperature. The reaction was then quenched by the addition of water (50 mL). The resulting solution was extracted with dichloromethane (100 mL×3) and the organic layers combined and dried over anhydrous sodium sulfate and concentrated under vacuum. The crude product (4 mL) was purified by Prep-HPLC with the following conditions (2#-AnalyseHPLC-SHIMADZU (HPLC-10)): Column, XSelect CSH Prep C18 OBD Column, 5 um, 19×150 mm; mobile phase, Water (0.1% FA) and CAN (0.1% DEA) (5.0% ACN (0.1% DEA) up to 33.0% in 14 min); Detector, uv 254 nm.

Enantiomer A (184): The collected fraction was lyophilized to give 33 mg (8.5%) of ((6R*)-3-amino-6-hydroxy-4,5,6,7-tetrahydroindazol-2-yl)((4R*)-6-fluoro-1,2,3,4-tetrahydroquinolin-4-yl)methanone as a white solid. RT4: 13.10 min; MS (ES, m/z) [M+H]$^+$: 331; (DMSO, 400 MHz, ppm): δ 6.806-6.755 (m, 1H); 6.666-6.634 (m, 1H); 6.519-6.4484 (m, 1H); 6.379 (s, 2H); 5.786 (s, 1H); 4.999-4.971 (m, 1H); 4.839-4.830 (m, 1H); 3.951 (s, 1H); 3.326-3.145 (m, 2H); 2.730-2.678 (m, 1H); 2.510-2.38 (m, 2H); 2.371-2.184 (m, 1H); 2.075-1.980 (m, 2H); 1.798-1.771 (m, 1H); 1.642-1.609 (m, 1H).

Enantiomer B (185): The collected fraction was lyophilized to give 23.1 mg (5.9%) of ((6R*)-3-amino-6-hydroxy-4,5,6,7-tetrahydroindazol-2-yl)((4S*)-6-fluoro-1,2,3,4-tetrahydroquinolin-4-yl)methanone as a white solid. RT3: 11.38 min; MS (ES, m/z) [M+H]$^+$: 331; (DMSO, 400 MHz, ppm): δ 6.804-6.753 (m, 1H); 6.657-6.626 (m, 1H); 6.517-6.4483 (m, 1H); 6.381 (s, 2H); 5.789 (s, 1H); 4.999-4.971 (m, 1H); 4.833-4.824 (m, 1H); 3.957 (s, 1H); 3.326-3.145 (m, 2H); 2.735-2.694 (m, 1H); 2.510-2.376 (m, 2H); 2.255-2.197 (m, 1H); 2.075-1.983 (m, 2H); 1.808-1.780 (m, 1H); 1.630-1.597 (m, 1H).

Example 186, 187, 188 and 189. Benzyl (5R*)-3-amino-2-(6-fluoro-1,2,3,4-tetrahydroquinoline-4-carbonyl)-4,5,6,7-tetrahydro-2H-indazol-5-ylcarbamate; benzyl (5R*)-3-amino-1-(6-fluoro-1,2,3,4-tetrahydroquinoline-4-carbonyl)-4,5,6,7-tetrahydro-1H-indazol-5-ylcarbamate; ((5R*)-3,5-diamino-4,5,6,7-tetrahydroindazol-2-yl)((4R*)-6-fluoro-1,2,3,4-tetrahydroquinolin-4-yl)methanone and ((5R*)-3,5-diamino-4,5,6,7-tetrahydroindazol-2-yl)((4S*)-6-fluoro-1,2,3,4-tetrahydroquinolin-4-yl)methanone

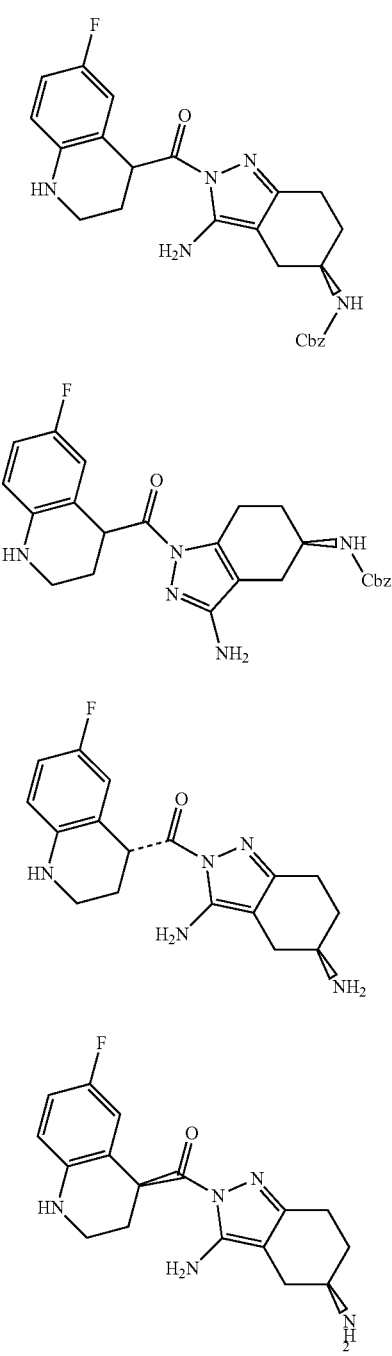

186

187

188

189

Step 1. Benzyl 3-formyl-4-oxocyclohexylcarbamate

Into a 250-mL 3-necked round-bottom flask purged and maintained with an inert atmosphere of nitrogen, was placed benzyl N-(4-oxocyclohexyl)carbamate (5 g, 20.22 mmol, 1.00 equiv) and toluene (100 mL). This was followed by the addition of methoxysodium (3.27 g, 60.53 mmol, 3.00 equiv) in 5 min. To this was added ethyl formate (8.98 g, 121.22 mmol, 6.00 equiv) in 2 h. The resulting solution was stirred for 5 min at 0° C. in a water/ice bath and then overnight at room temperature. The reaction was then quenched by the addition of water/ice (200 mL). The pH value of the solution was adjusted to 4~5 with HCl (1 mol/L). The resulting solution was extracted with ethyl acetate (100 mL×3), dried over anhydrous sodium sulfate and concentrated under vacuum. This resulted in 8.11 g (crude) of benzyl N-(3-formyl-4-oxocyclohexyl)carbamate as black crude oil. MS (ES, m/z) [M+H]$^+$: 276.

Step 2. (E)-benzyl 3-((hydroxyimino)methyl)-4-oxocyclohexylcarbamate

Into a 250-mL round-bottom flask, was placed benzyl N-(3-formyl-4-oxocyclohexyl)carbamate (8.11 g, 29.46 mmol, 1.00 equiv), hydroxylamine hydrochloride (2.44 g, 35.11 mmol, 1.20 equiv), acetic acid (0 mg). The resulting solution was stirred for 12 h at 100° C. The reaction mixture was cooled. The resulting mixture was concentrated under vacuum. The residue was dissolved in DCM (50 mL). The resulting solution was diluted with H$_2$O (200 mL). The pH value of the solution was adjusted to 6~7 with NaHCO$_3$. This resulted in 10.2 g (crude) of benzyl N-[3-[(1E)-(hydroxyimino)methyl]-4-oxocyclohexyl]carbamate as black oil. MS (ES, m/z) [M+H]$^+$: 291.

Step 3. Benzyl 3-cyano-4-oxocyclohexylcarbamate

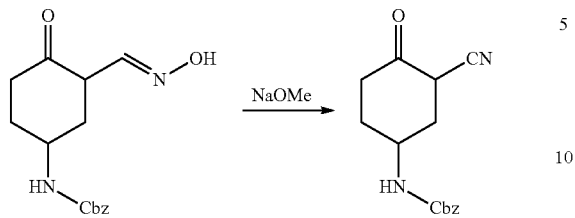

Into a 250-mL round-bottom flask, was placed benzyl N-[3-[(1E)-(hydroxyimino)methyl]-4-oxocyclohexyl]carbamate (7.5 g, 25.83 mmol, 1.00 equiv), toluene (150 mL), methanol (15 mL), methoxysodium (4.19 g, 77.56 mmol, 3.00 equiv). The resulting solution was stirred for 12 h at room temperature. The reaction was then quenched by the addition of water/ice (200 mL). The pH value of the solution was adjusted to 5~6 with HCl (1 mol/L). The resulting solution was extracted with ethyl acetate (100 mL×3) and the organic layers combined and dried over anhydrous sodium sulfate and concentrated under vacuum. This resulted in 5.9 g (crude) of benzyl N-(3-cyano-4-oxocyclohexyl)carbamate as black crude oil. MS (ES, m/z) [M+H]$^+$: 273.

Step 4. Benzyl 3-amino-4,5,6,7-tetrahydro-2H-indazol-5-ylcarbamate

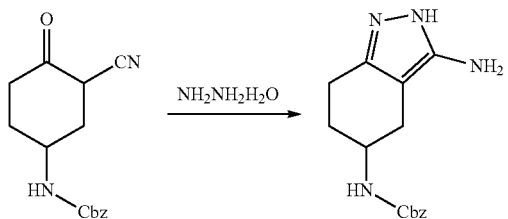 [SMILES: N#CC1CC(NC(=O)OCc2ccccc2)CCC1=O ; "NH2NH2H2O" ; Nc1[nH]nc2c1CC(NC(=O)OCc1ccccc1)CC2]

Into a 250-mL round-bottom flask, was placed benzyl N-(3-cyano-4-oxocyclohexyl)carbamate (4.91 g, 18.03 mmol, 1.00 equiv), ethanol (100 mL), hydrazine hydrate (4.91 g, 98.08 mmol, 5.00 equiv). The resulting solution was stirred for 12 h at room temperature. The resulting mixture was concentrated under vacuum. The residue was applied onto a silica gel column and eluted with dichloromethane/methanol (10:1). This resulted in 0.9 g (17%) of benzyl N-(3-amino-4,5,6,7-tetrahydro-2H-indazol-5-yl)carbamate as brown oil. MS (ES, m/z) [M+H]$^+$: 286.

Step 5. (S*)-benzyl 3-amino-4,5,6,7-tetrahydro-2H-indazol-5-ylcarbamate and (R*)-benzyl 3-amino-4,5,6,7-tetrahydro-2H-indazol-5-ylcarbamate

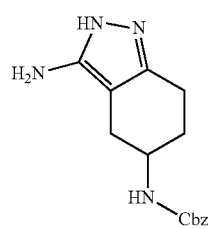

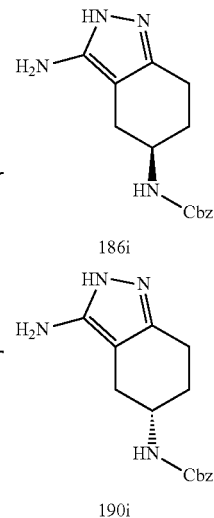

The racemic benzyl N-(3-amino-4,5,6,7-tetrahydro-2H-indazol-5-yl)carbamate (1.5 g) was separated by Prep-chiral-HPLC with the following conditions: Column: CHIRAL ART Cellulose-SB, 2×25 cm, 5 um; Mobile Phase A: Hex, Mobile Phase B: EtOH; Flow rate: 20 mL/min; Gradient: 30 B to 30 B in 13 min; 220/254 nm; The first eluting isomer (RT1:8.38 min) was collected and concentrated to give 400 mg (19%) of (R*)-benzyl 3-amino-4,5,6,7-tetrahydro-2H-indazol-5-ylcarbamate as a yellow solid. MS (ES, m/z) [M+H]$^+$: 286. And the second eluting isomer (RT2:9.56 min) was collected and concentrated to give 450 mg (19%) of (S*)-benzyl 3-amino-4,5,6,7-tetrahydro-2H-indazol-5-ylcarbamate as a yellow solid. MS (ES, m/z) [M+H]$^+$: 286.

Step 6. Benzyl (5R*)-3-amino-2-(6-fluoro-1,2,3,4-tetrahydroquinoline-4-carbonyl)-4,5,6,7-tetrahydro-2H-indazol-5-ylcarbamate and benzyl (5R*)-3-amino-1-(6-fluoro-1,2,3,4-tetrahydroquinoline-4-carbonyl)-4,5,6,7-tetrahydro-1H-indazol-5-ylcarbamate

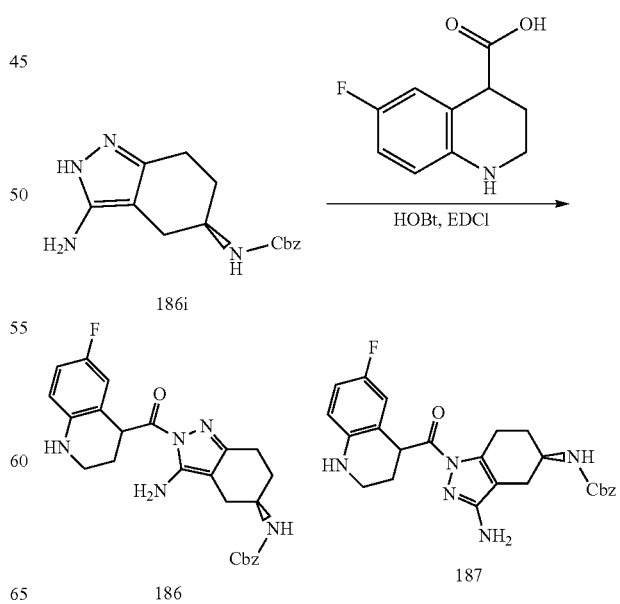

Into a 50-mL round-bottom flask, was placed benzyl N-[(5R*)-3-amino-4,5,6,7-tetrahydro-2H-indazol-5-yl]carbamate (200 mg, 0.70 mmol, 1.00 equiv), 6-fluoro-1,2,3,4-tetrahydroquinoline-4-carboxylic acid (205 mg, 1.05 mmol, 1.50 equiv), HOBT (145 mg, 1.07 mmol, 1.50 equiv), EDCI (200 mg, 1.04 mmol, 1.50 equiv), TEA (210 mg, 2.08 mmol, 3.00 equiv), N,N-dimethylformamide (8 mL). The resulting solution was stirred for 3 h at room temperature. The reaction was then quenched by the addition of water (50 mL). The resulting solution was extracted with ethyl acetate (50 mL×3) and concentrated under vacuum. The crude product was purified by Prep-HPLC with the following conditions: Column: XBridge Prep C18 OBD Column, 5 um, 19×150 mm; Mobile Phase A: water (10 mmoL/L NH₄HCO₃), Mobile Phase B: ACN; Flow rate: 20 mL/min; Gradient: 15% B to 32% B in 7 min; 220 nm;

Fraction A (186): The collected fraction was lyophilized to give 60 mg (19%) of benzyl (5R*)-3-amino-2-(6-fluoro-1,2,3,4-tetrahydroquinoline-4-carbonyl)-4,5,6,7-tetrahydro-2H-indazol-5-ylcarbamate as a white solid. RT2: 6.4 min; MS (ES, m/z) [M+H]⁺: 464; (DMSO-d₆, 400 MHz, ppm): δ 7.48-7.45 (m, 1H), 7.38-7.31 (m, 5H), 6.81-6.76 (m, 1H), 6.68-6.63 (m, 1H), 6.52-6.48 (m, 1H), 6.45 (s, 2H), 5.79 (s, 1H), 5.04 (s, 2H), 4.98-4.96 (m, 1H), 3.74-3.65 (m, 1H), 3.22-3.16 (m, 2H), 2.68-22.63 (m, 2H), 2.56-2.51 (m, 1H), 2.17-1.90 (m, 4H), 1.71-1.66 (m, 1H).

Fraction B (187): The collected fraction was lyophilized to give 50 mg (15%) of benzyl (5R*)-3-amino-1-(6-fluoro-1,2,3,4-tetrahydroquinoline-4-carbonyl)-4,5,6,7-tetrahydro-1H-indazol-5-ylcarbamate as a white solid. RT1: 5.5 min; MS (ES, m/z) [M+H]⁺: 464; (DMSO-d₆, 400 MHz, ppm): δ 7.47-7.44 (m, 1H), 7.39-7.31 (m, 5H), 6.79-6.74 (m, 1H), 6.65-6.63 (m, 1H), 6.50-6.47 (m, 1H), 5.76 (s, 1H), 5.63 (s, 2H), 5.03 (s, 2H), 4.91-4.89 (m, 1H), 3.74-3.71 (m, 1H), 3.27-3.24 (m, 1H), 3.13-3.11 (m, 1H), 3.04-2.99 (m, 1H), 2.83-2.79 (m, 1H), 2.59-2.51 (m, 1H), 2.16-2.12 (m, 1H), 2.01-1.88 (m, 3H), 1.68-1.66 (m, 1H).

Step 7. Benzyl (5R*)-3-amino-2-((4R*)-6-fluoro-1,2,3,4-tetrahydroquinoline-4-carbonyl)-4,5,6,7-tetrahydro-2H-indazol-5-ylcarbamate and benzyl (5R*)-3-amino-2-((4S*)-6-fluoro-1,2,3,4-tetrahydroquinoline-4-carbonyl)-4,5,6,7-tetrahydro-2H-indazol-5-ylcarbamate

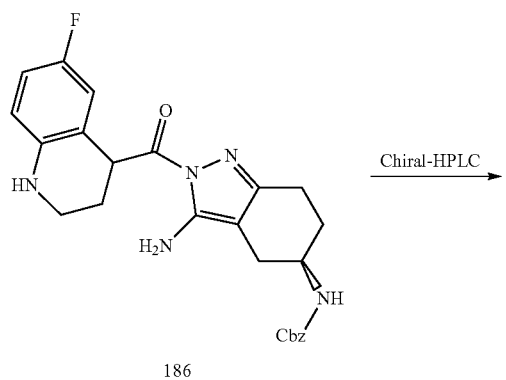

186

Chiral-HPLC →

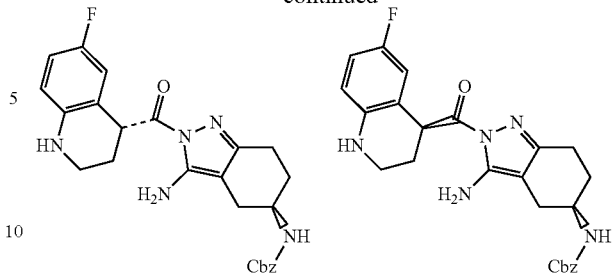

N-[(5R*)-3-amino-2-[(6-fluoro-1,2,3,4-tetrahydroquinolin-4-yl)carbonyl]-4,5,6,7-tetrahydro-2H-indazol-5-yl]carbamate (100 mg, 0.22 mmol, 1.00 equiv) was separated by Prep-chiral-HPLC with the following conditions: Column: Chiralpak ID-2, 2×25 cm, 5 um; Mobile Phase A: Hex, Mobile Phase B: EtOH; Flow rate: 15 mL/min; Gradient: 50 B to 50 B in 35.5 min; 220/254 nm. The first eluting isomer (RT1: 11.26 min) was collected and concentrated to give 30 mg (30%) of benzyl N-[(5R*)-3-amino-2-[[(4R)-6-fluoro-1,2,3,4-tetrahydroquinolin-4-yl]carbonyl]-4,5,6,7-tetrahydro-2H-indazol-5-yl]carbamate as a white solid. MS (ES, m/z) [M+H]: 464. The second eluting isomer (RT2: 29.79 min) was collected and concentrated to give 32 mg (32%) of benzyl N-[(5R*)-3-amino-2-[[(4S)-6-fluoro-1,2,3,4-tetrahydroquinolin-4-yl]carbonyl]-4,5,6,7-tetrahydro-2H-indazol-5-yl]carbamate as a white solid. MS (ES, m/z) [M+H]: 464.

Step 8. ((5R*)-3,5-diamino-4,5,6,7-tetrahydroindazol-2-yl)((4R*)-6-fluoro-1,2,3,4-tetrahydroquinolin-4-yl)methanone

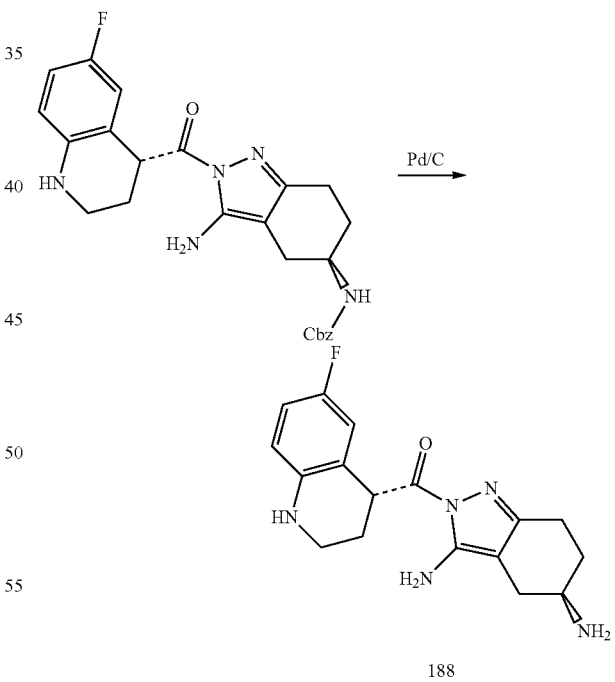

188

Into a 50-mL round-bottom flask, was placed benzyl N-[(5R*)-3-amino-2-[[(4S*)-6-fluoro-1,2,3,4-tetrahydroquinolin-4-yl]carbonyl]-4,5,6,7-tetrahydro-2H-indazol-5-yl]carbamate (32 mg, 0.07 mmol, 1.00 equiv), methanol (5 mL), Palladium carbon (10%) (20 mg). To the above hydrogen was introduced in. The resulting solution was stirred for 1 h at room temperature. The solids were filtered out. The filtrate was concentrated under vacuum. The crude product was purified by Prep-HPLC with the following conditions: Column: XBridge Prep C18 OBD Column, 5 um, 19×150 mm; Mobile Phase A: water (10 MMOL/L NH₄HCO₃), Mobile Phase B: ACN; Flow rate: 20 mL/min; Gradient: 15% B to 32% B in 7 min; 220 nm;

The collected fraction was lyophilized to give 5.2 mg (23%) of (5R*)-2-[[(4R*)-6-fluoro-1,2,3,4-tetrahydroquinolin-4-yl]carbonyl]-4,5,6,7-tetrahydro-2H-indazole-3,5-diamine as a white solid. Rt: 6.4 min. MS (ES, m/z) [M+H]⁺: 330; (DMSO-d₆, 400 MHz, ppm): δ 6.81-6.76 (m, 1H), 6.66-6.62 (m, 1H), 6.52-6.47 (m, 1H), 6.44 (s, 2H), 5.80 (s, 1H), 4.99-4.98 (m, 1H), 3.25-3.14 (m, 3H), 2.68-2.51 (m, 3H), 2.09-1.91 (m, 4H), 1.60-1.56 (m, 1H).

Step 9. ((5R*)-3,5-diamino-4,5,6,7-tetrahydroindazol-2-yl)((4S*)-6-fluoro-1,2,3,4-tetrahydroquinolin-4-yl)methanone

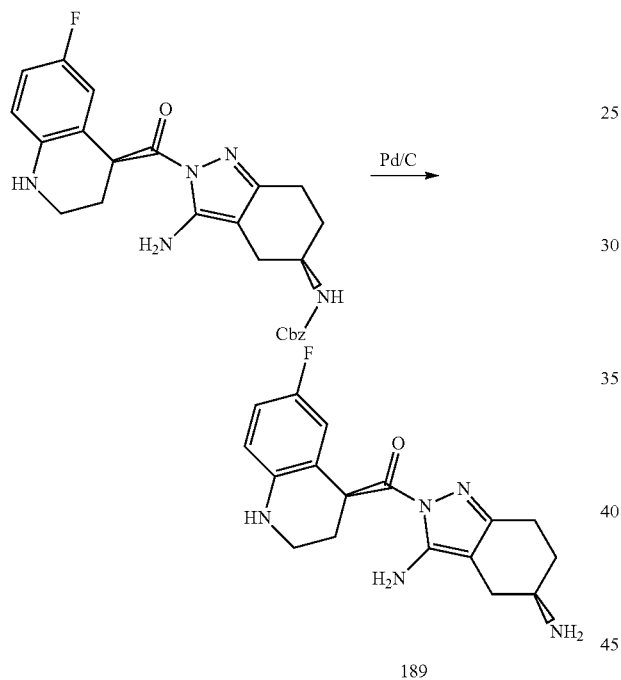

Into a 50-mL round-bottom flask, was placed benzyl N-[(5R*)-3-amino-2-[[(4R*)-6-fluoro-1,2,3,4-tetrahydroquinolin-4-yl]carbonyl]-4,5,6,7-tetrahydro-2H-indazol-5-yl]carbamate (30 mg, 0.06 mmol, 1.00 equiv), methanol (5 mL), Palladium carbon (10%) (20 mg). To the above hydrogen was introduced in. The resulting solution was stirred for 1 h at room temperature. The solids were filtered out. The filtrate was concentrated under vacuum. The crude product was purified by Prep-HPLC with the following conditions: Column: XBridge Prep C18 OBD Column, 5 um, 19×150 mm; Mobile Phase A: water (10 mmoL/L NH₄HCO₃), Mobile Phase B: ACN; Flow rate: 20 mL/min; Gradient: 15% B to 30% B in 7 min; 220 nm; The collected fraction was lyophilized to give 5.0 mg (23%) of ((5R*)-3,5-diamino-4,5,6,7-tetrahydroindazol-2-yl)((4S*)-6-fluoro-1,2,3,4-tetrahydroquinolin-4-yl)methanone (189) as a white solid. Rt: 6.5 min. MS (ES, m/z) [M+H]⁺: 330. (DMSO-d₆, 400 MHz, ppm): δ 6.81-6.75 (m, 1H), 6.66-6.63 (m, 1H), 6.52-6.48 (m, 1H), 6.38 (s, 2H), 5.79 (s, 1H), 4.99-4.96 (m, 1H), 3.22-3.16 (m, 2H), 2.95-2.94 (m, 1H), 2.63-2.54 (m, 2H), 2.47-2.41 (m, 1H), 2.08-1.84 (m, 4H), 1.51-1.48 (m, 1H).

Example 190, 191, 192 & 193. Benzyl N-[(5S*)-3-amino-2-[(6-fluoro-1,2,3,4-tetrahydroquinolin-4-yl)carbonyl]-4,5,6,7-tetrahydro-2H-indazol-5-yl]carbamate; benzyl N-[(5S*)-3-amino-1-[(6-fluoro-1,2,3,4-tetrahydroquinolin-4-yl)carbonyl]-4,5,6,7-tetrahydro-1H-indazol-5-yl]carbamate; ((5S*)-3,5-diamino-4,5,6,7-tetrahydroindazol-2-yl)((4S*)-6-fluoro-1,2,3,4-tetrahydroquinolin-4-yl)methanone; and ((5S*)-3,5-diamino-4,5,6,7-tetrahydroindazol-2-yl)((4R*)-6-fluoro-1,2,3,4-tetrahydroquinolin-4-yl)methanone

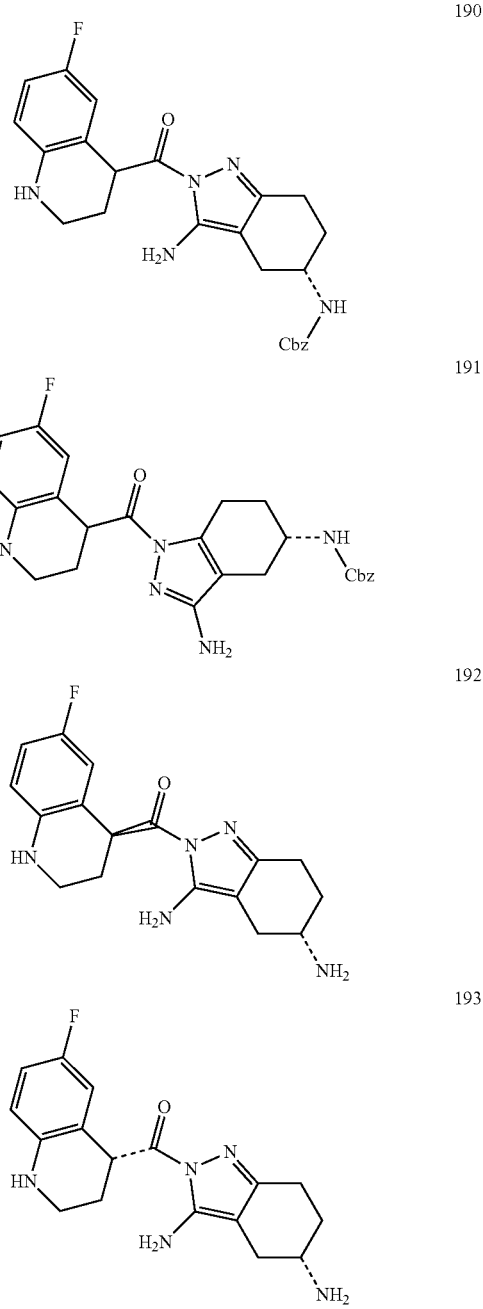

Step 1. Benzyl N-[(5S*)-3-amino-2-[(6-fluoro-1,2,3,4-tetrahydroquinolin-4-yl)carbonyl]-4,5,6,7-tetrahydro-2H-indazol-5-yl]carbamate and Benzyl N-[(5S*)-3-amino-1-[(6-fluoro-1,2,3,4-tetrahydroquinolin-4-yl)carbonyl]-4,5,6,7-tetrahydro-1H-indazol-5-yl]carbamate

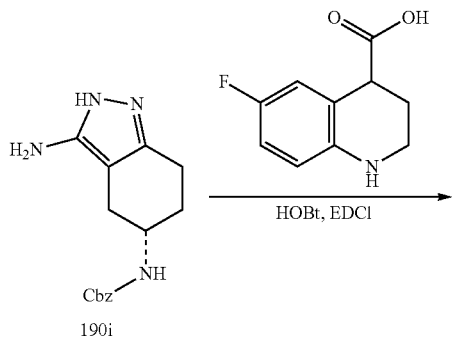

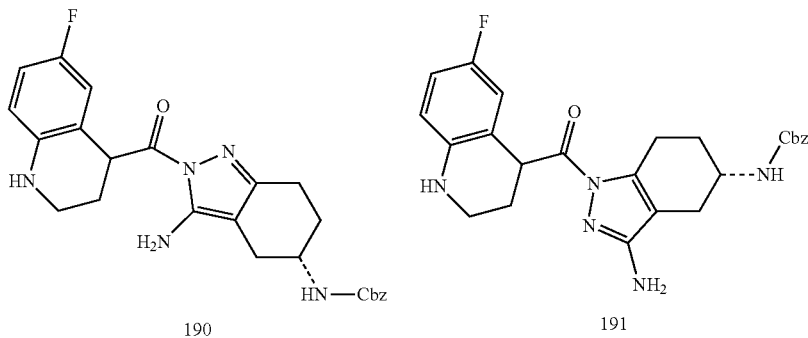

Into a 100-mL round-bottom flask, was placed benzyl N-[(5R)-3-amino-4,5,6,7-tetrahydro-2H-indazol-5-yl]carbamate (320 mg, 1.12 mmol, 1.00 equiv), 6-fluoro-1,2,3,4-tetrahydroquinoline-4-carboxylic acid (240 mg, 1.23 mmol, 1.10 equiv), EDCI (323 mg, 1.68 mmol, 1.50 equiv), HOBt (227 mg, 1.68 mmol, 1.50 equiv), TEA (566 mg, 5.60 mmol, 5.00 equiv), N,N-dimethylformamide (20 mL). The resulting solution was stirred for 2 h at room temperature. The reaction was then quenched by the addition of water (40 mL). The resulting solution was extracted with ethyl acetate (40 mL×3) and concentrated under vacuum. The crude product was purified by Flash-Prep-HPLC with the following conditions (IntelFlash-1): Column: XBridge C18 OBD Prep Column 100Å, 10 μm, 19 mm×250 mm; Mobile Phase A: Water (0.1% FA), Mobile Phase B: ACN; Flow rate: 20 mL/min; Gradient: 25% B to 45% B in 7 min; 254 nm;

Fraction A: The collected fraction was lyophilized to give 110.2 mg (21.2%) of benzyl N-[(5S*)-3-amino-2-[(6-fluoro-1,2,3,4-tetrahydroquinolin-4-yl)carbonyl]-4,5,6,7-tetrahydro-2H-indazol-5-yl]carbamate as a white solid. RT2: 6.45 min; MS (ES, m/z) [M+H]$^+$: 464. (DMSO-d$_6$, 400 MHz, ppm): δ 7.46-7.43 (m, 1H), 7.38-7.31 (m, 5H), 6.81-6.74 (m, 1H), 6.67-6.62 (m, 1H), 6.52-6.44 (m, 3H), 5.79 (s, 1H), 5.04-4.95 (m, 3H), 3.74-3.65 (m, 1H), 3.22-3.16 (m, 2H), 2.68-2.63 (m, 3H), 2.17-1.90 (m, 4H), 1.71-1.66 (m, 1H). Benzyl N-[(5S*)-3-amino-1-[(6-fluoro-1,2,3,4-tetrahydroquinolin-4-yl)carbonyl]-4,5,6,7-tetrahydro-1H-indazol-5-yl]carbamate as a white solid. RT1: 5.45 min; MS (ES, m/z) [M+H]$^+$: 464. (DMSO-d$_6$, 400 MHz, ppm): δ 7.44-7.30 (m, 6H), 6.79-6.74 (m, 1H), 6.65-6.63 (m, 1H), 6.50-6.47 (m, 1H), 5.59 (s, 1H), 5.74 (s, 2H), 5.03 (s, 2H), 4.93-4.89 (m, 1H), 3.74-3.71 (m, 1H), 3.27-3.24 (m, 1H), 3.13-3.11 (m, 1H), 3.04-2.99 (m, 1H), 2.83-2.79 (m, 1H), 2.59-2.51 (m, 1H), 2.16-2.12 (m, 1H), 2.01-1.88 (m, 3H), 1.68-1.66 (m, 1H).

Step 2. Benzyl N-[(5S*)-3-amino-2-[[(4S*)-6-fluoro-1,2,3,4-tetrahydroquinolin-4-yl]carbonyl]-4,5,6,7-tetrahydro-2H-indazol-5-yl]carbamate and benzyl N-[(5S*)-3-amino-2-[[(4R*)-6-fluoro-1,2,3,4-tetrahydroquinolin-4-yl]carbonyl]-4,5,6,7-tetrahydro-2H-indazol-5-yl]carbamate

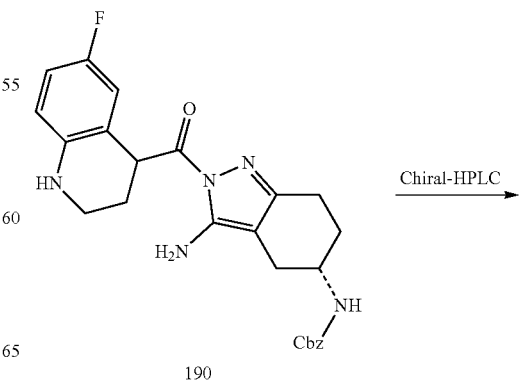

-continued

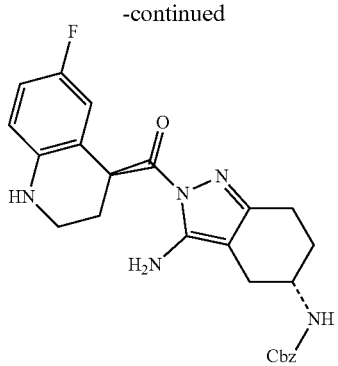

Benzyl N-[(5S*)-3-amino-2-[(6-fluoro-1,2,3,4-tetrahydroquinolin-4-yl)carbonyl]-4,5,6,7-tetrahydro-2H-indazol-5-yl]carbamate (100 mg, 0.22 mmol, 1.00 equiv) was separated by Prep-chiral-HPLC with the following conditions: Column: Chiralpak ID-2, 2×25 cm, 5 um; Mobile Phase A: Hex, Mobile Phase B: EtOH; Flow rate: 15 mL/min; Gradient: 50 B to 50 B in 35.5 min; 220/254 nm; The first eluting isomer (RT1: 11.26 min) was collected and concentrated under vacuum to give 40 mg (40%) of benzyl N-[(5S)-3-amino-2-[[(4R)-6-fluoro-1,2,3,4-tetrahydroquinolin-4-yl]carbonyl]-4,5,6,7-tetrahydro-2H-indazol-5-yl]carbamate (assumed) as a white solid. MS (ES, m/z) [M+H]+: 464. The second eluting isomer (RT2: 29.79 min) was collected and concentrated under vacuum to give 40 mg (40%) of benzyl N-[(5S*)-3-amino-2-[[(4S*)-6-fluoro-1,2,3,4-tetrahydroquinolin-4-yl]carbonyl]-4,5,6,7-tetrahydro-2H-indazol-5-yl]carbamate as a white solid. MS (ES, m/z) [M+H]+: 464.

Step 3. ((5S*)-3-amino-5,4,5,6,7-tetrahydroindazol-2-yl)((4S*)-6-fluoro-1,2,3,4-tetrahydroquinolin-4-yl)methanone

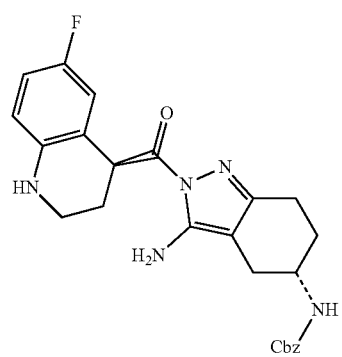

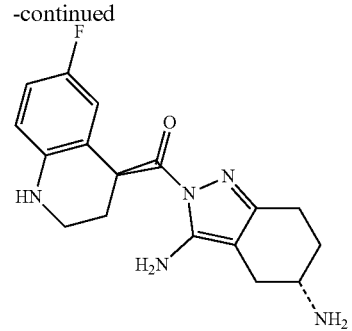

192

Into a 100-mL round-bottom flask, was placed benzyl N-[(5S*)-3-amino-2-[[(4S*)-6-fluoro-1,2,3,4-tetrahydroquinolin-4-yl]carbonyl]-4,5,6,7-tetrahydro-2H-indazol-5-yl]carbamate (40 mg, 0.09 mmol, 1.00 equiv), methanol (15 mL), Palladium carbon (10%) (30 mg). The flask was evacuated and flushed three times with nitrogen, followed by flushing with hydrogen. The mixture was stirred 2 h at room temperature under an atmosphere of hydrogen (balloon). The solid was filtered out. The filtrate was concentrated under vacuum. (2#-AnalyseHPLC-SHIMADZU (HPLC-10)): Column, XBridge Prep C18 OBD Column, 19×150 mm 5 um; mobile phase, water (10 mmoL/L NH$_4$HCO$_3$) and ACN (20.0% ACN up to 39.0% in 5 min); Detector, UV 254/220 nm. This resulted in 6.2 mg (22%) of ((5S*)-3,5-diamino-4,5,6,7-tetrahydroindazol-2-yl)((4S*)-6-fluoro-1,2,3,4-tetrahydroquinolin-4-yl)methanone as a white solid. MS (ES, m/z) [M+H]$^+$: 330; (DMSO-d$_6$, 300 MHz, ppm): δ 6.78-6.77 (m, 1H), 6.66-6.62 (m, 1H), 6.52-6.47 (m, 1H), 6.36 (s, 2H), 5.78 (s, 1H), 4.98-4.96 (m, 1H), 3.31-3.26 (m, 2H), 3.01-2.94 (m, 1H), 2.58-2.56 (m, 2H), 2.51-2.48 (m, 1H), 2.05-1.87 (m, 6H), 1.51-1.48 (m, 1H).

Step 4. ((5S*)-3,5-diamino-4,5,6,7-tetrahydroindazol-2-yl)((4R*)-6-fluoro-1,2,3,4-tetrahydroquinolin-4-yl)methanone

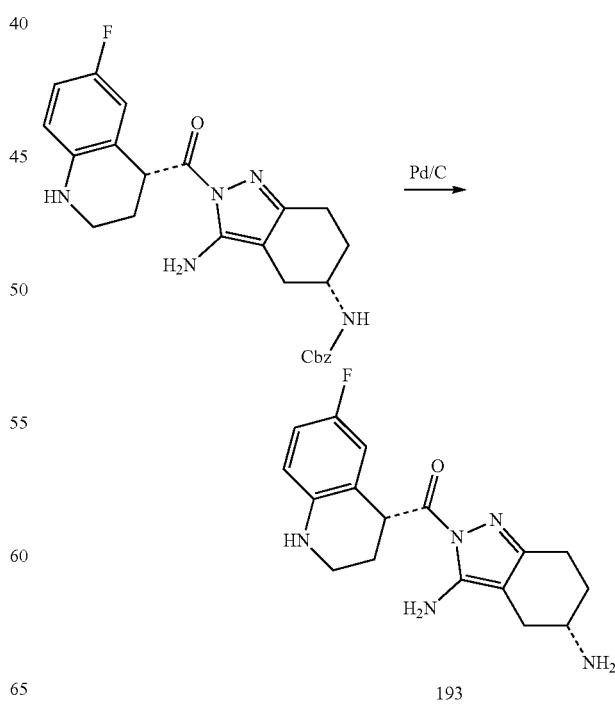

193

Into a 100-mL round-bottom flask, was placed benzyl N-[(5S*)-3-amino-2-[[(4R*)-6-fluoro-1,2,3,4-tetrahydroquinolin-4-yl]carbonyl]-4,5,6,7-tetrahydro-2H-indazol-5-yl]carbamate (40 mg, 0.09 mmol, 1.00 equiv), methanol (15 mL), Palladium carbon (10%) (30 mg). The flask was evacuated and flushed three times with nitrogen, followed by flushing with hydrogen. The mixture was stirred 2 h at room temperature under an atmosphere of hydrogen (balloon). The solid was filtered out. The filtrate was concentrated under vacuum. The crude product was purified by Prep-HPLC with the following conditions (2#-AnalyseHPLC-SHIMADZU (HPLC-10)): Column, XBridge Prep C18 OBD Column, 19×150 mm 5 um; mobile phase, water (10 mmoL/L NH4HCO3) and ACN (20.0% ACN up to 39.0% in 5 min); Detector, UV 254/220 nm. mL product was obtained. This resulted in 9.9 mg (35%) of ((5S*)-3,5-diamino-4,5,6,7-tetrahydroindazol-2-yl)((4R*)-6-fluoro-1,2,3,4-tetrahydroquinolin-4-yl)methanone as a white solid. MS (ES, m/z) [M+1]: 330. (DMSO-$d_6$, 300 MHz, ppm): δ 6.81-6.74 (m, 1H), 6.66-6.62 (m, 1H), 6.52-6.47 (m, 1H), 6.36 (s, 2H), 5.78 (s, 1H), 4.98-4.96 (m, 1H), 3.31-3.14 (m, 2H), 3.01-2.94 (m, 1H), 2.58-2.56 (m, 2H), 2.51-2.48 (m, 1H), 2.07-1.81 (m, 6H), 1.51-1.48 (m, 1H).

Example 194, 195 & 196. (R*)-(3-amino-6,7-dihydroindazol-2-yl)(8-methyl-1,2,3,4-tetrahydroquinolin-4-yl)methanone; (S*)-(3-amino-6,7-dihydroindazol-2-yl)(8-methyl-1,2,3,4-tetrahydroquinolin-4-yl)methanone; and (3-amino-6,7-dihydroindazol-1-yl)(8-methyl-1,2,3,4-tetrahydroquinolin-4-yl)methanone

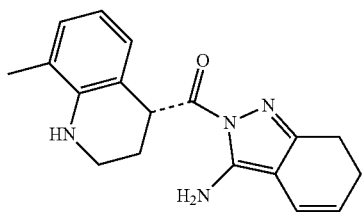

194

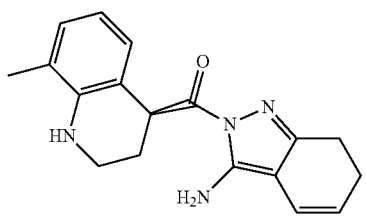

195

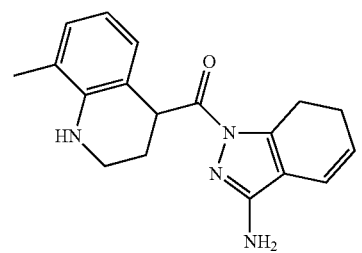

196

Step 1. 4-Bromo-8-methylquinoline

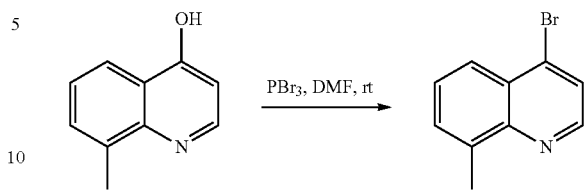

Into a 100-mL round-bottom flask, was placed 8-methylquinolin-4-ol (500 mg, 3.14 mmol, 1.00 equiv), N,N-dimethylformamide (20 mL). This was followed by the addition of tribromophosphane (851 mg, 3.14 mmol, 1.20 equiv) dropwise with stirring at room temperature. The resulting solution was stirred for 15 hours at room temperature. The reaction was then quenched by the addition of water/ice (100 mL). The pH value of the solution was adjusted to 10 with NaOH (2 mol/L). The precipitated solids were collected by filtration. This resulted in 660 mg (95%) of 4-bromo-8-methylquinoline as a light yellow solid. MS (ES, m/z) [M+1]: 222&224.

Step 2. Methyl 8-methylquinoline-4-carboxylate

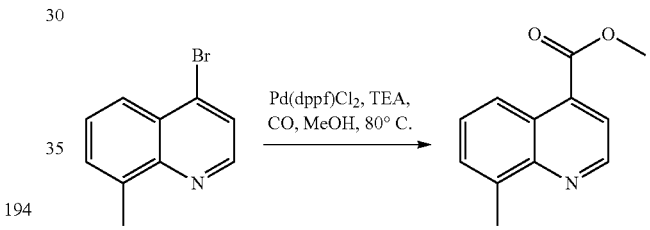

Into a 50-mL pressure tank reactor, was placed 4-bromo-8-methylquinoline (600 mg, 2.70 mmol, 1.00 equiv), Pd(dppf)Cl$_2$ (444 mg, 0.54 mmol, 0.20 equiv), TEA (1.4 g, 13.86 mmol, 5.00 equiv), methanol (15 mL). The flask was evacuated and flushed three times with nitrogen, followed by flushing with carbon monoxide (60 atm). The resulting solution was stirred for 16 hours at 80° C. After cooled to room temperature, the solvent was removed under vacuum, the residue was re-dissolved in ethyl acetate (20 mL), washed by brine (20 mL×3) and then applied onto a silica gel column with hexane/ethyl acetate (0-30%). This resulted in 350 mg (64%) of methyl 8-methylquinoline-4-carboxylate as a white solid. MS (ES, m/z) [M+1]: 202.

Step 3. 8-methylquinoline-4-carboxylic Acid

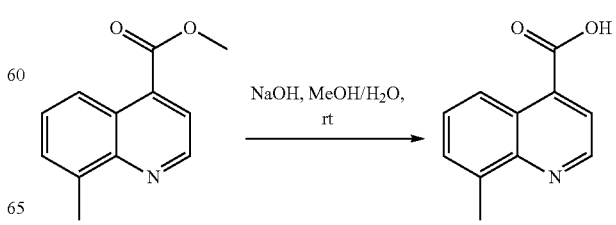

Into a 100-mL round-bottom flask, was placed methyl 8-methylquinoline-4-carboxylate (350 mg, 1.74 mmol, 1.00 equiv), NaOH (209 mg, 5.23 mmol, 3.00 equiv), water (20 mL), methanol (20 mL). The resulting solution was stirred for 14 hours at room temperature. The resulting mixture was concentrated under vacuum. The resulting solution was extracted with ethyl acetate (20 mL×2). The pH value of the aqueous phase was adjusted to 5-6 with hydrochloric acid (6 mol/L). The resulting solution was extracted with ethyl acetate (30 mL×3) and the organic phase combined. The resulting mixture was concentrated under vacuum. This resulted in 250 mg (77%) of 8-methylquinoline-4-carboxylic acid as a yellow solid. MS (ES, m/z) [M+1]: 188.

Step 4. 8-methyl-1,2,3,4-tetrahydroquinoline-4-carboxylic Acid

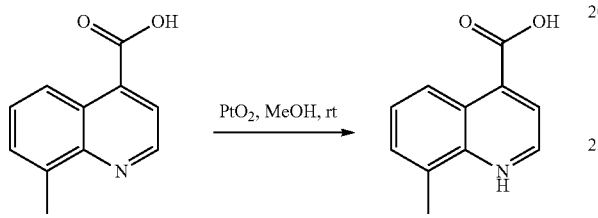

Into a 100-mL round-bottom flask, was placed 8-methylquinoline-4-carboxylic acid (250 mg, 1.34 mmol, 1.00 equiv), PtO$_2$ (40 mg), methanol (20 mL). The flask was evacuated and flushed three times with nitrogen, followed by flushing with hydrogen. The mixture was stirred 1 hour at room temperature under an atmosphere of hydrogen. The solids were filtered out. The resulting mixture was concentrated under vacuum. This resulted in 220 mg (86%) of 8-methyl-1,2,3,4-tetrahydroquinoline-4-carboxylic acid as a yellow solid. MS (ES, m/z) [M+1]: 192.

Step 5. Tert-butyl 3-amino-5-hydroxy-4,5,6,7-tetrahydro-2H-indazole-2-carboxylate

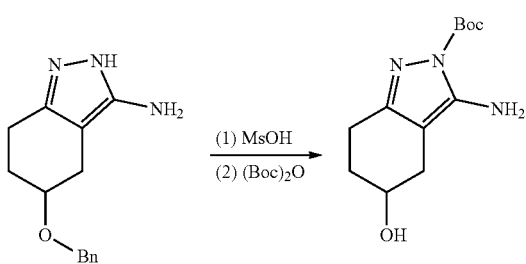 [SMILES: Nc1[nH]nc2c1CC(OCc1ccccc1)CC2 ; CC(C)(C)OC(=O)n1nc2c(c1N)CC(O)CC2]

Into a 500-mL round-bottom flask, was placed 5-(benzyloxy)-4,5,6,7-tetrahydro-2H-indazol-3-amine (10 g, 41.00 mmol, 1.00 equiv), DCM (200 mL), methanesulfonic acid (10 g, 104.06 mmol, 2.50 equiv). The resulting solution was stirred for 15 h at room temperature. The reaction liquid was used in the next step directly. MS (ES, m/z) [M+H]$^+$: 154. The reaction mixture was adjusted to pH 9 with TEA. A solution of di-tert-butyl dicarbonate (10.5 g, 48.1 mmol, 1.20 equiv) was added slowly. The resulting solution was stirred for 12 h at room temperature. The crude product was purified by reversed phase column with the following conditions: Column, C18 silica gel, 120 g, 20-45 um, 100 A; mobile phase, water with water (0.05% FA) and ACN (5% up to 85% ACN in 45 min); Detector, UV 220/254 nm. This resulted in 1 g (10%) of tert-butyl 3-amino-5-hydroxy-4,5,6,7-tetrahydro-2H-indazole-2-carboxylate as a yellow solid. MS (ES, m/z) [M+1]: 254.

Step 6. Tert-butyl 3-amino-6,7-dihydro-2H-indazole-2-carboxylate

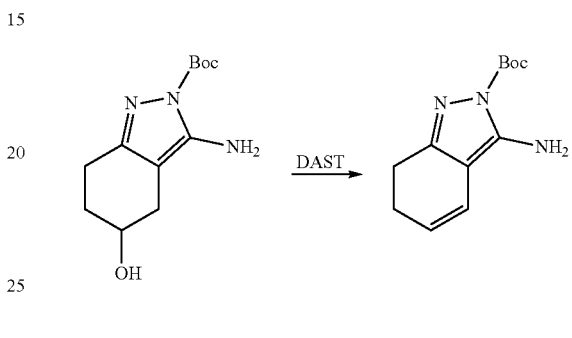

Into a 100-mL 3-necked round-bottom flask purged and maintained with an inert atmosphere of nitrogen, was placed DAST (1.1 g, 29.65 mmol, 3.00 equiv), dichloromethane (15 mL), a solution of tert-butyl 3-amino-5-hydroxy-4,5,6,7-tetrahydro-2H-indazole-2-carboxylate (600 mg, 2.37 mmol, 1.00 equiv) in dichloromethane (15 mL). The resulting solution was stirred for 5 h at room temperature. The crude product was purified by reversed phase column with the following conditions: Column, C18 silica gel, 120 g, 20-45 um, 100 A; mobile phase, water with water (0.05% NH$_4$HCO$_3$) and ACN (5% up to 95% ACN in 45 min); Detector, UV 220/254 nm. This resulted in 170 mg (31%) of tert-butyl 3-amino-6,7-dihydro-2H-indazole-2-carboxylate as a yellow solid. MS (ES, m/z) [M+1]: 236.

Step 7. 6,7-dihydro-2H-indazol-3-amine

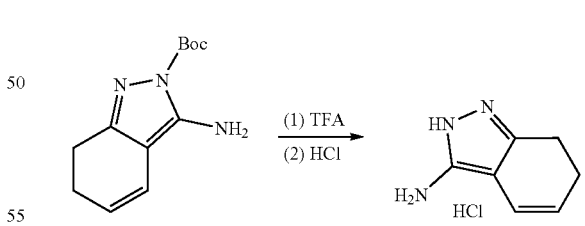

Into a 100-mL round-bottom flask, was placed tert-butyl 3-amino-6,7-dihydro-2H-indazole-2-carboxylate (170 mg, 0.72 mmol, 1.00 equiv), dichloromethane (20 mL), trifluoroacetic acid (244 mg, 2.16 mmol, 3.00 equiv). The resulting solution was stirred for 12 h at room temperature. The crude product was concentrated under vacuum. The reaction mixture was lyophilizated by the addition of ACN and HCl (2 mol/L). This resulted in 120 mg (crude) of 6,7-dihydro-2H-indazol-3-amine hydrochloride as a yellow solid.

MS (ES, m/z) [M+1]: 136.

Step 8. (3-amino-6,7-dihydroindazol-2-yl)(8-methyl-1,2,3,4-tetrahydroquinolin-4-yl)methanone and (3-amino-6,7-dihydroindazol-1-yl)(8-methyl-1,2,3,4-tetrahydroquinolin-4-yl)methanone Step 9. (R*)-(3-amino-6,7-dihydroindazol-2-yl)(8-methyl-1,2,3,4-tetrahydroquinolin-4-yl)methanone and (S*)-(3-amino-6,7-dihydroindazol-2-yl)(8-methyl-1,2,3,4-tetrahydroquinolin-4-yl)methanone

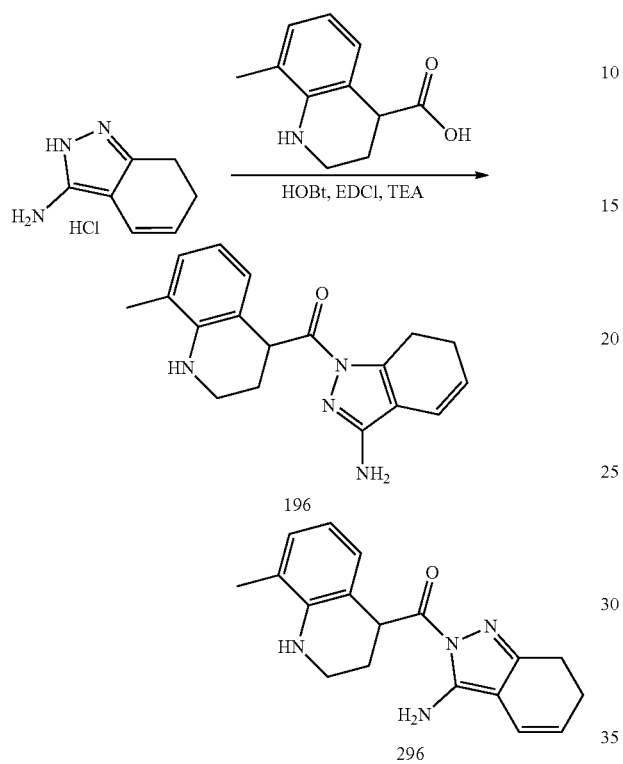

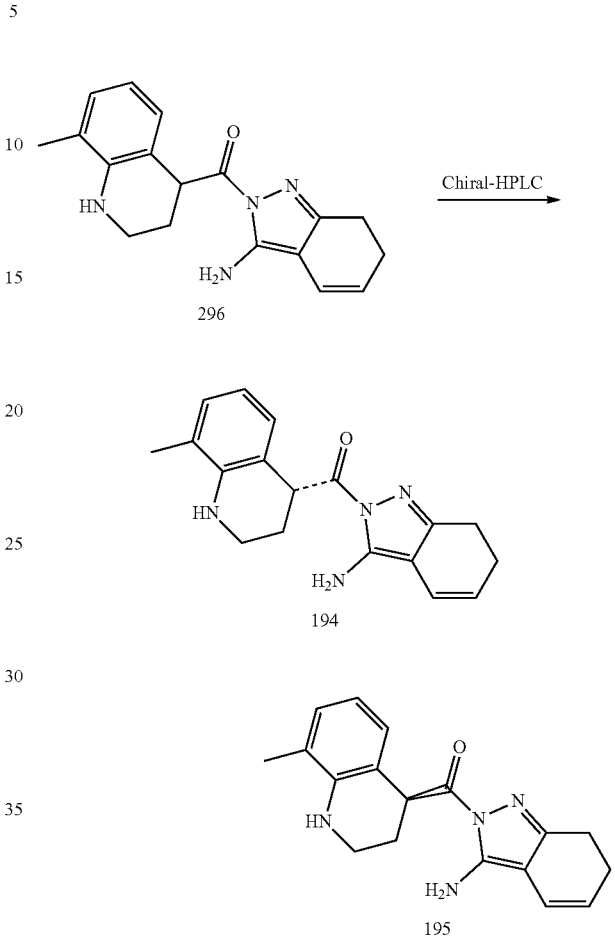

Into a 100-mL round-bottom flask, was placed 6,7-dihydro-2H-indazol-3-amine hydrochloride (110 mg, 0.64 mmol, 1.00 equiv), 8-methyl-1,2,3,4-tetrahydroquinoline-4-carboxylic acid (172 mg, 0.90 mmol, 1.40 equiv), EDCI (234 mg, 1.22 mmol, 1.88 equiv), HOBt (165 mg, 1.22 mmol, 1.88 equiv), TEA (409 mg, 4.04 mmol, 6.3 equiv), N,N-dimethylformamide (10 mL). The resulting solution was stirred for 2 h at room temperature. The reaction was then quenched by the addition of 30 mL of water. The resulting solution was extracted with 3×30 mL of ethyl acetate and the organic layers combined and concentrated under vacuum. The crude product was purified by Prep-HPLC with the following conditions (2#-AnalyseHPLC-SHIMADZU (HPLC-10)): Column: XBridge Shield RP18 OBD Column, 5 um, 19×150 mm; Mobile Phase A: water (0.1% FA), Mobile Phase B: ACN; Flow rate: 20 mL/min; Gradient: 33% B to 61% B in 9 min; 254 nm;

This resulted in 28.22 mg (11%) of (3-amino-6,7-dihydroindazol-1-yl)(8-methyl-1,2,3,4-tetrahydroquinolin-4-yl)methanone (196) as a white solid. RT1: 6.73 min. MS (ES, m/z) [M+H]$^+$: 309. (DMSO-d$_6$, 300 MHz, ppm): δ 6.80 (d, J=7.2, 1H); 6.66 (d, J=7.2, 1H); 6.36-6.31 (m, 1H); 5.85-5.75 (m, 2H); 5.61 (s, 2H); 5.17 (s, 1H); 5.00-4.96 (m, 1H); 3.51-3.46 (m, 2H); 3.39-3.31 (m, 1H); 3.27-3.24 (m, 1H); 3.00-2.94 (m, 2H); 2.07-1.93 (m, 5H). And 55 mg (22%) of (3-amino-6,7-dihydroindazol-2-yl)(8-methyl-1,2,3,4-tetrahydroquinolin-4-yl)methanone (296) as a white solid. RT2: 8.10 min.

(3-amino-6,7-dihydroindazol-2-yl)(8-methyl-1,2,3,4-tetrahydroquinolin-4-yl)methanone (296) was separated by Chiral-Prep-HPLC with the following conditions (Prep-HPLC-032): Column: CHIRALPAK IG UL001, 20×250 mm, 5 um; Mobile Phase A: Hex, Mobile Phase B: EtOH; Flow rate: 20 mL/min; Gradient: 30 B to 30 B in 14 min; 254/220 nm;

Enantiomer A (194): This resulted in 14.5 mg (6%) of (R*)-(3-amino-6,7-dihydroindazol-2-yl)(8-methyl-1,2,3,4-tetrahydroquinolin-4-yl)methanone as a white solid. RT2: 5.318 min; MS (ES, m/z) [M+H]$^+$: 309. (DMSO-d$_6$, 400 MHz, ppm): δ 6.82 (d, J=7.2, 1H); 6.66 (d, J=7.2, 1H); 6.48 (s, 2H); 6.36-6.33 (m, 1H); 5.90-5.83 (m, 2H); 5.21 (s, 1H); 5.07 (d, J=4.8, 1H); 3.38-3.35 (m, 1H); 3.28 (s, 1H); 3.16 (s, 2H); 2.94 (s, 2H); 2.07-2.03 (m, 5H).

Enantiomer B (195): This resulted in 18.7 mg (7%) of (S*)-(3-amino-6,7-dihydroindazol-2-yl)(8-methyl-1,2,3,4-tetrahydroquinolin-4-yl)methanone as a white solid. RT1: 4.983 min; MS (ES, m/z) [M+H]$^+$: 309; (DMSO-d$_6$, 400 MHz, ppm): δ 6.82 (d, J=7.2, 1H); 6.66 (d, J=7.2, 1H); 6.48 (s, 2H); 6.36-6.33 (m, 1H); 5.90-5.83 (m, 2H); 5.23 (s, 1H); 5.07 (d, J=4.8, 1H); 3.38-3.35 (m, 1H); 3.28 (s, 1H); 3.16 (s, 2H); 2.94 (s, 2H); 2.07-1.88 (m, 5H).

Example 197 & 198. ((6S*)-3-amino-6-hydroxy-4,5,6,7-tetrahydroindazol-2-yl)((4R*)-8-methyl-1,2,3,4-tetrahydroquinolin-4-yl)methanone and ((6S*)-3-amino-6-hydroxy-4,5,6,7-tetrahydroindazol-2-yl)((4S*)-8-methyl-1,2,3,4-tetrahydroquinolin-4-yl)methanone

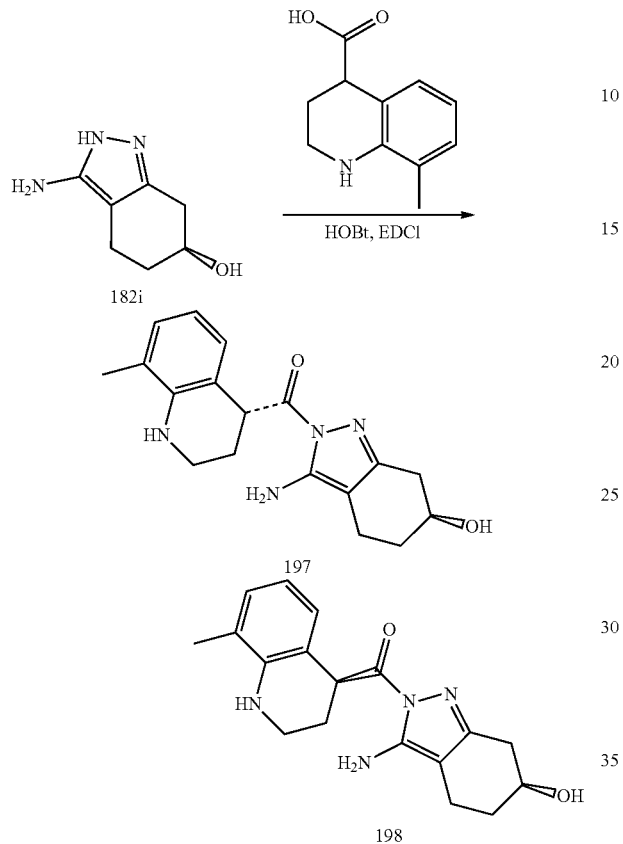

Into a 100-mL round-bottom flask, was placed 8-methyl-1,2,3,4-tetrahydroquinoline-4-carboxylic acid (194 mg, 1.01 mmol, 1.20 equiv), (6S*)-3-amino-4,5,6,7-tetrahydro-2H-indazol-6-ol (130 mg, 0.85 mmol, 1.00 equiv), HOBT (172 mg, 1.27 mmol, 1.50 equiv), EDCI (246 mg, 1.28 mmol, 1.50 equiv), N,N-dimethylformamide (6 mL), TEA (258 mg, 2.55 mmol, 3.00 equiv). The resulting solution was stirred for 2 h at 25° C. The reaction mixture was diluted with DCM (80 mL), washed with $H_2O$ (50 mL×3) and brine (50 mL×3) and dried with $Na_2SO_4$. After filtration, the filtrate was concentrated under reduced pressure. The crude product was purified by Prep-HPLC with the following conditions (Analyse HPLC-SHIMADZU): Column: XBridge Shield RP18 OBD Column, 5 um, 19×150 mm; Mobile Phase A: water (0.1% FA), Mobile Phase B: ACN; Flow rate: 20 mL/min; Gradient: 5% B to 30% B in 13 min; 254 nm;

Enantiomer A (197): The collected fraction was lyophilized to give 20.9 mg (8%) of ((6S*)-3-amino-6-hydroxy-4,5,6,7-tetrahydroindazol-2-yl)((4R*)-8-methyl-1,2,3,4-tetrahydroquinolin-4-yl)methanone as a white solid. RT4: 12.25 min; MS (ES, m/z) $[M+H]^+$: 327; (400 MHz, DMSO-$d_6$, ppm): δ 6.81 (d, J=7.2 Hz, 1H), 6.64 (d, J=7.2 Hz, 1H), 6.36-6.33 (m, 3H), 5.20 (s, 1H), 5.06-5.03 (m, 1H), 4.81-4.80 (m, 1H), 3.96 (s, 1H), 3.34-3.25 (m, 2H), 2.75-2.71 (m, 1H), 2.50-2.39 (m, 2H), 2.35-2.19 (m, 1H), 2.18-1.98 (m, 5H), 1.81-1.78 (m, 1H), 1.63-1.58 (m, 1H).

Enantiomer B (198): The collected fraction was lyophilized to give 20.3 mg (7%) of ((6S*)-3-amino-6-hydroxy-4,5,6,7-tetrahydroindazol-2-yl)((4S*)-8-methyl-1,2,3,4-tetrahydroquinolin-4-yl)methanone as a white solid. RT3: 11.15 min; MS (ES, m/z) $[M+H]^+$: 327; (400 MHz, DMSO-$d_6$, ppm): δ 6.81 (d, J=7.2 Hz, 1H), 6.65 (d, J=7.2 Hz, 1H), 6.37-6.33 (m, 3H), 5.19 (s, 1H), 5.06-5.03 (m, 1H), 4.82-4.81 (m, 1H), 3.96 (s, 1H), 3.33-3.25 (m, 2H), 2.73-2.72 (m, 1H), 2.50-2.39 (m, 2H), 2.38-2.19 (m, 1H), 2.19-1.97 (m, 5H), 1.80-1.77 (m, 1H), 1.64-1.60 (m, 1H).

Examples 199, 200, 201 &202. ((6R*)-3-amino-6-hydroxy-4,5,6,7-tetrahydroindazol-2-yl)((4S*)-8-methyl-1,2,3,4-tetrahydroquinolin-4-yl)methanone; ((6R*)-3-amino-6-hydroxy-4,5,6,7-tetrahydroindazol-2-yl)((4R*)-8-methyl-1,2,3,4-tetrahydroquinolin-4-yl)methanone; ((6R*)-3-amino-6-hydroxy-4,5,6,7-tetrahydroindazol-1-yl)((4S*)-8-methyl-1,2,3,4-tetrahydroquinolin-4-yl)methanone; and ((6R*)-3-amino-6-hydroxy-4,5,6,7-tetrahydroindazol-1-yl)((4R*)-8-methyl-1,2,3,4-tetrahydroquinolin-4-yl)methanone

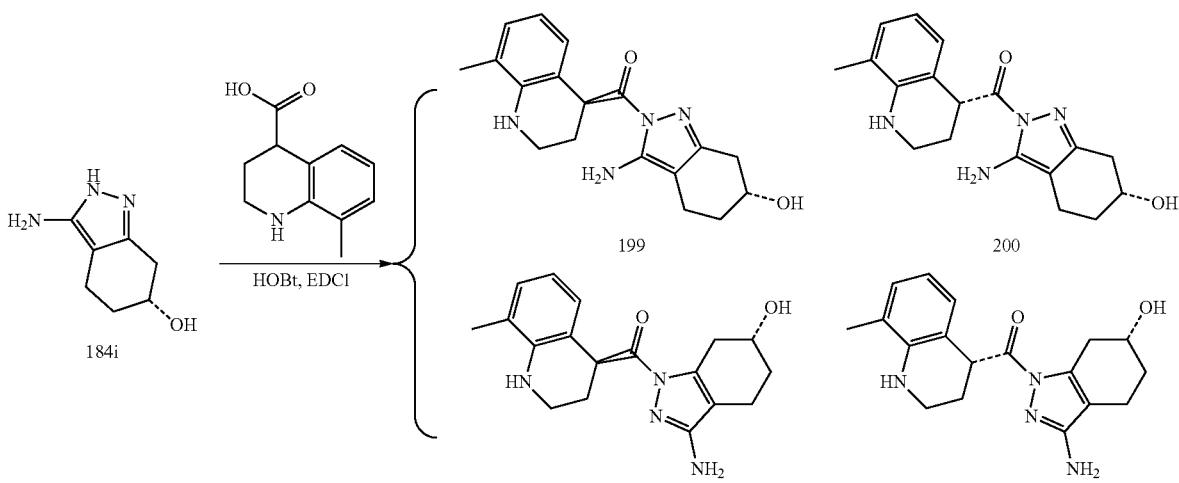

Into a 50-mL round-bottom flask, was placed (6R*)-3-amino-4,5,6,7-tetrahydro-2H-indazol-6-ol (150 mg, 0.98 mmol, 1.00 equiv), 8-methyl-1,2,3,4-tetrahydroquinoline-4-carboxylic acid (200 mg, 1.05 mmol, 1.20 equiv), TEA (300 mg, 2.97 mmol, 3.00 equiv), N,N-dimethylformamide (5 mL), HOBt (200 mg, 1.48 mmol, 1.50 equiv), EDCI (280 mg, 1.46 mmol, 1.50 equiv). The resulting solution was stirred for 2 h at room temperature. The reaction was then quenched by the addition of water (40 mL). The resulting solution was extracted with ethyl acetate (40 mL×3) and the organic layers combined. The resulting mixture was washed with Brine (100 mL×2). The mixture was dried over anhydrous sodium sulfate. The solids were filtered out. The resulting mixture was concentrated under vacuum. The crude product was purified by Prep-HPLC with the following conditions: Column: XBridge Shield RP18 OBD Column, 5 um, 19×150 mm; Mobile Phase A: water (0.1% FA), Mobile Phase B: ACN; Flow rate: 20 mL/min; Gradient: 5% B to 30% B in 13 min; 254 nm.

Enantiomer A (199): The collected fraction was lyophilized to give 28.2 mg (9%) of ((6R*)-3-amino-6-hydroxy-4,5,6,7-tetrahydroindazol-2-yl)((4S*)-8-methyl-1-1,2,3,4-tetrahydroquinolin-4-yl)methanone as a white solid. RT4: 12.25 min; MS (ES, m/z) [M+H]$^+$: 327; (DMSO-d$_6$, 400 MHz, ppm): δ 6.81-6.80 (m, 1H), 6.65-6.63 (m, 1H), 6.36-6.33 (m, 3H), 5.20 (s, 1H), 5.06-5.03 (m, 1H), 4.81-4.80 (m, 1H), 3.96-3.95 (m, 1H), 3.37-3.34 (m, 1H), 3.31-3.25 (m, 1H), 2.75-2.69 (m, 1H), 2.42-2.33 (m, 2H), 2.25-2.18 (m, 1H), 2.09-1.97 (m, 5H), 1.81-1.78 (m, 1H), 1.65-1.58 (m, 1H).

Enantiomer B (200): 26.5 mg (8%) of ((6R*)-3-amino-6-hydroxy-4,5,6,7-tetrahydroindazol-2-yl)((4R*)-8-methyl-1,2,3,4-tetrahydroquinolin-4-yl)methanone as a white solid. RT3: 11.15 min; MS (ES, m/z) [M+H]$^+$: 327; (DMSO-d$_6$, 400 MHz, ppm): δ 6.81-6.80 (m, 1H), 6.66-6.64 (m, 1H), 6.37-6.33 (m, 3H), 5.19 (s, 1H), 5.06-5.03 (m, 1H), 4.82-4.81 (m, 1H), 3.96-3.94 (m, 1H), 3.33-3.31 (m, 1H), 3.27-3.25 (m, 1H), 2.73-2.68 (m, 1H), 2.43-2.35 (m, 2H), 2.25-2.17 (m, 1H), 2.08-1.96 (m, 5H), 1.80-1.77 (m, 1H), 1.64-1.60 (m, 1H).

Enantiomer C (201): 13.7 mg (4%) of ((6R*)-3-amino-6-hydroxy-4,5,6,7-tetrahydroindazol-1-yl)((4S*)-8-methyl-1,2,3,4-tetrahydroquinolin-4-yl)methanone as a white solid. RT2: 9.78 min; MS (ES, m/z) [M+H]$^+$: 327; (DMSO-d$_6$, 400 MHz, ppm): δ 6.79-6.78 (m, 1H), 6.65-6.63 (m, 1H), 6.36-6.32 (m, 1H), 5.53 (m, 2H), 5.16 (s, 1H), 4.99-4.96 (m, 1H), 4.79-4.78 (m, 1H), 3.96-3.95 (m, 1H), 3.38-3.35 (m, 1H), 3.24-3.21 (m, 1H), 3.07-3.01 (m, 1H), 2.73-2.67 (m, 1H), 2.37-2.31 (m, 1H), 2.27-2.21 (m, 1H), 2.05-1.98 (m, 4H), 1.97-1.93 (m, 1H), 1.74-1.64 (m, 2H).

Enantiomer D (202): 13.9 mg (4%) of ((6R*)-3-amino-6-hydroxy-4,5,6,7-tetrahydroindazol-1-yl)((4R*)-8-methyl-1,2,3,4-tetrahydroquinolin-4-yl)methanone as a white solid. RT1: 9.12 min; MS (ES, m/z) [M+H]$^+$: 327; (DMSO-d$_6$, 400 MHz, ppm): δ 6.79-6.78 (m, 1H), 6.66-6.64 (m, 1H), 6.36-6.32 (m, 1H), 5.52 (m, 2H), 5.16 (s, 1H), 4.99-4.96 (m, 1H), 4.78-4.77 (m, 1H), 3.97-3.95 (m, 1H), 3.38-3.35 (m, 1H), 3.24-3.21 (m, 1H), 3.08-3.03 (m, 1H), 2.71-2.65 (m, 1H), 2.37-2.33 (m, 1H), 2.26-2.19 (m, 1H), 2.04-1.97 (m, 4H), 1.95-1.90 (m, 1H), 1.73-1.63 (m, 2H).

Example 203, 204 and 205. ((5R*)-3-amino-5-hydroxy-4,5,6,7-tetrahydroindazol-2-yl)((4R*)-8-chloro-1,2,3,4-tetrahydroquinolin-4-yl)methanone; ((5R*)-3-amino-5-hydroxy-4,5,6,7-tetrahydroindazol-2-yl)((4S*)-8-chloro-1,2,3,4-tetrahydroquinolin-4-yl)methanone; and ((5R*)-3-amino-5-hydroxy-4,5,6,7-tetrahydroindazol-1-yl)(8-chloro-1,2,3,4-tetrahydroquinolin-4-yl)methanone

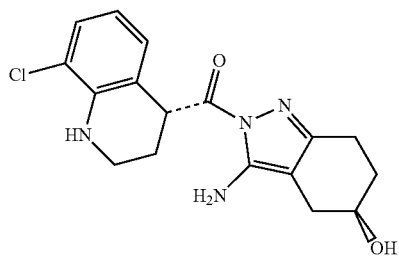

203

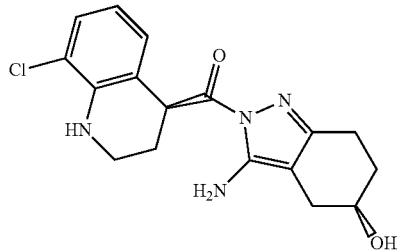

204

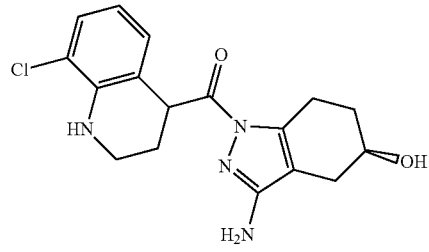

205

Preparation of 8-chloro-1,2,3,4-tetrahydroquinoline-4-carboxylic Acid

Step 1. methyl 8-chloroquinoline-4-carboxylate

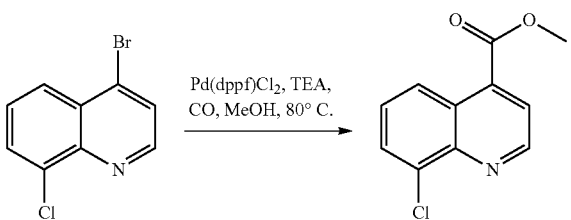

Into a 250-mL pressure tank reactor, was placed 4-bromo-8-chloroquinoline (4 g, 16.49 mmol, 1.00 equiv), Pd(dppf)Cl$_2$ (2 g, 2.45 mmol, 0.15 equiv), TEA (5 g, 49.50 mmol, 3.00 equiv), methanol (70 mL). The flask was evacuated and flushed three times with nitrogen, followed by flushing with carbon monoxide (60 atm). The resulting solution was stirred for 38 hours at 80° C. The reaction was cooled to room temperature. The resulting mixture was concentrated under vacuum. The residue was After cooled to room temperature, the solvent was removed under vacuum, the residue was re-dissolved in ethyl acetate (20 mL), washed by brine (20 mL×3) and then applied onto a silica gel column with ethyl acetate/petroleum ether (0-30%). This resulted in 3.5 g (96%) of methyl 8-chloroquinoline-4-carboxylate as a yellow solid. MS (ES, m/z) [M+1]: 222.

Step 2. Methyl 8-chloro-1,2,3,4-tetrahydroquinoline-4-carboxylate

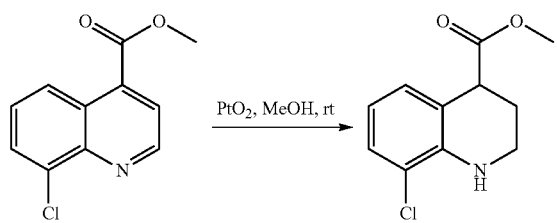

Into a 100-mL round-bottom flask, was placed methyl 8-chloroquinoline-4-carboxylate (400 mg, 1.80 mmol, 1.00 equiv), PtO$_2$ (200 mg), methanol (20 mL). The flask was evacuated and flushed three times with nitrogen, followed by flushing with hydrogen. The resulting solution was stirred for 1 h at room temperature. The solids were filtered out. The resulting mixture was concentrated under vacuum. This resulted in 320 mg (79%) of methyl 8-chloro-1,2,3,4-tetrahydroquinoline-4-carboxylate as a white solid. MS (ES, m/z) [M+1]: 226.

Step 3. 8-Chloro-1,2,3,4-tetrahydroquinoline-4-carboxylic Acid

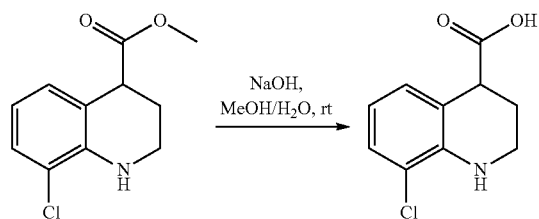

Into a 100-mL round-bottom flask, was placed methyl 8-chloro-1,2,3,4-tetrahydroquinoline-4-carboxylate (320 mg, 1.42 mmol, 1.00 equiv), methanol (15 mL), a solution of sodium hydroxide (175 mg, 4.38 mmol, 3.00 equiv) in water (10 mL). The resulting solution was stirred overnight at room temperature. The resulting mixture was concentrated under vacuum. The resulting solution was diluted with H$_2$O (20 mL). The resulting solution was extracted with ethyl acetate (30 mL×2). The pH value of the aqueous phase was adjusted to 5-6 with hydrochloric acid (6 mol/L). The resulting solution was extracted with ethyl acetate (40 mL×3) and the organic phase combined. The resulting mixture was concentrated under vacuum. This resulted in 220 mg (73%) of 8-chloro-1,2,3,4-tetrahydroquinoline-4-carboxylic acid as a yellow solid. MS (ES, m/z) [M+1]: 212.

Step 4. ((5R*)-3-amino-5-hydroxy-4,5,6,7-tetrahydroindazol-2-yl)(8-chloro-1,2,3,4-tetrahydroquinolin-4-yl)methanone and ((5R*)-3-amino-5-hydroxy-4,5,6,7-tetrahydroindazol-1-yl)(8-chloro-1,2,3,4-tetrahydroquinolin-4-yl)methanone

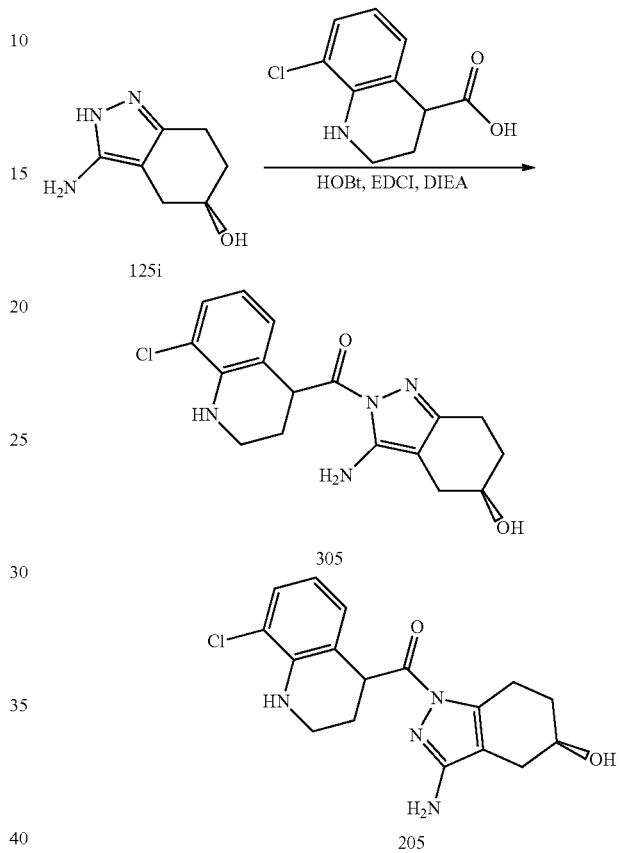

Into a 100-mL round-bottom flask, was placed (5R*)-3-amino-4,5,6,7-tetrahydro-2H-indazol-5-ol (120 mg, 0.78 mmol, 1.00 equiv), 8-chloro-1,2,3,4-tetrahydroquinoline-4-carboxylic acid (181 mg, 0.86 mmol, 1.10 equiv), EDCI (225 mg, 1.17 mmol, 1.50 equiv), HOBt (159 mg, 1.18 mmol, 1.50 equiv), TEA (101 mg, 1.00 mmol, 5.00 equiv), N,N-dimethylformamide. The resulting solution was stirred for 2 h at room temperature. The reaction was then quenched by the addition of water (30 mL). The resulting solution was extracted with ethyl acetate (30 mL×3). The organic layers combined and concentrated under vacuum. The crude product was purified by Prep-HPLC with the following conditions (2#-AnalyseHPLC-SHIMADZU (HPLC-10)): Column: XBridge Prep C18 OBD Column 19×150 mm 5 um; Mobile Phase A: water (10 mmoL/L NH$_4$HCO$_3$), Mobile Phase B: ACN; Flow rate: 20 mL/min; Gradient: 25% B to 50% B in 12 min; 254/220 nm. This resulted in 11.2 mg (4%) of ((5R*)-3-amino-5-hydroxy-4,5,6,7-tetrahydroindazol-1-yl)(8-chloro-1,2,3,4-tetrahydroquinolin-4-yl)methanone (205) as a white solid. RT1: 9.00; MS (ES, m/z) [M+H]$^+$: 347 & 349; (DMSO-d$_6$, 300 MHz, ppm): δ 7.09 (d, J=7.8, 1H); 6.79 (d, J=4.8, 1H); 6.44-6.39 (m, 1H); 5.69 (s, 1H); 5.56 (s, 2H); 5.00-4.96 (m, 1H); 4.78 (s, 1H); 3.89 (s, 1H); 3.30 (s, 2H); 2.94-2.72 (m, 2H); 2.50-2.49 (m, 1H); 2.09-1.94 (m, 3H); 1.81-1.62 (m, 2H). And 35 mg of ((5R*)-3-amino-5-hydroxy-4,5,6,7-tetrahydroindazol-2-yl)((4R*)-8-chloro-1,2,3,4-tetrahydroquinolin-4-yl)methanone (305) as a white solid. RT2: 10.08 min.

Step 5. ((5R*)-3-amino-5-hydroxy-4,5,6,7-tetrahydroindazol-2-yl)((4R*)-8-chloro-1,2,3,4-tetrahydroquinolin-4-yl)methanone and ((5R*)-3-amino-5-hydroxy-4,5,6,7-tetrahydroindazol-2-yl)((4S*)-8-chloro-1,2,3,4-tetrahydroquinolin-4-yl)methanone (5R*)-3-amino-2-[(8-chloro-1,2,3,4-tetrahydroquinolin-4-yl)carbonyl]-4,5,6,7-tetrahydro-2H-indazol-5-ol (305) was purified by Chiral-Prep-HPLC with the following conditions (Prep-HPLC-032): Column: CHIRALPAK IG, 20×250 mm, 5 um; Mobile Phase A: Hex-HPLC, Mobile Phase B: EtOH-HPLC; Flow rate: 20 mL/min; Gradient: 50 B to 50 B in 20 min; 254/220 nm;

Enantiomer A (203): This resulted in 9.8 mg (4%) of ((5R*)-3-amino-5-hydroxy-4,5,6,7-tetrahydroindazol-2-yl)((4R*)-8-chloro-1,2,3,4-tetrahydroquinolin-4-yl)methanone as a white solid. RT2: 13.194 min; MS (ES, m/z) [M+H]$^+$: 347 & 349; (DMSO-d$_6$, 300 MHz, ppm): δ 7.10 (d, J=6.9, 1H); 6.81 (d, J=7.2, 1H); 6.45-6.36 (m, 3H); 5.73 (s, 1H); 5.07-5.04 (m, 1H); 4.78 (d, J=3.9, 1H); 3.89 (s, 1H); 3.31 (s, 2H); 2.67-2.60 (m, 2H); 2.50-2.41 (m, 1H); 2.17-1.95 (m, 3H); 1.87-1.80 (s, 1H); 1.80-1.70 (m, 1H).

Enantiomer B (204): 11.2 mg (4%) of ((5R*)-3-amino-5-hydroxy-4,5,6,7-tetrahydroindazol-2-yl)((4S*)-8-chloro-1,2,3,4-tetrahydroquinolin-4-yl)methanone as a white solid. RT1: 8.66 min; MS (ES, m/z) [M+H]$^+$: 347 & 349; (DMSO-d$_6$, 300 MHz, ppm): δ 7.10 (d, J=6.9, 1H); 6.81 (d, J=7.2, 1H); 6.45-6.36 (m, 3H); 5.73 (s, 1H); 5.07-5.04 (m, 1H); 4.78 (d, J=3.9, 1H); 3.89 (s, 1H); 3.31 (s, 2H); 2.67-2.60 (m, 2H); 2.50-2.41 (m, 1H); 2.17-1.95 (m, 3H); 1.87-1.80 (s, 1H); 1.80-1.68 (m, 1H).

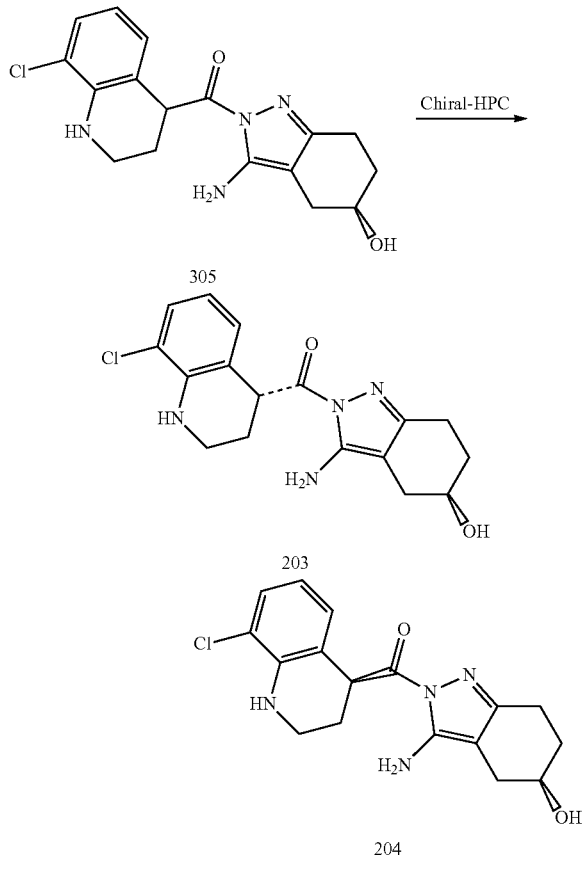

Example 206, 207 & 208 ((6S*)-3-amino-6-hydroxy-4,5,6,7-tetrahydroindazol-2-yl)((4R*)-8-chloro-1,2,3,4-tetrahydroquinolin-4-yl)methanone; ((6S*)-3-amino-6-hydroxy-4,5,6,7-tetrahydroindazol-2-yl)((4S*)-8-chloro-1,2,3,4-tetrahydroquinolin-4-yl)methanone and ((6S*)-3-amino-6-hydroxy-4,5,6,7-tetrahydroindazol-1-yl)(8-chloro-1,2,3,4-tetrahydroquinolin-4-yl)methanone

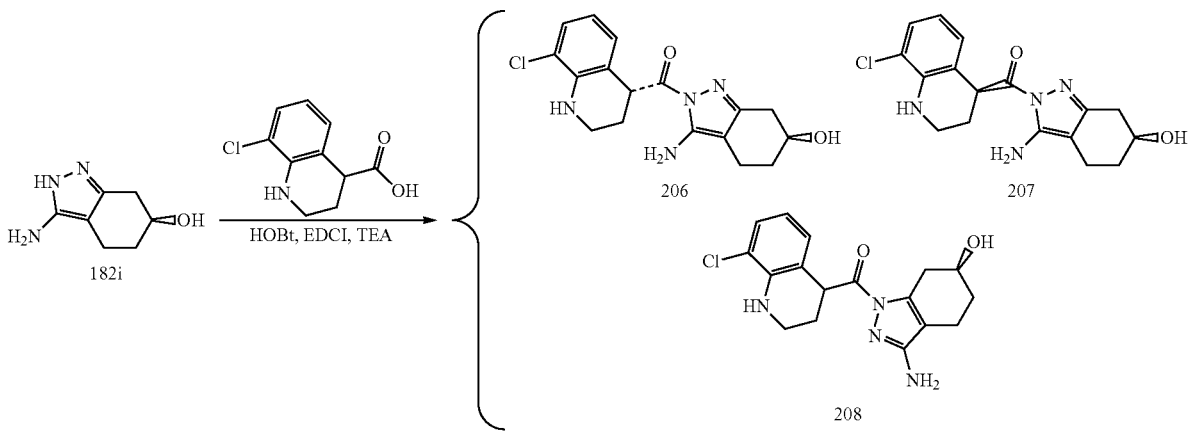 [SMILES: Nc1[nH]nc2c1CC[C@H](O)C2 ; O=C(O)C1CCNc2c(Cl)cccc21 ; Nc1c2c(nn1C(=O)[C@@H]1CCNc3c(Cl)cccc31)C[C@@H](O)CC2 ; Nc1nn(C(=O)C2CCNc3c(Cl)cccc32)c2c1CC[C@H](O)C2 ; Nc1c2c(nn1C(=O)[C@H]1CCNc3c(Cl)cccc31)C[C@@H](O)CC2]

Into a 50-mL round-bottom flask, was placed (6S*)-3-amino-4,5,6,7-tetrahydro-2H-indazol-6-ol (100 mg, 0.65 mmol, 1.00 equiv), HOBt (132 mg, 0.98 mmol, 1.50 equiv), EDCI (188 mg, 0.98 mmol, 1.50 equiv), 8-chloro-1,2,3,4-tetrahydroquinoline-4-carboxylic acid (165 mg, 0.78 mmol, 1.20 equiv), N,N-dimethylformamide (8 mL), TEA (196 mg, 1.94 mmol, 3.00 equiv). The resulting solution was stirred for 3 h at 25° C. The reaction mixture was diluted with DCM (80 mL), washed with water (50 mL×3) and brine (50 mL×3) and dried with $Na_2SO_4$. After filtration, the filtrate was concentrated under reduced pressure. The crude product was Example 209, 210, 211 & 212 ((6R*)-3-amino-6-hydroxy-4,5,6,7-tetrahydroindazol-2-yl)((4S*)-8-chloro-1,2,3,4-tetrahydroquinolin-4-yl)methanone; ((6R*)-3-amino-6-hydroxy-4,5,6,7-tetrahydroindazol-2-yl)((4R*)-8-chloro-1,2,3,4-tetrahydroquinolin-4-yl)methanone; ((6R*)-3-amino-6-hydroxy-4,5,6,7-tetrahydroindazol-1-yl)((4S*)-8-chloro-1,2,3,4-tetrahydroquinolin-4-yl)methanone; and ((6R*)-3-amino-6-hydroxy-4,5,6,7-tetrahydroindazol-1-yl)((4R*)-8-chloro-1,2,3,4-tetrahydroquinolin-4-yl)methanone

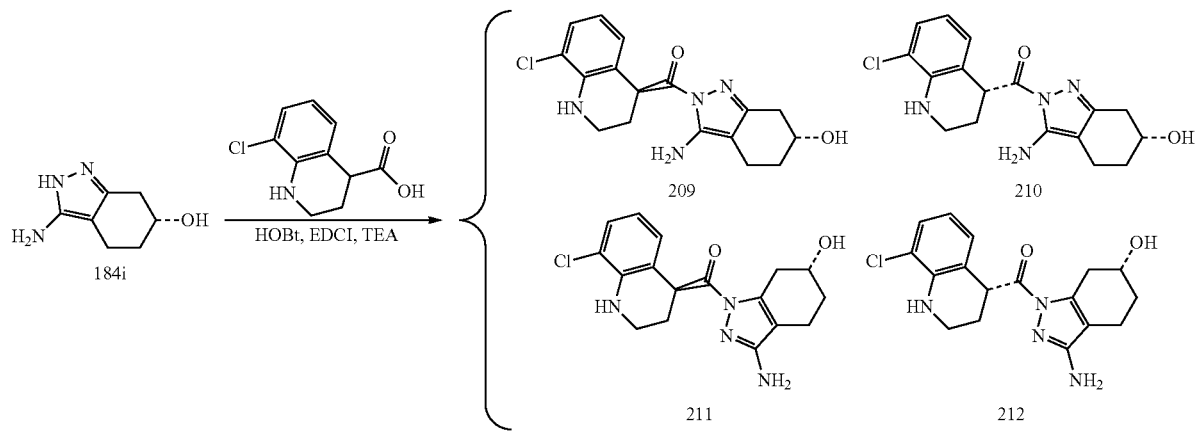 [SMILES: Nc1[nH]nc2c1CC[C@@H](O)C2 ; O=C(O)C1CCNc2c(Cl)cccc21 ; Nc1c2c(nn1C(=O)[C@H]1CCNc3c(Cl)cccc31)C[C@H](O)CC2 ; Nc1nn(C(=O)[C@H]2CCNc3c(Cl)cccc32)c2c1CC[C@@H](O)C2 ; Nc1c2c(nn1C(=O)[C@@H]1CCNc3c(Cl)cccc31)C[C@H](O)CC2 ; Nc1nn(C(=O)[C@@H]2CCNc3c(Cl)cccc32)c2c1CC[C@@H](O)C2]

purified by Prep-HPLC with the following conditions (Analyse HPLC-SHIMADZU): Column: XBridge Prep C18 OBD Column 19×150 mm 5 um; Mobile Phase A: water (10 mmoL/L $NH_4HCO_3$), Mobile Phase B: ACN; Flow rate: 20 mL/min; Gradient: 25% B to 40% B in 12 min; 254/220 nm.

Enantiomer A (206): The collected fraction was lyophilized to give 4.1 mg (2%) of ((6S*)-3-amino-6-hydroxy-4,5,6,7-tetrahydroindazol-2-yl)((4R*)-8-chloro-1,2,3,4-tetrahydroquinolin-4-yl)methanone as a white solid. RT3: 11.93 min; MS (ES, m/z) [M+H]$^+$: 347 & 349; (300 MHz, DMSO-$d_6$, ppm): δ 7.11 (d, J=7.8 Hz, 1H), 6.80 (d, J=7.5 Hz, 1H), 6.45-6.36 (m, 3H), 5.74 (s, 1H), 5.08-5.04 (m, 1H), 4.81 (d, J=3.6 Hz, 1H), 3.97 (s, 1H), 3.30-3.28 (m, 2H), 2.75-2.70 (m, 1H), 2.50-1.81 (m, 5H), 1.78-1.53 (m, 2H).

Enantiomer B (207): The collected fraction was lyophilized to give 2.4 mg (1%) of ((6S*)-3-amino-6-hydroxy-4,5,6,7-tetrahydroindazol-2-yl)((4S*)-8-chloro-1,2,3,4-tetrahydroquinolin-4-yl)methanone as a white solid. RT2: 11.50 min; MS (ES, m/z) [M+H]$^+$: 347 & 349; (300 MHz, DMSO-$d_6$, ppm): δ 7.11 (d, J=7.8 Hz, 1H), 6.81 (d, J=7.5 Hz, 1H), 6.46-6.36 (m, 3H), 5.73 (s, 1H), 5.08-5.05 (m, 1H), 4.82 (d, J=3.6 Hz, 1H), 3.97 (s, 1H), 3.30-3.28 (m, 2H), 2.74-2.67 (m, 1H), 2.50-1.92 (m, 5H), 1.90-1.50 (m, 2H).

Isomer C (208): The collected fraction was lyophilized to give 3.7 mg (1.8%) of ((6S*)-3-amino-6-hydroxy-4,5,6,7-tetrahydroindazol-1-yl)(8-chloro-1,2,3,4-tetrahydroquinolin-4-yl)methanone as a white solid. RT1: 10.37 min; MS (ES, m/z) [M+H]$^+$: 347 & 349; (300 MHz, DMSO-$d_6$, ppm): δ 7.09 (d, J=7.5 Hz, 1H), 6.79 (d, J=7.2 Hz, 1H), 6.45-6.42 (m, 1H), 5.70 (s, 1H), 5.57 (s, 2H), 5.02-4.98 (m, 1H), 4.78 (d, J=3.6 Hz, 1H), 3.97 (s, 1H), 3.10-3.00 (m, 1H), 2.50-1.88 (m, 6H), 1.70-1.55 (m, 2H).

Into a 50-mL round-bottom flask, was placed (6R*)-3-amino-4,5,6,7-tetrahydro-2H-indazol-6-ol (130 mg, 0.85 mmol, 1.00 equiv), 8-chloro-1,2,3,4-tetrahydroquinoline-4-carboxylic acid (200 mg, 0.94 mmol, 1.10 equiv), HOBT (170 mg, 1.26 mmol, 1.50 equiv), EDCI (240 mg, 1.25 mmol, 1.50 equiv), TEA (260 mg, 2.57 mmol, 3.00 equiv), N,N-dimethylformamide (5 mL). The resulting solution was stirred for 2 h at room temperature. The reaction was then quenched by the addition of water (40 mL). The resulting solution was extracted with ethyl acetate (40 mL×3) and the organic layers combined. The resulting mixture was washed with Brine (100 mL×2). The mixture was dried over anhydrous sodium sulfate. The solids were filtered out. The resulting mixture was concentrated under vacuum. The crude product was purified by Prep-HPLC with the following conditions: Column: XBridge Prep C18 OBD Column 19×150 mm 5 um; Mobile Phase A: water (10 mmoL/L $NH_4HCO_3$), Mobile Phase B: ACN; Flow rate: 20 mL/min; Gradient: 5% B to 25% B in 7 min; 254 nm;

Enantiomer A (209): The collected fraction was lyophilized to give 24.8 mg (8%) of ((6R*)-3-amino-6-hydroxy-4,5,6,7-tetrahydroindazol-2-yl)((4S*)-8-chloro-1,2,3,4-tetrahydroquinolin-4-yl)methanone as a white solid. RT4: 17.98 min; MS (ES, m/z) [M+H]$^+$: 347 & 349; (DMSO-$d_6$, 300 MHz, ppm): δ 7.11 (d, J=7.8 Hz, 1H), 6.80 (d, J=7.5 Hz, 1H), 6.45-6.40 (m, 1H), 6.36 (s, 2H), 5.74 (s, 1H), 5.08-5.04 (m, 1H), 4.82-4.81 (m, 1H), 3.97-3.96 (m, 1H), 3.35-3.34 (m, 1H), 3.28-3.26 (m, 1H), 2.76-2.69 (m, 1H), 2.44-2.33 (m, 2H), 2.26-1.94 (m, 3H), 1.85-1.79 (m, 1H), 1.65-1.59 (m, 1H).

219

Enantiomer B (210): 24.7 mg (8%) of ((6R*)-3-amino-6-hydroxy-4,5,6,7-tetrahydroindazol-2-yl)((4R*)-8-chloro-1,2,3,4-tetrahydroquinolin-4-yl)methanone as a white solid. RT3; 17.40 min; MS (ES, m/z) [M+H]$^+$: 347 & 349; (DMSO-d$_6$, 300 MHz, ppm): δ 7.11 (d, J=7.8 Hz, 1H), 6.80 (d, J=7.2 Hz, 1H), 6.46-6.41 (m, 1H), 6.36 (s, 2H), 5.74 (s, 1H), 5.08-5.05 (m, 1H), 4.83-4.82 (m, 1H), 3.96-3.95 (m, 1H), 3.29-3.26 (m, 2H), 2.74-2.67 (m, 1H), 2.44-2.34 (m, 2H), 2.26-1.96 (m, 3H), 1.85-1.78 (m, 1H), 1.68- 1.60 (m, 1H).

Enantiomer C (211): 10.0 mg (3%) of ((6R*)-3-amino-6-hydroxy-4,5,6,7-tetrahydroindazol-1-yl)((4S*)-8-chloro-1,2,3,4-tetrahydroquinolin-4-yl)methanone as a white solid. RT2: 16.02 min; MS (ES, m/z) [M+H]$^+$: 347 & 349; (DMSO-d$_6$, 300 MHz, ppm): δ 7.09 (d, J=7.8 Hz, 1H), 6.79 (d, J=7.5 Hz, 1H), 6.44-6.39 (m, 1H), 5.70 (s, 1H), 5.57 (s, 2H), 5.00-4.96 (m, 1H), 4.80-4.78 (m, 1H), 3.96-3.95 (m, 1H), 3.38-3.36 (m, 1H), 3.28-3.25 (m, 1H), 3.08-3.00 (m, 1H), 2.73-2.65 (m, 1H), 2.39-2.20 (m, 2H), 2.09- 1.95 (m, 2H), 1.70-1.68 (m, 2H).

Enantiomer D (212): 9.8 mg (3%) of ((6R*)-3-amino-6-hydroxy-4,5,6,7-tetrahydroindazol-1-yl)((4R*)-8-chloro-1,2,3,4-tetrahydroquinolin-4-yl)methanone as a white solid. RT1: 15.37 min; MS (ES, m/z) [M+H]$^+$: 347 & 349; (DMSO-d$_6$, 300 MHz, ppm): δ 7.09 (d, J=7.2 Hz, 1H), 6.79 (d, J=7.2 Hz, 1H), 6.45-6.39 (m, 1H), 5.70 (s, 1H), 5.57 (s, 2H), 5.00-4.97 (m, 1H), 4.80-4.78 (m, 1H), 3.95-3.94 (m, 1H), 3.37-3.35 (m, 1H), 3.29-3.25 (m, 1H), 3.09-3.02 (m, 1H), 2.72-2.64 (m, 1H), 2.38-2.17 (m, 2H), 2.10- 1.91 (m, 2H), 1.71-1.65 (m, 2H).

Example 213 & 214. ((5S*)-3,5-diamino-4,5,6,7-tetrahydroindazol-2-yl)((4S*)-8-methyl-1,2,3,4-tetrahydroquinolin-4-yl)methanone and ((5S*)-3,5-diamino-4,5,6,7-tetrahydroindazol-2-yl)((4R*)-8-methyl-1,2,3,4-tetrahydroquinolin-4-yl)methanone

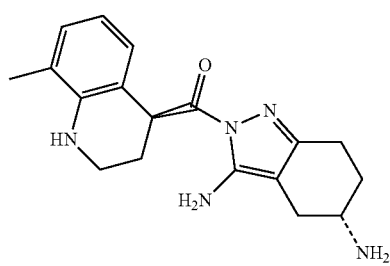

213

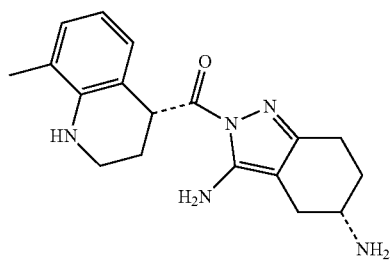

214

220

Step 1. Benzyl (S*)-3-amino-1-(8-methyl-1,2,3,4-tetrahydroquinoline-4-carbonyl)-4,5,6,7-tetrahydro-1H-indazol-5-ylcarbamate and benzyl (S*)-3-amino-2-(8-methyl-1,2,3,4-tetrahydroquinoline-4-carbonyl)-4,5,6,7-tetrahydro-2H-indazol-5-ylcarbamate

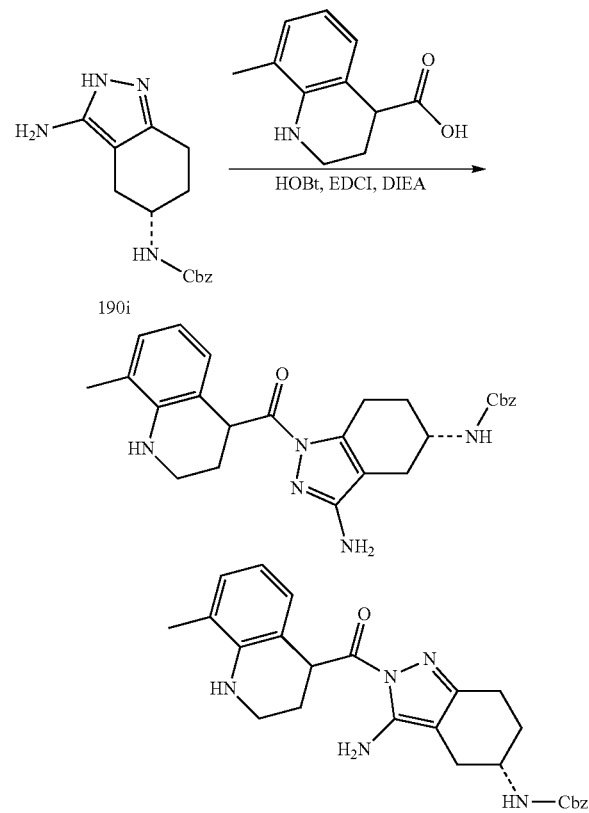

Into a 50-mL round-bottom flask, was placed benzyl N-[(5S*)-3-amino-4,5,6,7-tetrahydro-2H-indazol-5-yl]carbamate (150 mg, 0.52 mmol, 1.00 equiv), 8-methyl-1,2,3,4-tetrahydroquinoline-4-carboxylic acid (100 mg, 0.52 mmol, 1.00 equiv), HOBt (106 mg, 0.78 mmol, 1.50 equiv), EDCI (150 mg, 0.78 mmol, 1.50 equiv), DIEA (160 mg, 1.24 mmol, 3.00 equiv), N,N-dimethylformamide (5 mL). The resulting solution was stirred for 4 h at room temperature. The reaction was then quenched by the addition of water (40 mL). The resulting solution was extracted with ethyl acetate (40 mL×3), washed with brine (100 mL×2), dried over anhydrous sodium sulfate and concentrated under vacuum. The crude product was purified by Prep-HPLC with the following conditions: Column: XSelect CSH Prep C18 OBD Column, 5 um, 19×150 mm; Mobile Phase A: water (0.1% FA), Mobile Phase B: ACN; Flow rate: 20 mL/min; Gradient: 40% B to 70% B in 7 min; 254 nm; The collected fraction was lyophilized to give 50 mg (21%) of benzyl (S*)-3-amino-1-(8-methyl-1,2,3,4-tetrahydroquinoline-4-carbonyl)-4,5,6,7-tetrahydro-1H-indazol-5-ylcarbamate as a white solid. RT1: 5.68 min; MS (ES, m/z) [M+H]$^+$: 460. And 25 mg (10%) of benzyl (S*)-3-amino-2-(8-methyl-1,2,3,4-tetrahydroquinoline-4-carbonyl)-4,5,6,7-tetrahydro-1H-indazol-5-ylcarbamate as a white solid. RT2: 6.63 min; MS (ES, m/z) [M+H] 460.

Step 2. benzyl (S*)-3-amino-2-((S*)-8-methyl-1,2,3,4-tetrahydroquinoline-4-carbonyl)-4,5,6,7-tetrahydro-2H-indazol-5-ylcarbamate and benzyl (S*)-3-amino-2-((R*)-8-methyl-1,2,3,4-tetrahydroquinoline-4-carbonyl)-4,5,6,7-tetrahydro-2H-indazol-5-ylcarbamate

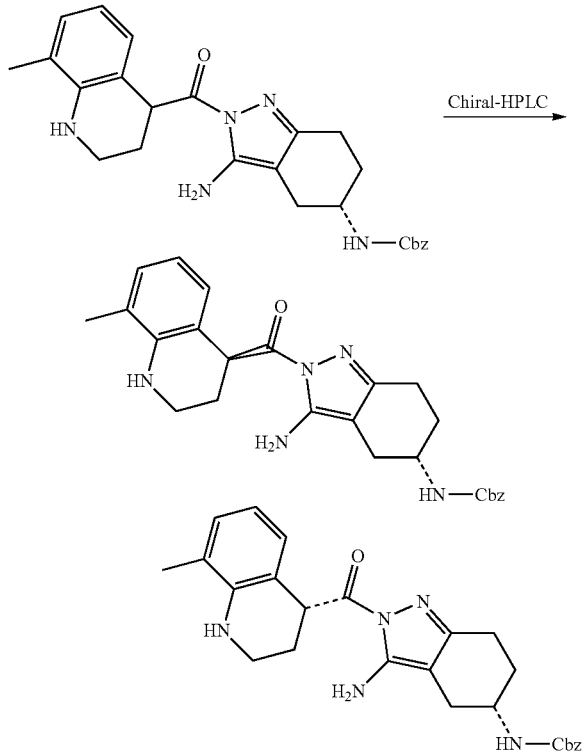

Benzyl N-[(5S*)-3-amino-2-[(8-methyl-1,2,3,4-tetrahydroquinolin-4-yl)carbonyl]-4,5,6,7-tetrahydro-2H-indazol-5-yl]carbamate (50 mg, 0.11 mmol, 1.00 equiv) was separated by Prep-chiral-HPLC with the following conditions: Column: Chiralpak IA, 2×25 cm, 5 um; Mobile Phase A: MeOH-HPLC, Mobile Phase B: DCM-HPLC; Flow rate: 20 mL/min; Gradient: 10 B to 10 B in 10 min; 254/220 nm; This resulted in 20 mg (40%) of benzyl (5S*)-3-amino-2-((4S*)-8-methyl-1,2,3,4-tetrahydroquinoline-4-carbonyl)-4,5,6,7-tetrahydro-2H-indazol-5-ylcarbamate as a white solid. RT1: 6.101 min; MS (ES, m/z) [M+H]+: 460. And 17 mg (34%) of benzyl (5S*)-3-amino-2-((4R*)-8-methyl-1,2,3,4-tetrahydroquinoline-4-carbonyl)-4,5,6,7-tetrahydro-2H-indazol-5-ylcarbamate as a white solid. RT2: 7.29 min; MS (ES, m/z) [M+H]+: 460.

Step 3. ((5S*)-3,5-diamino-4,5,6,7-tetrahydroindazol-2-yl)((4S*)-8-methyl-1,2,3,4-tetrahydroquinolin-4-yl)methanone

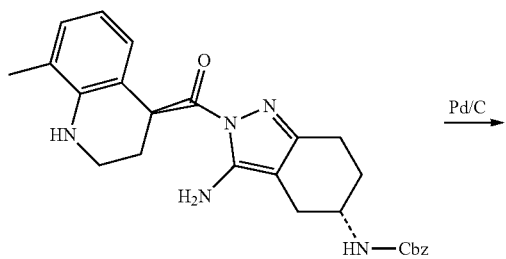

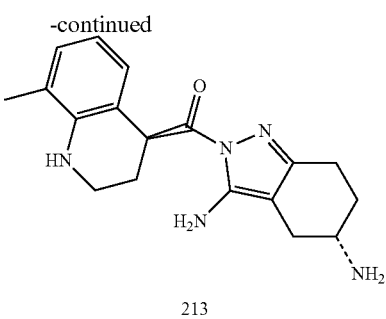

213

Into a 50-mL round-bottom flask, was placed benzyl N-[(5S*)-3-amino-2-[[(4S*)-8-methyl-1,2,3,4-tetrahydroquinolin-4-yl]carbonyl]-4,5,6,7-tetrahydro-2H-indazol-5-yl]carbamate (20 mg, 0.04 mmol, 1.00 equiv), methanol (5 mL), Palladium carbon (10%, 20 mg). To the above hydrogen was introduced in. The resulting solution was stirred for 1.5 h at room temperature. The solids were filtered out. The resulting mixture was concentrated under vacuum. The crude product was purified by Prep-HPLC with the following conditions: Column: XBridge Shield RP18 OBD Column 30×150 mm, 5 um; Mobile Phase A: water (10 MMOL/L NH4HCO3), Mobile Phase B: ACN; Flow rate: 60 mL/min; Gradient: 15% B to 34% B in 7 min; 254.220 nm; The collected fraction was lyophilized to give 5.6 mg (40%) of ((5S*)-3,5-diamino-4,5,6,7-tetrahydroindazol-2-yl)((4S*)-8-methyl-1,2,3,4-tetrahydroquinolin-4-yl)methanone (213) as a white solid. Rt: 6.03 min; MS (ES, m/z) [M+H]+: 326. (DMSO-$d_6$, 400 MHz, ppm): δ 6.82-6.81 (m, 1H), 6.65-6.63 (m, 1H), 6.39-6.33 (m, 3H), 5.19 (s, 1H), 5.05-5.03 (m, 1H), 3.36-3.34 (m, 1H), 3.27-3.26 (m, 1H), 2.97-2.95 (m, 1H), 2.67-2.57 (m, 2H), 2.44-2.43 (m, 1H), 2.08-2.00 (m, 5H), 1.99-1.92 (m, 2H), 1.50-1.47 (m, 1H).

Step 4. ((5S*)-3,5-diamino-4,5,6,7-tetrahydroindazol-2-yl)((4R*)-8-methyl-1,2,3,4-tetrahydroquinolin-4-yl)methanone

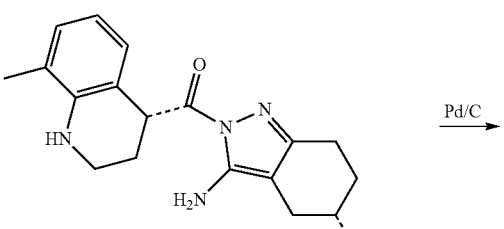

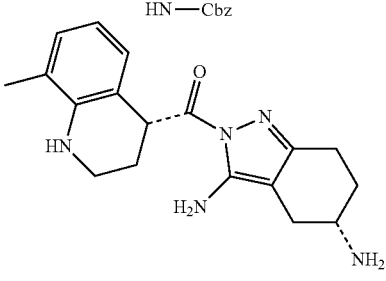

214

Into a 50-mL round-bottom flask, was placed benzyl N-[(5S*)-3-amino-2-[[(4R)-8-methyl-1,2,3,4-tetrahydroquinolin-4-yl]carbonyl]-4,5,6,7-tetrahydro-2H-indazol-5-yl]carbamate (17 mg, 0.04 mmol, 1.00 equiv), methanol (5 mL), Palladium carbon (10%, 17 mg). To the above hydrogen was introduced in. The resulting solution was stirred for 1.5 h at room temperature. The solids were filtered out. The resulting mixture was concentrated under vacuum. The crude product was purified by Prep-HPLC with the following conditions: Column: XBridge Shield RP18 OBD Column, 5 um, 19×150 mm; Mobile Phase A: water (10 MMOL/L NH₄HCO₃), Mobile Phase B: ACN; Flow rate: 20 mL/min; Gradient: 20% B to 50% B in 7 min; 254 nm; Rt: 6.4 min. The collected fraction was lyophilized to give 5.8 mg (48%) of ((5S*)-3,5-diamino-4,5,6,7-tetrahydroindazol-2-yl)((4R*)-8-methyl-1,2,3,4-tetrahydroquinolin-4-yl)methanone (214) as a white solid. MS (ES, m/z) [M+H]$^+$: 326. (DMSO-d$_6$, 300 MHz, ppm): δ 6.81-6.80 (m, 1H), 6.65-6.63 (m, 1H), 6.40-6.32 (m, 3H), 5.20 (s, 1H), 5.06-5.02 (m, 1H), 3.28-3.22 (m, 2H), 2.98-2.95 (m, 1H), 2.65-2.54 (m, 2H), 2.46-2.42 (m, 1H), 2.03-1.91 (m, 6H), 1.88-1.82 (m, 1H), 1.56-1.43 (m, 1H).

Example 215 & 216. ((4S*)-8-chloro-1,2,3,4-tetrahydroquinolin-4-yl)((5S*)-3,5-diamino-4,5,6,7-tetrahydroindazol-2-yl)methanone and ((4R*)-8-chloro-1,2,3,4-tetrahydroquinolin-4-yl)((5S*)-3,5-diamino-4,5,6,7-tetrahydroindazol-2-yl)methanone

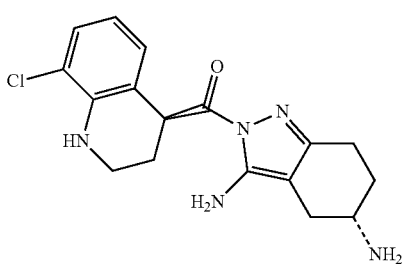

215

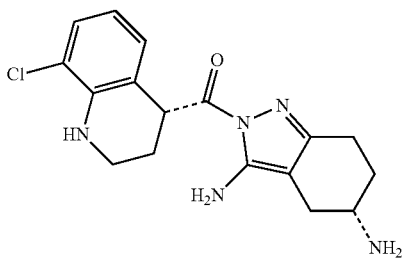

216

Step 1. Benzyl (S*)-3-amino-1-(8-chloro-1,2,3,4-tetrahydroquinoline-4-carbonyl)-4,5,6,7-tetrahydro-1H-indazol-5-ylcarbamate and benzyl (S*)-3-amino-2-(8-chloro-1,2,3,4-tetrahydroquinoline-4-carbonyl)-4,5,6,7-tetrahydro-2H-indazol-5-ylcarbamate

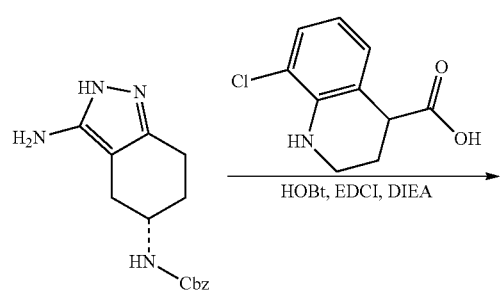

190i
from Ex. 186-189 step 5

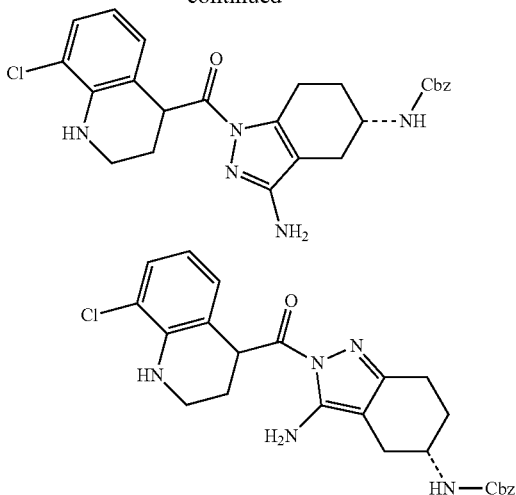

Into a 50-mL round-bottom flask, was placed benzyl N-[(5S*)-3-amino-4,5,6,7-tetrahydro-2H-indazol-5-yl]carbamate (270 mg, 0.94 mmol, 1.00 equiv), 8-chloro-1,2,3,4-tetrahydroquinoline-4-carboxylic acid (200 mg, 0.94 mmol, 1.00 equiv), N,N-dimethylformamide (5 mL), HOBt (140 mg, 1.04 mmol, 1.50 equiv), EDCI (270 mg, 1.41 mmol, 1.50 equiv), TEA (290 mg, 2.87 mmol, 3.00 equiv). The resulting solution was stirred for 2 h at room temperature. The reaction was then quenched by the addition of water (40 mL). The resulting solution was extracted with ethyl acetate (40 mL×3) and the organic layers combined. The resulting mixture was washed with brine (100 mL×2). The solid was dried in an oven under reduced pressure. The solids were filtered out. The resulting mixture was concentrated under vacuum. The crude product was purified by Prep-HPLC with the following conditions: Column: XSelect CSH Prep C18 OBD Column, 5 um, 19×150 mm; Mobile Phase A: water (0.1% FA), Mobile Phase B: ACN; Flow rate: 20 mL/min; Gradient: 45% B to 80% B in 7 min; 254 nm; The collected fraction was lyophilized to give 110 mg (24%) of benzyl (5S*)-3-amino-2-(8-chloro-1,2,3,4-tetrahydroquinoline-4-carbonyl)-4,5,6,7-tetrahydro-2H-indazol-5-ylcarbamate as a white solid. RT2: 6.4 min; MS (ES, m/z) [M+H]$^+$: 480 & 482. And 70 mg (15%) of benzyl (S*)-3-amino-1-(8-chloro-1,2,3,4-tetrahydroquinoline-4-carbonyl)-4,5,6,7-tetrahydro-1H-indazol-5-ylcarbamate as a white solid. RT1: 5.68 min; MS (ES, m/z) [M+H]$^+$: 480 & 482.

Step 2. Benzyl (5S*)-3-amino-2-((4S*)-8-chloro-1,2,3,4-tetrahydroquinoline-4-carbonyl)-4,5,6,7-tetrahydro-2H-indazol-5-ylcarbamate and benzyl (5S*)-3-amino-2-((4R*)-8-chloro-1,2,3,4-tetrahydroquinoline-4-carbonyl)-4,5,6,7-tetrahydro-2H-indazol-5-ylcarbamate

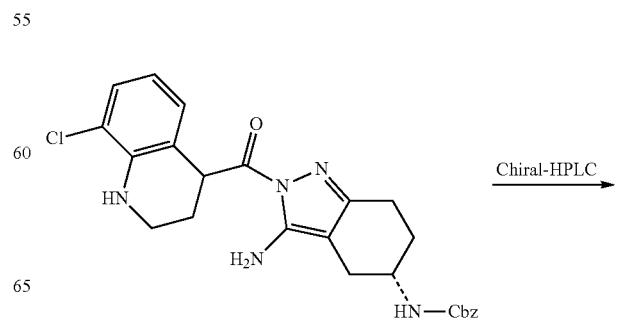

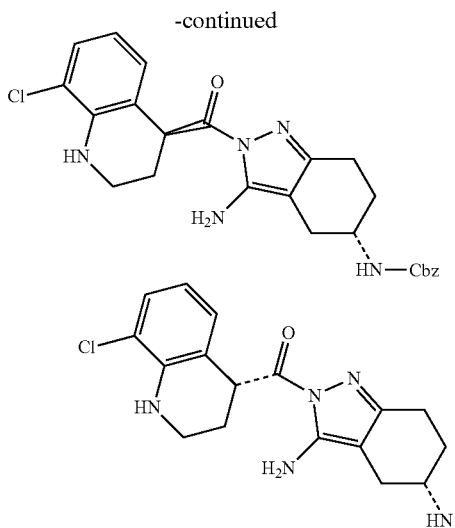

N-[(5S*)-3-amino-2-[(8-chloro-1,2,3,4-tetrahydroquinolin-4-yl)carbonyl]-4,5,6,7-tetrahydro-2H-indazol-5-yl]carbamate (110 mg, 0.23 mmol, 1.00 equiv) was separated by Prep-chiral-HPLC with the following conditions: Column: Chiralpak IA, 2×25 cm, 5 um; Mobile Phase A: MeOH-HPLC, Mobile Phase B: DCM-HPLC; Flow rate: 20 mL/min; Gradient: 10 B to 10 B in 9 min; 254/220 nm. This resulted in 42 mg (38%) of benzyl (5S*)-3-amino-2-((4S*)-8-chloro-1,2,3,4-tetrahydroquinoline-4-carbonyl)-4,5,6,7-tetrahydro-2H-indazol-5-ylcarbamate as a white solid. RT2: 7.219 min. MS (ES, m/z) [M+H]+: 480 & 482. And 38 mg (35%) of (5S*)-3-amino-2-((4R*)-8-chloro-1,2,3,4-tetrahydroquinoline-4-carbonyl)-4,5,6,7-tetrahydro-2H-indazol-5-ylcarbamate as a white solid. RT1: 6.299 min. MS (ES, m/z) [M+H]+: 480 & 482.

Step 3. ((4S*)-8-chloro-1,2,3,4-tetrahydroquinolin-4-yl)((5S*)-3,5-diamino-4,5,6,7-tetrahydroindazol-2-yl)methanone

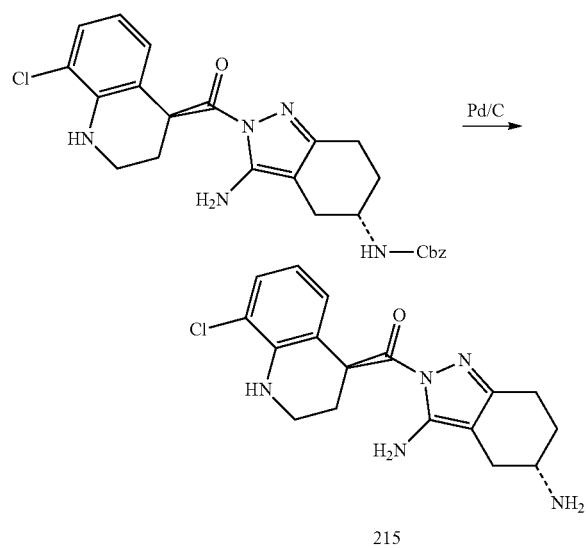

Into a 50-mL round-bottom flask, was placed benzyl N-[(5S)-3-amino-2-[[(4S)-8-chloro-1,2,3,4-tetrahydroquinolin-4-yl]carbonyl]-4,5,6,7-tetrahydro-2H-indazol-5-yl]carbamate (42 mg, 0.09 mmol, 1.00 equiv), methanol (10 mL), Palladium carbon (10%, 20 mg). To the above hydrogen was introduced in. The resulting solution was stirred for 40 min at room temperature. The solids were filtered out. The resulting mixture was concentrated under vacuum. The crude product was purified by Prep-HPLC with the following conditions: Column: XBridge Prep C18 OBD Column 19×150 mm 5 um; Mobile Phase A: water (10 MMOL/L NH4HCO3), Mobile Phase B: ACN; Flow rate: 20 mL/min; Gradient: 30% B to 50% B in 5 min; 254/220 nm; Rt: 4.67 min. The collected fraction was lyophilized to give 6.9 mg (23%) of ((4S*)-8-chloro-1,2,3,4-tetrahydroquinolin-4-yl) ((5S*)-3,5-diamino-4,5,6,7-tetrahydroindazol-2-yl)methanone (215) as a white solid. MS (ES, m/z) [M+H]+: 346 & 348. (DMSO-d6, 300 MHz, ppm): δ 7.12-7.09 (m, 1H), 6.81-6.79 (m, 1H), 6.45-6.40 (m, 1H), 6.36 (s, 2H), 5.74 (s, 1H), 5.07-5.04 (m, 1H), 2.99-2.96 (m, 1H), 2.65-2.55 (m, 2H), 2.44-2.40 (m, 1H), 2.27-1.82 (m, 6H), 1.54-1.47 (m, 1H).

Step 4. ((4R*)-8-chloro-1,2,3,4-tetrahydroquinolin-4-yl)((5S*)-3,5-diamino-4,5,6,7-tetrahydroindazol-2-yl)methanone

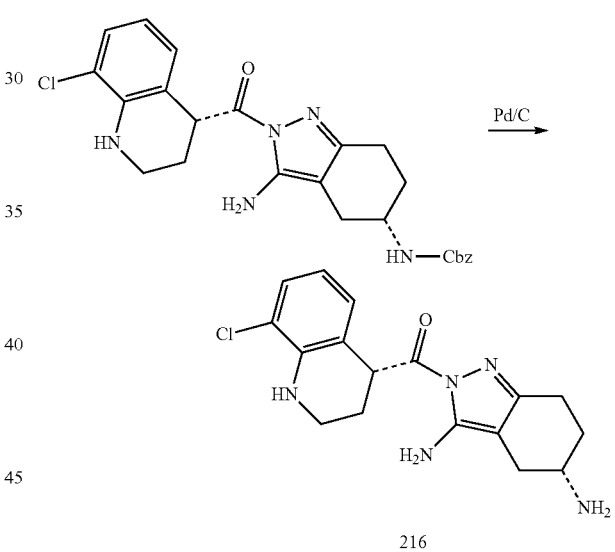

Into a 50-mL round-bottom flask, was placed benzyl N-[(5S)-3-amino-2-[[(4R)-8-chloro-1,2,3,4-tetrahydroquinolin-4-yl]carbonyl]-4,5,6,7-tetrahydro-2H-indazol-5-yl]carbamate (42 mg, 0.09 mmol, 1.00 equiv), methanol (10 mL), Palladium carbon (10%, 20 mg). To the above hydrogen was introduced in. The resulting solution was stirred for 40 min at room temperature. The solids were filtered out. The resulting mixture was concentrated under vacuum. The crude product was purified by Prep-HPLC with the following conditions: Column: XBridge Prep C18 OBD Column 19×150 mm 5 um; Mobile Phase A: water (10 mmoL/L NH4HCO3), Mobile Phase B: ACN; Flow rate: 20 mL/min; Gradient: 30% B to 50% B in 5 min; 254/220 nm; Rt: 4.65 min. The collected fraction was lyophilized to give 10.4 mg (34%) of ((4R*)-8-chloro-1,2,3,4-tetrahydroquinolin-4-yl) ((5S*)-3,5-diamino-4,5,6,7-tetrahydroindazol-2-yl)methanone (216) as a white solid. MS (ES, m/z) [M+H]+: 346 & 348. (DMSO-d6, 300 MHz, ppm): δ 7.12-7.09 (m, 1H), 6.82-6.79 (m, 1H), 6.46-6.40 (m, 1H), 6.35 (s, 2H), 5.74 (s, 1H), 5.07-5.04 (m, 1H), 2.96-2.95 (m, 1H), 2.66-2.54 (m, 2H), 2.46-2.42 (m, 1H), 2.13-1.82 (m, 6H), 1.53-1.44 (m, 1H).

Example 217 & 218. ((5R*)-3-amino-5-hydroxy-4,5,6,7-tetrahydro-2H-indazol-2-yl)((4R*)-8-methyl-1,2,3,4-tetrahydroquinolin-4-yl)methanone and ((5R*)-3-amino-5-hydroxy-4,5,6,7-tetrahydro-2H-indazol-2-yl)((4S*)-8-methyl-1,2,3,4-tetrahydroquinolin-4-yl)methanone

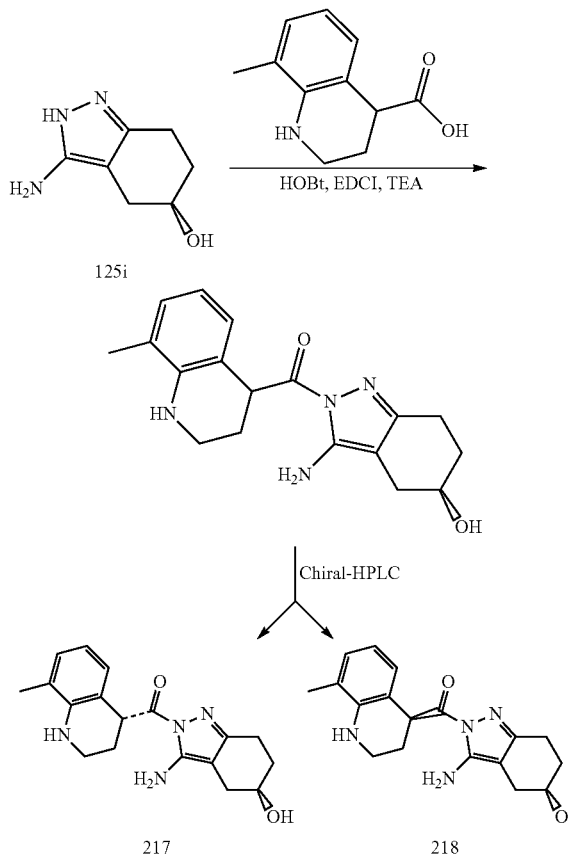

Into a 100-mL round-bottom flask, was placed (5R*)-3-amino-4,5,6,7-tetrahydro-2H-indazol-5-ol (400 mg, 2.61 mmol, 1.00 equiv), 8-methyl-1,2,3,4-tetrahydroquinoline-4-carboxylic acid (1 equiv), EDCI (752 mg, 3.92 mmol, 1.50 equiv), HOBt (527 mg, 3.90 mmol, 1.50 equiv), TEA (1.3 g, 12.85 mmol, 5.00 equiv), N,N-dimethylformamide (20 mL). The resulting solution was stirred for 2 h at room temperature. The reaction was then quenched by the addition of water (100 mL). The resulting solution was extracted with ethyl acetate (60 mL×3) and the organic layers combined and concentrated under vacuum. The crude product was purified by Prep-HPLC with the following conditions (2#-AnalyseHPLC-SHIMADZU (HPLC-10)): Column, XBridge Shield RP18 OBD Column, 5 um, 19×150 mm; mobile phase, water (0.1% FA) and ACN (5.0% ACN up to 30.0% in 15 min); Detector, UV 254 nm. The fraction collected was lyophilized to give 200 mg (25%) of ((R*)-3-amino-5-hydroxy-4,5,6,7-tetrahydro-2H-indazol-2-yl)(8-methyl-1,2,3,4-tetrahydroquinolin-4-yl)methanone. RT2: 14.50 min; The racemic product was separated by Chiral-Prep-HPLC with the following conditions (Prep-HPLC-032): Column, Chiralpak ID-2, 2×25 cm, 5 um; mobile phase, Hex and ethanol (hold 30.0% ethanol in 20 min); Detector, UV 254/220 nm.

Enantiomer A (217): This resulted in 81.2 mg (10%) of ((5R*)-3-amino-5-hydroxy-4,5,6,7-tetrahydro-2H-indazol-2-yl)((4R*)-8-methyl-1,2,3,4-tetrahydroquinolin-4-yl)methanone as a white solid. RT2: 15.07 min; MS (ES, m/z) [M+H]+: 327; (DMSO-d6, 400 MHz, ppm): δ 6.82 (d, J=7.2 Hz, 1H), 6.65 (d, J=7.6 Hz, 1H), 6.37-6.33 (m, 3H), 5.19 (s, 1H), 5.06-5.03 (m, 1H), 4.78 (d, J=4.0 Hz, 1H), 3.89 (m, 1H), 3.36-3.33 (m, 1H), 3.26-3.25 (m, 1H), 2.66-2.50 (m, 2H), 2.66-2.50 (m, 2H), 2.16-2.11 (m, 1H), 2.08-1.97 (m, 5H), 1.90-1.77 (m, 1H), 1.72-1.58 (m, 1H).

Enantiomer B (218): This resulted in 84.9 mg (10%) of ((5R*)-3-amino-5-hydroxy-4,5,6,7-tetrahydro-2H-indazol-2-yl)((4S*)-8-methyl-1-1,2,3,4-tetrahydroquinolin-4-yl) methanone as a white solid. RT1: 12.58 min; MS (ES, m/z) [M+H]+: 327; (DMSO-d6, 400 MHz, ppm): δ 6.82 (d, J=7.2 Hz, 1H), 6.64 (d, J=7.2 Hz, 1H), 6.36-6.33 (m, 3H), 5.19 (s, 1H), 5.06-5.03 (m, 1H), 4.77 (d, J=4.0 Hz, 1H), 3.89 (m, 1H), 2.65-2.50 (m, 2H), 2.47-2.45 (m, 1H), 2.15-2.11 (m, 1H), 2.09-1.99 (m, 5H), 1.90-1.77 (m, 1H), 1.72-1.58 (m, 1H).

In similar fashion the compounds in Table 3 may be synthesized.

TABLE 3

| Examples | Structure | Name |
| --- | --- | --- |
| 219 | 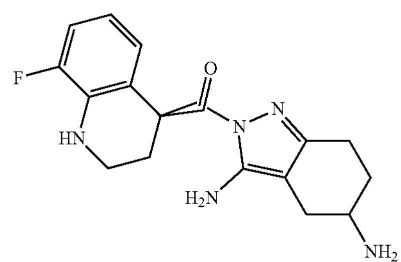 | ((5R/S)-3,5-diamino-4,5,6,7-tetrahydroindazol-2-yl)((4S*)-8-fluoro-1,2,3,4-tetrahydroquinolin-4-yl)methanone |

TABLE 3-continued

| Examples | Structure | Name |
|---|---|---|
| 220 | 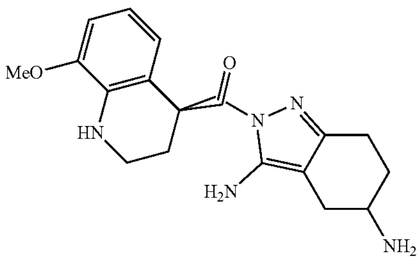 | ((5R/S)-3,5-diamino-4,5,6,7-tetrahydroindazol-2-yl)((4S*)-8-methoxy-1,2,3,4-tetrahydroquinolin-4-yl)methanone |
| 221 | 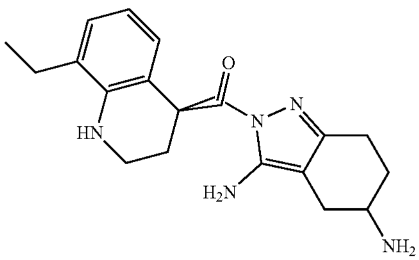 | ((5R/S)-3,5-diamino-4,5,6,7-tetrahydroindazol-2-yl)((4S*)-8-ethyl-1,2,3,4-tetrahydroquinolin-4-yl)methanone |
| 222 | 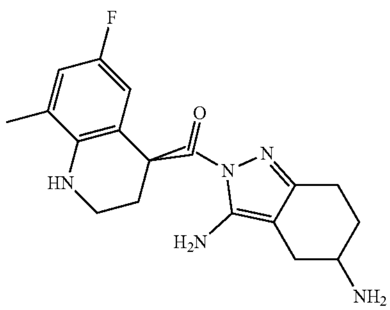 | ((5R/S)-3,5-diamino-4,5,6,7-tetrahydroindazol-2-yl)((4S*)-6-fluoro-8-methyl-1,2,3,4-tetrahydroquinolin-4-yl)methanone |
| 223 | 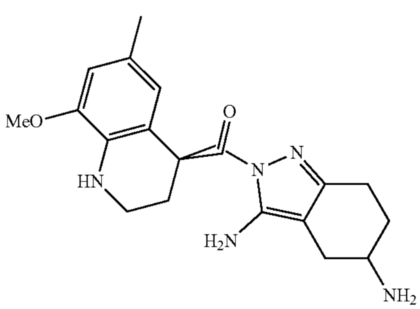 | ((5R/S)-3,5-diamino-4,5,6,7-tetrahydroindazol-2-yl)((4S*)-8-methoxy-6-methyl-1,2,3,4-tetrahydroquinolin-4-yl)methanone |
| 224 | 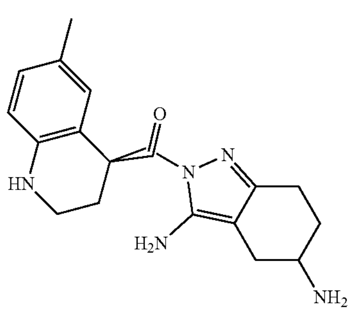 | ((5R/S)-3,5-diamino-4,5,6,7-tetrahydroindazol-2-yl)((4S*)-6-methyl-1,2,3,4-tetrahydroquinolin-4-yl)methanone |

TABLE 3-continued

| Examples | Structure | Name |
|---|---|---|
| 226 | 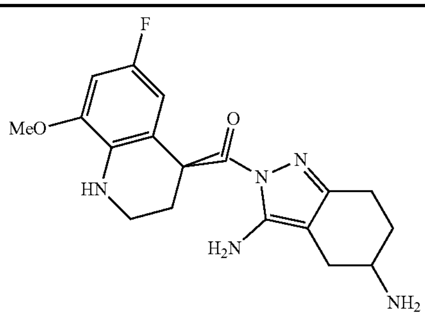 | ((5R/S)-3,5-diamino-4,5,6,7-tetrahydroindazol-2-yl)((4S*)-6-fluoro-8-methoxy-1,2,3,4-tetrahydroquinolin-4-yl)methanone |
| 227 | 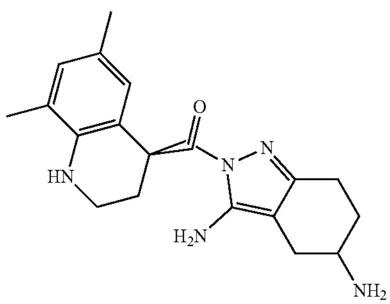 | ((5R/S)-3,5-diamino-4,5,6,7-tetrahydroindazol-2-yl)((4S*)-6,8-dimethyl-1,2,3,4-tetrahydroquinolin-4-yl)methanone |
| 228 | 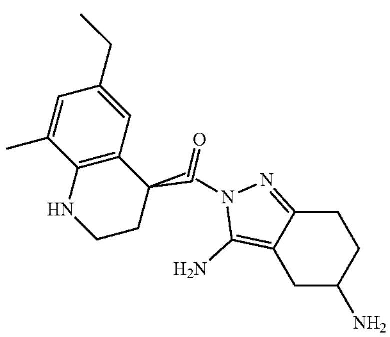 | ((5R/S)-3,5-diamino-4,5,6,7-tetrahydroindazol-2-yl)((4S*)-6-ethyl-8-methyl-1,2,3,4-tetrahydroquinolin-4-yl)methanone |
| 229 | 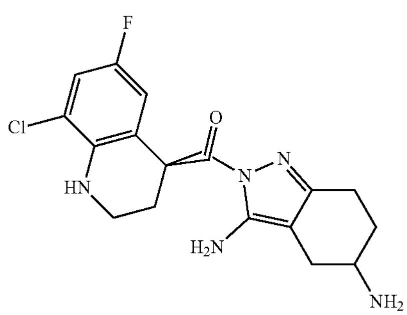 | ((4S*)-8-chloro-6-fluoro-1,2,3,4-tetrahydroquinolin-4-yl)((5R/S)-3,5-diamino-4,5,6,7-tetrahydroindazol-2-yl)methanone |
| 230 | 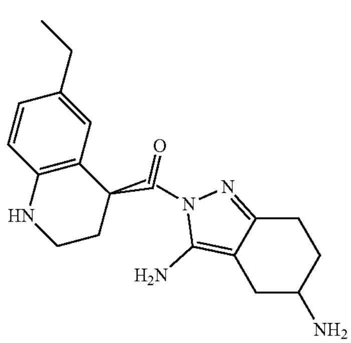 | ((5R/S)-3,5-diamino-4,5,6,7-tetrahydroindazol-2-yl)((4S*)-6-ethyl-1,2,3,4-tetrahydroquinolin-4-yl)methanone |

TABLE 3-continued

| Examples | Structure | Name |
|---|---|---|
| 231 | 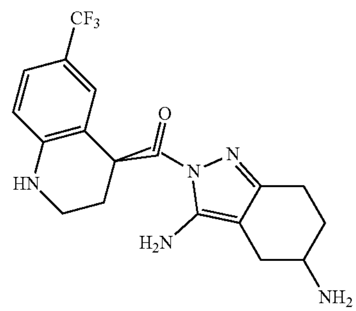 | ((5R/S)-3,5-diamino-4,5,6,7-tetrahydroindazol-2-yl)((4S*)-6-tri-fluoromethyl-1,2,3,4-tetrahydroquinolin-4-yl)methanone |
| 232 | 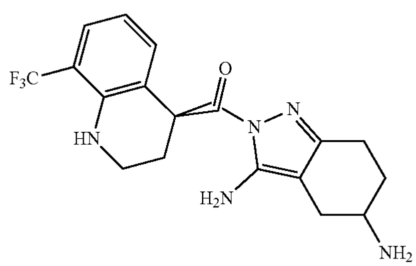 | ((5R/S)-3,5-diamino-4,5,6,7-tetrahydroindazol-2-yl)((4S*)-8-tri-fluoromethyl-1,2,3,4-tetrahydroquinolin-4-yl)methanone |
| 233 | 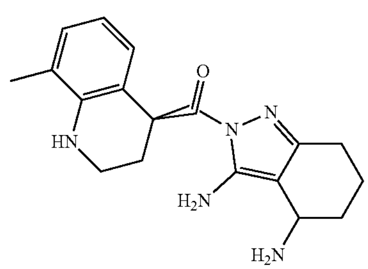 | ((4R/S)-3,4-diamino-4,5,6,7-tetrahydroindazol-2-yl)((4S*)-8-methyl-1,2,3,4-tetrahydroquinolin-4-yl)methanone |
| 234 | 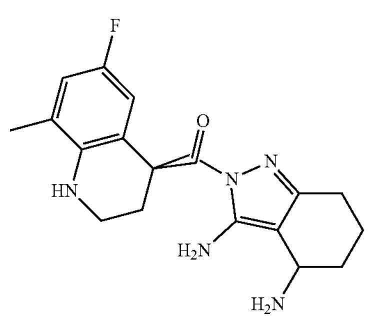 | ((4R/S)-3,4-diamino-4,5,6,7-tetrahydroindazol-2-yl)((4S*)-6-fluoro-8-methyl-1,2,3,4-tetrahydroquinolin-4-yl)methanone |
| 235 | 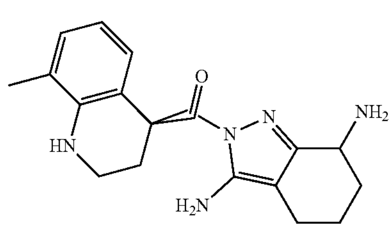 | ((7R/S)-3,7-diamino-4,5,6,7-tetrahydroindazol-2-yl)((4S*)-8-methyl-1,2,3,4-tetrahydroquinolin-4-yl)methanone |

TABLE 3-continued

| Examples | Structure | Name |
|---|---|---|
| 236 | 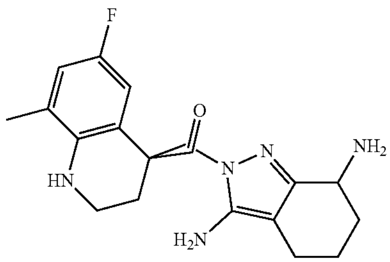 | ((7R/S)-3,7-diamino-4,5,6,7-tetrahydroindazol-2-yl)((4S*)-6-fluoro-8-methyl-1,2,3,4-tetrahydroquinolin-4-yl)methanone |
| 238 | 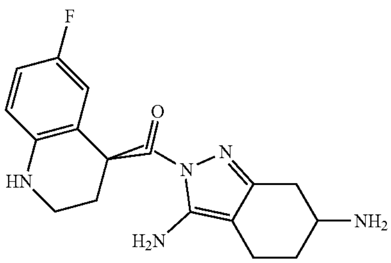 | ((6R/S)-3,6-diamino-4,5,6,7-tetrahydroindazol-2-yl)((4S*)-6-fluoro-1,2,3,4-tetrahydroquinolin-4-yl)methanone |
| 239 | 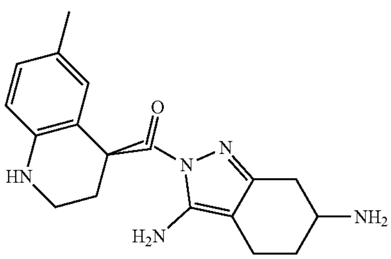 | ((6R/S)-3,6-diamino-4,5,6,7-tetrahydroindazol-2-yl)((4S*)-6-methyl-1,2,3,4-tetrahydroquinolin-4-yl)methanone |
| 241 | 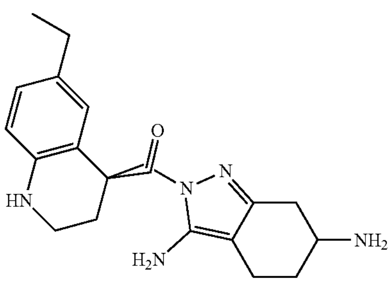 | ((6R/S)-3,6-diamino-4,5,6,7-tetrahydroindazol-2-yl)((4S*)-6-ethyl-1,2,3,4-tetrahydroquinolin-4-yl)methanone |
| 242 | 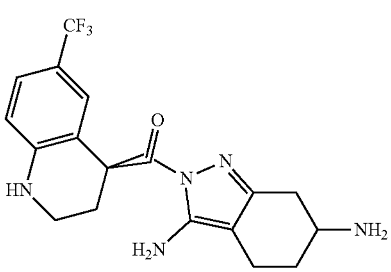 | ((6R/S)-3,6-diamino-4,5,6,7-tetrahydroindazol-2-yl)((4S*)-6-tri-fluoromethyl-1,2,3,4-tetrahydroquinolin-4-yl)methanone |
| 243 | 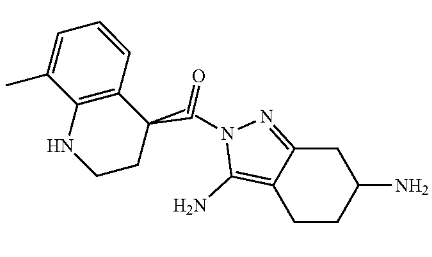 | ((6R/S)-3,6-diamino-4,5,6,7-tetrahydroindazol-2-yl)((4S*)-8-methyl-1,2,3,4-tetrahydroquinolin-4-yl)methanone |

TABLE 3-continued

| Examples | Structure | Name |
|---|---|---|
| 244 | 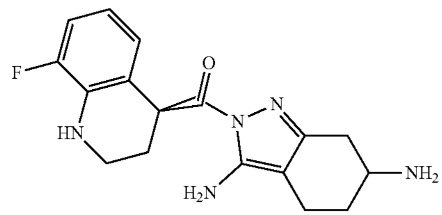 | ((6R/S)-3,6-diamino-4,5,6,7-tetrahydroindazol-2-yl)((4S*)-8-fluoro-1,2,3,4-tetrahydroquinolin-4-yl)methanone |
| 245 | 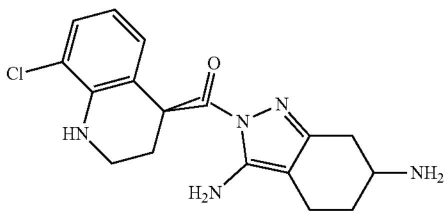 | ((4S*)-8-chloro-1,2,3,4-tetrahydroquinolin-4-yl)((6R/S)-3,6-diamino-4,5,6,7-tetrahydroindazol-2-yl)methanone |
| 246 | 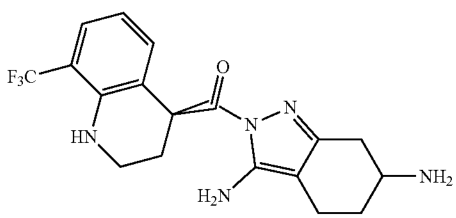 | ((6R/S)-3,6-diamino-4,5,6,7-tetrahydroindazol-2-yl)((4S*)-8-tri-fluoromethyl-1,2,3,4-tetrahydroquinolin-4-yl)methanone |
| 247 | 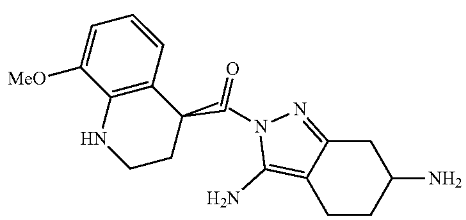 | ((6R/S)-3,5-diamino-4,5,6,7-tetrahydroindazol-2-yl)((4S*)-8-methoxy-1,2,3,4-tetrahydroquinolin-4-yl)methanone |
| 248 | 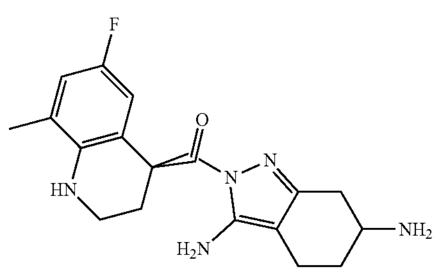 | ((6R/S)-3,6-diamino-4,5,6,7-tetrahydroindazol-2-yl)((4S*)-6-fluoro-8-methyl-1,2,3,4-tetrahydroquinolin-4-yl)methanone |
| 249 | 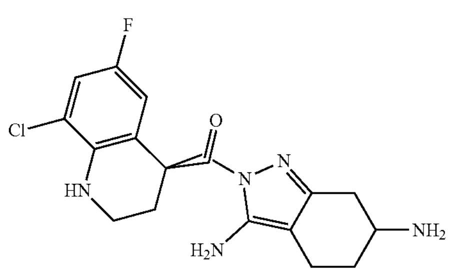 | ((4S*)-8-chloro-6-fluoro-1,2,3,4-tetrahydroquinolin-4-yl)((6R/S)-3,6-diamino-4,5,6,7-tetrahydroindazol-2-yl)methanone |

TABLE 3-continued

| Examples | Structure | Name |
|---|---|---|
| 250 | 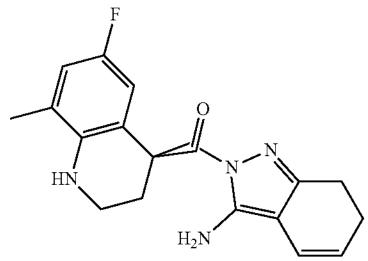 | (S*)-(3-amino-6,7-dihydroindazol-2-yl)(6-fluoro-8-methyl-1,2,3,4-tetrahydroquinolin-4-yl)methanone |
| 251 | 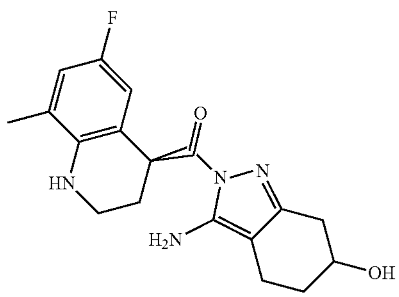 | ((6R/S)-3-amino-6-hydroxy-4,5,6,7-tetrahydroindazol-2-yl)((4S*)-6-fluoro-8-methyl1,2,3,4-tetrahydroquinolin-4-yl)methanone |
| 252 | 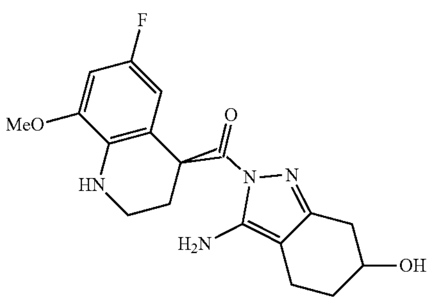 | ((6R/S)-3-amino-6-hydroxy-4,5,6,7-tetrahydroindazol-2-yl)((4S*)-6-fluoro-8-methoxy-1,2,3,4-tetrahydroquinolin-4-yl)methanone |
| 253 | 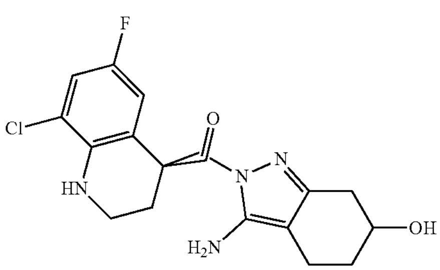 | ((4S*)-8-chloro-6-fluoro-1,2,3,4-tetrahydroquinolin-4-yl)((6R/S)-3-amino-6-hydroxy-4,5,6,7-tetrahydroindazol-2-yl)methanone |
| 254 | 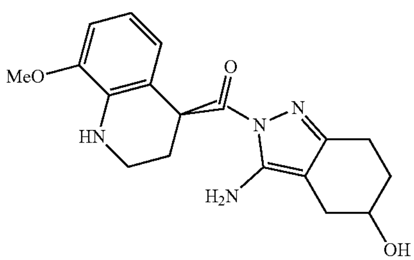 | ((5R/S)-3-amino-5-hydroxy-4,5,6,7-tetrahydro-2H-indazol-2-yl)((4S*)-8-methoxy-1,2,3,4-tetrahydroquinolin-4-yl)methanone |

TABLE 3-continued

| Examples | Structure | Name |
|---|---|---|
| 255 | 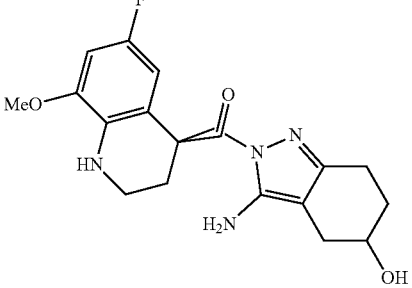 | ((5R/S)-3-amino-5-hydroxy-4,5,6,7-tetrahydro-2H-indazol-2-yl)((4S*)-6-fluoro-8-methoxy-1,2,3,4-tetrahydroquinolin-4-yl)methanone |
| 256 | 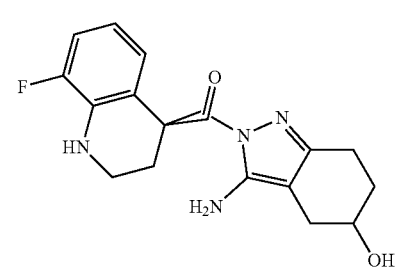 | ((5R/S)-3-amino-5-hydroxy-4,5,6,7-tetrahydro-2H-indazol-2-yl)((4S*)-8-fluoro-1,2,3,4-tetrahydroquinolin-4-yl)methanone |
| 257 | 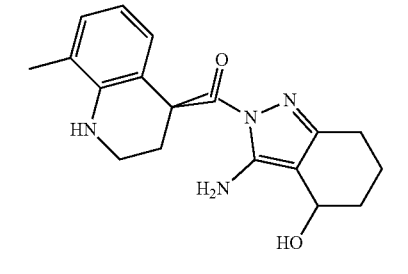 | ((4R/S)-3-amino-4-hydroxy-4,5,6,7-tetrahydro-2H-indazol-2-yl)((4S*)-8-methyl-1,2,3,4-tetrahydroquinolin-4-yl)methanone |
| 258 | 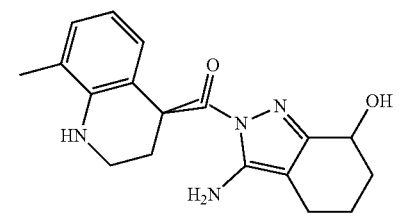 | ((7R/S)-3-amino-7-hydroxy-4,5,6,7-tetrahydro-2H-indazol-2-yl)((4S*)-8-methyl-1,2,3,4-tetrahydroquinolin-4-yl)methanone |
| 259 | 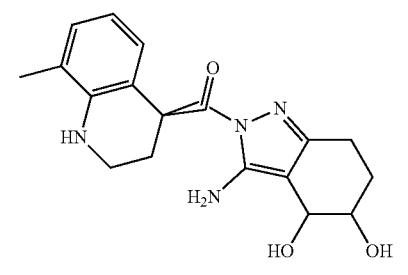 | ((4R/S, 5R/S)-3-amino-4,5-di-hydroxy-4,5,6,7-tetrahydro-2H-indazol-2-yl)((4S*)-8-methyl-1,2,3,4-tetrahydroquinolin-4-yl)methanone |

TABLE 3-continued

| Examples | Structure | Name |
|---|---|---|
| 260 | 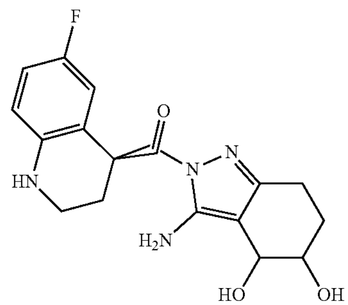 | ((4R/S, 5R/S)-3-amino-4,5-di-hydroxy-4,5,6,7-tetrahydro-2H-indazol-2-yl)((4S*)-6-fluoro-1,2,3,4-tetrahydroquinolin-4-yl)methanone |
| 261 | 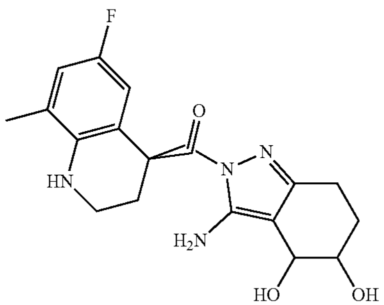 | ((4R/S, 5R/S)-3-amino-4,5-di-hydroxy-4,5,6,7-tetrahydro-2H-indazol-2-yl)((4S*)-6-fluoro-1,2,3,4-tetrahydroquinolin-4-yl)methanone |

The compounds of the invention were tested in the following screens.

Factor XIIa (FXIIa) Inhibitory Activity:

In a 96-well clear bottom plate, 80 µl of assay buffer was added to each well. Assay buffer consists of 0.5× Hank's Balanced Salt Solution (Invitrogen), buffered with 25 mM HEPES pH 7.4 (Invitrogen) and 0.5× Tris-buffered saline with Tween-20 0.05% (Santa Cruz Biotechnology). Test compounds were first dissolved in DMSO (Sigma) and then 4 µl were added to test wells containing assay buffer. Serial dilutions using an automated multi-channel pipette were used to generate a concentration range of approximately 1-100 µM. Human FXIIa (Enzyme Research Labs) was diluted in assay buffer to a final concentration of 12.5 nM. 80 µl of this enzyme solution was added to the assay wells. The enzyme/compound mixtures were incubated for 10 minutes at room temperature. Chromogenic substrate (Pefachrome XIIa; Enzyme Research Labs) was added to assay wells at a final concentration of 400 µM. The assay plate was spun for 1 minute at 1500 g and then read at 37° C. in a SpectraMax M2 plate reader ($\lambda$=405 nm). Activity was quantified as the rate of change in absorbance, which corresponds to the rate of substrate cleavage. IC$_{50}$ values were determined as the concentration of inhibitor that produced 50% of the rate of change of control wells without any inhibitor. For compounds with activity <1 µM, the assay was repeated with a lower concentration range, typically from 10-1000 nM.

Counterscreens for Selectivity:

Thrombin.

In a 96-well white opaque plate, 80 µl of assay buffer was added to each well. Test compounds were added, and serially diluted as above, to generate a concentration range of approximately 1-100 µM. Human alpha-thrombin (Enzyme Research Labs) was diluted in assay buffer to a final concentration of 12.5 nM. 80 µl of this enzyme solution was added to the assay wells. The enzyme/compound mixtures were incubated for 10 minutes at room temperature. Fluorogenic substrate (Boc-Val-Pro-Arg-7-amido-4-methylcoumarin; Sigma) was added to assay wells at a final concentration of 20 µM. The assay plate was spun for 1 minute at 1500 g and then read at 37° C. in a SpectraMax M2 plate reader ($\lambda_{ex}$=380 nm and $\lambda_{em}$=460 nm). Activity was quantified as the rate of change in fluorescence, which corresponds to the rate of substrate cleavage. IC$_{50}$ values were determined as the concentration of inhibitor that produced 50% of the rate of change of control wells without any inhibitor. For compounds with activity <1 µM, the assay was repeated with a lower concentration range, typically from 10-1000 nM.

Factor Xa.

In a 96-well white opaque plate, 80 µl of assay buffer was added to each well. Test compounds were added, and serially diluted as above, to generate a concentration range of approximately 1-100 µM. Human FXa (Enzyme Research Labs) was diluted in assay buffer to a final concentration of 12.5 nM. 80 µl of this enzyme solution was added to the assay wells. The enzyme/compound mixtures were incubated for 10 minutes at room temperature. Fluorogenic substrate (Pefafluor FXa; Enzyme Research Labs) was added to assay wells at a final concentration of 80 µM. The assay plate was spun for 1 minute at 1500 g and then read at 37° C. in a SpectraMax M2 plate reader ($\lambda_{ex}$=380 nm and $\lambda_{em}$=460 nm). Activity was quantified as the rate of change in fluorescence, which corresponds to the rate of substrate cleavage. IC$_{50}$ values were determined as the concentration of inhibitor that produced 50% of the rate of change of control wells without any inhibitor.

Factor XIa.

In a 96-well clear-bottom plate, 80 µl of assay buffer was added to each well. Test compounds were added, and serially diluted as above, to generate a concentration range of approximately 1-100 µM. Human FXIa (Enzyme Research Labs) was diluted in assay buffer to a final concentration of 12.5 nM. 80 μl of this enzyme solution was added to the assay wells. The enzyme/compound mixtures were incubated for 10 minutes at room temperature. Chromogenic substrate (Pefachrome FXIa 3371; Enzyme Research Labs) was added to assay wells at a final concentration of 100 μM. The assay plate was spun for 1 minute at 1500 g and then read at 37° C. in a SpectraMax M2 plate reader (λ=405). Activity was quantified as the rate of change in absorbance, which corresponds to the rate of substrate cleavage. $IC_{50}$ values were determined as the concentration of inhibitor that produced 50% of the rate of change of control wells without any inhibitor.

Plasma Kallikrein.

In a 96-well white opaque plate, 80 μl of assay buffer was added to each well. Test compounds were added, and serially diluted as above, to generate a concentration range of approximately 1-100 μM. Human plasma kallikrein (Enzyme Research Labs) was diluted in assay buffer to a final concentration of 12.5 nM. 80 μl of this enzyme solution was added to the assay wells. The enzyme/compound mixtures were incubated for 10 minutes at room temperature. Fluorogenic substrate (Z-Phe-Arg 7-amido-4-methylcoumarin; Sigma) was added to assay wells at a final concentration of 50 μM. The assay plate was spun for 1 minute at 1500 g and then read at 37° C. in a SpectraMax M2 plate reader ($\lambda_{ex}$=380 nm and $\lambda_{em}$=460 nm). Activity was quantified as the rate of change in fluorescence, which corresponds to the rate of substrate cleavage. $IC_{50}$ values were determined as the concentration of inhibitor that produced 50% of the rate of change of control wells without any inhibitor.

Results of testing of some embodiments in the foregoing screens are shown in Table 4, wherein the $IC_{50}$s are given in μM:

TABLE 4

| example number | AT # | Factor XIIa $IC_{50}$ μM | Thrombin $IC_{50}$ μM |
|---|---|---|---|
| 1 | 286 | 0.1 | 25 |
| 2 | 324 | >50 | >50 |
| 3 | 315 | 5 | 33 |
| 4 | 433 | 65 | 45 |
| 5 | 380 | 1.7 | >50 |
| 6 | 430 | 50 | >>50 |
| 7 | 381 | 0.15 | 30 |
| 8 | 418 | >50 | >50 |
| 9 | 385 | 0.02 | 40 |
| 10 | 431 | 90 | >100 |
| 11 | 388 | 0.2 | >50 |
| 12 | 424 | >50 | >50 |
| 13 | 389 | 5.6 | 77 |
| 14 | 428 | >10 | >10 |
| 15 | 429 | >100 | >100 |
| 16 | 394 | 15 | 100 |
| 17 | 425 | >100 | >100 |
| 18 | 421 | 5 | >100 |
| 19 | 427 | >100 | >100 |
| 20 | 456 | 17.5 | >100 |
| 21 | 515 | 40 | >100 |
| 22 | 471 | 0.04 | 20 |
| 23 | 492 | 5 | >100 |
| 24 | 506 | >100 | >100 |
| 25 | 495 | 0.3 | 80 |
| 26 | 538 | 80 | >80 |
| 27 | 311 | 0.4 | 6 |
| 28 | 382 | 0.06 | 36 |
| 29 | 383 | 0.15 | >50 |
| 30 | 384 | 5 | >70 |
| 31 | 386 | 0.15 | >50 |
| 32 | 387 | 0.15 | >50 |
| 33 | 391 | >125 | >125 |
| 34 | 392 | >150 | >150 |
| 35 | 395 | >100 | >100 |
| 36 | 453 | 0.2 | >80 |
| 37 | 454 | 2.5 | >75 |
| 38 | 472 | 0.04 | 44 |
| 39 | 484 | 4 | 75 |
| 40 | 487 | 15 | >100 |
| 41 | 488 | 1.2 | >100 |
| 42 | 489 | 11 | >100 |
| 43 | 490 | 7.5 | >100 |
| 44 | 493 | 11 | 90 |
| 45 | 494 | 12 | >100 |
| 46 | 496 | 7.5 | >50 |
| 47 | 458 | 0.03 | 50 |
| 48 | 459 | >100 | >100 |
| 49 | 473 | 0.02 | 90 |
| 50 | 476 | 0.01 | 25 |
| 51 | 477 | 0.4 | >50 |
| 52 | 536 | NA | NA |
| 53 | 479 | 0.02 | 28 |
| 54 | 539 | 30 | >85 |
| 55 | 482 | 0.01 | 20 |
| 56 | 537 | 29 | >100 |
| 57 | 524 | 0.06 | 60 |
| 58 | 525 | 0.06 | 40 |
| 59 | 571 | >100 | >100 |
| 60 | 572 | 17 | 22 |
| 61 | 573 | >50 | 20 |
| 62 | 527 | 0.01 | 20 |
| 63 | 540 | 65 | >100 |
| 64 | 528 | 0.2 | 60 |
| 65 | 541 | >100 | >100 |
| 66 | 542 | 0.01 | 75 |
| 67 | 567 | >50 | >50 |
| 68 | 543 | 0.01 | 40 |
| 69 | 568 | 35 | >100 |
| 70 | 544 | 0.02 | 13 |
| 71 | 569 | 55 | 55 |
| 72 | 582 | 0.15 | 75 |
| 73 | 583 | >50 | >50 |
| 74 | 586 | 0.5 | >100 |
| 75 | 590 | >100 | >100 |
| 76 | 587 | 0.3 | >100 |
| 77 | 589 | >100 | >100 |
| 78 | 678 | 0.15 | NT |
| 79 | 679 | 40 | NT |
| 80 | 393 | 0.25 | 68 |
| 81 | 580 | 0.3 | >50 |
| 82 | 581 | 0.04 | 80 |
| 83 | 624 | 0.02 | 60 |
| 84 | 625 | 3.3 | 100 |
| 85 | 584 | 0.4 | 30 |
| 86 | 585 | 0.5 | >80 |
| 87 | 588 | 5 | NT |
| 88 | 593 | 0.85 | 50 |
| 89 | 596 | 40 | NT |
| 90 | 597 | 0.3 | 18 |
| 91 | 761 | 50 | NT |
| 92 | 574 | NT | NT |
| 93 | 598 | >100 | 75 |
| 94 | 599 | 0.25 | NT |
| 95 | 600 | NT | NT |
| 96 | 575 | NT | NT |
| 97 | 601 | 0.4 | NT |
| 98 | 602 | NT | NT |
| 99 | 603 | 1 | 22 |
| 100 | 632 | NT | NT |
| 101 | 618 | 0.9 | NT |
| 102 | 733 | NT | NT |
| 103 | 619 | 0.7 | NT |
| 104 | 736 | >50 | NT |
| 105 | 620 | 1.8 | 50 |
| 106 | 626 | 0.04 | NT |
| 107 | 627 | 8 | NT |
| 108 | 628 | 0.07 | NT |
| 109 | 629 | 10 | NT |
| 110 | 633 | 0.25 | NT |
| 111 | 712 | >100 | NT |

TABLE 4-continued

| example number | AT # | Factor XIIa IC$_{50}$ μM | Thrombin IC$_{50}$ μM |
|---|---|---|---|
| 112 | 658 | 0.18 | NT |
| 113 | 660 | 0.05 | NT |
| 114 | 681 | >100 | NT |
| 115 | 683 | 0.4 | NT |
| 116 | 737 | NT | NT |
| 117 | 704 | 0.03 | NT |
| 118 | 724 | 20 | NT |
| 119 | 706 | 0.05 | 100 |
| 120 | 758 | 10 | >80 |
| 121 | 707 | 0.02 | 9 |
| 122 | 875 | 0.7 | 25 |
| 123 | 722 | 2.5 | NT |
| 124 | 749 | 60 | 60 |
| 125 | 738 | 1.4 | >100 |
| 126 | 739 | 0.02 | 37 |
| 127 | 740 | 0.35 | >80 |
| 128 | 741 | 30 | >65 |
| 129 | 858 | 0.05 | >150 |
| 130 | 857 | 45 | NT |
| 131 | 878 | >90 | NT |
| 132 | 879 | >90 | NT |
| 133 | 855 | 33 | NT |
| 134 | 856 | 1.2 | >75 |
| 135 | 876 | 24 | NT |
| 136 | 877 | >90 | NT |
| 137 | 860 | 0.06 | 29 |
| 138 | 906 | 16 | NT |
| 139 | 917 | 85 | NT |
| 140 | 908 | 0.2 | >60 |
| 141 | 910 | 17 | NT |
| 142 | 918 | 65 | NT |
| 143 | 948 | 1.3 | >80 |
| 144 | 949 | 9 | NT |
| 145 | 965 | >80 | NT |
| 146 | 966 | >80 | NT |
| 147 | 950 | 33 | NT |
| 148 | 951 | 0.04 | >80 |
| 149 | 967 | >40 | NT |
| 150 | 968 | 23 | NT |
| 152 | 504 | 25 | >100 |
| 154 | 507 | 17 | >50 |
| 155 | 512 | 90 | >100 |
| 156 | 549 | 100 | 100 |
| 157 | 516 | 30 | >100 |
| 158 | 635 | 13 | NT |
| 159 | 650 | 0.15 | NT |
| 160 | 677 | 6 | NT |
| 161 | 705 | 0.06 | >100 |
| 162 | 750 | 50 | NT |
| 163 | 734 | 1.5 | NT |
| 164 | 735 | 10 | NT |
| 165 | 742 | 0.35 | >80 |
| 166 | 743 | 50 | >100 |
| 167 | 791 | >80 | >80 |
| 168 | 792 | >100 | >100 |
| 169 | 744 | 60 | >100 |
| 170 | 745 | 6 | >150 |
| 171 | 793 | >90 | >90 |
| 172 | 794 | >100 | >100 |
| 173 | 859 | 0.1 | 30 |
| 174 | 880 | >80 | NT |
| 175 | 916 | 16 | NT |
| 176 | 952 | >100 | NT |
| 177 | 953 | 2 | >100 |
| 178 | 1019 | NT | NT |
| 179 | 955 | 28 | NT |
| 180 | 954 | 0.09 | >80 |
| 181 | 1020 | NT | NT |
| 182 | 969 | >100 | NT |
| 183 | 970 | 0.6 | >100 |
| 184 | 971 | >100 | NT |
| 185 | 972 | 0.07 | >100 |
| 186 | 1033 | 2.5 | NT |
| 187 | 1038 | NT | NT |
| 188 | 979 | >80 | NT |
| 189 | 980 | 3 | NT |
| 190 | 1034 | 0.4 | >60 |
| 191 | 1039 | >55 | NT |
| 192 | 981 | 0.08 | >90 |
| 193 | 982 | 4 | NT |
| 194 | 1061 | 7 | NT |
| 195 | 1062 | 0.04 | NT |
| 196 | 1141 | 7.5 | NT |
| 197 | 1070 | 1.5 | >150 |
| 198 | 1071 | 0.1 | >100 |
| 199 | 1072 | 0.04 | NT |
| 200 | 1073 | 3.3 | NT |
| 201 | 1082 | >150 | NT |
| 202 | 1083 | >175 | NT |
| 203 | 1095 | 55 | NT |
| 204 | 1096 | 0.04 | NT |
| 205 | 1128 | >100 | NT |
| 206 | 1099 | 2.8 | NT |
| 207 | 1100 | 0.16 | NT |
| 208 | 1132 | >100 | NT |
| 209 | 1101 | 0.04 | >100 |
| 210 | 1102 | 3.3 | >100 |
| 211 | 1133 | >100 | NT |
| 212 | 1134 | >100 | NT |
| 213 | 1103 | 0.06 | NT |
| 214 | 1104 | NT | NT |
| 215 | 1105 | 0.07 | NT |
| 216 | 1106 | 3 | NT |
| 217 | 1063 | 35 | NT |
| 218 | 1064 | 0.05 | >90 |

A predictive correlation between inhibition of Factor XIIa and efficacy in vivo in the mouse experimental autoimmune encephalomyelitis (EAE) model has been published by Gobel et al. in Nature Communications 7:11626 (18 May 2016). Experimental autoimmune encephalomyelitis (EAE) is the most commonly used experimental model for the human inflammatory demyelinating disease, multiple sclerosis (MS). Many of the drugs that are in current or imminent use in MS have been developed, tested or validated on the basis of EAE studies [Constantinescu et al., British Journal of Pharmacology (2011) 164 1079-1106]. Thus the results shown above would indicate to the person of skill that the compounds would be useful to treat CNS inflammatory diseases and thromboses. Our own PCT (PCT/US2017/12796), filed Jan. 10, 2017, discloses the correlation of inhibition of Factor XIIa with efficacy in vivo in the mouse experimental autoimmune encephalomyelitis (EAE) model for a series of 1-acyl-3-(heteroaryl)-1H-1,2,4-triazol-5-amines that selectively inhibit Coagulation Factor XIIa. Briefly, female mice approximately 10 weeks old are immunized with a fragment of myelin oligodendrocyte glycoprotein (MOG), residues 35-55 in an emulsion with Freund's Complete adjuvant. Two subcutaneous injections are performed, one on the upper back, and one on the lower back. Approximately 2 hours later, animals receive an intraperitoneal injection of pertussis toxin. Twenty-four hours later, animals receive a second dose of pertussis toxin. Disease onset occurs within approximately 10-14 days, and disease severity is scored using a standard EAE scoring guide:

| EAE SCORE | CLINICAL SIGNS |
|---|---|
| 0 | Normal; no signs of disease |
| 1 | Limp tail |
| 2 | Paraparesis: limp tail and hind limb weakness; Waddling gait |

-continued

| EAE SCORE | CLINICAL SIGNS |
|---|---|
| 3 | Hind limb Paralysis Total loss of movement in hind limbs. Mouse moves itself with forelimbs. |
| 4 | Quadriplegia |
| 5 | Moribund, or complete hind limb paralysis with moderate to severe forelimb paresis |

Test compounds are administered either with MOG inoculation (prophylactic model), or beginning at the earliest sign of disease (therapeutic model). Compound efficacy is assessed by determining the EAE severity score 4 weeks after inoculation, as well as by determining EAE onset and peak severity in relation to comparator and/or control groups. A compound that showed an $IC_{50}$ versus FXIIa of 0.055 µM was evaluated in this test with the following results:

| Treatment | EAE incidence (%) | p value | Median day of onset (all mice) | p value | MMS +/− SD | p value | End score +/− SD | p value | End % body weight +/− SD | p value |
|---|---|---|---|---|---|---|---|---|---|---|
| Vehicle | 91.7 | | 16.0 | | 2.75 +/− 1.25 | | 1.33 +/− 1.27 | | 91.4 +/− 11.2 | |
| Example from US2017/ 12796 | 25.0 | 0.0005 | >28.0* | 0.0013 | 0.79 +/− 1.44 | 0.0018 | 0.71 +/− 1.32 | 0.0103 | 105.2 +/− 8.7 | 0.0026 |

*Median day of onset cannot be calculated because 50% or less of mice developed disease The compounds provided herein can be used for treating inflammation, for treating an immunological disorder, for treating pathologies associated with vasodilatation, or for treating thrombosis. The method includes, for example, administering to a patient a therapeutically effective amount of a compound of formula I or formula II.

What is claimed is:
1. A compound of formula I or formula II:

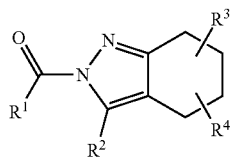

Formula I

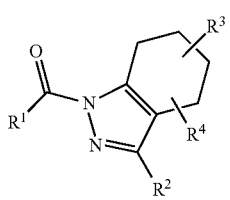

Formula II wherein
$R^1$ is an optionally substituted bicyclic ring system chosen from an optionally substituted indole, isoindole, oxindole, tetrahydroindole, tetralin, indoline, isoindoline, tetrahydroquinoline, tetrahydroisoquinoline, 3,4-dihydro-1H-isochromene, 3,4-dihydro-2H-chromene, benzofuran, dihydrobenzofuran, tetrahydrobenzofuran, benzothiophene, tetrahydrobenzothiophene, indazole, tetrahydroindazole, 2,3-dihydro-1H-indene, naphthalene, tetrahydronaphthalene, and isochroman, said ring system attached to the carbonyl through a carbon, or, when $R^2$ is amino, $R^1$ may additionally be meta- or para-substituted phenyl or an optionally substituted monocyclic heteroaryl ring; wherein $R^1$ is optionally substituted with one or more of halogen, hydroxy, amino, cyano, $(C_1-C_8)$hydrocarbyl, $(C_1-C_8)$hydrocarbyloxy, $(C_1-C_4)$alkylamino, $di(C_1-C_4)$alkylamino, $(C_1-C_4)$acylamino, $(C_1-C_4)$alkylsulfonyl, $(C_1-C_4)$fluoroalkyl, $(C_1-C_4)$fluoroalkoxy, $(C_1-C_6)$oxaalkyl, $(C_3-C_6)$carbocycle, and $(C_1-C_4)$alkenyl;

$R^2$ is chosen from hydrogen, amino and methyl; and $R^3$ and $R^4$ are chosen independently from hydrogen, halogen, hydroxy, amino, cyano, $(C_1-C_4)$alkyl, $(C_1-C_4)$alkoxy, $(C_1-C_4)$alkylamino, $di(C_1-C_4)$alkylamino, $(C_1-C_7)$acylamino, $((C_1-C_7)$hydrocarbyloxy)carbonylamino, $(C_1-C_4)$fluoroalkyl, $(C_1-C_4)$fluoroalkoxy, and $(C_1-C_6)$oxaalkyl, or, taken together, $R^3$ and $R^4$ on adjacent carbons form a double bond.

2. A compound according to claim 1 wherein $R^1$ is an optionally substituted bicyclic ring system.

3. A compound according to claim 2 wherein $R^1$ is optionally substituted indole, benzofuran, or benzothiophene.

4. A compound according to claim 1 wherein, when $R^1$ is substituted with one or more $(C_1-C_8)$hydrocarbyl, said $(C_1-C_8)$hydrocarbyl substituent is chosen from straight chain $(C_1-C_8)$alkyl, branched $(C_1-C_8)$alkyl, $(C_3-C_6)$cycloalkyl, and $(C_3-C_6)$cycloalkyl$(C_1-C_3)$alkyl.

5. The compound of claim 1, wherein $R^1$ is

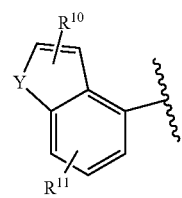

wherein
$R^{10}$ is —H, halogen, —O—$(C_1-C_8)$hydrocarbyl, or —$(C_1-C_8)$hydrocarbyl;

Y is chosen from S, O, NH, and N$(C_1-C_8)$hydrocarbyl; and $R^{11}$ is —H, halogen, —$(C_1-C_8)$hydrocarbyl, or —O$(C_1-C_8)$hydrocarbyl.

6. The compound of claim 5, wherein R¹ is

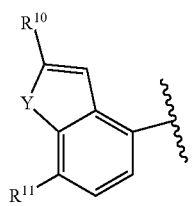

wherein

R¹⁰ is chosen from —H, —(C₁-C₄)alkyl, and (C₃-C₆)cycloalkyl; and

R¹¹ is chosen from —H and —O(C₁-C₄)alkyl.

7. The compound of claim 1, wherein R¹ is

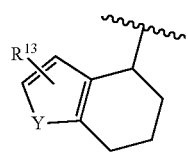

wherein

R¹³ is —H, halogen, —O—(C₁-C₈)hydrocarbyl, or —(C₁-C₈)hydrocarbyl; and

Y is chosen from S, O, NH, and N(C₁-C₈)hydrocarbyl.

8. The compound of claim 7, wherein R¹ is

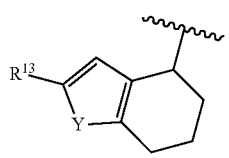

wherein

R¹³ is chosen from —H, —(C₁-C₄)alkyl, and (C₃-C₆)cycloalkyl.

9. The compound of claim 1, wherein R¹ is

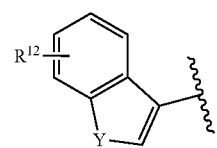

wherein

Y is chosen from S, O, NH, and N(C₁-C₈)hydrocarbyl; and

R¹² is chosen from —H, —(C₁-C₈)hydrocarbyl and —O(C₁-C₈)hydrocarbyl.

10. The compound of claim 9, wherein R¹ is

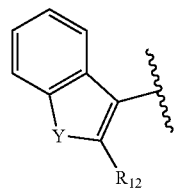

wherein R¹² is —H or (C₁-C₄)alkyl.

11. The compound of claim 1, wherein R¹ is chosen from optionally substituted naphthalene, tetralin, tetrahydrobenzofuran, benzothiophene, tetrahydrobenzothiophene, tetrahydroindole, tetrahydroquinoline and 3,4-dihydro-1H-isochromene.

12. A compound according to claim 1, wherein R² is —NH₂.

13. A compound according to claim 12 of formula V

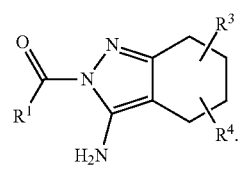

V

14. A compound according to claim 12 of formula III

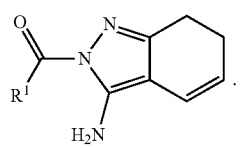

III

15. A compound according to claim 1, wherein R³ and R⁴ are chosen independently from hydrogen, halogen, hydroxy, amino, (C₁-C₄)alkoxy, (C₁-C₄)alkylamino, di(C₁-C₄)alkylamino, (C₁-C₄)acylamino, (C₁-C₄)fluoroalkyl, (C₁-C₄)fluoroalkoxy, and (C₁-C₆)oxaalkyl.

16. A compound according to claim 11 wherein R¹ is

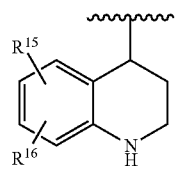

and R¹⁵ and R¹⁶ are independently selected from hydrogen, halogen, hydroxy, amino, cyano, (C₁-C₄)alkyl, (C₁-C₄)alkoxy, (C₁-C₄)fluoroalkyl, and (C₁-C₄)fluoroalkoxy.

17. A compound of at least 80% e.e. according to claim 1 of formula

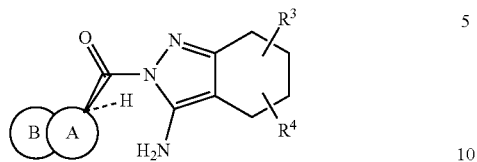

wherein AB is an optionally substituted 6,5-5,6- or 6,6 bicycle in which ring A is non-aromatic and ring B is aromatic, wherein said 6,5-5,6- or 6,6 bicycle is optionally substituted with one or more of halogen, hydroxy, amino, cyano, $(C_1-C_8)$hydrocarbyl, $(C_1-C_8)$hydrocarbyloxy, $(C_1-C_4)$alkylamino, di$(C_1-C_4)$alkylamino, $(C_1-C_4)$acylamino, $(C_1-C_4)$alkylsulfonyl, $(C_1-C_4)$fluoroalkyl, $(C_1-C_4)$fluoroalkoxy, $(C_1-C_6)$oxaalkyl, $(C_3-C_6)$ carbocycle, and $(C_1-C_4)$alkenyl and the carbon at its point of attachment is of a single absolute configuration.

18. A method for treating autoimmune inflammatory diseases of the CNS in a patient, said method comprising administering to said patient a therapeutically effective amount of a compound according to claim 1.

* * * * *